US005637686A

United States Patent [19]
Tjian et al.

[11] Patent Number: 5,637,686
[45] Date of Patent: Jun. 10, 1997

[54] TATA-BINDING PROTEIN ASSOCIATED FACTOR, NUCLEIC ACIDS

[75] Inventors: Robert Tjian, Berkeley; Lucio Comai, El Cerrito, both of Calif.; Brian D. Dynlact, Charlestown, Mass.; Timothy Hoey, San Francisco, Calif.; Siegfried Ruppert; Naoko Tanese, both of Berkeley, Calif.; Edith Wang, San Francisco, Calif.; Robert O. J. Weinzierl, Berkeley, Calif.

[73] Assignee: The Regents of the University of California, Oakland, Calif.

[21] Appl. No.: 646,715

[22] Filed: May 9, 1996

Related U.S. Application Data

[60] Division of Ser. No. 188,582, Jan. 28, 1994, Pat. No. 5,534,410, which is a continuation-in-part of Ser. No. 87,119, Jun. 30, 1993, abandoned, which is a continuation-in-part of Ser. No. 13,412, Jan. 28, 1993, abandoned.

[51] Int. Cl.$^6$ ............................ C12N 15/12; C12N 15/11
[52] U.S. Cl. ................................ 536/23.5; 536/23.1
[58] Field of Search ................................ 536/23.1, 23.5

[56] References Cited

PUBLICATIONS

Dynlacht et al, Isolation of Coactivators Associated with the TATA–Binding Protein That Mediate Transcriptional Activation, Cell, vol. 66: pp. 563–576.

*Primary Examiner*—Mindy Fleisher
*Assistant Examiner*—Terry A. McKelvey
*Attorney, Agent, or Firm*—Richard Aron Osman

[57] ABSTRACT

TATA-binding protein associated factors, TAFs, nuclear proteins involved in RNA polymerase I, II, and III transcription, and nucleic acids encoding TAFs are disclosed. The disclosed methods and compositions find use in developing pharmaceuticals, diagnosis and therapy.

18 Claims, No Drawings

TATA-BINDING PROTEIN ASSOCIATED FACTOR, NUCLEIC ACIDS

CROSS-REFERENCE TO RELATED APPLICATION

This Application is a division of application Ser. No. 08/188,582, filed Jan. 28, 1994 now U.S. Pat. No. 5,534,410 which is a continuation-in-part of application Ser. No. 08/087,119 filed Jun. 30, 1993 now abandoned which is a continuation-in-part of application Ser. No. 08/013,412 filed Jan. 28, 1993 now abandoned.

The research carried out in the subject application was supported in part by grants from the National Institutes of Health. The government may have rights in any patent issuing on this application.

INTRODUCTION

1. Technical Field

The technical field of this invention concerns TATA-binding protein associated factors, proteins involved in gene transcription.

2. Background

Gene transcription requires the concerted action of a number of molecules. DNA provides regulatory sequences and a coding sequence, or template, from which an RNA polymerase synthesizes corresponding RNA. Regulatory sequences generally include sites for sequence-specific transcriptional control, including promoters, enhancers, suppressors, etc; and also a site for transcription initiation. For review, see Mitchell and Tjian (1989), Science 245, 371–378.

RNA polymerases alone appear incapable of initiating transcription. However, in vitro transcriptional activity of RNA polymerases can be restored by the addition of nuclear extracts or fractions thereof. For example, under certain conditions, in vitro transcription by RNA polymerase II (Pol II) can be at least partially restored by the addition of what have variously been reported to be four, five, six or seven nuclear fractions [See e.g. Matsui et al. (1980), Biol Chem 255, 1192], herein referred to as TFIIA, TFIIB, TFIID, TFIIE, TFIIF, TFIIH and TFIIJ. Pol I and Pol III appear to require at least two fractions, called respectively SL1 and UBF, and TFIIIA and TFIIIB.

Many of these transcription fractions remain only partially characterized. For example, all but one of the Pol II fractions remain incompletely characterized or comprise multiple components. The fractions TFIID, SL1 and TFIIIB have been reported to contain a TATA binding component, henceforth, TATA-binding protein, or TBP. Groups of the present Applicants have reported anti-TBP antibodies capable of immunoprecipitating TBP from TFIID, SL1, and TFIIIB.

TFIID, SL1 and TFIIIB immunoprecipitates have revealed TBP and numerous associated factors, tentatively called TBP-associated factors, or TAFs. Furthermore, preliminary experiments indicated that the TBP and non-TBP (TAF) fractions, when combined, facilitated at least some sequence-specific transcription activation.

Unfortunately, it is not clear from the above art that there is any transcriptional activity in the non-TBP fractions of TFIID, SL1 or TFIIIB immunoprecipitates. For example, the reported apparent functional complementarity of the TBP and non-TBP fractions might result from the influence of antirepressors, inhibitor inhibition, etc. Furthermore, the coactivator transcriptional activity attributed to the non-TBP fractions could result from one or more components unrelated to the electrophoretically resolved TAF components. Nor does the literature provide any suggestion as to which, if any, of the electrophoretically resolved components of the non-TBP fraction provide(s) transcriptional activity, nor means for identifying bands resolvable from the non-TBP fractions.

Relevant Literature

Pugh and Tjian (1990), Cell 61:1187–1197; Tanese et al. (1991), Genes and Devel 5:2212–2224; Pugh and Tjian (1991), Genes and Devel 5:1935–1945; Dynlacht et al. (1991), Cell 66:563–576; Timmers et al. (1991), Genes and Devel 5:1946–1956; Zhou et al. (1992), Genes and Devel 6:1964–1974; and Takada et al. (1992), Proc Natl Acad Sci USA 89:11809–11813, relate to factors associated with Pol II transcription. Comai et al. (1992) Cell 6:965–976 relates to factors associated with Pol I transcription. Lobo et al. (1991), Genes and Devel, 5:1477–1489; Margotin et al. (1991), Science 251:424–426; Simmen et al. (1991), EMBO J 10:1853–1862; and Taggart et al. (1992), Cell 71:1015; Lobo et al. (1992), Cell 71:1029; and White and Jackson (1992), Cell 71:1041 relate to factors associated with Pol III transcription. Sekiguchi et al. (1988), EMBO J 7:1683–1687 and Sekiguchi et al. (1991), Mol and Cellular Biol 11:3317–3325 disclose the cloning of the CCG1 gene encoding a protein reported to be involved in cell cycle progression.

SUMMARY OF THE INVENTION

Substantially pure and biologically active TATA-binding protein associated factors (TAFs), eukaryotic nuclear proteins involved in RNA polymerase I, II, and III transcription, nucleic acids encoding TAFs, and methods of using TAFs and TAF-encoding nucleic acids are provided. Recombinant TAFs, anti-TAF antibodies and TAF-fusion products find use in drug screening, dignostics and therapeutics. In particular, the disclosed TAFs provide valuable reagents in developing specific biochemical assays for screening compounds that agonize or antagonize selected transcription factors involved in regulating gene expression associated with human pathology.

DESCRIPTION OF SPECIFIC EMBODIMENTS

Substantially pure and biologically active TATA-binding protein associated factors (TAFs) and portions thereof, nucleic acids encoding TAFs and portions thereof, and methods of use are provided.

As used herein, a given TAF refers to the TAF protein, recombinant or purified from a natural source, and functional and xenogeneic analogs thereof. For example "dTAFII110" refers to a Pol II TAF, derivable from Drosophila, with an apparent molecular weight of about 110 kD, generally as determined by SDS-PAGE under conditions described herein, in Dynlacht et al. (1991), Comai et al. (1992), or otherwise identified by functional, sequence, etc. data herein. It is understood that these molecular weight designations are for the convenience of nomenclature and may not necessarily correspond to actual or predicted molecular weight. Other TAFs are analogously identified herein.

A "portion" of a given TAF is a peptide comprising at least about a six, preferably at least about an eighteen, more preferably at least about a thirty-six amino acid sequence of the TAF. Of particular interest are portions of the TAF that facilitate functional or structural interaction with activators, TAFs, TBP, Pol I, II or III, the TATA box and surrounding DNA sequences, etc. Methods for identifying such preferred portions are described below.

By substantially full-length is meant a polypeptide or polynucleotide that comprises at least 50%, preferably at least 70% and more preferably at least 90% of the natural TAF polypeptide or polynucleotide length.

"Xenogeneic" TAF analogs are nonhuman-, nonDrosophila-derived proteins with substantial functional or sequence identity to human and Drosophila TAFs. Of particular interest are xenogeneic TAF analogs derived from rodents, primates, and livestock animals including bovine, ovine, equine and avian species.

"Functional" analogs of a given TAF or proteins with "substantial functional identity" to a given TAF are compounds that exhibit one or more biochemical properties specific to such TAF, such as the ability of dTAFII110 to interact with Sp1.

"Modulating transcription" means altering transcription, and includes changing the rate of transcription initiation, the level of transcription, or the responsiveness of transcription/transcription initiation to regulatory controls.

The terms "substantially pure" or "isolated" mean that the TAF, TAF portion, or nucleic acid encoding a TAF or TAF portion is unaccompanied by at least some of the material with which it is normally associated in its natural state. While a composition of a substantially pure TAF or portion thereof is preferably substantially free of polyacrylamide, such composition may contain excipients and additives useful in diagnostic, therapeutic and investigative reagents. A substantially pure TAF composition subject to electrophoresis or reverse phase HPLC provides such TAF as a single discernable proteinaceous band or peak.

Generally, a substantially pure TAF composition is at least about 1% protein weight said TAF; preferably at least about 10%; more preferably at least about 50%; and most preferably at least 90%. Protein weight percentages are determined by dividing the weight of the TAF or TAF portion, including alternative forms and analogs of the TAF such as proteolytic breakdown products, alternatively spliced; differentially phosphorylated or glycosylated, or otherwise post-translationally modified forms of the TAF, present in a fraction by the total protein weight present.

A biologically active TAF or TAF portion retains one or more of the TAF's native function such as the ability to specifically bind TBP, transcription factors (activators), other TAFs or anti-TAF antibodies, or to modulate or facilitate transcription or transcription initiation. Exemplary assays for biological activity are described below and in the working exemplification.

Specific binding is empirically determined by contacting, for example a TAF, with a mixture of components and identifying those components that preferentially bind the TAF. Specific binding may be conveniently shown by competitive binding studies, for example, immobilizing a TAF, on a solid matrix such as a polymer bead or microtiter plate and contacting the immobilized TAF with a mixture. Often, one or more components of the mixture will be labeled. Another useful approach is to displace labeled ligand. Generally, specific binding of a TAF will have binding affinity of $10^{-6}$M, more preferably $10^{-8}$M, more preferably $10^{-10}$M under optimized reaction conditions and temperature.

Portions of TAFs find use in screening TAF expression libraries, defining functional domains of TAFs, identifying compounds that bind or associate with TAFs and the like.

Accordingly, peptides encoding a portion of a TAF are provided that are capable of modulating transcription including transcription initiation. Typically, such peptides are effective by binding to a TAF, an activator, or TBP or competitively inhibiting a TAF domain's association with another compound, typically a protein like TBP or another TAF, an activator, or DNA. For example, TAF-TAF interactions may be exploited to purify TAFs, e.g. immobilized TAF200 is used to purify TAF110.

Associational domains of TAFs are ascertainable by those skilled in the art using the methods and compositions disclosed herein. Useful methods include in vitro mutagenesis such as deletion mutants, secondary and tertiary structural predictions, antibody and solvent accessibility, etc. For example, peptides derived from highly charged regions find particular use as immunogens and as modulators of TAF-protein interactions. Also, TAF mutants are used to identify regions important for specific protein interactions or otherwise involved in transcription. Here, useful assays include column binding assay and transfection studies.

The invention provides recombinantly produced TAFs, TAF analogs and portions thereof. These recombinant products are readily modified through physical, chemical, and molecular techniques disclosed or cited herein or otherwise known to those skilled in the relevant art. According to a particular embodiment of the invention, portions of the TAF-encoding sequences are spliced with heterologous sequences to produce fusion proteins. Such fusion proteins find particular use in modulating gene transcription in vitro and in vivo.

For example, many eukaryotic sequence-specific transcription factors have separable DNA binding and activation domains. A TAF or domain thereof can be fused to a well-characterized DNA binding domain (see, e.g., Sadowski et al., (1988) Nature 335, 563–564) and the resulting fusion protein can be tested for its ability to modulate transcription or transcriptional initiation. For example, we disclose the fusion of the N-terminal region of TAF110 to the DNA binding domain of the GAL4 protein. Alternatively, an TAF domain can be fused with a domain having endonuclease activity for site-specific DNA cleaving. Other useful TAF fusion partners include GST, Lerner epitope, an epitope recognized by a monoclonal antibody (e.g. hemagglutinin epitope and 12CA5 monoclonal antibody), glutathione S-transferase for immobilization, the SP1 or VP16 activation domains, etc.

TAFs can be further modified by methods known in the art. For example, TAFs may be phosphorylated or dephosphorylated, glycosylated or deglycosylated, with or without radioactive labeling, etc. The disclosed TAF serine residues in particular provide useful phosphorylation sites. See e.g. methods disclosed in Roberts et al. (1991) Science 253, 1022–1026 and in Wegner et al. (1992) Science 256, 370–373. Especially useful are modifications that alter TAF solubility, membrane transportability, stability, and binding specificity and affinity. Some examples include fatty acid-acylation, proteolysis, and mutations in TAF-TAF or TAF-TBP interaction domains that stabilize binding.

TAFs may also be modified with a label capable of providing a detectable signal, for example, at a heart muscle kinase labeling site, either directly or indirectly. Exemplary labels include radioisotopes, fluorescers, etc. Alternatively, a TAF may be expressed in the presence of a labeled amino acid such as $^{35}$S-methionine. Such labeled TAFs and analogs thereof find use, for example, as probes in expression screening assays for proteins that interact with TAFs, or, for example, TAF binding to other transcription factors in drug screening assays.

Specific polyclonal or monoclonal antibodies that can distinguish TAFs from other nuclear proteins are conveniently made using the methods and compositions disclosed in Harlow and Lane, Antibodies, A Laboratory Manual, Cold Spring Harbor Laboratory, 1988, other references cited herein, as well as immunological and hybridoma technologies known to those in the art. In particular, TAFs and analogs and portions thereof also find use in raising anti-TAF antibodies in laboratory animals such as mice and rabbits as well as the production of monoclonal antibodies by cell fusion or transformation.

Anti-TAF antibodies and fragments (Fab, etc) thereof find use in modulating TAF involvement in transcription complexes, screening TAF expression libraries, etc. In addition, these antibodies can be used to identify, isolate, and purify structural analogs of TAFs. Anti-TAF antibodies also find use for subcellular localization of TAFs under various conditions such as infection, during various cell cycle phases, induction with cytokines, protein kinases such as C and A, etc. Other exemplary applications include using TAF-specific antibodies (including monoclonal or TAF-derived peptide specific antibodies) to immuno-deplete in vitro transcription extracts and using immuno-affinity chromatography to purify TAFs, including analogs, or other nuclear factors which interact with TAFs.

Compositions are also provided for therapeutic intervention in disease, for example, by modifying TAFs or TAF encoding nucleic acids. Oligopeptides can be synthesized in pure form and can find many uses in diagnosis and therapy. These oligopeptides can be used, for example, to modulate native TAF interaction with other TAFs, TBP, other transcription factors or DNA. The oligopeptides will generally be more than six and fewer than about 60 amino acids, more usually fewer than about 30 amino acids, although large oligopeptides may be employed. A TAF or a portion thereof may be used in purified form, generally greater than about 50%, usually greater than about 90% pure. Methods for purifying such peptides to such purities include various forms of chromatographic, chemical, and electrophoretic separations disclosed herein or otherwise known to those skilled in the art.

Experimental methods for purifying TAFs are set out briefly below and in detail in the following working exemplification. Generally, TBP-TAF complexes are immunopurified (generally, by immunoprecipitation) using polyclonal or monoclonal antibodies directed against a native TAF or TBP epitope. Alternatively, monoclonal antibodies directed against an epitope-tagged TBP or TAF may be used. See e.g. Zhou, et al. (1992). At least three complementary experimental approaches are employed for isolating cDNAs encoding TAFs: (1) TAF-specific binding proteins (e.g. antibodies directed against TAF proteins, TAF-binding TAFs, TBP, TAF-binding activators, or TAF-binding coactivators) are used for screening expression libraries; (2) cDNA libraries are screened with potentially homologous TAF oligonucleotide sequences (alternatively, a series of degenerate oligonucleotide PCR primers derived from the homologous TAF sequence may be used to amplify probes from cDNA. See Peterson et al. (1990) Science, 248, 1625–1630, FIG. 1.); and, (3) TAF proteins are purified to homogeneity for protein microsequencing.

TAF ENCODING NUCLEIC ACID

The invention provides nucleic acid sequences encoding TAFs and portions of TAFs. By "encoding a portion of a TAF" is meant to include sequences substantially identical to sequences encoding at least a portion of a TAF. Included are DNA and RNA sequences, sense and antisense.

"Substantial sequence identity" means that a portion of the protein or nucleic acid presents at least about 70%, more preferably at least about 80%, and most preferably at least about 90% sequence identity with a TAF sequence portion. Where the sequence diverges from native TAF sequences disclosed herein, the differences are preferably conservative, i.e. an acidic for an acidic amino acid substitution or a nucleotide change providing a redundant codon. Dissimilar sequences are typically aggregated within regions rather than being distributed evenly over the polymer.

A substantially identical sequence hybridizes to a complementary TAF-encoding sequence under low stringency conditions, for example, at 50° C. and 6× SSC (0.9M saline/0.09M sodium citrate) and that remains bound when subject to washing at 55° C. with 1× SSC.

The invention's TAF encoding polynucleotides are isolated; meaning that the claimed sequence is present as other than a naturally occurring chromosome o transcript in its natural environment. Typically isolated sequences are removed from at least some of the nucleotide sequences with which they are normally associated with on a natural chromosome.

A substantially pure or isolated TAF- or TAF portion-encoding nucleic acid is generally at least about 1% nucleic acid weight said TAF-encoding nucleic acid; preferably at least about 10%; more preferably at least about 50%; and most preferably at least 90%. Nucleic acid weight percentages are determined by dividing the weight of the TAF or TAF portion-encoding nucleic acid, including alternative forms and analogs such as alternatively spliced or partially transcribed forms, by the total nucleic acid weight present.

The invention also provides for TAF sequences modified by transitions, transversions, deletions, insertions, or other modifications such as alternative splicing and such alternative forms, genomic TAF sequences, TAF gene flanking sequences, including TAF regulatory sequences and other non-transcribed TAF sequences, TAF mRNA sequences, and RNA and DNA antisense sequences complementary to TAF encoding sequences, sequences encoding xenogeneic TAFs and TAF sequences comprising synthetic nucleotides, e.g., the oxygen of the phosphate group may be replaced with sulfur, methyl, or the like.

For modified TAF-encoding sequences or related sequences encoding proteins with TAF-like functions, there will generally be substantial sequence identity between at least a portion thereof and a portion of a TAF, preferably at least about 40%, more preferably at least 80%, most preferably at least 90%, particularly conservative substitutions, particularly within regulatory regions and regions encoding protein domains involved in protein-protein interactions, particularly TAF-transcription factor interactions.

Typically, the invention's TAF encoding polynucleotides are associated with heterologous sequences. Examples of such heterologous sequences include regulatory sequences such as promoters, enhancers, response elements, signal sequences, polyadenylation sequences, etc., introns, 5' and 3' noncoding regions, etc. Other useful heterologous sequences are known to those skilled in the art or otherwise disclosed references cited herein. See for example, Russel Doolittle, Of URFs and ORFs, A Primer on How to Analyze Derived Amino Acid Sequences, University Science Books, Mill Valley, Calif.

TAF encoding nucleic acids can be subject to alternative purification, synthesis, modification or use by methods disclosed herein or otherwise known in the art. For example, the nucleic acids can be modified to alter stability, solubility, binding affinity and specificity, methylation, etc. The nucleic acid sequences of the present invention may also be modified with a label capable of providing a detectable signal, either directly or indirectly. Exemplary labels include radioisotopes, fluorescers, biotinylation, etc.

Nucleic acids encoding at least a portion of a TAF are used to identify nuclear factors which interact with that TAF using expression screening in yeast as described in Current Protocols in Molecular Biology. In this example, a yeast cDNA library containing fusion genes of cDNA joined with DNA encoding the activation domain of a transcription factor (e.g. Gal4) are transfected with fusion genes encoding a portion of a TAF and the DNA binding domain of a transcription factor. Clones encoding TAF binding proteins provide for the complementation of the transcription factor and are identified through transcription of a reporter gene. See, e.g. Fields and Song (1989) Nature 340, 245–246 and Chien et al. (1991) Proc Natl Acad Sci USA 88, 9578–9582.

The invention also provides vectors comprising nucleic acids encoding a TAF or portion or analog thereof. A large number of vectors, including plasmid and viral vectors, have been described for expression in a variety of eukaryotic and prokaryotic hosts. Vectors will often include one or more replication systems for cloning or expression, one or more markers for selection in the host, e.g. antibiotic resistance, and one or more expression cassettes. The inserted TAF coding sequences may be synthesized, isolated from natural sources, prepared as hybrids, etc. Ligation of the coding sequences to the transcriptional regulatory sequences may be achieved by known methods. Advantageously, vectors may also include a promotor operably linked to the TAF encoding portion.

Suitable host cells may be transformed/transfected/infected by any suitable method including electroporation, $CaCl_2$ mediated DNA uptake, viral infection, microinjection, microprojectile, or other established methods. Alternatively, nucleic acids encoding one or more TAFs may be introduced into cells by recmonbination events. For example, a sequence can be microinjected into a cell, and thereby effect homologous recombination at the site of an endogenous gene encoding a TAF, an analog or pseudogene thereof, or a sequence with substantial identity to a TAF-encoding gene. Other recombination-based methods such as nonhomologous recombinations, deletion of endogenous gene by homologous recombination, especially in pluripotent cells, etc., provide additional applications.

Appropriate host cells include bacteria, archebacteria, fungi, especially, yeast, and plant and animal cells, especially mammalian cells. Of particular interest are *E. coli, B. stutilis, Saccharomyces cerevisiae*, SF9 and SF21 cells, C129 cells, 293 cells, Neurospora, and CHO, COS, HeLa cells and immortalized mammalian myeloid and lymphoid cell lines. Preferred replication systems include M13, CO1E1, SV40, baculovirus, vaccinia, lambda, adenovirus, AAV, BPV, etc. A large number of transcription initiation and termination regulatory elements/regions have been isolated and shown to be effective in the transcription and translation of heterologous proteins in the various hosts. Examples of these regions, methods of isolation, manner of manipulation, etc. are known in the art. The particular choice of vector/host cell is not critical to the invention.

Under appropriate expression conditions, host cells are used as a source of recombinantly produced TAFs or TAF analogs. Preferred expression systems include *E. Coli*, vaccinia, or baculovirus; the latter two permitting the recombinant TAFs to be modified, processed and transported within a eukaryotic system.

TAF-encoding oligonucleotides also used to identify other TAFs or transcription factors. For example, $^{32}$P-labeled TAF-encoding nucleic acids are used to screen cDNA libraries at low stringency to identify similar cDNAs that encode proteins with TAF-related domains. Additionally, TAF related proteins, are isolated by PCR amplification with degenerate oligonucleotide probes using the sequences disclosed herein. Other experimental methods for cloning TAFs, sequencing DNA encoding TAFs, and expressing recombinant TAFs are also set out in the working exemplification below. Other useful cloning, expression, and genetic manipulation techniques for practicing the inventions disclosed herein are known to those skilled in the art.

The compositions and methods disclosed herein may be used to effect gene therapy. See, e.g. Gutierrez et al. (1992) Lancet 339, 715–721. For example, cells are transfected with TAF sequences operably linked to gene regulatory sequences capable of effecting altered TAF expression or regulation. To modulate TAF translation, cells may be transfected with TAF complementary antisense polynucleotides.

Antisense modulation may employ TAF antisense sequences operably linked to gene regulatory sequences. Cells are transfected with a vector comprising a TAF sequence with a promoter sequence oriented such that transcription of the gene yields an antisense transcript capable of binding to TAF encoding mRNA. Transcription may be constitutive or inducible and the vector may provide for stable extrachromosomal maintenance or integration. Alternatively, single-stranded antisense nucleic acid sequences that bind to genomic DNA or mRNA encoding at least a portion of TAF may be administered to the target cell at a concentration that results in a substantial reduction in TAF expression.

ASSAYS FOR IDENTIFYING TRANSCRIPTION FACTORS AND THERAPEUTIC AGENTS

The invention provides methods and compositions for identifying agents useful in modulating gene transcription. Such agents find use in the diagnosis or treatment of broad range of disease including cancer, cardiovascular diseases, microbial and fungal infections and particularly viral infections, inflammatory disease, immune disease, etc. The ability to develop rapid and convenient high-throughput biochemical assays for screening compounds that interfere with the process of transcription in human cells opens a new avenue for drug development. An overview of this therapeutic approach is presented in Peterson & Baichwal (1993), Trends in Biotechnology, in press. Typically, prospective agents are screened from large libraries of synthetic or natural compounds. For example, numerous means are available for random and directed synthesis of saccharide, peptide, and nucleic acid based compounds, see, e.g. Lam et al., (1991) Nature 354, 82–86. Alternatively, libraries of natural compounds in the form of bacterial, fungal, plant and animal extracts are available or readily predicable. Additionally, natural and synthetically produced libraries and compounds are readily modified through conventional chemical, physical, and biochemical means. Examples of such modifications are disclosed herein.

Useful agents are identified with a range of assays employing TAFs or TAF encoding nucleic acids. As examples, protein binding assays, nucleic acid binding assays and gel shift assays are useful approaches. Exemplary assays include assaying labeled TBP binding to immobilized TAF, labeled TAF or TAF peptide binding immobilized TBP, etc. Many appropriate assays are amenable to scaled-up, high throughput usage suitable for volume drug screening. Such screening will typically require the screening of at least about 10, preferably at least about 100, and more preferably at least about 1000 prospective agents per week. The particular assay used will be determined by the particular nature of the TAF interactions. For instance, a prospective agent may modify with the function of a TAF but not with transcription complex assembly. For example, a molecule that binds to a TAF but does not disrupt complex assembly is identified more readily through labeled binding assays than through gel retardation assay. Assays may employ single TAFS, TAF portions, TAF fusion products, partial TAF complexes, or the complete TFIID transcription complex, depending on the associational requirements of the subject transcription factor.

Useful agents are typically those that bind to or modify the association of transcription associated factors, especially TAFs. Preferred agents include those capable of modulating the expression of Pol II genes, particularly oncogenes (including viral oncogenes such as adenovirus EIA, human papilloma E7, and cellular onogenes such Rb, P53, E2F, myc, fos/jun (AP1), abl, etc.), genes transcribed during viral infection or activation, and sterol regulated genes. Preferred agents modify, preferably disrupt, TAF-TAF, TAF-activator, TAF-coactivator (coactivators include OCA-B, dTAFII110, etc.) or TAF-TBP binding. An especially preferred useful agent disrupts the association of a disclosed hTAF, with an activator, particularly a viral-specific activator, particularly an HIV-specific activator such as tat.

Useful agents are found within numerous chemical classes, though typically they are organic compounds; preferably small organic compounds. Small organic compounds have a molecular weight of more than 50 yet less than about 2,500, preferably less than about 750, more preferably, less than about 250. Exemplary classes include peptides, saccharides, steroids, and the like.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxyl terminus, e.g., for the amino group; acylation or alkylation, and for the carboxyl group, esterfication or amidification, or the like. Other methods of stabilization may include encapsulation, for example, in liposomes, etc.

Agents may be prepared in a variety of ways known to those skilled in the art. For example, peptides under about 60 amino acids can be readily synthesized today using conventional commercially available automatic synthesizers. Alternatively, peptide (and protein and nucleic acid agents are readily produced by known recombinant technologies.

For therapeutic uses, the compositions and selected agents disclosed herein may be administered by any convenient way that will depend upon the nature of the compound. For small molecular weight agents, oral administration is preferred and enteric coatings may be indicated where the compound is not expected to retain activity after exposure to the stomach environment. Generally the amount administered will be empirically determined, typically in the range of about 1 to 1000 ug/kg of recipient.

Large proteins are preferably administered parenterally, conveniently in a physiologically acceptable carrier, e.g., phosphate buffered saline, saline, deionized water, or the like. Typically, such compositions are added to a retained physiological fluid such as blood or synovial fluid. Generally, the amount administered will be empirically determined; typically in the range of about 10 to 1000 µ/kg of the recipient. Other additives may be included, such as stabilizers, bactericides, etc. These additives will be present in conventional amounts.

The following examples are offered by way of illustration and not by way of limitation.

EXAMPLES

Additional exemplary materials and methods for the purification, cloning and expression of TAFs are described below. Additional exemplary functional assays are described in detail. While exemplified primarily for dTAFII110, the disclosed methods find ready application to other TAFs by those skilled in the art and familiar with the methods hereinor found in standard manuals such as Molecular Cloning, A Laboratory Manual (2nd Ed., Sambrook, Fritsch and Maniatis, Cold Spring Harbor), Current Protocols in Molecular Biology (Eds. Ausubel, Brent, Kingstoan, Moore, Seidman, Smith and Struhl, Greene Publ. Assoc., Wiley -Interscience, NY, N.Y. 1992)

Immunopurified dTFIID complex is necessary and sufficient to mediate Sp1 activation in vitro.

In order to determine if the TFIID complex is sufficient to substitute for a partially-purified TFIID fraction, we have purified the TBP-TAF complex extensively by using an affinity resin coupled to a specific monoclonal antibody directed against TBP. Transcriptionally active TFIID purified from Drosophila embryos was obtained by eluting the complex from the antibody affinity resin with a low concentration (0.5 M) of guanidine hydrochloride in the presence of a sythetic peptide corresponding to the epitope recognized by monoclonal 42A11. The antibody used for the immunopurification remained bound to the protein G-sepharose beads and was found in the pellet. The proteins were electrophoresed on an 8% polyacrylamide-SDS gel and detected by silver staining. The resultant gels reveal seven major TAFs in the complex ranging in size from 30 to over 200 kD.

After dialysis of the purified TFIID complex to remove the peptide and denaturant, in vitro transcription reactions were carried out in the presence of basal factors that were isolated from Drosophila embryo nuclear extracts (Dynlacht et al., 1991; Wampler et al., 1990). Without the TFIID fraction there is no detectable transcription. Purified, recombinant dTBP is able to direct basal but not activated transcription. In contrast, immunopurified TFIID complex is able to mediate basal expression and Sp1 activation. Sp1-dependent activation with the TFIID fraction is shown in lanes 7 and 8 . For the in vitro transcription assay 2 ul of the immunopurified TFIID complex was assayed. Transcription was assayed by primer extension. The results demonstrate that the immunopurified TFIID complex containing TBP and at least 7 specific TAFs is necessary and sufficient for Sp1-dependent activation of transcription in vitro. As expected, the impure TFIID fraction also mediates transcriptional activation by Sp1, while the recombinant TBP protein is only able to direct basal, but not activated transcription. The immunopurified complex is also able to support activation by other transcription factors such as NTF-1.

Cloning and expression of Drosophila TAF110 cDNAs

Purified TFIID complex was used to immunize a mouse, and monoclonal antibodies were generated against TAF110

(see Experimental Procedures below). The serum from the immunized mouse was also collected and polyclonal antibodies used to screen a λgt11 expression library constructed from Drosophila embryo cDNA (Zinn et al., 1988). One clone was tentatively classified as a TAF110 cDNA because it produced protein that cross-reacted with independently isolated anti-TAF110 monoclonal antibodies. This partial cDNA clone was subsequently used as a probe to isolate full-length cDNAs from a λgt10 library (Poole et al., 1985). The longest clone obtained was 4.6 kb. This cDNA is polyadenylated at the 3' end and appears to be nearly full-length, based on the size of the mRNA, as determined by Northern blot analysis. The 4.6 kb. This cDNA clone contains a long open reading frame coding for a protein of 921 amino acids SEQ. ID NOS: 1 and 2), with a calculated molecular weight of 99.4 kD and an estimated pI of 10.1. Within the predicted amino acid sequence, there are 3 peptides that correspond to amino acid sequences determined from lys C peptides generated from HPLC purified TAF110. For microsequencing, the TFIID complex was immunopurified from fractionated embryo nuclear extract, and the TAFs were separated from TBP and the antibody by elution with 1M guanidine-HCl. The purified TAFs were fractionated on a C4 reverse phase HPLC column. Three adjacent fractions containing TAF 110 as the major species were cleaved with the protease lys-C, and the resulting peptides were purified and sequenced. Three peptide sequences were found that match the predicted amino acid sequence of the TAF110 cDNA.

We have expressed TAF 110 protein in a variety of cell types. The protein was expressed from the cloned gene in a baculovirus expression system and detected by western blot using a TAF110 monoclonal antibody. The protein encoded by the TAF110 cDNA has the same apparent molecular weight as the endogenous protein in the TFIID fraction derived from Drosophila cells, and the protein produced from the cloned gene cross-reacts with monoclonal antibodies directed against the TAF110 protein isolated from embryos. These results taken together demonstrate that the 4.6 kb cDNA encodes the full-length TAF110 protein.

TAF110 appears to be a single copy gene in Drosophila bases on low-strengency Southern blot analysis. The TAF110 gene is located at 72D,4–5 on the left arm of the third chromosome. There are not any previously identified Drosophila genes assigned to this chromosomal location (Lindsey and Zimm, 1992).

Hybridomas producing antibodies against TAF110 were selected by screening cell culture supernatants for those containing antibodies that specifically recognize the 110 kd protein in a western blot. For westerns, approximately 50 ug of the TFIID fraction was immunoprecipitated with antibodies against dTBP or TAF110. The α-TAF110 monoclonal antibody 33G8 was obtained from a hybridoma culture medium and purified by binding to protein G-sepharose. Proteins were eluted from the resin by boiling in sample buffer, electrophoresed on 8% polyacrylamide gel, and silver stained. Several of the a-TAF110 monoclonals that were obtained by this method specifically immunoprecipitate the same set of proteins as a-dTBP antibodies. This demonstrates that at least part of TAF110 is accessible to our antibodies, and therefore exposed in the native TFIID complex and positioned for interaction with activators.

Monoclonal antibodies specific for other Drosophila TAFs can also immunopurify the same TFIID complex as a-TBP and α-TAF110 antibodies. Thus, there appears to be one predominant TBP-containing complex in the TFIID fraction, as opposed to a heterogeneous set of complexes containing different sets of TAFs bound to TBP. Our methods are also used to determine if there are rare, perhaps tissue-specific, TBP-containing complexes that might contain different collections of TAFs or if the activity of the TAFs could be modulated by post-translational modifications. For example, TAF200 does not stain as intensely as the other TAFs and TBP, and, on this basis, might not be present in all complexes. However, this protein seems to be an authentic member of the major TFIID complex since antibodies directed against TAF200 immunopurify a set of proteins that appear to be identical to complexes purified by antibodies directed against TBP or other TAFs. The preparations of the purified TFIID complex contain some polypeptides that are less abundant than the major TAF proteins. Based on western analyses with α-TAF antibodies, these minor species appear to be proteolytic breakdown products of larger TAFs or substoichiometric TAFs.

The TAF110 coding sequence (SEQ ID NO: 1, residues 538-3300) contains several regions which are rich in glutamine residues or rich in serine and threonine residues, and the C-terminal third of the protein is highly charged. The C-terminal region of the molecule contains 32% acidic or basic residues. We searched the existing data bases for genes similar to the TAF110 gene, and found that it is not highly homologous to any previously identified genes. In particular, TAF110 did not show any similarity to any DNA binding domains. Interestingly, Sp1 received one of the highest scores in the NBRF protein sequence data base search for similarity to TAF110. The amino terminal third of TAF110 has an organization similar to the activation domains of Sp1, consisting of glutamine-rich regions flanked by serine-threonine rich domains. The two proteins share 21% amino acid identity and 35% similarity over 260 residues.

This unexpected similarity to Sp1 prompted us to consider a possible functional relationship between Sp1 and TAF110. In particular, whether the amino-terminal region of TAF110 might contain interaction surfaces for activators such as Sp1, especially since the A and B glutamine-rich domains are responsible for mediating Sp1-Sp1 interactions as well as activation. Indeed, one of the unique properties of Sp1 activation domains is their capacity to mediate a phenomenon called superactivation, in which a truncated form of Sp1 lacking the zinc fingers but containing glutamine-rich domains A and B is able to interact directly with DNA-bound full length Sp1. This interaction increases the number of activation domains at the promoter and can greatly enhance expression of a gene regulated by Sp1 binding sites. This type of interaction also appears to be involved in synergistic activation mediated by distally and proximally bound Sp1.

?dTAF110 can function as a target for the Sp1 activation domains

To test for functional homology between the similar domains, we asked if the N-terminal region of TAF110 could function as a target for the Sp1 activation domains in a superactivation assay. The amino terminal 308 residues of TAF110 (SEQ ID NO: 2) were fused to the DNA binding domain of the GAL4 protein, G4(1–147), and tested in a transient cotransfection assay in Drosophila Schneider cells. This hybrid construct, by itself, weakly activates (4 fold) a reporter gene which is dependent on GAL4 binding sites. This low level of activity is similar to the modest activation observed with constructs containing the Sp1 B domain fused to GAL4. When this TAF110 hybrid construct is cotransfected with DNA expressing the gln-rich A and B domains of Sp1, (N539), a 60 fold increase in transcription is observed. This 15 fold superactivation is dependent on the TAF110 sequences since Sp1(N539) is unable to stimulate transcription when cotransfected with G4(1-147) alone. The interaction with Sp1 apparently requires an extended region of TAF110 (SEQ ID NO: 2) since GAL4 fusion proteins bearing TAF110 residues 1-137, 138-308, or 87-308 are unable to mediate superactivation by Sp1.

These results indicate that the N-terminal 308 amino acids of TAF110 are sufficient for mediating an interaction with the glutamine-rich activation domains of Sp1 that lead to superactivation. In the positive control for this experiment, a GAL4-Sp1B domain fusion is superactivated approximately 50 fold by the fingerless Sp1 mutant. In a search for other potential targets of Sp1, we have tested some additional members of the TFIID complex for the ability to mediate superactivation by Sp1. For example, GAL4 hybrids containing TAF40, TAF80, or the amino-terminal region of dTBP were found to be inactive in the superactivation assay. This results shows that the interaction between TAF110 and Sp1 in Drosophila cells is quite specific and that other subunits of the TBP-TAF complex that we tested are unable to interact with the glutamine-rich activation domains of Sp1.

dTAF110 and Sp1 interact in yeast

The superactivation assay in Drosophila Schneider cells provided the first hint that TAF110 may serve as a coactivator for Sp1. However, it is difficult to assess in this assay whether TAF110 can interact with Sp1 in the absence of the other TAFs which are present in Drosophila cells. The superactivation assay also imposes certain limitations to the number and types of constructs that can be tested. Moreover, it seemed prudent to establish several independent assays to investigate the relationship between TAF110 and transcription activation domains. Therefore, we carried out two additional types of assays, one in vivo and one in vitro, to test the results obtained in Schneider cells. First, we tested the ability of TAF110 and Sp1 to interact in a versatile assay for protein-protein interaction which is carried out in yeast cells (Fields and Song, 1989). This strategy takes advantage of the modular organization of eukaryotic transcription factors. In this assay, one of the partners to be tested is fused to the DNA binding domain of GAL4 and, in a separate molecule, the other partner is fused to the acidic activation domain (AAD). A functional activation domain is recruited to the target promoter bearing GAL4 binding sites and the lacZ reporter gene is expressed only if there is a protein-protein interaction between the partners being tested.

Full-length TAF110 as well as a variety of deletion mutants were fused to the DNA binding domain of GAL4, G4(1-147). In contrast to the situation in Drosophila cells, the amino terminal region of TAF110 cannot activate transcription by itself in yeast. This result was anticipated since glutamine-rich activation domains have not been observed to function it yeast. As potential partners for TAF110, the Sp1 activation domains were fused to the acidic activation domain of GAL4. Each of the Sp1 glutamine-rich activation domains A or B can independently interact with full-length TAF110 as judged by activation of the reporter gene. In these experiments, yeast bearing an integrated GAL1:lacZ fusion were transformed with two plasmids: (1) fusions to the DNA binding domain of GAL4 (residues 1-147), and (2) fusions to the acidic activation domain (AAD; residues 768-881 of GAL4), and the resulting β-gal activity was measured (expressed in units/mg of protein). Interestingly, domain A of Sp1 appears to interact more efficiently than domain B, and this correlates well with the previous finding that A is a better activator for transcription than domain B (Courey and Tjian, 1988). As in Drosophila cells, residues 1-308 of TAF110 are sufficient for the interaction, while regions 1-137 and 138-308 are inactive. The full-length TAF110 fusion is more active than the N308 construct in this assay. Although this effect may be due to differential protein expression, it is possible that the C-terminal regions of TAF110 contribute to interactions with Sp1. The protein-protein interaction assay in yeast further supports the idea that TAF110 interacts, directly or indirectly, with the activation domains of Sp1, and the strength of this interaction appears to be correlated with transcriptional function.

The other TAF proteins that have been tested in the superactivation assay or the yeast assay displayed no detectable interaction with Sp1. However, the GAL4 fusion proteins that these assays rely on might not be able to participate in all the correct interactions because some surfaces could be sterically blocked. Therefore, additional strategies, such as the use of full length Sp1, are used to test for other potential interactions.

dTAF110 does not interact with other activators tested

To determine whether the interaction between Sp1 and TAF110 is specific, or whether other types of activators also interact with TAF110, we used the yeast assay to test a variety of other activation domains including the acidic activation domain of GAL4 (Ma and Plashne, 1987) and the proline-rich activation domain of CTF (Mermod et al. 1989). Neither of these two activators displayed any interaction with TAF110 in the yeast assay. In addition we tested activation domains from the Drosophila proteins Antennapedia (Antp) and bicoid (bcd), both of which are glutamine-rich. Surprisingly, both of these glutamine-rich domains failed to interact with TAF110 in the yeast assay. Since TAF110 can interact with both Sp1 domains A and B, which have no significant homology other than high glutamine content, but not Antp and bcd which are even more glutamine-rich than Sp1, it appears that glutamine content alone may not be a sufficient criterion for the classification of functionally similar activation domains. In this regard, it may be useful to draw a distinction between the Sp1 activation domains, which are approximately 25% glutamine and flanked by serine/threonine rich sequences, and the bcd and Antp sequences, which are partially composed of uninterrupted stretches of glutamines and lack adjacent serine/threonine sequences.

The N-terminal region of TAF110, containing the glutamine-and serine/threonine-rich sequences, is able to function as a weak activation domain in Drosophila cells, suggesting that this region can interact with a component of the native TFIID complex. To determine whether the N-terminal region of TAF110 is similar to the Sp1 activation domains which can mediate multimerization, we tested for TAF110-TAF110 interactions. We found that the N-terminal region of TAF110 is able to interact with itself as judged by activation of the lacZ reporter gene in the yeast assay (FIG. 6A). This is another example of functional similarity between the Sp1 activation domains and the N-terminal region of TAF110, which can interact with each other as well themselves.

TBP and other TAFs tested do not interact with Sp1 in yeast

Since Sp1 synergistically activates transcription through multiple sites even though it does not bind cooperatively to DNA, we sought to determine whether Sp1 works via interactions with multiple targets or coactivators. We therefore tested two other members of the TFIID complex, TAF40 and TAF80. Similar to the superactivation assay in Drosophila cells, neither TAF40 or TAF80 displayed any ability to interact with Sp1 under the conditions of the yeast assay. In addition, the conserved C-terminal domain of TBP was tested for Sp1 interaction in yeast but no interaction was observed. We were unable to test full-length dTBP in this assay because it functions as an activator in yeast when fused to the GAL4 DNA binding domain. These results show that the interaction between TAF110 and Sp1 is quite specific, and that TAF80, TAF40, and the conserved region of TBP do not appear to be targets for Sp1.

Since the TFIID complex is also required at promoters that lack a TATA box, one of the TAFs might be required for promoter recognition through the initiator element. In addition to communicating with promoter-selective factors, the TAFs interact with each other, at least one TAF interacts with TBP, and one interacts with RNA polymerase II or one of the basal factors.

Sp1 binds dTAF110 in vitro

The superactivation assay in Schneider cells and the yeast experiments are both indirect assays for protein-protein interactions. Therefore, we also determined the ability of Sp1 to bind directly to TAF110 in vitro. Biotinylated oligonucleotides containing Sp1 binding sites were coupled to streptavidin-agarose resin. The resin was incubated with Sp1 that had been over-expressed and purified from HeLa cells infected with a vaccinia virus expression vector (Jackson et al. 1990). After allowing Sp1 to bind DNA on the beads, the unbound Sp1 was washed away. Control resin that lacked Sp1 was also prepared and tested in parellel. These resins were incubated in batch with $^{35}$S-labeled TAF110 synthesized in vitro in a reticulocyte lysate. After incubation with the labeled protein, the beads were extensively washed and the bound proteins were eluted in two steps with buffer containing 0.2M KCl followed by 1.0M KCl. The 1.0M salt incubation elutes Sp1 from the DNA. The input, unbound supernatant, and eluted fractions were subsequently analyzed by SDS-PAGE and autoradiography. Samples from the binding reaction were also analyzed by silver staining to detect non-specific binding of proteins present in the reticulocyte lysate.

$^{35}$S-labeled TAF110 synthesized in vitro in a reticulocyte lysate and incubated with streptavidin-agarose beads with or without DNA-bound Sp1. Protein fractions were run on SDS-PAGE and analyzed by autoradiography or by silver staining. After allowing TAF110 to bind Sp1, the beads were pelleted and the supernatant containing the unbound proteins was collected. The resin was washed 4 time. The specifically bound proteins were eluted by incubating the beads in buffer containing 0.2M KCl, followed by 1.0M KCl. The Sp1 protein bound to the DNA is eluted by treatment with 1.0M salt. Labeled TAF110 protein is detectable in the eluted fractions. No detectable TAF110 protein bound to the DNA affinity resin in the absence of Sp1 protein. Quantitation of these results by analysis of the gel in a PhosphorImager (Molecular Dynamics) scintillation gel scanner indicate a 60-fold greater binding by labeled TAF110 to the Sp1-containing resin. The silver stained gel showed that Sp1 is the major species in the eluate indicating that the unlabeled proteins in the extract are not able to bind Sp1.

These data show that TAF110 is selectively retained on the resin containing DNA-bound Sp1, but TAF110 does not bind the control resin that lacks Sp1. Most of the bound TAF110 elutes with the Sp1 at 1.0M KCl with a lower amount eluting at 0.2M KCl. Analysis of the fractions by silver staining indicates that Sp1 is the major protein detectable in the high salt eluate, indicating that the unlabeled proteins present the reticulocyte lysate, which constitute the vast majority of the total protein in the input, are not non-specifically binding to Sp1 in this assay. To rule out the possibility that an intermediary protein, perhaps some other TAF or other eukaryotic protein, was required for the Sp1-TAF110 interaction, this experiment was repeated using $^{35}$S-labeled TAF110 synthesized in an in vitro transcription/translation extract derived from $E.\ coli$ (Skelly et al., 1987). The TAF110 protein synthesized in the prokaryotic system was also specifically retained on the Sp1 affinity resin providing further evidence that Sp1 can bind directly to TAF110.

As an additional test of specificity, we also determined if deletion mutants of TAF110 could bind to Sp1 in this in vitro assay (mutants are expressed from the N-terminal). A 1–137 mutant was not able to bind Sp1 in vitro, while some binding was obtained with a 1–308 mutant. Mutants of 308–921, 447–921, and 571–921 were all effective in binding Sp1, while C-termina deletions beyond 852 from these mutants eliminated Sp1 binding. These results indicate the importance of a 852–921 region and a 137–308 region of TAF110 in transcription activator interaction.

TAF110 does not directly bind TBP

Our experiments indicate that TAF110 cannot directly bind to TBP by itself and that at least one additional TAF is required to connect TAF110 and TBP. For example, α-TAF110 antibodies fail to coprecipitate both in vitro expressed TAF110 and TBP and similarly with α-TBP antibody.

Exemplary Experimental Procedures

Purification of the TFIID complex

For the in vitro transcription assay, the TFIID complex was immunopurified from the partially purified TFIID fraction (Q-sepharose fraction, 0.3M KCl eluate) (Dynlacht et al., 1991) using the α-dTBP monoclonal antibody 42A11 coupled to protein G sepharose (Pharmacia). The immunoprecipitates were washed with 0.1M KCl-HEMG-ND buffer (25 mM HEPES pH 7.6, 0.1 mM EDTA, 12.5 mM $MgCl_2$, 10% glycerol, 0.1% mM DTT) and the TFIID complex was eluted from the antibody by addition 10 mg/ml of the peptide mimicking the epitope of 42A11 in HEMG buffer containing 0.5M guanidine-HCl. The eluate was dialyzed against 0.1M KCl-HEMG-ND, and then assayed for transcription activity.

Purification of dTAF110

Nuclear extracts derived from approximately 1 kg of Drosophila embryos were prepared and fractionated as previously described (Dynlacht et al., 1991; Wampler et al., 1990). For protein sequencing, the TFIID complex was purified with polyclonal α-dTBP antibodies as previously described (Dynlacht et al., 1991) or with a monoclonal antibody as described above. The TAFs were separated from TBP by elution of the protein A-antibody resin with 0.1M KCl-HEMG buffer containing 1.5 mM DTT, 0.1% LDAO (lauryl dimethylamineoxide), and 1M Gd-HCl. The TAFs were eluted by batch incubation of the resin with an equal volume of buffer for 25 min at 4° C. This procedure was repeated and the two supernatants were combined. Urea was added to 8M, DTT to 10 mM, and cysteines were modified with 4-vinylpyridine.

Two approaches were used to separate the TAFs: HPLC and PAGE. Under the HPLC approach, the TAFs were fractionated by reverse phase HPLC on a 300 angstrom C4 column (2.1×30 mm). The proteins were eluted with a gradient from 20–70% buffer B (buffer A=0.1% TFA, 1% n-propanol; buffer B=0.1% TFA, 1% n-propanol, 60% isopropanol, 30% acetonitrile). TAF110 consistently eluted at 35% buffer B. Fractions containing TAF110 (approximately 5 µg) were lyophilized, resuspended in 100 mM TRIS, pH 8.0, and 2M urea, and incubated at 55° C. for 10 min. 150 ng of the protease lys C was added and the protein was digested for 20 hr at 37° C. Peptides were chromatographed and sequenced as previously described (Williams et al., 1988).

Under the gel electrophoresis approach, the TAFs were separated by electrophoesis and transferred to membranes. The separated TAFs were digested with LysC or trypsin and the resultant peptides eluted, chromatographed and sequenced. See Fernandez et al., (1992) Analytical Biochemistry 201, 255–264.

In vitro transcription assay

Transcription factor fractions were reconstituted with basal factor fractions derived from 0–12 hr Drosophila embryo nuclear extracts essentially as previously described (Dynlacht et al., 1991) except that TFIIB was separated from TFIIE/TFIIF and pol II was fractionated further on a phosphocellulose column. Each reaction contained 0.5 ug of the TFIIB fraction (S-sepharose 0.5M eluate), 1.5 ug of the TDIIE/TFIIF fraction (S-sepharose 0.25M eluate), and 0.25 mg of the pol II fraction (phosphocellulose 0.4M eluate). Some reactions contained 1.5 ug of the TFIID fraction or 2 ng of purified, recombinant dTBP that had been expressed in E. coli (Hoey et al., 1990). The template for the in vitro transcription reaction was BCAT (Lillie and Green, 1989) containing 3 Sp1 binding sites, and transcription was assayed by primer extension.

Generation of antibodies against the TAFs

Immunopurified TFIID complex (approximately 10 ug/injection) was mixed with Ribi's adjuvant and injected intraperitoneally into a Swiss-Webster mouse at days 0, 7, and 21. The initial immune response was monitored at day 28 and boosted further by two biweekly injections of more antigen. After an intravenous injection of one further dose of antigen the spleen was dissected out and electrofused with myeloma cells. Approximately 600 supernatants from 96-well dishes (each well containing on average 5 independent hybridomas) were assayed on western strip blots for cross-reactivity with immunopurified TFIID complex proteins. Hybridomas from wells producing anti-TAF and/or anti-TBP antibodies were cloned by limited dilution and tested by Western blotting and immunoprecipitation assays.

Cloning of TAF110 cDNAs

The polyclonal antiserum obtained from the immunization scheme described above was used at a 1/1000 dilution to screen approximately $5 \times 10^5$ plaques of a size-selected (>1.8 kb) 9–12 hr lgt11 Drosophila cDNA library (Zinn et al., 1988). Positive clones were plaque-purified to homogeneity and tested for cross-reactivity against anti-TAF monoclonal antibodies of known specificity. One clone, λ106, cross-reacted strongly with several independent anti-TAF110 hybridomas.

Insert DNA (2.6 kb) from λ106 was purified and labeled using Klenow polymerase and random hexamer priming (Amersham). $10^6$ recombinant phage from a cDNA library (Poole, et al., 1985) prepared from 3–9 hour Drosophila embryos were screened as previously described (Kadonaga et al., 1987). 24 positives were obtained in duplicate on the primary screen; 12 of these were randomly selected for rescreening, and 10 of 12 were positive on the secondary screen. All 10 of these cDNA clones were found to be related to each other on the basis of restriction mapping and cross-hybridization. The largest cDNA clone of 4.6 kb, λ110-5, was completely sequenced, and two other clones of 3.1 kb, λ110-1, and 2.1 kb, λ110-2, were partially sequenced. The inserts were subcloned into pBS-SK (Stratagene) in both orientations, a nested set of deletions was constructed with exonuclease III, and the clones were sequenced by the dideoxy method. The λ110-1 clone was found to be 37 nucleotides longer at the 5' end than the λ110-5 clone and missing 1.5 kb on the 3' end. The SEQ ID NO: 1 is a composite of the λ110-1 and λ110-5 sequence.

Expression of dTAF110 protein

An NdeI site was created at the initiating methionine using a PCR based strategy. A 3.1 kb NdeI-BssHII fragment containing the entire coding sequence was subcloned into the SmaI site of the baculovirus expression vector pVL1392 (Pharmingen). Recombinant baculoviruses were selected by co-transfection of Sf9 cells with the expression vector and linear viral DNA as described by the supplier (Pharmingen). Samples for the western blot were prepared by infecting SF9 cells with recombinant virus obtained from the transfection supernatant. Three days after infection the cells were harvested, washed, resuspended in HEMG buffer, and lysed by sonication. The protein concentration was measured by Bradford assay. After electrophoresis proteins were transferred to nitrocellulose; TAF110 protein was detected using the monoclonal antibody 3E7.

Transfections

Transfection of Schneider cells (line SL2) was carried out as previously described (Courey and Tjian, 1988) except that the transfections were performed in 60 mm dishes. The expression vector for all proteins used in this study was pPac, which contains the Drosophila actin 5c promoter. TAF110 sequences were fused in frame to GAL4 DNA binding domain, residues 1–147. The following restriction fragments of the TAF110 cDNA were used: N137, NdeI-ClaI; N308, NdeI-SalI, 138–308, ClaI-SalI; 87–308, HincII. The constructs were checked by sequencing across the fusion junctions. The amounts of DNA used were as follows: 100 ng of the pPacGAL4 derivatives, 500 ng of the pPacSp1N539, and 2.5 ug of the reporter gene pG5BCAT (Lillie and Green, 1989). CAT assays were performed and quantitated as previously described (Courey and Tjian, 1988).

Yeast Methods

The yeast strain Y153 (a, gal4, gal80, his3, trpl-901, ade2-101, ura3-52, leu2-3, 112, URA3::Gall:lacZ, LYS2::Gal-His3) was transformed with two plasmids according to the method of Shiestl and Gietz (Schiestl and Gietz, 1989). The Gal4 DNA binding domain hybrids were constructed in the vector pAS1. pAS1 is a 2µ plasmid with TRP selection that expresses fusions to Gal4(1–147) from the ADH promoter. For expression of GAL4(1–147), an XbaI linker containing stop codons in all three reading frames was inserted in pAS1 immediately downstream of the GAL4(1–147) coding sequence. G4-110 (fl) contains the entire coding region of the TAF110 on an NdeI-BssHII fragment, and the shorter G4-110 fusions contain fragments as described for the Drosophila expression vectors. G4-80 (fl) contains an NdeI-XbaI fragment that includes the entire coding region of Drosophila TAF80. G4-40 (fl) contains an NdeI-EcoRV fragment encoding Drosophila TAF40. G4-dTBP(191C) contains an NdeI fragment derived from pAR-191C containing the conserved C-terminal domain (Hoey et al., 1990). The reading frame across all fusion junctions was verified by sequencing, and the protein expression was verified by western blot analyses with either α-TAF or α-GAL4 antibodies, with the exception of G4-110 (N137).

The acidic activation domain fusions were constructed in the vectors pGAD1F, pGAD2F or pGAD3F which differ only in the reading frame of a unique Bam site (Chien et al., 1991). These 2µ plasmids with LEU2 selection express fusions to activating region II (residues 768–881) of GAL4 from the ADH promoter. Sp1 region A consists of amino acids 83–262 and Sp1 region B consists of residues 263–542; these were cloned as BamHI-BglII fragments from the plasmids pKSABg10 and pKSBG respectively. The C-terminal 100 amino acids of CTF1 (residues 399–499) were cloned as a BglII-EcoRI fragment (Mermod et al., 1989). The Antp construct was made by subcloning a BamHI fragment containing the activation domain (Courey et al., 1989). Bcd residues 249–489 (Driever et al., 1989) were cloned on a SalI fragment derived from pPac-bcd. The reading frame across all fusion junctions was verified by sequencing.

Transformed yeast were assayed qualitatively after growth on media containing X-gal. Quantitative β-galactosidase assays were performed as described (Himmelfarb et al., 1990) except cells were grown to mid log in selective media containing 2% glucose. Assays were performed in triplicate and activity is expressed as units/mg of total protein.

In vitro protein-protein interaction assay

A 3.1 kb NdeI-BssHII fragment containing the entire TAF110 coding region was subcloned into the plasmid pTbSTOP (Jantzen et al., 1992), which contains the b-globin untranslated leader downstream of a T7 promoter. The plasmid was linearized with XbaI, and, the gene was transcribed in vitro with T7 RNA polymerase. $^{35}$S-met labeled protein was synthesized in vitro in a rabbit reticulocyte lysate (Promega). Alternatively, TAF110 was synthesized in vitro in an E. coli derived S30 transcription/translation extract (Skelly et al., 1987). Sp1 protein was overexpressed in HeLa cells using a vaccinia virus expression vector (Jackson et al., 1990) and purified by wheat germ agglutinin (WGA) affinity chromatography (Jackson and Tjian 1990), prior to DNA affinity purification as outlined below.

DNA affinity resin was prepared as follows: 5' biotinylated oligonucleotides containing 4 Sp1 binding sites, and its complement, were annealed and coupled to streptavidin-agarose beads (Pierce) by incubating overnight at room temperature. The beads were incubated with WGA-purified Sp1 in buffer Z' (25 mM HEPES, pH 7.6 20% glycerol, 0.1% NP-40, 10 mM ZnSO$_4$, 1 mM DTT) containing 0.1M KCl for 2 hours at 4° C. Sp1 was bound to the resin at a concentration of approximately 1 mg/ml of beads. $^{35}$S-labeled TAF110 was incubated in batch with 15 ml of the DNA affinity resin in Z'+50 mM KCl, with or without Sp1, for 4 hours at 4° C. The beads were washed 4 times with 1 ml of the same buffer, and eluted with Z'+0.2M KCl, followed by Z'+1.0M KCl. The eluted proteins were TCA-precipitated and analyzed by SDS-PAGE. Before autoradiography, the gel was fixed and treated with Amplify (Amersham).

Detection of Direct TBP/TAF Interactions on Protein Blots

Immunopurification of the Drosophila TFIID complex using anti-TBP antibodies results in the purification of a large multiprotein complex consisting of TBP and 7 major TAFs. To identify TAFs which can bind directly to TBP we probed a blot containing renatured TAFs with a 32P-labelled TBP-GST fusion protein. After washing off unbound TBP-fusion protein and exposing the blot to X-ray film a strong signal was seen which coincided with the position of dTAFII-250K on the gel. Further experiments revealed that a truncated version of TBP, consisting of the highly conserved C-terminal domain, is sufficient to mediate this interaction. We also tested other fractions containing basal factors (Wampler et al., 1990; Dynlacht et al., 1991), including TFIIB, E/F and RNA polymerase II, and failed to detect specific signals. We conclude that TBP and TAFII-250K interact directly and that TAFII-250K is present in the TFIID fraction but not associated with TFIIB, E, F or RNA polymerase II.

Molecular Cloning and Characterization of the dTAFII-250K Gene

Having identified dTAFII-250K as a candidate for a direct TBP-TAF interaction we decided to clone the corresponding gene. The low abundance and large size of dTAF(II)-250K disfavours cloning strategies based on protein microsequencing. Instead, we were able to obtain monoclonal antibodies which specifically (and exclusively) recognize dTAF(II)-250K on Western blots. To show that dTAF(II)-250K is indeed a genuine component of the TFIID complex, we used two of these monoclonal antibodies, 2B2 and 30H9, to carry out immunoprecipitations from the TFIID fraction. The pattern and stoichiometry of TAFs and TBP is indistinguishable from the ones described previously using either anti-TBP (Dynlacht et al., 1991) or anti-dTAF(II)-110K (Hoey et al., 1993) antibodies. We cloned the gene encoding the Drosophila dTAF(II)-250K by screening a lgt11 expression library prepared from 6–12 hour old embryos (Zinn et al., 1988) with hybridoma supernatants containing either 2B 2 and 30H9 anti-dTAF(II)-250K monoclonal antibodies. Five partial cDNA clones were obtained, which all cross-hybridized with each other at high stringency. Restriction mapping and sequence analysis confirmed that they were indeed derived from the same gene. Two of these cDNAs, 1D-1 and 1D-2, allowed us to establish a composite open reading frame spanning 4.5 kb (FIG. 2). Attempts to isolate additional cDNA clones encoding N-terminal regions of dTAF(II)250 or 5'-RACE experiments have so far been unsuccessful. Genomic DNA sequencing allowed us to extend the open reading frame by approximately 1 kb before encountering noncoding (presumanbly intronic) sequences. Inspection of the open reading frame encoded by the cDNA clones reveals a protein sequence which displays an extensive similarity to the human 'Cell Cycle Gene 1'(CCG1) gene previously described by Sekiguchi et al., 1991. Many of the sequence elements defined in the CCG1 genes are also present in the dTAF-250K encoding sequence. Interestingly, however, we detected a 35 amino acid insertion in the region which Sekiguchi et al. putatively identified as an HMG box. This insertion causes substantial disruption of the spatial alignment with the consensus sequence. We also used the 1D-2 cDNA fragment to map the dTAFII-250K gene to position 32E1-2 (left arm of chromosome II) by in situ hybridization. This location does not contain any previously characterized genes and currently no deletions spanning that regions are available. Since dTAF-250 seems to be present in all or the majority of the TFIID complexes present within cells and seems to provide essential contact points with TBP and TAFs (see below) we expect that a deletion of the 32E1-2 locus would cause a lethal phenotype.

Expression of the C-terminal domain of dTAF(II)-250K in Insect Cells

To study the functional properties of the proteins encoded by these cDNAs we decided to express the protein encoded by the reading frame of our longest cDNA, 1D-1. Because of the expected large size of the protein encoded we chose the baculovirus system. After subcloning of the fragment into expression vector pVL1393 and transfecting the construct into Sf9 cells we detected expression of a 180K protein (subsequently referred to as DN250) which cross reacted strongly with several anti-TAF250 monoclonal antibodies recognizing a variety of epitopes in different parts of the 250K TAF. We detected no cross-reactivity between our antibodies and any endogenous Spodoptera TAF250 homologs which might be present in Sf9 cells.

The C-terminal Domain of the dTAF(II)250K Is Sufficient for TBP Binding

To study whether DN250 was capable of interacting with TBP we immunopurified the protein from infected cells. Monoclonal antibody 30H9 was bound to protein A or G beads and incubated with extracts from baculovirus infected cells. Under these conditions DN250 is specifically immobilized on the beads. After washing off unbound material we added an extract containing partially purified TBP (also expressed in the baculovirus system). TBP was specifically bound to beads carrying the immunopurified TAF250-C180 protein whereas beads containing antibody only failed to do so. Further evidence for this direct TBP-TAF interaction by carrying out protein blots. The ability of a protein representing appr. 60% of the full-length 250K protein to bind TBP demonstrates conclusively that the cloned C-terminal part is sufficient for TBP binding Gelshift Analysis of the DN250/TBP Complex TBP is the only component of the general transcriptional machinery capable of sequence-specific binding to the TATA box. We therefore were interested to see how interaction of TBP with TAF250-C180 affected the specificity and affinity of DNA binding. TBP was added to a 32-P labelled DNA fragment containing the −33 to +55 region of the adenovirus major late promoter and DNA-binding was monitored using a gelshift assay. The intensity of probe DNA shifted by TBP increased substantially in presence of purified TAF250-C180 wheras TAF250-C180 alone did not detectably bind to DNA. To investigate whether this enhanced affinity of the TBP/TAF250-C180 complex for DNA was due to additional contacts with DNA provided by the TAF250-C180 protein we carried out footprinting studies, again using the adenovirus major later promoter region as a probe.

TAF250 and TAF110 Specifically Interact With Each Other, even in Absence of TBP

Since we have not observed any of the cloned Drosophila TAFs to bind to TBP we investigated whether they would interact with the TBP/ d250KdeltaC180 complex. 35S-labelled 110K protein (Hoey et al., 1993) was synthesized in an in-vitro translation system and incubated with TAF250-C180 protein in presence and absence of TBP. As shown in FIG. 5 we found that the 110K TAF binds specifically to dTAF(II)250K-C180 in the presence and absence of TBP thus indicating that the two proteins bind independently to two distinct domains within the 250K TAF. The affinity and specificity of this interaction is sufficiently high to allow selective purification of TAF110 from a crude baculovirus extract expressing the recombinant protein by using TAF250-C180 immobilized on beads.

Protein Blot Analysis pGEX-2TK was linearized with SmaI, phosphatase-treated and the ligated with gel-purified NdeI fragments of either pARdTFIID or pARdTFIID-191C (Hoey et al., 1990). Generation of 32-P labelled GST fusion protein, protein blotting and hybridization were carried out essentially as described in Kaelin et al., 1992.

Generation of anti-dTAFII-250K Hybridoma Cell Lines

The monoclonal antibodies described in this study were derived as described in Hoey et al.(1993). Briefly, a Swiss-Webster mouse was immunized with intact immunopurified Drosophila TFIID complex. After fusion hybridoma supernatants containing anti-dTAFII-250K antibodies were selected using stripblots containing SDS-gel-separated TBP and TAFs. Two such cell lines, 2B2 and 30H9, were then cloned to homogeneity by limited dilution.

Isolation of dTAFII-250K cDNA and Genomic Clones

Approximately 5×105 independent plaques of a size-selected (<=1.8 kb) Drosophila lgt11 library prepared from Drosophila embryos (Zinn et al., 19..) were screened with two independent anti-dTAFII-250K monoclonal antibodies, 2B2 and 30H9. All the positives identified cross-hybridized at high stringency with each other on the DNA level. Restriction mapping and sequence analysis showed that all of the clones were derived from the same gene. cDNA clones 1D1 and 1D2 contained inserts of 1.5 and 4.0 kb, respectively, and were sequenced to completion. 1D2 was found to extend 500 bp further towards the 5' end of the gene and was used to isolate genomic clones 1DASH3 and 1DASH4 (Sau3A partially digested DNA cloned into 1DASH).

Sequencing Strategy

We employed the gd transposon-directed sequencing strategy (Gold Biosystems) as described in Strathmann et al., 1991. DNA fragments of interest were subcloned into the plasmid vector pMOB1 and electroporated into DPWC cells. After conjugation with the recipient host BW26 the mixture was plated out on kanamycin/carbenicillin plates. Transposon insertion points were mapped by PCR. Clones with the desired transposon locations were grown up and sequenced using transposon-specific primers with 35S-dATP or the Pharmacia A. L. F. Sequencer.

Expression of a Truncated Version of dTAFII-250K (DN250) in the Baculovirus System cDNA #5 was inserted into the EcoRI site of Baculovirus-expression plasmid pVL1393 (Pharmingen). The resulting construct was co-transfected with 'BaculoGold' viral DNA (Pharmingen) into Sf9 cells. After 3 days cells were harvested and expression of the DN250 protein was monitored by Western blotting using the anti-dTAFII-250K monoclonal antibody 2B2. The recombinant virus-containing supernatant was used to infect large scale cultures of Sf9 cells. We typically prepared whole cell extracts from 1 liter of plate cultures of infected Sf9-cells by sonicating them in HEMG-ND/0.1M KCl (HEMG-ND contains 25 mM HEPES, pH 7.6, mM MgCl2 0.1 mM EDTA, 0.1% NP40, 1 mM PMSF, 1.5 mM DTT, 5 mg/ml leupeptin). The supernatant was partially purified (approximately 5 fold) by chromatography over Q-sepharose (Pharmacia) with step gradient elution (HEMG containing 0.1M, 0.2, 0.4 and 1.0M KCl, respectively). dTAFII-250K(C180) eluted in the 0.4M step('Q.4' fraction). After dialysis against HEMG-0.1M KCl the extract was frozen in aliquots and used for the immunopurification/coprecipitation studies.

Coimmunopreciptiation Studies

Protein G-beads were preloaded with monoclonal antibodies and incubated with various cell extracts from Baculovirus-infected cell fractions or 35S-labelled dTAFII110 prepared by in vitro translation. After 45 minutes on ice, unbound protein was removed with several washes with HEMG-ND.

hTAFII250 purification and cloning

We previously reported the isolation of hTFIID by affinity chromatography using antibodies specific to TBP. The purified complex contains at least seven distinct TAFs ranging in molecular weight from 30–250 kD which copurify with TBP. We were particularly interested in characterizing the 250 kD species because this subunit of TFIID appears to bind TBP directly as determined by Far Western analysis. Using affinity-purified TAFs to immunize mice, we generated both polyclonal and monoclonal antibodies that cross-react with different TAFs. We used these antibodies to screen lgt11 expression cDNA libraries and several clones were isolated, including 1H1 which contains a 1.1 kb insert. To determine which, if any, TAF is encoded by 1H1, we expressed this cDNA as a GST fusion protein, purified the tagged protein by glutathione affinity chromatography, and raised antibodies against this recombinant protein. Antisera directed against GST-lH1 specifically crossreacted with the 250 kD TAF, indicating that a portion of the gene encoding hTAFII250 had been isolated.

Next, we determined the DNA sequence of lH1 and discovered that this open reading frame is related to the previously identified human gene, CCG1, which had been implicated in cell cycle regulation. Specifically, a temperature-sensitive mutant hamster cell line, ts13, is arrested at G1 a few hours before entering S phase at the non-permissive temperature. Expression of human CCG1 in ts13 overcomes this cell cycle block. Since lH1 only encoded a small portion of hTAFII250, we isolated several additional clones from a primary HeLa cDNA library, including lH2, which contained a 5.3 kb insert. The construction of a full-length hTAFII250 cDNA revealed the predominant hTAFII250 RNA species characterized in HeLa cells encodes 21 additional amino acids between residues 177 and 178 relative to CCG1. Interestingly, we sequenced several other cDNAs containing internal insertions or deletions when compared to CCG1. This finding suggests that multiple hTAFII250-related proteins may be generated by alternate splicing of a primary transcript.

Although the finding that a cDNA isolated by antibodies directed against TAFs encodes a cell cycle gene is exciting, it was important to provide some functional evidence that this clone indeed encodes a bona fide TAF which is a subunit of TFIID. We first asked whether the recombinant hTAFII250 expressed in a vaccinia virus system becomes associated with the endogenous TFIID complex in HeLa cells. To distinguish between the recombinant and endogenous protein, we engineered a version containing a hemagglutinin antigen (HA) epitope at the N-terminus of hTAFII250. Antibodies against TBP were used to immunopurify the TFIID complex from HeLa cells infected with either recombinant or control vaccinia virus. The immunopurified complexes were subjected to gel electrophoresis and analyzed by Western blot analysis using either a monoclonal anti-HA antibody to detect the HA-tagged molecule or monoclonal antibody 6B3, raised against the endogenous hTAFII250. The anti-HA antibody crossreacted specifically with a 250 kD protein only in the TFIID complex prepared from recombinant hTAFII250 virus infected HeLa cells but not control infected cells. As expected, 6B3 recognized both the recombinant hTAFII250 and the endogenous protein. Thus, we conclude that the recombinant hTAFII250 associates with TBP in vivo and is part of the TFIID complex.

To test for a direct interaction between hTAFII250 and TBP, we performed a Far Western analysis with radiolabelled TBP and antibody immunopurified HA-tagged hTAFII250. The full-length hTAFII250 is capable of interacting directly with TBP in vitro, even in the absence of other TAFs or coactivators. These results and the analysis of the independently cloned Drosophila TAFII250 suggest that this largest TAF is responsible for the initial assembly of the TFIID complex by binding directly to TBP and other TAFs.

The important role of hTAFII250 in the formation of a TFIID complex prompted us to define more precisely its interaction with TBP. For these studies we employed the two hybrid system carried out in yeast cells. Using this rapid and convenient assay for protein:protein interactions, we observed that a hybrid construct containing hTAFII250 fused to the DNA binding domain of GAL4, G4(1–147), interacted selectively and efficiently with human TBP attached to the acidic activation domain of GAL4, G4(768–881). Yeast expressing both of these proteins produced high levels of b-galactosidase due to increased transcription of a lacZ reporter construct, containing GAL4 binding sites. Interestingly, hTAFII250 also interacts efficiently with a truncated version of human TBP which contains only the conserved C-terminal 180 amino acids. By contrast, a construct containing the "species-specific" N-terminal domain of human TBP failed to interact with hTAFII250. These results are in agreement with Far Western experiments using radiolabelled cTBP and nTBP as probes and suggest that residues 160 to 339 on the outer surface of TBP may be responsible for hTAFII250 binding.

Our unexpected finding that hTAFII250 is related to CCG1 suggests a rather intriguing link between a subunit of TFIID and expression of genes involved in cell cycle control. Interestingly, CCG1 is a nuclear phosphoprotein with several domains characteristic of transcription factors including a putative HMG-box and a proline-rich cluster. Based on these structural motifs, Sekiguchi et al. suggested that CCG1 might work as a sequence-specific transcription factor needed for regulating genes involved in the progression through G1. However, it now seems clear that CCG1 or a related product is part of the TFIID complex and is not a promoter-specific transcription factor. Therefore, it seems more likely that the G1 arrest in ts13 is due to the failure of a defective TFIID complex to mediate activation by a subset of cellular transcription factors that govern cell cycle genes, e.g. thymidine kinase and dihydrofolate reductase genes. The presence of a putative DNA binding domain, the HMG box, may suggest that once hTAFII250 forms a complex with TBP, some portion of this large subunit of TFIID may contact DNA, perhaps downstream of the initiation site.

Immunoaffinity purified hTFIID complex: Interaction with hTBP and production of hTAFs-specific antibodies A. Immunoprecipitation reactions were carried out according to a modified version of previously described procedures (Tanese et. al.). 0.5 mg of affinity purified a-hTBP antibody was added to 200 mg of hTFIID (phosphocellulose 0.48–1.0M KCl) fraction, and the mixture nutated for 2–4 hrs at 4° C. Protein A Sepharose was then added and nutation continued for an additional 2–4 hrs.

Antibody-antigen complexes were pelleted by low-speed centrifugation, washed four times with 0.1M KCl-HEMG (25 mM Hepes, 12.5 mM Mg Cl2, 0.1 mM EDTA, 10% glycerol) containing 0.1% NP-40 and 1 mM DTT. The immunoprecipitated hTFIID complex was subjected to 8% SDS-PAGE and silver stained. For Far Western analysis, the proteins were blotted onto nitrocellulose membrane and hybridized with 35S-labeled hTBP (Kaelin et al.). pTbhTBP was used to in vitro transcribe hTBP RNA which was in vitro translated using 120 mCi 35S-methionine (>1000 Ci/mMol, Amersham) in reticulocyte lysate (Promega).

B. Antigen used to immunize mice for antibody production was prepared as follows. The immunoprecipitated hTFIID complex, purified from 250 liters of HeLa cells, was eluted from the Protein A Sepharose—antibody complex with 0.1 M KCl-HEMG containing 1M guadidine-HCl, 0.1% NP-40, and 1 mM DTT. Under these conditions TBP remained bound to the antibody. The eluted TAFs were dialized against 0.1M KCl-HEMG containing 0.1% NP-40 and 1 mM DTT. The mixture of proteins containing 1–2 mg of each TAF was used to immunize a mouse. Test bleeds were taken and the immune response monitored by Western blot analysis. After a series of five boosts, the mouse was sacrificed and the spleen was used for the production of monoclonal antibody producing hybridoma cells lines. The identification of hybridoma cell lines producing hTAF specific antibodies was determined by Western blot analysis of eluted TAFs.

Cloning and identification of the 250 kD subunit of hTFIID complex as CCG1

A. An expression screen of 2.4×106 PFU from a λgt11 HeLa S3 cDNA library (Clontech) was carried out using the a-hTAFs polyclonal serum described above. 38 primary signals were identified of which 6 were plaque purified. 1 phage DNA was prepared and analyzed by EcoRI restriction enzyme digestion. 1H1 contained a 1.1 kb insert which was subcloned into the EcoRI site of pGEX1 (Pharmacia) to express a GST-1H1 fusion protein. The resulting construct was transformed into Escherichia coli TG2, and following induction with 0.5 mM IPTG, the induced protein was purified on glutathione Sepharose 4B beads (Pharmacia). 2 mg (per injection) of the fusion protein was used to immunize a mouse. Test bleeds were taken and used for Western blot analyses.

B. Poly(A)+RNA from HeLa cells was used for construction of a directional cDNA library in lZAPII (Stratagene) as described previously (Ruppert et al. 1992). Using a randomly 32P-labeled probe derived from the 1H1 cDNA insert, 15 independent cDNA clones were isolated from 1.2×106 original PFU. The cDNA inserts were rescued by the zapping procedure (Short et al.) and characterized extensively by restriction enzyme analysis and Southern blotting. The longest cDNA clone isolated from 1H2 contains a 5.3 kb insert, revealing an extended 3' untranslated region but missing about 1.15 kb of 5' sequences when compared to CCG1. This 5' region was generated by PCR using conditions described previously (Ruppert et al.). Two set of PCR primers were designed according to the CCG1 cDNA sequence (Sekiguchi et al). PCR I forward primer #1:5'-TATTTCCGGCATATGGGACCCGGCTG-3' (see SEQ ID NO:10) (position 40 to 65, containing an engineered NdeI restriction site at the translation start codon) and reverse primer #2:5'-GAAGTCCACTTTCTCACCAG-3' (see SEQ ID NO:10) (position 578 to 597). PCR-II, forward primer #3:5'-TACCAGCAGCATATGGGGAGCTTGCAG-3' (see SEQ ID NO:10) (position 421 to 447) and reverse primer #4: 5'-GCTCTAAGGAAGCCAGCCTGCCAGGCTTG-3' (see SEQ ID NO:10) (position 1343 to 1371). All PCR products were subcloned into pBluescript KS (Stratagene) and sequenced. The most abundant product of PCR-II, a 1 kb fragment, included a 63 in frame insertion, while a minor 330 bp fragment revealed a 618 bp in frame deletion with respect to the CCG1 cDNA. To generate a full-length hTAFII250 cDNA, the product of PCR-I and the 1 kb PCR-II product were joined via the shared SmaI restriction site. Subsequently the 1.2 kb XbaI fragment of the resulting plasmid was cloned into XbaI cut pH2 to generate the full-length cDNA clone phTAFII250.

Analyses of hTAFII250 and hTBP interaction

A. To construct an HA-tagged version of hTAFII250 we generated a plasmid, pSK-HAX, containing the hemagglutinin antigen (HA) epitope, factor X cleavage site, and in frame NdeI cloning site. A 6.3 kb NdeI/Asp718 fragment from phTAFII250 was inserted into pSK-HAX to generate pHAX-hTAFII250. A 6.0 kb SpeI fragment thereof containing the complete coding region of hTAFII250, was inserted into the XbaI site of the vaccina virus expression vector pAbT4537 (Applied bioTechnology Inc.). Extracts from recombinant virus, vhTAFII250, or control virus (New York City Board of Health strain of vaccina virus) infected HeLa cells (Dynlacht 1989) were fractionated by phosphocellulose chromatography as described (Tanese et al.). hTFIID complexes from the 0.48–1.0M KCl fraction were immunoprecipitated with affinity-purified a-hTBP antibodies, subjected to 8% SDS-PAGE and analyzed by Western blotting.

B. To generate an HA-tagged version of hTAFII250 in the baculovirus expression system, we first generated new baculovirus vectors, pVL1392HAX and pVL1393HAX, derived from pVL1392 and pVL1393 (Pharmingen), respectively. These vectors contain the HA antigen epitope, factor X cleavage site, and unique in frame NcoI and NdeI restriction sites. A 6.0 kb NdeI/SpeI fragment from phTAFII250 was inserted into pVL1392HAX creating pbHAX-hTAFII250. Whole cell extracts from either SF9 cells or SF9 cells infected with recombinant baculovirus were prepared in 0.4M KCl-HEMG (including 0.04% NP-40, 1 mM DTT, 0.2 mM AEBSF. 0.1 mM NaMBS) and used directly for immunoprecipitation with the a-HA antibody. The precipitate was subjected to 8% SDS-PAGE and blotted onto nitrocellulose membrane. The filter was probed first with 35S-labeled hTBP, and subsequently with the monoclonal antibody 6B3.

hTAFII250 interacts with hTBP in yeast hTAFII250, fused to the DNA binding domain of GAL4 (residues 1–147), was constructed by inserting a 6.0 kb NdeI/BamHI fragment derived from pvhTAFII250 into the pASI vector. The activation domain fusions were obtained by cloning inserts into the pGADIF vector (Chien et al.). The hybird proteins generated included the acidic activation domain of GAL4 (residues 768–881) fused to either full-length, residues 160–339, or residues 1–159 of hTBP. The above described constructs were transformed into the yeast strain Y153 (a, gal 4, gal80, his3, trp1–901, ade2–101, ura3–52, leu2–3, 112, URA3::Gal1:1acZ, LYS2::Gal-His3: as described (Chien et al.) and b-galactosidase assays performed according to published procedures (Hoey et al).

Drosophila TBP and dTAFII250 interact with the C-terminal portion of dTAFII150

Radiolabeled in vitro translated dTAFII150 bound efficiently to immobilized HA-dTBP or dTAFII250ΔN (see Weinzierl et al (1993) Nature 362, 511–517). In contrast, dTAFII110 and other TAFs failed to interact selectively with dTAFII150, showing that dTAFII150 interacts with at least two subunits of the TFIID complex, dTBP and dTAFII250, which also contact each other.

We also carried out in vivo experiments in which insect Sf9 cells were co-infected with two recombinant baculoviruses, one expressing dTAFII150 and the second expressing either TBP or one of the other TAFs. Complexes were subsequently immunopurified from cellular lysates and analyses by SDS PAGE followed by immunoblotting using antibodies directed against dTAFII150. Coinfection of virus expressing dTAFII150 and either HA-dTBP or dTAFII250ΔN resulted in efficient formation and copurification of heteromeric complexes. Similarly, full-length hTAFII250 bound efficiently to dTAFII150.

Radiolabeled in vitro translated C-terminal 369 residue portion (dTAFII150ΔN) of this protein binds TBP and dTAFII250ΔN with the same efficiency as the full length protein. No significant binding of a N-terminal 786 residue portion (dTAFII150ΔC) was observed: i.e. the interaction interfaces from these proteins are located in the C-terminal portion of dTAFII150.

TSM-1 associates with TBP and TAFII250

Like dTAFII150. TSM1ΔN (C-terminal 920 residue portion) bound efficiently to yTBP as well as HA-dTBP; hence we conclude that yeast contain a TAFII250 and TSM-1 is a TAF.

The activation domain of the Drosophila regulator NTF-1 (Neurogenic Element Binding Transcription Factor-1) interacts with dTAFII150.

NTF-1 immuno-copurifies with dTFIID using anti-dTBP, indicatin that one or more subunits of the dTFIID interacts directly with NTF-1. Using coimmunoprecipitation experiments: dTAFII150 was immunopurified from Sf9 extracts containing dTAFII150, the immobilized TAF was mixed with recombinant NTF-1, the isolated complex was analyzed by SDS-PAGE, and the presence of NTF-1 was detected by protein immunoblot anaysis, showing that NTF-1 directly interacts with dTAFII150.

Next we used a GST-NTF-1 fusion protein containing the N-terminal 284 amino acids of NTF-1 to bind various truncated bersions of dTAFII150, showing that the N-terminal, but not the C-terminal region of dTAFII150 bound to the N-terminal terminal extended activation domain of NTF-1. Neither dTAFII80 nor dTAFII40 bound significantly under these conditions.

Using an affinity resin containing a covalently attached synthetic peptide corresponding to the 56 amino acid minimal activation domain of NTF-1, we showed that this region is sufficient to interact with dTAFII150 and that the activator interface of dTAFII150 is distinct from the C-terminal region with interacts with dTBP and dTAFII250. Hence, the requirement for TAFs during NTF-1 activation is at least in part mediated by NTF-1:dTAFII150 interactions.

TAF Sequence Data

Nucleotide and amino acid sequences of:

dTAFII30α.(SEQ ID NO:21, 22)

dTAFII30β.(SEQ ID NO:23, 24)

dTAFII40 (SEQ ID NO:8, 9)

dTAFII60 (SEQ ID NO:6, 7)

dTAFII80 (SEQ ID NO:4, 5)

dTAFII110 (SEQ ID NO:1, 2)

dTAF150 (SEQ ID NO:19, 20)

dTAFII250 (SEQ ID NO:3, 14)

hTAFII30α.(SEQ ID NOS:28, 33 and 34)

hTAFII30β.(SEQ ID NOS:27, 35 and 36)

hTAFII40 (SEQ ID NO:25, 26)

hTAFII70 (SEQ ID NO:12, 13)

hTAFII100 (SEQ ID NO:17, 18)

hTAFII130 (SEQ ID NO:15, 16)

hTAFII250 (SEQ ID NO:10, 11)

hTAFI48 (SEQ ID NO:29, 30)

hTAFI110 (SEQ ID NO:31, 32)

were obtained as described above. Additional methods relating to PolI TAFs may be found in Comai et al. (1992) Cell 68, 965–976.

It is evident from the above results that one can use the methods and compositions disclosed herein for making and identifying diagnostic probes and therapeutic drugs. It will also be clear to one skilled in the art from a reading of this disclosure that advantage can be taken to effect alterations of gene expression: both genes encoding TAF and genes amenable to TAF-mediated transcriptional modulation. Such alterations can be effected for example, using a small molecule drug identified with disclosed TAF-based screening assays.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid encoding a biologically active polypeptide consisting of a sequence of six or more consecutive amino acids of a human TATA-Binding Protein Associated Factor (TAF) polypeptide selected from the group consisting of hTAFII30α peptide 1 (SEQ ID NO:28), hTAFII30α peptide 2 (SEQ ID NO:33), hTAFII30α peptide 3 (SEQ ID NO:34), hTAFII30β peptide 1 (SEQ ID NO:27), hTAFII30β peptide 2 (SEQ ID NO:35), hTAFII30β peptide 3 (SEQ ID NO:36), hTAFII40 (SEQ ID NO:26), hTAFII70 (SEQ ID NO:13), hTAFII100 (SEQ ID NO:18), hTAFII130 (SEQ ID NO:16), hTAFII250 (SEQ ID NO:11), hTAFI48 (SEQ ID NO:30), and hTAFI110 (SEQ ID NO:32).

2. The nucleic acid according to claim 1 wherein said TAF polypeptide is hTAFII30α peptide 1 (SEQ ID NO:28), hTAFII30α peptide 2 (SEQ ID NO:33)or hTAFII30α peptide 3 (SEQ ID NO:34).

3. The nucleic acid according to claim 1 wherein said TAF polypeptide is is hTAFII30β peptide 1 (SEQ ID NO:27), hTAFII30β peptide 2 (SEQ ID NO:35) or hTAFII30β peptide 3 (SEQ ID NO:36).

4. The nucleic acid according to claim 1 wherein said TAF polypeptide is hTAFII40 (SEQ ID NO:26).

5. The nucleic acid according to claim 1 wherein said TAF polypeptide is hTAFII70 (SEQ ID NO:13).

6. The nucleic acid according to claim 1 wherein said TAF polypeptide is hTAFII100 (SEQ ID NO:18).

7. The nucleic acid according to claim 1 wherein said TAF polypeptide is hTAFII130 (SEQ ID NO:16).

8. The nucleic acid according to claim 1 wherein said TAF polypeptide is hTAFII250 (SEQ ID NO:11).

9. The nucleic acid according to claim 1 wherein said TAF polypeptide is hTAFI48 (SEQ ID NO:30).

10. The nucleic acid according to claim 1 wherein said TAF polypeptide is hTAFI110 (SEQ ID NO:32).

11. An isolated recombinant nucleic acid comprising a human TAF gene sequence which hybridizes under high stringency conditions with a TAF gene selected from the group consisting of hTAFII40 (SEQ ID NO:25), hTAFII70 (SEQ ID NO: 12), hTAFII100 (SEQ ID NO:17), hTAFII130 (SEQ ID NO:15), hTAFII250 (SEQ ID NO:10), hTAFI48 (SEQ ID NO:29), and hTAFI110 (SEQ ID NO:31).

12. The nucleic acid according to claim 11 wherein said TAF gene is hTAFII40 (SEQ ID NO:25).

13. The nucleic acid according to claim 11 wherein said TAF gene is hTAFII70 (SEQ ID NO:12).

14. The nucleic acid according to claim 11 wherein said TAF gene is hTAFII100 (SEQ ID NO:17).

15. The nucleic acid according to claim 11 wherein said TAF gene is hTAFII130 (SEQ ID NO:15).

16. The nucleic acid according to claim 11 wherein said TAF gene is hTAFII250 (SEQ ID NO:10).

17. The nucleic acid according to claim 11 wherein said TAF gene is hTAFI48 (SEQ ID NO:29).

18. The nucleic acid according to claim 11 wherein said TAF gene is hTAFI110 (SEQ ID NO:31).

* * * * *

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
( A ) LENGTH: 4615 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 538..3300

( x i ) SEQUENCE DESCRIPTION: SEQ ID NO:1:

```
CAACTCGTCC  GTACCTCGGC  GGTCCGTAAA  CAATATTTAC  TCGGTTTTCG  GCTAAATCGC    60

CAGAGAAACG  CAACGGGAAA  TCGTTTAAAA  TGCGCCCCAG  TGCACCGAGT  TTGAACGCAA   120

AATGAATTGA  ATGCTCAACA  ATCAGTCCGT  GCGAGCACGC  GCGAGTGTGT  GTGTGCGCAG   180

GAAACCCGC   CGATCGGGAA  AAGTGTAGAA  AGGCTTAGCG  GCGCAAACAA  AAGGCAGCGA   240

ATTAGCGAGA  TAACACACAC  GCGACAACGA  CTGCAACGGA  TGCGCCAGGA  GAAAGGCCGA   300

CGACAGTGAC  GGCAAAGGCG  AGTGCGAGTG  AGCCAGCGCA  GCACCAATTC  AGCGGAGCAC   360

CCGCTTTTTT  GGCCAAGTTC  GCTTCTGGAG  CGCACAGCAT  GCAACAACTC  CGCCAACACC   420
```

-continued

```
AACACAGGAT GTGCGCAACT AGTTGATCGG AACAGGATCG CTCGCCCACA CCAACACACA        480

GAAGTCAGTG GAATAGGAGA AACACACTCG CCAATAACAT AAACACCACA CAGCACG          537

ATG AAC ACC AGC CAG ACA GCT GCC GGC AAT CGC ATC ACC TTC ACC AGC         585
Met Asn Thr Ser Gln Thr Ala Ala Gly Asn Arg Ile Thr Phe Thr Ser
 1            5                  10                  15

CAG CCG CTG CCC AAT GGC ACC ATC AGC ATA GCC GGC AAT CCC GGC GCG         633
Gln Pro Leu Pro Asn Gly Thr Ile Ser Ile Ala Gly Asn Pro Gly Ala
             20                  25                  30

GTC ATC TCC ACG GCC CAG CTA CCG AAT ACC ACC ACC ATC AAG ACG ATC         681
Val Ile Ser Thr Ala Gln Leu Pro Asn Thr Thr Thr Ile Lys Thr Ile
         35                  40                  45

CAG GCG GGG ATC GGT GGT CAG CAT CAG GGA CTT CAG CAG GTG CAT CAT         729
Gln Ala Gly Ile Gly Gly Gln His Gln Gly Leu Gln Gln Val His His
     50                  55                  60

GTC CAA CAG CAG CAG CAG TCG CAA CAG CAA CAA CAG CAG CAA CAG CAG         777
Val Gln Gln Gln Gln Gln Ser Gln Gln Gln Gln Gln Gln Gln Gln Gln
 65                  70                  75                  80

ACG CAA TCC GCC GGT CAA CCG CTG CTC AAT TCA ATG CTG CCG GCT GGC         825
Thr Gln Ser Ala Gly Gln Pro Leu Leu Asn Ser Met Leu Pro Ala Gly
             85                  90                  95

GTG GTG GTG GGC ATG CGC CAA CAG GCG CCG TCA CAG CAG CAG CAG AAG         873
Val Val Val Gly Met Arg Gln Gln Ala Pro Ser Gln Gln Gln Gln Lys
            100                 105                 110

AAT GTG CCC ACC AAC CCG CTC AGT CGC GTG GTG ATC AAC TCC CAC ATG         921
Asn Val Pro Thr Asn Pro Leu Ser Arg Val Val Ile Asn Ser His Met
        115                 120                 125

GCG GGC GTG AGA CCG CAG AGT CCA TCG ATA ACT TTA AGC ACA CTT AAT         969
Ala Gly Val Arg Pro Gln Ser Pro Ser Ile Thr Leu Ser Thr Leu Asn
    130                 135                 140

ACG GGT CAG ACC CCG GCA TTG CTG GTC AAG ACG GAT AAC GGA TTC CAG        1017
Thr Gly Gln Thr Pro Ala Leu Leu Val Lys Thr Asp Asn Gly Phe Gln
145                 150                 155                 160

CTG TTG CGC GTG GGC ACG ACG ACG GGT CCG CCG ACG GTG ACA CAG ACT        1065
Leu Leu Arg Val Gly Thr Thr Thr Gly Pro Pro Thr Val Thr Gln Thr
            165                 170                 175

ATA ACC AAC ACC AGC AAT AAC AGC AAC ACG ACA AGC ACC ACA AAC CAT        1113
Ile Thr Asn Thr Ser Asn Asn Ser Asn Thr Thr Ser Thr Thr Asn His
        180                 185                 190

CCC ACA ACC ACA CAG ATC CGT CTG CAA ACT GTG CCG GCT GCA GCT TCT        1161
Pro Thr Thr Thr Gln Ile Arg Leu Gln Thr Val Pro Ala Ala Ala Ser
    195                 200                 205

ATG ACC AAC ACG ACC GCC ACC AGC AAC ATC ATT GTC AAT TCG GTG GCA        1209
Met Thr Asn Thr Thr Ala Thr Ser Asn Ile Ile Val Asn Ser Val Ala
210                 215                 220

AGC AGT GGA TAT GCA AAC TCT TCG CAG CCG CCG CAT CTG ACG CAA CTA        1257
Ser Ser Gly Tyr Ala Asn Ser Ser Gln Pro Pro His Leu Thr Gln Leu
225                 230                 235                 240

AAT GCG CAG GCG CCA CAA CTG CCG CAG ATT ACG CAG ATT CAA ACA ATA        1305
Asn Ala Gln Ala Pro Gln Leu Pro Gln Ile Thr Gln Ile Gln Thr Ile
            245                 250                 255

CCG GCC CAG CAG TCT CAG CAG CAG CAG GTG AAC AAT GTA AGC TCC GCG        1353
Pro Ala Gln Gln Ser Gln Gln Gln Gln Val Asn Asn Val Ser Ser Ala
        260                 265                 270

GGA GGA ACG GCA ACG GCG GTC AGC AGT ACG ACG GCA GCG ACG ACG ACG        1401
Gly Gly Thr Ala Thr Ala Val Ser Ser Thr Thr Ala Ala Thr Thr Thr
    275                 280                 285

CAG CAG GGC AAT ACC AAA GAA AAG TGT CGC AAG TTT CTA GCC AAT TTA        1449
Gln Gln Gly Asn Thr Lys Glu Lys Cys Arg Lys Phe Leu Ala Asn Leu
290                 295                 300
```

| | | | | | | | | | | | | | | | | |
|---|---|---|---|---|---|---|---|---|---|---|---|---|---|---|---|---|
| ATC | GAA | TTG | TCG | ACA | CGG | GAA | CCG | AAG | CCG | GTG | GAG | AAG | AAC | GTG | CGC | 1497 |
| Ile | Glu | Leu | Ser | Thr | Arg | Glu | Pro | Lys | Pro | Val | Glu | Lys | Asn | Val | Arg | |
| 305 | | | | | 310 | | | | 315 | | | | | | 320 | |
| ACC | CTC | ATC | CAG | GAG | CTG | GTC | AAT | GCG | AAT | GTC | GAG | CCG | GAG | GAG | TTT | 1545 |
| Thr | Leu | Ile | Gln | Glu | Leu | Val | Asn | Ala | Asn | Val | Glu | Pro | Glu | Glu | Phe | |
| | | | | 325 | | | | | 330 | | | | | 335 | | |
| TGT | GAC | CGC | CTG | GAG | CGC | TTG | CTC | AAC | GCC | AGC | CCG | CAG | CCG | TGT | TTG | 1593 |
| Cys | Asp | Arg | Leu | Glu | Arg | Leu | Leu | Asn | Ala | Ser | Pro | Gln | Pro | Cys | Leu | |
| | | | 340 | | | | | 345 | | | | | 350 | | | |
| ATT | GGA | TTC | CTT | AAG | AAG | AGT | TTG | CCT | CTG | CTA | CGA | CAA | GCC | CTC | TAC | 1641 |
| Ile | Gly | Phe | Leu | Lys | Lys | Ser | Leu | Pro | Leu | Leu | Arg | Gln | Ala | Leu | Tyr | |
| | | 355 | | | | | 360 | | | | | 365 | | | | |
| ACA | AAG | GAG | CTG | GTC | ATC | GAA | GGC | ATT | AAA | CCT | CCG | CCG | CAG | CAC | GTT | 1689 |
| Thr | Lys | Glu | Leu | Val | Ile | Glu | Gly | Ile | Lys | Pro | Pro | Pro | Gln | His | Val | |
| | 370 | | | | | 375 | | | | | 380 | | | | | |
| CTC | GGC | CTG | GCC | GGA | CTC | TCT | CAA | CAG | TTG | CCT | AAA | ATC | CAA | GCG | CAA | 1737 |
| Leu | Gly | Leu | Ala | Gly | Leu | Ser | Gln | Gln | Leu | Pro | Lys | Ile | Gln | Ala | Gln | |
| 385 | | | | | 390 | | | | | 395 | | | | | 400 | |
| ATC | CGT | CCG | ATC | GGT | CCT | AGC | CAG | ACA | ACG | ACC | ATT | GGA | CAG | ACG | CAG | 1785 |
| Ile | Arg | Pro | Ile | Gly | Pro | Ser | Gln | Thr | Thr | Thr | Ile | Gly | Gln | Thr | Gln | |
| | | | | 405 | | | | | 410 | | | | | 415 | | |
| GTG | CGT | ATG | ATA | ACG | CCG | AAT | GCC | TTG | GGC | ACG | CCG | CGA | CCC | ACC | ATT | 1833 |
| Val | Arg | Met | Ile | Thr | Pro | Asn | Ala | Leu | Gly | Thr | Pro | Arg | Pro | Thr | Ile | |
| | | | 420 | | | | | 425 | | | | | 430 | | | |
| GGC | CAC | ACC | ACG | ATA | TCG | AAG | CAG | CCA | CCG | AAT | ATT | CGG | TTG | CCT | ACG | 1881 |
| Gly | His | Thr | Thr | Ile | Ser | Lys | Gln | Pro | Pro | Asn | Ile | Arg | Leu | Pro | Thr | |
| | | 435 | | | | | 440 | | | | | 445 | | | | |
| GCC | CCG | CGT | CTC | GTC | AAC | ACT | GGA | GGA | ATT | CGC | ACC | CAG | ATA | CCC | TCG | 1929 |
| Ala | Pro | Arg | Leu | Val | Asn | Thr | Gly | Gly | Ile | Arg | Thr | Gln | Ile | Pro | Ser | |
| | 450 | | | | | 455 | | | | | 460 | | | | | |
| TTG | CAG | GTG | CCT | GGT | CAG | GCG | AAC | ATT | GTG | CAA | ATA | CGT | GGA | CCG | CAG | 1977 |
| Leu | Gln | Val | Pro | Gly | Gln | Ala | Asn | Ile | Val | Gln | Ile | Arg | Gly | Pro | Gln | |
| 465 | | | | | 470 | | | | | 475 | | | | | 480 | |
| CAT | GCT | CAG | CTG | CAG | CGT | ACT | GGA | TCG | GTC | CAG | ATC | CGG | GCC | ACC | ACT | 2025 |
| His | Ala | Gln | Leu | Gln | Arg | Thr | Gly | Ser | Val | Gln | Ile | Arg | Ala | Thr | Thr | |
| | | | | 485 | | | | | 490 | | | | | 495 | | |
| CGT | CCG | CCA | AAC | AGT | GTG | CCC | ACC | GCG | AAC | AAA | CTC | ACT | GCC | GTC | AAG | 2073 |
| Arg | Pro | Pro | Asn | Ser | Val | Pro | Thr | Ala | Asn | Lys | Leu | Thr | Ala | Val | Lys | |
| | | | 500 | | | | | 505 | | | | | 510 | | | |
| GTG | GGA | CAG | ACG | CAA | ATC | AAA | GCG | ATT | ACG | CCC | AGC | CTG | CAT | CCA | CCC | 2121 |
| Val | Gly | Gln | Thr | Gln | Ile | Lys | Ala | Ile | Thr | Pro | Ser | Leu | His | Pro | Pro | |
| | | 515 | | | | | 520 | | | | | 525 | | | | |
| TCG | CTG | GCG | GCA | ATC | TCA | GGT | GGA | CCA | CCG | CCG | ACA | CCC | ACG | CTG | TCT | 2169 |
| Ser | Leu | Ala | Ala | Ile | Ser | Gly | Gly | Pro | Pro | Pro | Thr | Pro | Thr | Leu | Ser | |
| | 530 | | | | | 535 | | | | | 540 | | | | | |
| GTT | TTG | TCT | ACG | TTG | AAC | TCC | GCC | TCG | ACC | ACA | ACG | CTG | CCC | ATA | CCA | 2217 |
| Val | Leu | Ser | Thr | Leu | Asn | Ser | Ala | Ser | Thr | Thr | Thr | Leu | Pro | Ile | Pro | |
| 545 | | | | | 550 | | | | | 555 | | | | | 560 | |
| TCG | TTA | CCC | ACG | GTC | CAC | CTT | CCC | CCC | GAA | GCT | CTT | CGA | GCC | CGT | GAG | 2265 |
| Ser | Leu | Pro | Thr | Val | His | Leu | Pro | Pro | Glu | Ala | Leu | Arg | Ala | Arg | Glu | |
| | | | | 565 | | | | | 570 | | | | | 575 | | |
| CAG | ATG | CAA | AAT | TCG | CTG | AAC | CAC | AAC | AGC | AAT | CAC | TTC | GAT | GCA | AAA | 2313 |
| Gln | Met | Gln | Asn | Ser | Leu | Asn | His | Asn | Ser | Asn | His | Phe | Asp | Ala | Lys | |
| | | | 580 | | | | | 585 | | | | | 590 | | | |
| CTG | GTG | GAG | ATC | AAG | GCG | CCG | TCG | CTG | CAT | CCG | CCG | CAC | ATG | GAG | CGG | 2361 |
| Leu | Val | Glu | Ile | Lys | Ala | Pro | Ser | Leu | His | Pro | Pro | His | Met | Glu | Arg | |
| | | 595 | | | | | 600 | | | | | 605 | | | | |
| ATC | AAC | GCA | TCT | CTC | ACA | CCG | ATT | GGA | GCC | AAG | ACG | ATG | GCA | AGG | CCG | 2409 |
| Ile | Asn | Ala | Ser | Leu | Thr | Pro | Ile | Gly | Ala | Lys | Thr | Met | Ala | Arg | Pro | |
| | | | 610 | | | | | 615 | | | | | 620 | | | |

| | | | | | | | | | | | | | | | | |
|---|---|---|---|---|---|---|---|---|---|---|---|---|---|---|---|---|
| CCG | CCT | GCG | ATC | AAC | AAG | GCG | ATA | GGG | AAA | AAG | AAA | CGC | GAC | GCC | ATG | 2457 |
| Pro 625 | Pro | Ala | Ile | Asn | Lys 630 | Ala | Ile | Gly | Lys | Lys 635 | Lys | Arg | Asp | Ala | Met 640 | |
| GAA | ATG | GAC | GCC | AAA | TTG | AAC | ACA | TCG | AGC | GGA | GGA | GCG | GCG | TCC | GCT | 2505 |
| Glu | Met | Asp | Ala | Lys 645 | Leu | Asn | Thr | Ser | Ser 650 | Gly | Gly | Ala | Ala | Ser 655 | Ala | |
| GCG | AAC | TCG | TTT | TTC | CAG | CAG | AGC | TCC | ATG | TCC | TCG | ATG | TAC | GGT | GAC | 2553 |
| Ala | Asn | Ser | Phe 660 | Phe | Gln | Gln | Ser | Ser | Met 665 | Ser | Ser | Met | Tyr 670 | Gly | Asp | |
| GAT | GAT | ATC | AAC | GAT | GTT | GCC | GCC | ATG | GGA | GGT | GTT | AAC | TTG | GCG | GAG | 2601 |
| Asp | Asp | Ile 675 | Asn | Asp | Val | Ala | Ala | Met 680 | Gly | Gly | Val | Asn 685 | Leu | Ala | Glu | |
| GAG | TCG | CAG | CGA | ATT | CTC | GGC | TGT | ACC | GAA | AAC | ATC | GGC | ACG | CAG | ATT | 2649 |
| Glu | Ser | Gln | Arg 690 | Ile | Leu | Gly | Cys 695 | Thr | Glu | Asn | Ile 700 | Gly | Thr | Gln | Ile | |
| CGA | TCC | TGC | AAA | GAT | GAG | GTT | TTT | CTT | AAT | CTC | CCC | TCG | CTG | CAA | GCT | 2697 |
| Arg 705 | Ser | Cys | Lys | Asp | Glu 710 | Val | Phe | Leu | Asn | Leu 715 | Pro | Ser | Leu | Gln | Ala 720 | |
| AGA | ATA | CGG | GCA | ATT | ACT | TCG | GAG | GCG | GGA | CTG | GAT | GAG | CCG | TCG | CAG | 2745 |
| Arg | Ile | Arg | Ala | Ile 725 | Thr | Ser | Glu | Ala | Gly 730 | Leu | Asp | Glu | Pro | Ser 735 | Gln | |
| GAT | GTG | GCC | GTT | CTG | ATA | TCG | CAC | GCC | TGT | CAG | GAG | CGC | CTG | AAG | AAC | 2793 |
| Asp | Val | Ala | Val 740 | Leu | Ile | Ser | His | Ala 745 | Cys | Gln | Glu | Arg | Leu 750 | Lys | Asn | |
| ATC | GTT | GAG | AAG | TTG | GCT | GTG | ATA | GCG | GAG | CAC | CGC | ATT | GAT | GTC | ATC | 2841 |
| Ile | Val | Glu | Lys 755 | Leu | Ala | Val | Ile | Ala 760 | Glu | His | Arg | Ile 765 | Asp | Val | Ile | |
| AAG | TTG | GAT | CCA | CGC | TAT | GAG | CCC | GCC | AAG | GAT | GTG | CGC | GGT | CAG | ATC | 2889 |
| Lys | Leu 770 | Asp | Pro | Arg | Tyr | Glu 775 | Pro | Ala | Lys | Asp | Val 780 | Arg | Gly | Gln | Ile | |
| AAG | TTT | CTC | GAG | GAG | CTG | GAC | AAG | GCC | GAG | CAG | AAG | CGA | CAC | GAG | GAA | 2937 |
| Lys 785 | Phe | Leu | Glu | Glu 790 | Leu | Asp | Lys | Ala | Glu 795 | Gln | Lys | Arg | His | Glu 800 | Glu | |
| CTG | GAG | CGT | GAG | ATG | CTG | CTG | CGG | GCA | GCC | AAG | TCA | CGG | TCG | AGG | GTG | 2985 |
| Leu | Glu | Arg | Glu | Met 805 | Leu | Leu | Arg | Ala | Ala 810 | Lys | Ser | Arg | Ser | Arg 815 | Val | |
| GAA | GAT | CCC | GAG | CAG | GCC | AAG | ATG | AAG | GCG | AGG | GCC | AAG | GAG | ATG | CAA | 3033 |
| Glu | Asp | Pro | Glu 820 | Gln | Ala | Lys | Met | Lys 825 | Ala | Arg | Ala | Lys | Glu 830 | Met | Gln | |
| CGC | GCC | GAA | ATG | GAG | GAG | TTG | CGT | CAA | CGA | GAT | GCC | AAT | CTG | ACG | GCG | 3081 |
| Arg | Ala | Glu | Met 835 | Glu | Glu | Leu | Arg | Gln 840 | Arg | Asp | Ala | Asn 845 | Leu | Thr | Ala | |
| CTG | CAG | GCG | ATT | GGA | CCT | CGG | AAA | AAG | CTG | AAG | CTG | GAC | GGC | GAA | ACA | 3129 |
| Leu | Gln 850 | Ala | Ile | Gly | Pro | Arg 855 | Lys | Lys | Leu | Lys | Leu 860 | Asp | Gly | Glu | Thr | |
| GTC | AGT | TCG | GGA | GCG | GGT | TCA | AGT | GGC | GGC | GGA | GTG | CTA | AGC | AGC | TCG | 3177 |
| Val 865 | Ser | Ser | Gly | Ala | Gly 870 | Ser | Ser | Gly | Gly | Gly 875 | Val | Leu | Ser | Ser | Ser 880 | |
| GGA | TCT | GCG | CCG | ACG | ACG | TTA | CGG | CCT | CGC | ATA | AAA | CGT | GTG | AAC | CTG | 3225 |
| Gly | Ser | Ala | Pro | Thr 885 | Thr | Leu | Arg | Pro | Arg 890 | Ile | Lys | Arg | Val | Asn 895 | Leu | |
| CGC | GAC | ATG | CTC | TTC | TAC | ATG | GAG | CAA | GAG | CGG | GAG | TTC | TGT | CGC | AGT | 3273 |
| Arg | Asp | Met | Leu | Phe 900 | Tyr | Met | Glu | Gln | Glu 905 | Arg | Glu | Phe | Cys | Arg 910 | Ser | |
| TCC | ATG | CTG | TTC | AAG | ACA | TAC | CTC | AAG | TGATCGCTGC | | | TGTTGCCCAT | | | | 3320 |
| Ser | Met | Leu | Phe 915 | Lys | Thr | Tyr | Leu | Lys 920 | | | | | | | | |
| CAATCGCACC | GTCTTCTCCT | CGCCGATCCT | CCTACTCCGT | GGACTGTCGT | GTTGTTGTTT | | | | | | | | | | | 3380 |
| TATACAGCTT | TACGATTTCA | TCCACTTGCA | ATATATTTTA | GCCTCAACTT | TAAATGCGTC | | | | | | | | | | | 3440 |

-continued

```
GCGTGTCCCC TGTTGTTGTT TCTTTTTAGT TAGGCGGCTC TATTTAATTT CTATTTTTAC   3500
ATTTATTTAC ATAAATCCTA AATTCTAATC GTATTGATT  TTAAGCCTAA TTTAAAGCTC   3560
GTTTATTTTT CCAATAAATT CTCTGTAAAA CTTAAACCAA ACCAATCCAA AAACAAAACA   3620
AAACCAGAGT AAACGAAGAG AATAAAATAA TAGAGAGGAA AGTAAAAGAA GGTAAAAGAG   3680
AGCGCGCAGT CAGCGGTCGT TTGATTTGTA ATTTGTAACA TAATAATGTT TGCATCAACT   3740
GCATTGACGG CCTTATCTAA ACGATATAAA CATAATTATT AATATTTAAT TATTTAGCTT   3800
AGTTTGTTAA ACGAAAACGA ACCATAATTC CTAGATTTTA AGTAAAAAGC AAGGGCGCGT   3860
GAAGAGAAAT CGAAACCGAA TTACAGATAA AGGTTTTTAA AACCAACTAG ATCGAAACAA   3920
GTTCAGCAAC AGCAAAACAA AAGAACACAT CAAAAAAGA  ACCGAAAAAT ATCCATTTAA   3980
ACATCCATTG AATTAGGTTT AGTTGTTTAA AAAAGATGTA ATTTTAATT  ACCCATAATG   4040
TATAAACGGA AATCAATCGT TAGGCAAGAC CACAACAAAC CCAACAAATT GTAAATACAT   4100
TCTAGGCTAC GGTTTTTCTA ATAGATAACT AGGTAAAAAC GCAAACGTAA TTAACAAATT   4160
ATCGATGGCA AGGAGCGATG CGAGCGCAGA CAACTTGGCA CACCGAAAAA ATATGTTTTT   4220
ATTAGTGGCG CTCGTTCATC CATTAAGAAT GGCGATTCAT TAGGCTCCAT AGATCCATAA   4280
ATCCCCTAAT CCAATCTGAA CTACACACAA AATAGACAAA TTTTATACAA TTAGCTCGAT   4340
AAATCTTGTA AAATAGAGTC CCGTAAAAAA TTATAACAAA TAAATTGACA ACAATTGATG   4400
TAATTCAGTA AACCTAAGCA AAAGTGAAA  CCATTCTAAG CAAATTCTTT GTGTGTAAAA   4460
ATTAATATGA TAAACAAAAT GCAGATGCAA CCGTAAACAG CGCATAGTTT GGTAGGCATA   4520
TAACTGAATA TATATATATT ATTATTATTA TGTTTAACA  TTAAGCAAAA AATAAAAGA   4580
AAAAATTGAG AAAACTTCAA AAAAAAAAA  AAAAA                              4615
```

( 2 ) INFORMATION FOR SEQ ID NO:2:

( i ) SEQUENCE CHARACTERISTICS:
        ( A ) LENGTH: 921 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asn Thr Ser Gln Thr Ala Ala Gly Asn Arg Ile Thr Phe Thr Ser
 1               5                  10                  15

Gln Pro Leu Pro Asn Gly Thr Ile Ser Ile Ala Gly Asn Pro Gly Ala
            20                  25                  30

Val Ile Ser Thr Ala Gln Leu Pro Asn Thr Thr Thr Ile Lys Thr Ile
        35                  40                  45

Gln Ala Gly Ile Gly Gly Gln His Gln Gly Leu Gln Gln Val His His
    50                  55                  60

Val Gln Gln Gln Gln Gln Ser Gln Gln Gln Gln Gln Gln Gln Gln Gln
65                  70                  75                  80

Thr Gln Ser Ala Gly Gln Pro Leu Leu Asn Ser Met Leu Pro Ala Gly
                85                  90                  95

Val Val Val Gly Met Arg Gln Gln Ala Pro Ser Gln Gln Gln Gln Lys
            100                 105                 110

Asn Val Pro Thr Asn Pro Leu Ser Arg Val Val Ile Asn Ser His Met
        115                 120                 125

Ala Gly Val Arg Pro Gln Ser Pro Ser Ile Thr Leu Ser Thr Leu Asn
    130                 135                 140
```

-continued

```
Thr Gly Gln Thr Pro Ala Leu Leu Val Lys Thr Asp Asn Gly Phe Gln
145                 150                 155                 160

Leu Leu Arg Val Gly Thr Thr Thr Gly Pro Pro Thr Val Thr Gln Thr
                165                 170                 175

Ile Thr Asn Thr Ser Asn Asn Ser Asn Thr Thr Ser Thr Thr Asn His
            180                 185                 190

Pro Thr Thr Thr Gln Ile Arg Leu Gln Thr Val Pro Ala Ala Ala Ser
        195                 200                 205

Met Thr Asn Thr Thr Ala Thr Ser Asn Ile Ile Val Asn Ser Val Ala
    210                 215                 220

Ser Ser Gly Tyr Ala Asn Ser Ser Gln Pro Pro His Leu Thr Gln Leu
225                 230                 235                 240

Asn Ala Gln Ala Pro Gln Leu Pro Gln Ile Thr Gln Ile Gln Thr Ile
                245                 250                 255

Pro Ala Gln Gln Ser Gln Gln Gln Gln Val Asn Asn Val Ser Ser Ala
                260                 265                 270

Gly Gly Thr Ala Thr Ala Val Ser Ser Thr Thr Ala Ala Thr Thr Thr
            275                 280                 285

Gln Gln Gly Asn Thr Lys Glu Lys Cys Arg Lys Phe Leu Ala Asn Leu
    290                 295                 300

Ile Glu Leu Ser Thr Arg Glu Pro Lys Pro Val Glu Lys Asn Val Arg
305                 310                 315                 320

Thr Leu Ile Gln Glu Leu Val Asn Ala Asn Val Glu Pro Glu Glu Phe
                325                 330                 335

Cys Asp Arg Leu Glu Arg Leu Leu Asn Ala Ser Pro Gln Pro Cys Leu
                340                 345                 350

Ile Gly Phe Leu Lys Lys Ser Leu Pro Leu Leu Arg Gln Ala Leu Tyr
            355                 360                 365

Thr Lys Glu Leu Val Ile Glu Gly Ile Lys Pro Pro Gln His Val
    370                 375                 380

Leu Gly Leu Ala Gly Leu Ser Gln Gln Leu Pro Lys Ile Gln Ala Gln
385                 390                 395                 400

Ile Arg Pro Ile Gly Pro Ser Gln Thr Thr Ile Gly Gln Thr Gln
                405                 410                 415

Val Arg Met Ile Thr Pro Asn Ala Leu Gly Thr Pro Arg Pro Thr Ile
            420                 425                 430

Gly His Thr Thr Ile Ser Lys Gln Pro Pro Asn Ile Arg Leu Pro Thr
        435                 440                 445

Ala Pro Arg Leu Val Asn Thr Gly Gly Ile Arg Thr Gln Ile Pro Ser
450                 455                 460

Leu Gln Val Pro Gly Gln Ala Asn Ile Val Gln Ile Arg Gly Pro Gln
465                 470                 475                 480

His Ala Gln Leu Gln Arg Thr Gly Ser Val Gln Ile Arg Ala Thr Thr
                485                 490                 495

Arg Pro Pro Asn Ser Val Pro Thr Ala Asn Lys Leu Thr Ala Val Lys
            500                 505                 510

Val Gly Gln Thr Gln Ile Lys Ala Ile Thr Pro Ser Leu His Pro Pro
        515                 520                 525

Ser Leu Ala Ala Ile Ser Gly Pro Pro Pro Thr Pro Thr Leu Ser
    530                 535                 540

Val Leu Ser Thr Leu Asn Ser Ala Ser Thr Thr Thr Leu Pro Ile Pro
545                 550                 555                 560

Ser Leu Pro Thr Val His Leu Pro Pro Glu Ala Leu Arg Ala Arg Glu
                565                 570                 575
```

```
Gln  Met  Gln  Asn  Ser  Leu  Asn  His  Asn  Ser  Asn  His  Phe  Asp  Ala  Lys
               580                      585                      590

Leu  Val  Glu  Ile  Lys  Ala  Pro  Ser  Leu  His  Pro  Pro  His  Met  Glu  Arg
          595                      600                      605

Ile  Asn  Ala  Ser  Leu  Thr  Pro  Ile  Gly  Ala  Lys  Thr  Met  Ala  Arg  Pro
     610                      615                      620

Pro  Pro  Ala  Ile  Asn  Lys  Ala  Ile  Gly  Lys  Lys  Arg  Asp  Ala  Met
625                      630                      635                      640

Glu  Met  Asp  Ala  Lys  Leu  Asn  Thr  Ser  Ser  Gly  Gly  Ala  Ala  Ser  Ala
                    645                      650                      655

Ala  Asn  Ser  Phe  Phe  Gln  Gln  Ser  Ser  Met  Ser  Ser  Met  Tyr  Gly  Asp
               660                      665                      670

Asp  Asp  Ile  Asn  Asp  Val  Ala  Ala  Met  Gly  Gly  Val  Asn  Leu  Ala  Glu
          675                      680                      685

Glu  Ser  Gln  Arg  Ile  Leu  Gly  Cys  Thr  Glu  Asn  Ile  Gly  Thr  Gln  Ile
     690                      695                      700

Arg  Ser  Cys  Lys  Asp  Glu  Val  Phe  Leu  Asn  Leu  Pro  Ser  Leu  Gln  Ala
705                      710                      715                      720

Arg  Ile  Arg  Ala  Ile  Thr  Ser  Glu  Ala  Gly  Leu  Asp  Glu  Pro  Ser  Gln
                    725                      730                      735

Asp  Val  Ala  Val  Leu  Ile  Ser  His  Ala  Cys  Gln  Glu  Arg  Leu  Lys  Asn
               740                      745                      750

Ile  Val  Glu  Lys  Leu  Ala  Val  Ile  Ala  Glu  His  Arg  Ile  Asp  Val  Ile
          755                      760                      765

Lys  Leu  Asp  Pro  Arg  Tyr  Glu  Pro  Ala  Lys  Asp  Val  Arg  Gly  Gln  Ile
     770                      775                      780

Lys  Phe  Leu  Glu  Glu  Leu  Asp  Lys  Ala  Glu  Gln  Lys  Arg  His  Glu  Glu
785                      790                      795                      800

Leu  Glu  Arg  Glu  Met  Leu  Leu  Arg  Ala  Ala  Lys  Ser  Arg  Ser  Arg  Val
                    805                      810                      815

Glu  Asp  Pro  Glu  Gln  Ala  Lys  Met  Lys  Ala  Arg  Ala  Lys  Glu  Met  Gln
               820                      825                      830

Arg  Ala  Glu  Met  Glu  Glu  Leu  Arg  Gln  Arg  Asp  Ala  Asn  Leu  Thr  Ala
          835                      840                      845

Leu  Gln  Ala  Ile  Gly  Pro  Arg  Lys  Lys  Leu  Lys  Leu  Asp  Gly  Glu  Thr
     850                      855                      860

Val  Ser  Ser  Gly  Ala  Gly  Ser  Ser  Gly  Gly  Val  Leu  Ser  Ser  Ser
865                      870                      875                      880

Gly  Ser  Ala  Pro  Thr  Thr  Leu  Arg  Pro  Arg  Ile  Lys  Arg  Val  Asn  Leu
               885                      890                      895

Arg  Asp  Met  Leu  Phe  Tyr  Met  Glu  Gln  Glu  Arg  Glu  Phe  Cys  Arg  Ser
          900                      905                      910

Ser  Met  Leu  Phe  Lys  Thr  Tyr  Leu  Lys
          915                 920
```

( 2 ) INFORMATION FOR SEQ ID NO:3:

( i ) SEQUENCE CHARACTERISTICS:
        ( A ) LENGTH: 4164 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

```
TTCGCTGTAC GAGGTACCCG GTCCGAATTC CAAAAGGGCC AACAACTTCA CCCGTGACTT      60
TCTGCAGGTG TTTATTTACC GCCTGTTCTG GAAAAGTCGC GACAACCCGC CCCGCATTCG     120
AATGGACGAT ATAAACAGG  CTTTTCCCGC TCATTCCGAG AGCAGCATCC GCAAGCGTTT     180
AAAGCAGTGC GCTGACTTCA AGCGAACAGG CATGGACTCC AATTGGTGGG TTATAAAGCC     240
AGAGTTTCGC CTTCCATCCG AGGAGGAGAT CCGAGCCATG GTGTCACCTG AGCAGTGTTG     300
CGGTACTTCA GCATGATAGC GGCGGAACAA CGCTTAAAGG ATGCTGGGTA TGGAGAAAAG     360
TTTTTGTTCG CACCTCAGGA AGATGACGAC GAGGAGGCGC AGTGAAAGCT TGACGACGAA     420
GTAAAGGTGG CTCCTTGGAA CACGACTCGC GCATATATCC AAGCCATGCG GGGAAAGTGT     480
TTACTCCAGT TGAGTGGTCC AGCCGATCCA ACGGGATGTG GAGAGGGATT TTCATATGTT     540
CGAGTGCCAA ACAAGCCCAC GCAAACCAAG GAGGAGCAAG AGTCGCAGCC TAAACGTTCG     600
GTCACAGGAA CAGATGCAGA TTTGCGTCGT CTGCCACTCC AGCGTGCAAA AGAGCTGTTG     660
CGGCAGTTCA AGGTGCCCGA GGAGGAGATC AAAAAGCTTT CCCGCTGGGA GGTCATTGAC     720
GTGGTGCGCA CCCTGTCCAC AGAAAAGGCC AAGGCCGGTG AAGAGGGAAT GGATAAGTTT     780
TCTCGTGGCA ACCGGTTCTC CATTGCAGAG CATCAGGAGC GTTATAAGGA AGAGTGCCAG     840
CGCATATTCG ATCTGCAAAA CAGAGTGCTG GCCAGCTCTG AGGTGCTGTC CACAGATGAG     900
GCAGAGTCCT CGGCCTCTGA GGAATCTGAT CTCGAAGAAC TTGGCAAGAA TCTTGAGAAC     960
ATGCTGTCAA ACAAGAAAAC CTCGACGCAA TTGTCAAGGG AACGTGAAGA GCTGGAGCGT    1020
CAGGAGTTGC TTCGCCAGCT TGACGAAGAA CACGGCGGAC CAAGTGGTAG TGGAGGAGCC    1080
AAGGGAGCCA AAGGAAAGGA TGATCCGGGA CAGCAAATGC TGGCAACCAA CAACCAGGGC    1140
AGGATCCTTC GCATTACGCG TACCTTTAGA GGTAACGATG GCAAGGAATA TACTCGCGTG    1200
GAGACTGTGC GGCGGCAACC AGTTATCGAC GCCTACATCA AGATTCGCAC CACTAAGGAC    1260
GAGCAGTTCA TCAAGCAGTT CGCAACGCTA GATGAGCAGC AGAAGGAGGA GATGAAGCGC    1320
GAAAAGAGAC GCATTCAGGA GCAGCTACGT CGCATCAAGC GCAACCAGGA GCGCGAACGC    1380
CTGGCGCAGC TGGCCCAGAA CCAGAAGCTT CAGCCAGGTG GCATGCCCAC TTCCTTGGGT    1440
GATCCTAAGA GCTCGGGCGG TCATTCGCAC AAGGAGCGGG ATAGCGGCTA CAAGGAGGTC    1500
AGCCCTTCGC GCAAGAAGTT CAAGCTTAAG CCAGACCTAA AGCTGAAGTG CGGCGCCTGT    1560
GGACAGGTTG GTCACATGCG CACAAACAAA GCCTGTCCCT TGTATTCTGG CATGCAAAGC    1620
AGTCTGTCCC AGTCGAACCC ATCTCTGGCT GACGATTTTG ACGAACAGAG CGAAAAGGAG    1680
ATGACAATGG ATGACGATGA TCTTGTGAAT GTCGATGGCA CCAAAGTAAC GCTCAGCAGT    1740
AAGATTCTCA AGCGTCATGG TGGTGATGAT GGCAAGCGTC GCAGCGGATC TAGCTCTGGT    1800
TTCACCTTGA AGGTTCCCCG AGATGCGATG GGCAAGAAGA AACGCAGAGT GGGTGGCGAT    1860
CTTCATTGTG ACTATCTGCA GCGACACAAT AAAACGGCCA ATCGCAGGCG CACGGACCCC    1920
GTTGTGGTAC TGTCCTCTAT CCTGGAGATT ATCCATAATG AGCTGCGATC TATGCCAGAT    1980
GTATCGCCAT TCCTGTTCCC GGTAAGCGCA AAAAGGTTC  CCGACTACTA CCGCGTGGTG    2040
ACCAAGCCCA TGGATCTGCA AACGATGAGG GAGTATATCG CCAAAGGCTA ACACGAGTCG    2100
CGAGATGTTC CTCGAGGATC TCAAGCAGAT TGTGGACAAC TCGCTGATCT ACAATGGACC    2160
GCAGAGTGCA TACACCTTGG CTGCCCAACG CATGTTCAGC AGTTGTTTTG AATTGCTCGC    2220
AGAGGCGAAG ACAAACTGAT GCGCCTCGAG AAGGCAATTA CCCGCTGCTG GACGACGAT     2280
GACCAAGTGG CACTCTCCTT TATCTTTGAC AAGCTGCACT CGCAGATTAA GCAATTACCA    2340
GAGAGCTGGC CTTTCCTTAA GCCTGTCAAC AAGAAACAGG TTAAGGACTA CTACACGGTT    2400
```

| | | | | | |
|---|---|---|---|---|---|
| ATCAAGCGAC | CCATGGACCT | CGAAACTATC | GGCAAAAACA | TTGAAGCTCA | TCGCTATCAC | 2460 |
| AGTCGTGCCG | AGTATCTGGC | TGATATCGAG | TTGATCGCCA | CCAACTGTGA | GCAGTACAAC | 2520 |
| GGCAGTGACA | CCCGCTACAC | CAAGTTCTCA | AAGAAGATAC | TTGAGTATGC | CCAAACCCAG | 2580 |
| TTAATTGAGT | TTTCGGAGCA | CTGCGGCCAG | TTGGAAAATA | ACATAGCTAA | GACGCAGGAG | 2640 |
| CGTGCTAGGG | AAAATGCACC | AGAGTTTGAT | GAAGCCTGGG | GCAATGATGA | TTACAACTTT | 2700 |
| GACCGTGGCA | GTAGGGCCAG | TTCACCCGGA | GATGACTACA | TCGACGTCGA | GGGTCATGGG | 2760 |
| GGGCATGCCT | CCTCATCGAA | CTCTATCCAT | CGCAGCATGG | GCGCCGAGGC | CGGTTCGTCA | 2820 |
| CATACGGCGC | CGGCGGTGCG | AAAACCAGCT | CCTCCTGGTC | CTGGTGAGGT | GAAGCGCGGA | 2880 |
| AGGGGTAGGC | CCCGCAAGCA | GCGCGACCCC | GTGGAGGAGG | TCAAATCCCA | GAATCCGGTT | 2940 |
| AAGCGTGGTC | GGGGGCGTCC | GAGGAAGGAC | AGCCTTGCCT | CAAACATGAG | TCACACGCAA | 3000 |
| GCTTACTTCC | TGGATGAAGA | TCTCCAATGC | TCCACAGATG | ACGAGGACGA | CGACGAGGAG | 3060 |
| GAGGACTTCC | AGGAGGTCTC | CGAAGACGAG | AACAATGCGG | CGAGCATTTT | AGATCAGGGC | 3120 |
| GAACGTATCA | ATGCGCCTGC | CGATGCCATG | GATGGCATGT | TGACCCCAA | GAACATCAAG | 3180 |
| ACAGAGATTG | ACCTAGAGGC | TCACCAGATG | GCAGAGGAGC | CGATCGGCGA | GGATGACAGC | 3240 |
| CAGCAGGTGG | CCGAAGCAAT | GGTGCAGTTG | AGTGGCGTGG | GCGGCTACTA | TGCTCAACAG | 3300 |
| CAGCAAGATG | AATCCATGGA | TGTGGACCCC | AACTACGATC | CCTCAGATTT | CCTCGCCATG | 3360 |
| CACAAGCAGC | GCCAGAGCCT | CGGCGAGCCC | AGCAGCTTGC | AGGGTGCTTT | CACCAACTTC | 3420 |
| CTATCGCACG | AGCAGGATGA | TAATGGGCCT | TACAATCCCG | CCGAAGCCAG | CACAAGTGCC | 3480 |
| GCTTCCGGTG | CAGACTTAGG | AATGGACGCT | TCAATGGCCA | TGCAAATGGC | GCCGGAAATG | 3540 |
| CCTGTCAATA | CCATGAACAA | CGGAATGGGC | ATCGATGATG | ATCTGGATAT | TTCGGAGAGT | 3600 |
| GACGAGGAAG | ACGATGGTTC | TCGAGTGCGT | ATCAAAAGG | AGGTCTTCGA | CGACGGGGAT | 3660 |
| TACGCCTTGC | AGCACCAGCA | GATGGGACAG | GCAGCATCGC | AGTCGCAGAT | ATACATGGGG | 3720 |
| ATTCGTCCAA | CGAGCCCACG | ACTCTCGACT | ACCAGCAACC | ACCGCAACTG | GACTTCCAAC | 3780 |
| AAGTGCAGGA | AATGGAGCAG | TTGCAGCACC | AAGTGATGCC | ACCAATGCAA | TCAGAGCAAC | 3840 |
| TGCAGCAGCA | ACAGACGCCG | CAGGAGACAA | TGATTATGCC | TGGACTTTTT | AGTGATAGGG | 3900 |
| AATAATTGTT | AGTTGTTAGA | AAATAAAACG | TCGATTTAAT | AATAGGATTG | AGCTTCGCTG | 3960 |
| TGAAACAATT | TTATACACTT | TTTACAATGC | ATTGTTTTAA | CGGATTTGA | AATACTACAA | 4020 |
| TATGTTCTCT | GAAAAAATAT | TTCCTTTTCA | TGCCAATATG | TTTTTAATTT | TACACTTTAC | 4080 |
| AATTTATGAA | ATCTAATTCA | AAATATGTTT | TTAAAATATA | ATTTTCATAA | CTTTAAATAA | 4140 |
| TGCCTAGAAA | AAAAAAAAA | AAAA | | | | 4164 |

( 2 ) INFORMATION FOR SEQ ID NO:4:

( i ) SEQUENCE CHARACTERISTICS:
        ( A ) LENGTH: 2359 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 49..2160

( x i ) SEQUENCE DESCRIPTION: SEQ ID NO:4:

| | | | | | | |
|---|---|---|---|---|---|---|
| GATAACAAAA | TAGTACACAA | GTTCCATATA | TTTCAATTTT | CCGCGAAA | ATG AGC CTG | 57 |
| | | | | | Met Ser Leu | |
| | | | | | 1 | |

| | | | | | | | | | | | | | | | | |
|---|---|---|---|---|---|---|---|---|---|---|---|---|---|---|---|---|
| GAA | GTG | AGC | AAT | ATC | AAC | GGG | GGA | AAC | GGT | ACT | CAA | TTG | TCC | CAC | GAC | 105 |
| Glu | Val | Ser | Asn | Ile | Asn | Gly | Gly | Asn | Gly | Thr | Gln | Leu | Ser | His | Asp | |
| | 5 | | | | 10 | | | | | 15 | | | | | | |
| AAG | CGT | GAG | CTG | CTA | TGC | CTG | CTG | AAA | CTC | ATC | AAA | AAG | TAC | CAG | CTG | 153 |
| Lys | Arg | Glu | Leu | Leu | Cys | Leu | Leu | Lys | Leu | Ile | Lys | Lys | Tyr | Gln | Leu | |
| 20 | | | | | 25 | | | | | 30 | | | | | 35 | |
| AAG | AGC | ACT | GAG | GAG | CTG | CTC | TGC | CAA | GAG | GCG | AAT | GTG | AGC | AGT | GTG | 201 |
| Lys | Ser | Thr | Glu | Glu | Leu | Leu | Cys | Gln | Glu | Ala | Asn | Val | Ser | Ser | Val | |
| | | | | 40 | | | | | 45 | | | | | 50 | | |
| GAA | TTG | TCG | GAA | ATC | AGC | GAA | AGT | GAT | GTT | CAG | CAG | GTG | CTG | GGC | GCA | 249 |
| Glu | Leu | Ser | Glu | Ile | Ser | Glu | Ser | Asp | Val | Gln | Gln | Val | Leu | Gly | Ala | |
| | | | 55 | | | | | 60 | | | | | 65 | | | |
| GTT | TTG | GGA | GCT | GGC | GAT | GCC | AAC | CGG | GAG | CGG | AAA | CAT | GTC | CAA | TCT | 297 |
| Val | Leu | Gly | Ala | Gly | Asp | Ala | Asn | Arg | Glu | Arg | Lys | His | Val | Gln | Ser | |
| | | 70 | | | | | 75 | | | | | 80 | | | | |
| CCG | GCG | CAG | GGT | CAT | AAA | CAG | TCC | GCG | GTG | ACG | GAG | GCC | AAT | GCT | GCA | 345 |
| Pro | Ala | Gln | Gly | His | Lys | Gln | Ser | Ala | Val | Thr | Glu | Ala | Asn | Ala | Ala | |
| | 85 | | | | | 90 | | | | | 95 | | | | | |
| GAG | GAA | CTG | GCC | AAG | TTC | ATC | GAC | GAC | GAC | AGC | TTT | GAT | GCT | CAG | CAC | 393 |
| Glu | Glu | Leu | Ala | Lys | Phe | Ile | Asp | Asp | Asp | Ser | Phe | Asp | Ala | Gln | His | |
| 100 | | | | | 105 | | | | | 110 | | | | | 115 | |
| TAT | GAG | CAG | GCA | TAC | AAG | GAG | CTG | CGC | ACT | TTC | GTT | GAG | GAC | TCC | CTG | 441 |
| Tyr | Glu | Gln | Ala | Tyr | Lys | Glu | Leu | Arg | Thr | Phe | Val | Glu | Asp | Ser | Leu | |
| | | | | 120 | | | | | 125 | | | | | 130 | | |
| GAC | ATA | TAC | AAG | CAT | GAG | CTG | TCC | ATG | GTT | CTG | TAC | CCA | ATT | CTG | GTG | 489 |
| Asp | Ile | Tyr | Lys | His | Glu | Leu | Ser | Met | Val | Leu | Tyr | Pro | Ile | Leu | Val | |
| | | | 135 | | | | | 140 | | | | | 145 | | | |
| CAG | ATC | TAC | TTC | AAG | ATC | CTC | GCC | AGT | GGA | CTA | AGG | GAG | AAG | GCC | AAA | 537 |
| Gln | Ile | Tyr | Phe | Lys | Ile | Leu | Ala | Ser | Gly | Leu | Arg | Glu | Lys | Ala | Lys | |
| | | 150 | | | | | 155 | | | | | 160 | | | | |
| GAA | TTC | ATT | GAG | AAG | TAC | AAA | TGC | GAT | CTC | GAC | GGC | TAC | TAC | ATA | GAG | 585 |
| Glu | Phe | Ile | Glu | Lys | Tyr | Lys | Cys | Asp | Leu | Asp | Gly | Tyr | Tyr | Ile | Glu | |
| | 165 | | | | | 170 | | | | | 175 | | | | | |
| GGT | CTT | TTC | AAC | CTT | CTT | TTG | CTG | TCT | AAG | CCC | GAG | GAG | CTG | CTG | GAG | 633 |
| Gly | Leu | Phe | Asn | Leu | Leu | Leu | Leu | Ser | Lys | Pro | Glu | Glu | Leu | Leu | Glu | |
| 180 | | | | | 185 | | | | | 190 | | | | | 195 | |
| AAT | GAC | CTC | GTA | GTA | GCC | ATG | GAG | CAG | GAT | AAG | TTT | GTC | ATT | CGC | ATG | 681 |
| Asn | Asp | Leu | Val | Val | Ala | Met | Glu | Gln | Asp | Lys | Phe | Val | Ile | Arg | Met | |
| | | | | 200 | | | | | 205 | | | | | 210 | | |
| TCC | AGG | GAC | TCG | CAC | TCT | CTG | TTC | AAG | CGA | CAC | ATT | CAG | GAT | CGC | CGG | 729 |
| Ser | Arg | Asp | Ser | His | Ser | Leu | Phe | Lys | Arg | His | Ile | Gln | Asp | Arg | Arg | |
| | | | 215 | | | | | 220 | | | | | 225 | | | |
| CAG | GAA | GTG | GTG | GCA | GAT | ATT | GTT | TCC | AAG | TAC | TTG | CAT | TTC | GAC | ACA | 777 |
| Gln | Glu | Val | Val | Ala | Asp | Ile | Val | Ser | Lys | Tyr | Leu | His | Phe | Asp | Thr | |
| | | 230 | | | | | 235 | | | | | 240 | | | | |
| TAC | GAG | GGC | ATG | GCG | CGC | AAC | AAG | CTG | CAG | TGC | GTC | GCC | ACC | GCG | GGC | 825 |
| Tyr | Glu | Gly | Met | Ala | Arg | Asn | Lys | Leu | Gln | Cys | Val | Ala | Thr | Ala | Gly | |
| | 245 | | | | | 250 | | | | | 255 | | | | | |
| TCG | CAC | CTC | GGA | GAG | GCC | AAG | CGA | CAG | GAC | AAC | AAA | ATG | CGG | GTG | TAC | 873 |
| Ser | His | Leu | Gly | Glu | Ala | Lys | Arg | Gln | Asp | Asn | Lys | Met | Arg | Val | Tyr | |
| 260 | | | | | 265 | | | | | 270 | | | | | 275 | |
| TAC | GGA | CTG | CTC | AAG | GAG | GTG | GAC | TTT | CAG | ACT | CTG | ACC | ACT | CCA | GCG | 921 |
| Tyr | Gly | Leu | Leu | Lys | Glu | Val | Asp | Phe | Gln | Thr | Leu | Thr | Thr | Pro | Ala | |
| | | | | 280 | | | | | 285 | | | | | 290 | | |
| CCG | GCA | CCA | GAG | GAG | GAG | GAC | GAT | GAT | CCG | GAT | GCC | CCG | GAT | CGT | CCG | 969 |
| Pro | Ala | Pro | Glu | Glu | Glu | Asp | Asp | Asp | Pro | Asp | Ala | Pro | Asp | Arg | Pro | |
| | | | 295 | | | | | 300 | | | | | 305 | | | |
| AAA | AAG | AAA | AAG | CCA | AAA | AAG | GAT | CCC | CTG | CTG | TCG | AAA | AAG | TCC | AAG | 1017 |
| Lys | Lys | Lys | Lys | Pro | Lys | Lys | Asp | Pro | Leu | Leu | Ser | Lys | Lys | Ser | Lys | |
| | | 310 | | | | | 315 | | | | | 320 | | | | |

|  |  |  |  |  |  |  |  |  |  |  |  |  |  |  |  |
|---|---|---|---|---|---|---|---|---|---|---|---|---|---|---|---|
| TCG | GAT | CCG | AAT | GCT | CCA | TCC | ATC | GAC | AGA | ATT | CCC | CTG | CCG | GAA | CTG | 1065
| Ser | Asp | Pro | Asn | Ala | Pro | Ser | Ile | Asp | Arg | Ile | Pro | Leu | Pro | Glu | Leu |
| 325 |  |  |  | 330 |  |  |  |  |  | 335 |  |  |  |  |  |

```
TCG GAT CCG AAT GCT CCA TCC ATC GAC AGA ATT CCC CTG CCG GAA CTG       1065
Ser Asp Pro Asn Ala Pro Ser Ile Asp Arg Ile Pro Leu Pro Glu Leu
325             330                 335

AAG GAT TCG GAC AAG TTG CTA AAG CTT AAG GCT CTC AGG GAA GCC AGC       1113
Lys Asp Ser Asp Lys Leu Leu Lys Leu Lys Ala Leu Arg Glu Ala Ser
340             345                 350                 355

AAG CGT TTA GCC CTC AGC AAG GAT CAA CTG CCC TCT GCC GTC TTC TAC       1161
Lys Arg Leu Ala Leu Ser Lys Asp Gln Leu Pro Ser Ala Val Phe Tyr
                360                 365                 370

ACG GTG CTT AAT TCC CAT CAG GGC GTA ACC TGT GCC GAG ATT TCA GAC       1209
Thr Val Leu Asn Ser His Gln Gly Val Thr Cys Ala Glu Ile Ser Asp
                375                 380                 385

GAT TCC ACG ATG TTG GCC TGT GGA TTT GGC GAT TCT AGC GTG AGG ATT       1257
Asp Ser Thr Met Leu Ala Cys Gly Phe Gly Asp Ser Ser Val Arg Ile
        390                 395                 400

TGG TCA TTG ACG CCC GCG AAG CTG CGT ACG CTG AAG GAT GCA GAT TCC       1305
Trp Ser Leu Thr Pro Ala Lys Leu Arg Thr Leu Lys Asp Ala Asp Ser
    405                 410                 415

CTT CGC GAA CTG GAC AAG GAA TCG GCG GAT ATC AAT GTG CGT ATG CTG       1353
Leu Arg Glu Leu Asp Lys Glu Ser Ala Asp Ile Asn Val Arg Met Leu
420                 425                 430                 435

GAT GAC CGA AGT GGT GAG GTA ACC AGG AGC TTA ATG GGT CAC ACC GGA       1401
Asp Asp Arg Ser Gly Glu Val Thr Arg Ser Leu Met Gly His Thr Gly
                440                 445                 450

CCC GTA TAC CGC TGT GCC TTT GCC CCC GAG ATG AAC CTG TTG CTC TCA       1449
Pro Val Tyr Arg Cys Ala Phe Ala Pro Glu Met Asn Leu Leu Leu Ser
            455                 460                 465

TGT TCC GAG GAC AGC ACC ATA AGG CTG TGG TCT CTG CTC ACC TGG TCC       1497
Cys Ser Glu Asp Ser Thr Ile Arg Leu Trp Ser Leu Leu Thr Trp Ser
        470                 475                 480

TGC GTA GTC ACC TAC CGC GGG CAC GTT TAC CCG GTG TGG GAT GTT CGC       1545
Cys Val Val Thr Tyr Arg Gly His Val Tyr Pro Val Trp Asp Val Arg
485                 490                 495

TTT GCG CCG CAT GGC TAC TAT TTT GTT TCT TGT TCG TAC GAC AAA ACT       1593
Phe Ala Pro His Gly Tyr Tyr Phe Val Ser Cys Ser Tyr Asp Lys Thr
500                 505                 510                 515

GCT CGT CTG TGG GCC ACG GAT TCC AAT CAA GCG TTG CGC GTA TTC GTG       1641
Ala Arg Leu Trp Ala Thr Asp Ser Asn Gln Ala Leu Arg Val Phe Val
            520                 525                 530

GGT CAC TTG TCG GAC GTG GAT TGT GTA CAA TTT CAT CCC AAT TCC AAT       1689
Gly His Leu Ser Asp Val Asp Cys Val Gln Phe His Pro Asn Ser Asn
            535                 540                 545

TAT GTG GCC ACC GGT TCT AGC GAT CGC ACG GTA CGC CTG TGG GAC AAC       1737
Tyr Val Ala Thr Gly Ser Ser Asp Arg Thr Val Arg Leu Trp Asp Asn
        550                 555                 560

ATG ACC GGT CAG TCG GTA CGC CTG ATG ACG GGC CAC AAG GGA TCG GTG       1785
Met Thr Gly Gln Ser Val Arg Leu Met Thr Gly His Lys Gly Ser Val
    565                 570                 575

AGT TCT CTG GCC TTC TCC GCC TGC GGC CGG TAT CTG GCC TCG GGT TCA       1833
Ser Ser Leu Ala Phe Ser Ala Cys Gly Arg Tyr Leu Ala Ser Gly Ser
580                 585                 590                 595

GTA GAT CAC AAT ATC ATC ATC TGG GAT CTG TCG AAC GGA TCC CTG GTC       1881
Val Asp His Asn Ile Ile Ile Trp Asp Leu Ser Asn Gly Ser Leu Val
            600                 605                 610

ACC ACC CTG TTG AGG CAC ACT AGC ACT GTG ACC ACG ATC ACC TTT AGT       1929
Thr Thr Leu Leu Arg His Thr Ser Thr Val Thr Thr Ile Thr Phe Ser
        615                 620                 625

CGC GAT GGA ACA GTC CTG GCT GCA GCC GGC TTG GAT AAC AAT CTA ACT       1977
Arg Asp Gly Thr Val Leu Ala Ala Ala Gly Leu Asp Asn Asn Leu Thr
        630                 635                 640
```

```
CTG TGG GAC TTT CAC AAG GTT ACC GAA GAC TAT ATC AGC AAT CAC ATC       2025
Leu Trp Asp Phe His Lys Val Thr Glu Asp Tyr Ile Ser Asn His Ile
    645             650                 655

ACT GTG TCG CAC CAT CAG GAT GAG AAC GAC GAG GAC GTC TAC CTC ATG       2073
Thr Val Ser His His Gln Asp Glu Asn Asp Glu Asp Val Tyr Leu Met
660                 665                 670                 675

CGT ACT TTC CCC AGC AAG AAC TCG CCA TTT GTC AGC CTG CAC TTT ACG       2121
Arg Thr Phe Pro Ser Lys Asn Ser Pro Phe Val Ser Leu His Phe Thr
            680                 685                 690

CGC CGA AAT CTC CTG ATG TGC GTG GGT CTA TTC AAG AGT TAGGAGCACA        2170
Arg Arg Asn Leu Leu Met Cys Val Gly Leu Phe Lys Ser
                695                 700

GATAAGCTTA TTTGGTATAC GTAATGTAGT GTTAAGGAAT GCTCGGAATG TTTAGGATTA     2230

ATGTTTTGTA TTTCGTTTGT GACCCATCCC CCCTGAAATG TCGATTAGTT GTTTAAGCAT     2290

AAAAGTGTAA AGTGCATATA TGCGCAAGTT ATCAATAAAT TTTAATTAAT ATAAAAGTCA     2350

AAAAAAAAA                                                             2359
```

( 2 ) INFORMATION FOR SEQ ID NO:5:

( i ) SEQUENCE CHARACTERISTICS:
        ( A ) LENGTH: 704 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Ser Leu Glu Val Ser Asn Ile Asn Gly Gly Asn Gly Thr Gln Leu
1               5                   10                  15

Ser His Asp Lys Arg Glu Leu Leu Cys Leu Leu Lys Leu Ile Lys Lys
            20                  25                  30

Tyr Gln Leu Lys Ser Thr Glu Glu Leu Leu Cys Gln Glu Ala Asn Val
        35                  40                  45

Ser Ser Val Glu Leu Ser Glu Ile Ser Glu Ser Asp Val Gln Gln Val
    50                  55                  60

Leu Gly Ala Val Leu Gly Ala Gly Asp Ala Asn Arg Glu Arg Lys His
65                  70                  75                  80

Val Gln Ser Pro Ala Gln Gly His Lys Gln Ser Ala Val Thr Glu Ala
                85                  90                  95

Asn Ala Ala Glu Glu Leu Ala Lys Phe Ile Asp Asp Ser Phe Asp
                100                 105                 110

Ala Gln His Tyr Glu Gln Ala Tyr Lys Glu Leu Arg Thr Phe Val Glu
            115                 120                 125

Asp Ser Leu Asp Ile Tyr Lys His Glu Leu Ser Met Val Leu Tyr Pro
        130                 135                 140

Ile Leu Val Gln Ile Tyr Phe Lys Ile Leu Ala Ser Gly Leu Arg Glu
145                 150                 155                 160

Lys Ala Lys Glu Phe Ile Glu Lys Tyr Lys Cys Asp Leu Asp Gly Tyr
                165                 170                 175

Tyr Ile Glu Gly Leu Phe Asn Leu Leu Leu Ser Lys Pro Glu Glu
            180                 185                 190

Leu Leu Glu Asn Asp Leu Val Val Ala Met Glu Gln Asp Lys Phe Val
        195                 200                 205

Ile Arg Met Ser Arg Asp Ser His Ser Leu Phe Lys Arg His Ile Gln
210                 215                 220
```

```
Asp Arg Arg Gln Glu Val Val Ala Asp Ile Val Ser Lys Tyr Leu His
225                 230                 235                 240

Phe Asp Thr Tyr Glu Gly Met Ala Arg Asn Lys Leu Gln Cys Val Ala
            245                 250                 255

Thr Ala Gly Ser His Leu Gly Glu Ala Lys Arg Gln Asp Asn Lys Met
                260                 265                 270

Arg Val Tyr Tyr Gly Leu Leu Lys Glu Val Asp Phe Gln Thr Leu Thr
            275                 280                 285

Thr Pro Ala Pro Ala Pro Glu Glu Glu Asp Asp Pro Asp Ala Pro
290                 295                 300

Asp Arg Pro Lys Lys Lys Pro Lys Lys Asp Pro Leu Leu Ser Lys
305                 310                 315                 320

Lys Ser Lys Ser Asp Pro Asn Ala Pro Ser Ile Asp Arg Ile Pro Leu
                325                 330                 335

Pro Glu Leu Lys Asp Ser Asp Lys Leu Leu Lys Leu Lys Ala Leu Arg
            340                 345                 350

Glu Ala Ser Lys Arg Leu Ala Leu Ser Lys Asp Gln Leu Pro Ser Ala
            355                 360                 365

Val Phe Tyr Thr Val Leu Asn Ser His Gln Gly Val Thr Cys Ala Glu
    370                 375                 380

Ile Ser Asp Asp Ser Thr Met Leu Ala Cys Gly Phe Gly Asp Ser Ser
385                 390                 395                 400

Val Arg Ile Trp Ser Leu Thr Pro Ala Lys Leu Arg Thr Leu Lys Asp
                405                 410                 415

Ala Asp Ser Leu Arg Glu Leu Asp Lys Glu Ser Ala Asp Ile Asn Val
            420                 425                 430

Arg Met Leu Asp Asp Arg Ser Gly Glu Val Thr Arg Ser Leu Met Gly
        435                 440                 445

His Thr Gly Pro Val Tyr Arg Cys Ala Phe Ala Pro Glu Met Asn Leu
450                 455                 460

Leu Leu Ser Cys Ser Glu Asp Ser Thr Ile Arg Leu Trp Ser Leu Leu
465                 470                 475                 480

Thr Trp Ser Cys Val Val Thr Tyr Arg Gly His Val Tyr Pro Val Trp
                485                 490                 495

Asp Val Arg Phe Ala Pro His Gly Tyr Tyr Phe Val Ser Cys Ser Tyr
            500                 505                 510

Asp Lys Thr Ala Arg Leu Trp Ala Thr Asp Ser Asn Gln Ala Leu Arg
        515                 520                 525

Val Phe Val Gly His Leu Ser Asp Val Asp Cys Val Gln Phe His Pro
    530                 535                 540

Asn Ser Asn Tyr Val Ala Thr Gly Ser Ser Asp Arg Thr Val Arg Leu
545                 550                 555                 560

Trp Asp Asn Met Thr Gly Gln Ser Val Arg Leu Met Thr Gly His Lys
                565                 570                 575

Gly Ser Val Ser Ser Leu Ala Phe Ser Ala Cys Gly Arg Tyr Leu Ala
            580                 585                 590

Ser Gly Ser Val Asp His Asn Ile Ile Trp Asp Leu Ser Asn Gly
        595                 600                 605

Ser Leu Val Thr Thr Leu Leu Arg His Thr Ser Thr Val Thr Thr Ile
    610                 615                 620

Thr Phe Ser Arg Asp Gly Thr Val Leu Ala Ala Ala Gly Leu Asp Asn
625                 630                 635                 640

Asn Leu Thr Leu Trp Asp Phe His Lys Val Thr Glu Asp Tyr Ile Ser
                645                 650                 655
```

| Asn | His | Ile | Thr | Val | Ser | His | His | Gln | Asp | Glu | Asn | Asp | Glu | Asp | Val |
|     |     |     | 660 |     |     |     |     | 665 |     |     |     |     | 670 |     |     |

| Tyr | Leu | Met | Arg | Thr | Phe | Pro | Ser | Lys | Asn | Ser | Pro | Phe | Val | Ser | Leu |
|     |     |     | 675 |     |     |     |     | 680 |     |     |     |     | 685 |     |     |

| His | Phe | Thr | Arg | Arg | Asn | Leu | Leu | Met | Cys | Val | Gly | Leu | Phe | Lys | Ser |
|     |     |     | 690 |     |     |     | 695 |     |     |     |     | 700 |     |     |     |

( 2 ) INFORMATION FOR SEQ ID NO:6:

( i ) SEQUENCE CHARACTERISTICS:
        ( A ) LENGTH: 2018 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 70..1842

( x i ) SEQUENCE DESCRIPTION: SEQ ID NO:6:

GGAATTCGAG TTGGCCAAAG TGGCGCAATC CGGTATCAAT TGTTCAAACC GAGCAGCCCC     60

| TCCAGCAGC | ATG | CTG | TAC | GGC | TCC | AGC | ATC | TCG | GCG | GAG | TCC | ATG | AAG | 108 |
|           | Met | Leu | Tyr | Gly | Ser | Ser | Ile | Ser | Ala | Glu | Ser | Met | Lys |     |
|           | 1   |     |     | 5   |     |     |     |     |     | 10  |     |     |     |     |

| GTG | ATC | GCG | GAG | AGC | ATC | GGA | GTG | GGC | TCC | CTG | TCG | GAT | GAC | GCC | GCC | 156 |
| Val | Ile | Ala | Glu | Ser | Ile | Gly | Val | Gly | Ser | Leu | Ser | Asp | Asp | Ala | Ala |     |
|     | 15  |     |     |     |     | 20  |     |     |     |     | 25  |     |     |     |     |     |

| AAG | GAA | CTA | GCG | GAG | GAT | GTG | TCC | ATC | AAG | CTG | AAG | AGG | ATT | GTA | CAG | 204 |
| Lys | Glu | Leu | Ala | Glu | Asp | Val | Ser | Ile | Lys | Leu | Lys | Arg | Ile | Val | Gln |     |
| 30  |     |     |     |     | 35  |     |     |     |     | 40  |     |     |     |     | 45  |     |

| GAT | GCG | GCC | AAG | TTC | ATG | AAC | CAC | GCC | AAG | CGG | CAG | AAG | CTC | TCA | GTG | 252 |
| Asp | Ala | Ala | Lys | Phe | Met | Asn | His | Ala | Lys | Arg | Gln | Lys | Leu | Ser | Val |     |
|     |     |     |     | 50  |     |     |     |     | 55  |     |     |     |     | 60  |     |     |

| CGG | GAC | ATC | GAC | ATG | TCC | CTT | AAG | GTG | CGA | AAT | GTG | GAG | CCG | CAG | TAC | 300 |
| Arg | Asp | Ile | Asp | Met | Ser | Leu | Lys | Val | Arg | Asn | Val | Glu | Pro | Gln | Tyr |     |
|     |     |     | 65  |     |     |     |     | 70  |     |     |     |     | 75  |     |     |     |

| GGT | TTC | GTA | GCC | AAG | GAC | TTC | ATT | CCA | CTC | CGC | TTC | GCA | TCT | GGC | GGA | 348 |
| Gly | Phe | Val | Ala | Lys | Asp | Phe | Ile | Pro | Leu | Arg | Phe | Ala | Ser | Gly | Gly |     |
|     |     | 80  |     |     |     |     | 85  |     |     |     |     | 90  |     |     |     |     |

| GGA | CGG | GAG | CTG | CAC | TTC | ACC | GAG | GAC | AAG | GAA | ATC | GAC | CTA | GGA | GAA | 396 |
| Gly | Arg | Glu | Leu | His | Phe | Thr | Glu | Asp | Lys | Glu | Ile | Asp | Leu | Gly | Glu |     |
|     | 95  |     |     |     |     | 100 |     |     |     |     | 105 |     |     |     |     |     |

| ATC | ACA | TCC | ACC | AAC | TCT | GTA | AAA | ATT | CCC | CTG | GAT | CTC | ACC | CTG | CGC | 444 |
| Ile | Thr | Ser | Thr | Asn | Ser | Val | Lys | Ile | Pro | Leu | Asp | Leu | Thr | Leu | Arg |     |
| 110 |     |     |     |     | 115 |     |     |     |     | 120 |     |     |     |     | 125 |     |

| TCC | CAT | TGG | TTT | GTT | GTG | GAG | GGA | GTG | CAA | CCC | ACT | GTG | CCC | GAA | AAC | 492 |
| Ser | His | Trp | Phe | Val | Val | Glu | Gly | Val | Gln | Pro | Thr | Val | Pro | Glu | Asn |     |
|     |     |     |     | 130 |     |     |     |     | 135 |     |     |     |     | 140 |     |     |

| CCC | CCT | CCG | CTC | TCG | AAG | GAT | TCC | CAG | TTA | CTG | GAC | TCG | GTC | AAT | CCA | 540 |
| Pro | Pro | Pro | Leu | Ser | Lys | Asp | Ser | Gln | Leu | Leu | Asp | Ser | Val | Asn | Pro |     |
|     |     |     | 145 |     |     |     |     | 150 |     |     |     |     | 155 |     |     |     |

| GTT | ATT | AAG | ATG | GAT | CAA | GGC | CTA | AAC | AAA | GAT | GCG | GCA | GGC | AAA | CCC | 588 |
| Val | Ile | Lys | Met | Asp | Gln | Gly | Leu | Asn | Lys | Asp | Ala | Ala | Gly | Lys | Pro |     |
|     |     | 160 |     |     |     |     | 165 |     |     |     |     | 170 |     |     |     |     |

| ACC | ACC | GGC | AAG | ATA | CAC | AAG | CTG | AAA | AAC | GTG | GAG | ACC | ATT | CAT | GTC | 636 |
| Thr | Thr | Gly | Lys | Ile | His | Lys | Leu | Lys | Asn | Val | Glu | Thr | Ile | His | Val |     |
|     | 175 |     |     |     |     | 180 |     |     |     |     | 185 |     |     |     |     |     |

| AAG | CAA | CTG | GCC | ACG | CAC | GAG | TTG | TCC | GTG | GAG | CAG | CAG | TTG | TAC | TAC | 684 |
| Lys | Gln | Leu | Ala | Thr | His | Glu | Leu | Ser | Val | Glu | Gln | Gln | Leu | Tyr | Tyr |     |
| 190 |     |     |     |     | 195 |     |     |     |     | 200 |     |     |     |     | 205 |     |

| | | | | | | | | | | | | | | | | |
|---|---|---|---|---|---|---|---|---|---|---|---|---|---|---|---|---|
| AAG | GAG | ATC | ACC | GAG | GCG | TGC | GTG | GGA | TCT | GAT | GAG | CCG | CGG | CGC | GGG | 732 |
| Lys | Glu | Ile | Thr | Glu | Ala | Cys | Val | Gly | Ser | Asp | Glu | Pro | Arg | Arg | Gly | |
| | | | 210 | | | | | 215 | | | | | 220 | | | |
| GAA | GCG | CTG | CAG | TCG | CTG | GGA | TCC | GAT | CCT | GGC | CTG | CAC | GAA | ATG | CTT | 780 |
| Glu | Ala | Leu | Gln | Ser | Leu | Gly | Ser | Asp | Pro | Gly | Leu | His | Glu | Met | Leu | |
| | | | 225 | | | | | 230 | | | | | 235 | | | |
| CCC | CGC | ATG | TGC | ACC | TTC | ATT | GCC | GAG | GGA | GTT | AAG | GTC | AAT | GTG | GTT | 828 |
| Pro | Arg | Met | Cys | Thr | Phe | Ile | Ala | Glu | Gly | Val | Lys | Val | Asn | Val | Val | |
| | | 240 | | | | | 245 | | | | | 250 | | | | |
| CAG | AAC | AAC | TTG | GCG | TTG | CTT | ATT | TAC | CTC | ATG | CGC | ATG | GTT | CGT | GCG | 876 |
| Gln | Asn | Asn | Leu | Ala | Leu | Leu | Ile | Tyr | Leu | Met | Arg | Met | Val | Arg | Ala | |
| | 255 | | | | | 260 | | | | | 265 | | | | | |
| CTT | CTG | GAT | AAT | CCT | TCG | CTG | TTT | CTG | GAG | AAA | TAC | CTC | CAC | GAA | CTG | 924 |
| Leu | Leu | Asp | Asn | Pro | Ser | Leu | Phe | Leu | Glu | Lys | Tyr | Leu | His | Glu | Leu | |
| 270 | | | | | 275 | | | | | 280 | | | | | 285 | |
| ATA | CCC | TCG | GTG | ATG | ACG | TGC | ATT | GTG | TCC | AAA | CAG | CTG | TGT | ATG | CGC | 972 |
| Ile | Pro | Ser | Val | Met | Thr | Cys | Ile | Val | Ser | Lys | Gln | Leu | Cys | Met | Arg | |
| | | | | 290 | | | | | 295 | | | | | 300 | | |
| CCC | GAG | CTG | GAC | AAT | CAC | TGG | GCC | CTG | CGA | GAC | TTT | GCC | TCC | CGA | CTG | 1020 |
| Pro | Glu | Leu | Asp | Asn | His | Trp | Ala | Leu | Arg | Asp | Phe | Ala | Ser | Arg | Leu | |
| | | | 305 | | | | | 310 | | | | | 315 | | | |
| ATG | GCT | CAA | ATC | TGC | AAG | AAC | TTC | AAT | ACC | CTA | ACC | AAC | AAT | CTG | CAA | 1068 |
| Met | Ala | Gln | Ile | Cys | Lys | Asn | Phe | Asn | Thr | Leu | Thr | Asn | Asn | Leu | Gln | |
| | | | 320 | | | | | 325 | | | | | 330 | | | |
| ACC | CGT | GTC | ACC | CGC | ATC | TTC | AGC | AAG | GCC | CTG | CAG | AAC | GAC | AAG | ACC | 1116 |
| Thr | Arg | Val | Thr | Arg | Ile | Phe | Ser | Lys | Ala | Leu | Gln | Asn | Asp | Lys | Thr | |
| | | 335 | | | | | 340 | | | | | 345 | | | | |
| CAC | CTG | TCC | TCG | CTT | TAC | GGC | TCT | ATT | GCG | GGT | CTC | TCG | GAG | CTG | GGG | 1164 |
| His | Leu | Ser | Ser | Leu | Tyr | Gly | Ser | Ile | Ala | Gly | Leu | Ser | Glu | Leu | Gly | |
| 350 | | | | | 355 | | | | | 360 | | | | | 365 | |
| GGC | GAA | GTC | ATA | AAG | GTT | TTC | ATC | ATA | CCC | CGC | CTT | AAG | TTC | ATA | TCG | 1212 |
| Gly | Glu | Val | Ile | Lys | Val | Phe | Ile | Ile | Pro | Arg | Leu | Lys | Phe | Ile | Ser | |
| | | | | 370 | | | | | 375 | | | | | 380 | | |
| GAG | CGC | ATT | GAA | CCT | CAC | CTG | CTC | GGC | ACC | TCC | ATC | AGC | AAC | ACT | GAC | 1260 |
| Glu | Arg | Ile | Glu | Pro | His | Leu | Leu | Gly | Thr | Ser | Ile | Ser | Asn | Thr | Asp | |
| | | | 385 | | | | | 390 | | | | | 395 | | | |
| AAG | ACA | GCA | GCA | GGT | CAC | ATC | CGC | GCC | ATG | CTT | CAG | AAG | TGC | TGT | CCC | 1308 |
| Lys | Thr | Ala | Ala | Gly | His | Ile | Arg | Ala | Met | Leu | Gln | Lys | Cys | Cys | Pro | |
| | | | 400 | | | | | 405 | | | | | 410 | | | |
| CCG | ATT | CTC | AGG | CAA | ATG | CTC | AGC | GCC | AGA | TAC | AGC | GGA | GGA | CTA | CAA | 1356 |
| Pro | Ile | Leu | Arg | Gln | Met | Leu | Ser | Ala | Arg | Tyr | Ser | Gly | Gly | Leu | Gln | |
| | | 415 | | | | | 420 | | | | | 425 | | | | |
| GAA | CGA | CTT | TGG | CTT | CCT | GGG | GCC | GTC | GCT | GTG | CCA | GGC | GTA | GTC | AAA | 1404 |
| Glu | Arg | Leu | Trp | Leu | Pro | Gly | Ala | Val | Ala | Val | Pro | Gly | Val | Val | Lys | |
| 430 | | | | | 435 | | | | | 440 | | | | | 445 | |
| GTT | CGA | AAT | GCG | CCC | GCC | TCA | AGC | ATT | GTA | ACC | CTG | TCA | TCC | AAC | ACT | 1452 |
| Val | Arg | Asn | Ala | Pro | Ala | Ser | Ser | Ile | Val | Thr | Leu | Ser | Ser | Asn | Thr | |
| | | | | 450 | | | | | 455 | | | | | 460 | | |
| ATC | AAC | ACG | GCA | CCC | ATC | ACG | AGT | GCA | GCA | CAA | ACA | GCA | ACA | ACC | ATC | 1500 |
| Ile | Asn | Thr | Ala | Pro | Ile | Thr | Ser | Ala | Ala | Gln | Thr | Ala | Thr | Thr | Ile | |
| | | | 465 | | | | | 470 | | | | | 475 | | | |
| GGA | CGA | GTG | TCC | ATG | CCC | ACC | ACA | CAG | AGA | CAG | GGA | AGT | CCC | GGA | GTC | 1548 |
| Gly | Arg | Val | Ser | Met | Pro | Thr | Thr | Gln | Arg | Gln | Gly | Ser | Pro | Gly | Val | |
| | | 480 | | | | | 485 | | | | | 490 | | | | |
| TCG | TCC | CTG | CCG | CAA | ATA | AGA | GCC | ATT | CAG | GCC | AAC | CAG | CCG | GCG | CAA | 1596 |
| Ser | Ser | Leu | Pro | Gln | Ile | Arg | Ala | Ile | Gln | Ala | Asn | Gln | Pro | Ala | Gln | |
| | 495 | | | | | 500 | | | | | 505 | | | | | |
| AAG | TTT | GTG | ATA | GTC | ACC | CAG | AAC | TCG | CCG | CAG | CAG | GGC | CAG | GCG | AAG | 1644 |
| Lys | Phe | Val | Ile | Val | Thr | Gln | Asn | Ser | Pro | Gln | Gln | Gly | Gln | Ala | Lys | |
| 510 | | | | | 515 | | | | | 520 | | | | | 525 | |

| | | | | | | | | | | | | | | | | |
|---|---|---|---|---|---|---|---|---|---|---|---|---|---|---|---|---|
| GTG | GTG | CGG | CGT | GGC | AGC | TCT | CCG | CAC | AGC | GTG | GTC | CTC | TCC | GCG | GCC | 1692 |
| Val | Val | Arg | Arg | Gly | Ser | Ser | Pro | His | Ser | Val | Val | Leu | Ser | Ala | Ala | |
| | | | | 530 | | | | | 535 | | | | | 540 | | |
| TCC | AAC | GCT | GCC | AGT | GCC | TCC | AAT | TCG | AAC | TCA | AGC | TCG | AGC | GGC | AGT | 1740 |
| Ser | Asn | Ala | Ala | Ser | Ala | Ser | Asn | Ser | Asn | Ser | Ser | Ser | Ser | Gly | Ser | |
| | | | 545 | | | | | 550 | | | | | 555 | | | |
| CTA | CTA | GCG | GCT | GCA | CAG | CGG | AGC | AGC | GAG | AAT | GTG | TGT | GTT | ATT | GCC | 1788 |
| Leu | Leu | Ala | Ala | Ala | Gln | Arg | Ser | Ser | Glu | Asn | Val | Cys | Val | Ile | Ala | |
| | | 560 | | | | | 565 | | | | | 570 | | | | |
| GGT | AGC | GAA | GCG | CCA | GCA | GTT | GAT | GGT | ATA | ACA | GTT | CAA | TCT | TTC | AGA | 1836 |
| Gly | Ser | Glu | Ala | Pro | Ala | Val | Asp | Gly | Ile | Thr | Val | Gln | Ser | Phe | Arg | |
| | 575 | | | | | 580 | | | | | 585 | | | | | |
| GCA | TCC | TAGACGCCAA | CTCGCTGATC | ATTGAGACGG | AGATTGTGCG | CGCACCGGCC | | | | | | | | | | 1892 |
| Ala | Ser | | | | | | | | | | | | | | | |
| 590 | | | | | | | | | | | | | | | | |

```
CGAGCTGGCG  GATCTCTCGC  ACCTGGAGTA  GCCAGCTTAG  TTCGTAGTCC  ACATTTGTC          1952

ATATTGTATG  CAATAAAATA  AAAAATGCGG  GTTCCTACCC  CAAAAAAATG  TAAAAAAAA          2012

AAAAAA                                                                         2018
```

( 2 ) INFORMATION FOR SEQ ID NO:7:

( i ) SEQUENCE CHARACTERISTICS:
        ( A ) LENGTH: 591 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| | | | | | | | | | | | | | | |
|---|---|---|---|---|---|---|---|---|---|---|---|---|---|---|
| Met | Leu | Tyr | Gly | Ser | Ser | Ile | Ser | Ala | Glu | Ser | Met | Lys | Val | Ile | Ala |
| 1 | | | | 5 | | | | | 10 | | | | | 15 | |
| Glu | Ser | Ile | Gly | Val | Gly | Ser | Leu | Ser | Asp | Asp | Ala | Ala | Lys | Glu | Leu |
| | | | 20 | | | | | 25 | | | | | 30 | | |
| Ala | Glu | Asp | Val | Ser | Ile | Lys | Leu | Lys | Arg | Ile | Val | Gln | Asp | Ala | Ala |
| | | | 35 | | | | 40 | | | | | 45 | | | |
| Lys | Phe | Met | Asn | His | Ala | Lys | Arg | Gln | Lys | Leu | Ser | Val | Arg | Asp | Ile |
| | 50 | | | | | 55 | | | | | 60 | | | | |
| Asp | Met | Ser | Leu | Lys | Val | Arg | Asn | Val | Glu | Pro | Gln | Tyr | Gly | Phe | Val |
| 65 | | | | | 70 | | | | 75 | | | | | 80 | |
| Ala | Lys | Asp | Phe | Ile | Pro | Leu | Arg | Phe | Ala | Ser | Gly | Gly | Gly | Arg | Glu |
| | | | | 85 | | | | | 90 | | | | | 95 | |
| Leu | His | Phe | Thr | Glu | Asp | Lys | Glu | Ile | Asp | Leu | Gly | Glu | Ile | Thr | Ser |
| | | | 100 | | | | | 105 | | | | | 110 | | |
| Thr | Asn | Ser | Val | Lys | Ile | Pro | Leu | Asp | Leu | Thr | Leu | Arg | Ser | His | Trp |
| | | 115 | | | | | 120 | | | | | 125 | | | |
| Phe | Val | Val | Glu | Gly | Val | Gln | Pro | Thr | Val | Pro | Glu | Asn | Pro | Pro | Pro |
| | 130 | | | | | 135 | | | | | 140 | | | | |
| Leu | Ser | Lys | Asp | Ser | Gln | Leu | Leu | Asp | Ser | Val | Asn | Pro | Val | Ile | Lys |
| 145 | | | | | 150 | | | | | 155 | | | | | 160 |
| Met | Asp | Gln | Gly | Leu | Asn | Lys | Asp | Ala | Ala | Gly | Lys | Pro | Thr | Thr | Gly |
| | | | | 165 | | | | | 170 | | | | | 175 | |
| Lys | Ile | His | Lys | Leu | Lys | Asn | Val | Glu | Thr | Ile | His | Val | Lys | Gln | Leu |
| | | | 180 | | | | | 185 | | | | | 190 | | |
| Ala | Thr | His | Glu | Leu | Ser | Val | Glu | Gln | Gln | Leu | Tyr | Tyr | Lys | Glu | Ile |
| | | | 195 | | | | 200 | | | | | 205 | | | |
| Thr | Glu | Ala | Cys | Val | Gly | Ser | Asp | Glu | Pro | Arg | Arg | Gly | Glu | Ala | Leu |
| | | 210 | | | | | 215 | | | | | 220 | | | |

| Gln | Ser | Leu | Gly | Ser | Asp | Pro | Gly | Leu | His | Glu | Met | Leu | Pro | Arg | Met |
| 225 | | | | 230 | | | | | 235 | | | | | | 240 |

| Cys | Thr | Phe | Ile | Ala | Glu | Gly | Val | Lys | Val | Asn | Val | Val | Gln | Asn | Asn |
| | | | | 245 | | | | | 250 | | | | | 255 | |

| Leu | Ala | Leu | Leu | Ile | Tyr | Leu | Met | Arg | Met | Val | Arg | Ala | Leu | Leu | Asp |
| | | | 260 | | | | | 265 | | | | | 270 | | |

| Asn | Pro | Ser | Leu | Phe | Leu | Glu | Lys | Tyr | Leu | His | Glu | Leu | Ile | Pro | Ser |
| | | 275 | | | | | 280 | | | | | 285 | | | |

| Val | Met | Thr | Cys | Ile | Val | Ser | Lys | Gln | Leu | Cys | Met | Arg | Pro | Glu | Leu |
| | 290 | | | | | 295 | | | | | 300 | | | | |

| Asp | Asn | His | Trp | Ala | Leu | Arg | Asp | Phe | Ala | Ser | Arg | Leu | Met | Ala | Gln |
| 305 | | | | | 310 | | | | | 315 | | | | | 320 |

| Ile | Cys | Lys | Asn | Phe | Asn | Thr | Leu | Thr | Asn | Asn | Leu | Gln | Thr | Arg | Val |
| | | | | 325 | | | | | 330 | | | | | 335 | |

| Thr | Arg | Ile | Phe | Ser | Lys | Ala | Leu | Gln | Asn | Asp | Lys | Thr | His | Leu | Ser |
| | | | 340 | | | | | 345 | | | | | 350 | | |

| Ser | Leu | Tyr | Gly | Ser | Ile | Ala | Gly | Leu | Ser | Glu | Leu | Gly | Gly | Glu | Val |
| | | | 355 | | | | | 360 | | | | | 365 | | |

| Ile | Lys | Val | Phe | Ile | Ile | Pro | Arg | Leu | Lys | Phe | Ile | Ser | Glu | Arg | Ile |
| | 370 | | | | | 375 | | | | | 380 | | | | |

| Glu | Pro | His | Leu | Leu | Gly | Thr | Ser | Ile | Ser | Asn | Thr | Asp | Lys | Thr | Ala |
| 385 | | | | | 390 | | | | | 395 | | | | | 400 |

| Ala | Gly | His | Ile | Arg | Ala | Met | Leu | Gln | Lys | Cys | Cys | Pro | Pro | Ile | Leu |
| | | | | 405 | | | | | 410 | | | | | 415 | |

| Arg | Gln | Met | Leu | Ser | Ala | Arg | Tyr | Ser | Gly | Gly | Leu | Gln | Glu | Arg | Leu |
| | | | 420 | | | | | 425 | | | | | 430 | | |

| Trp | Leu | Pro | Gly | Ala | Val | Ala | Val | Pro | Gly | Val | Val | Lys | Val | Arg | Asn |
| | | 435 | | | | | 440 | | | | | 445 | | | |

| Ala | Pro | Ala | Ser | Ser | Ile | Val | Thr | Leu | Ser | Ser | Asn | Thr | Ile | Asn | Thr |
| | 450 | | | | | 455 | | | | | 460 | | | | |

| Ala | Pro | Ile | Thr | Ser | Ala | Ala | Gln | Thr | Ala | Thr | Thr | Ile | Gly | Arg | Val |
| 465 | | | | | 470 | | | | | 475 | | | | | 480 |

| Ser | Met | Pro | Thr | Thr | Gln | Arg | Gln | Gly | Ser | Pro | Gly | Val | Ser | Ser | Leu |
| | | | | 485 | | | | | 490 | | | | | 495 | |

| Pro | Gln | Ile | Arg | Ala | Ile | Gln | Ala | Asn | Gln | Pro | Ala | Gln | Lys | Phe | Val |
| | | | 500 | | | | | 505 | | | | | 510 | | |

| Ile | Val | Thr | Gln | Asn | Ser | Pro | Gln | Gln | Gly | Gln | Ala | Lys | Val | Val | Arg |
| | | | 515 | | | | | 520 | | | | | 525 | | |

| Arg | Gly | Ser | Ser | Pro | His | Ser | Val | Val | Leu | Ser | Ala | Ala | Ser | Asn | Ala |
| | | 530 | | | | | 535 | | | | | 540 | | | |

| Ala | Ser | Ala | Ser | Asn | Ser | Asn | Ser | Ser | Ser | Ser | Gly | Ser | Leu | Leu | Ala |
| 545 | | | | | 550 | | | | | 555 | | | | | 560 |

| Ala | Ala | Gln | Arg | Ser | Ser | Glu | Asn | Val | Cys | Val | Ile | Ala | Gly | Ser | Glu |
| | | | | 565 | | | | | 570 | | | | | 575 | |

| Ala | Pro | Ala | Val | Asp | Gly | Ile | Thr | Val | Gln | Ser | Phe | Arg | Ala | Ser | |
| | | | 580 | | | | | 585 | | | | | 590 | | |

( 2 ) INFORMATION FOR SEQ ID NO:8:

( i ) SEQUENCE CHARACTERISTICS:
        ( A ) LENGTH: 1120 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
  ( A ) NAME/KEY: CDS
  ( B ) LOCATION: 80..913

( x i ) SEQUENCE DESCRIPTION: SEQ ID NO:8:

```
GATATGTACG TGCACAATTT CAATGGAATA AACAATCTTC TTGCAGCAAA GCCGACGTAA              60

ACATAATAAC TATAGAAGT ATG AGC GCA GAG AAG TCC GAT AAG GCC AAG ATC             112
                    Met Ser Ala Glu Lys Ser Asp Lys Ala Lys Ile
                     1               5                  10

AGT GCC CAA ATC AAG CAC GTG CCG AAG GAC GCG CAG GTG ATC ATG TCC              160
Ser Ala Gln Ile Lys His Val Pro Lys Asp Ala Gln Val Ile Met Ser
             15                  20                  25

ATC CTG AAG GAG CTG AAT GTC CAG GAG TAC GAG CCG CGC GTG GTC AAC              208
Ile Leu Lys Glu Leu Asn Val Gln Glu Tyr Glu Pro Arg Val Val Asn
         30                  35                  40

CAA CTG CTG GAG TTC ACC TTC CGC TAT GTC ACC TGC ATT CTG GAC GAC              256
Gln Leu Leu Glu Phe Thr Phe Arg Tyr Val Thr Cys Ile Leu Asp Asp
     45                  50                  55

GCC AAG GTA TAC GCC AAC CAT GCG CGC AAG AAG ACC ATC GAC TTG GAC              304
Ala Lys Val Tyr Ala Asn His Ala Arg Lys Lys Thr Ile Asp Leu Asp
 60              65                  70                      75

GAC GTG CGT CTG GCC ACC GAG GTT ACG CTG GAC AAG AGC TTC ACC GGG              352
Asp Val Arg Leu Ala Thr Glu Val Thr Leu Asp Lys Ser Phe Thr Gly
             80                  85                      90

CCG TTG GAG CGC CAC GTT CTA GCC AAG GTG GCC GAC GTG CGC AAC AGC              400
Pro Leu Glu Arg His Val Leu Ala Lys Val Ala Asp Val Arg Asn Ser
         95                 100                 105

ATG CCC CTG CCA CCC ATT AAG CCG CAC TGC GGT CTC CGA CTG CCG CCC              448
Met Pro Leu Pro Pro Ile Lys Pro His Cys Gly Leu Arg Leu Pro Pro
     110                 115                 120

GAC CGC TAC TGT CTC ACC GGC GTC AAC TAC AAA CTG CGG GCC ACT AAT              496
Asp Arg Tyr Cys Leu Thr Gly Val Asn Tyr Lys Leu Arg Ala Thr Asn
 125                 130                 135

CAG CCC AAG AAA ATG ACC AAG TCG GCG GTG GAG GGC CGT CCA CTG AAG              544
Gln Pro Lys Lys Met Thr Lys Ser Ala Val Glu Gly Arg Pro Leu Lys
140                 145                 150                 155

ACC GTC GTT AAG CCC GTC TCC AGC GCC AAT GGT CCG AAG AGG CCA CAC              592
Thr Val Val Lys Pro Val Ser Ser Ala Asn Gly Pro Lys Arg Pro His
                 160                 165                 170

TCC GTG GTG GCC AAG CAG CAG GTG GTG ACC ATT CCC AAG CCC GTC ATC              640
Ser Val Val Ala Lys Gln Gln Val Val Thr Ile Pro Lys Pro Val Ile
             175                 180                 185

AAG TTT ACC ACC ACT ACG ACA ACG AAA ACG GTG GGC AGC TCC GGC GGA              688
Lys Phe Thr Thr Thr Thr Thr Thr Lys Thr Val Gly Ser Ser Gly Gly
         190                 195                 200

TCT GGG GGC GGC GGT GGT CAG GAG GTT AAG AGC GAG AGC ACC GGC GCC              736
Ser Gly Gly Gly Gly Gly Gln Glu Val Lys Ser Glu Ser Thr Gly Ala
     205                 210                 215

GGC GGA GAT CTC AAG ATG GAG GTG GAC AGC GAT GCG GCG GCC GTG GGC              784
Gly Gly Asp Leu Lys Met Glu Val Asp Ser Asp Ala Ala Ala Val Gly
 220                 225                 230                 235

AGC ATC GCT GGC GCA TCC GGT TCG GGA GCA GGA AGT GCC AGC GGA GGA              832
Ser Ile Ala Gly Ala Ser Gly Ser Gly Ala Gly Ser Ala Ser Gly Gly
             240                 245                 250

GGA GGA GGA GGA GGA TCA TCT GGC GTT GGA GTG GCC GTC AAG CGG GAA              880
Gly Gly Gly Gly Gly Ser Ser Gly Val Gly Val Ala Val Lys Arg Glu
         255                 260                 265

CGT GAG GAG GAG GAG TTT GAG TTT GTG ACC AAC TAGCGAAACG ACATCATTTA            933
Arg Glu Glu Glu Glu Phe Glu Phe Val Thr Asn
     270                 275
```

```
CCTTAAATTA ATATTCTTAA ATCAGACCAA AGCACTTGCA TTTGGTTGAG CGAACTGGGG    993

GTCTAAATTT CAACTCGAAT GTGAAGTCCC AAAAACCTTA GTATAGATTC GCCCGTTAAT    1053

CATTATGAAA TCTACGTTTT ATACACAAAT ACAACTACCA GATTTCATA TTAAAAAAAA     1113

AAAAAA                                                                1120
```

( 2 ) INFORMATION FOR SEQ ID NO:9:

( i ) SEQUENCE CHARACTERISTICS:
        ( A ) LENGTH: 278 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met Ser Ala Glu Lys Ser Asp Lys Ala Lys Ile Ser Ala Gln Ile Lys
 1               5                  10                  15

His Val Pro Lys Asp Ala Gln Val Ile Met Ser Ile Leu Lys Glu Leu
                20                  25                  30

Asn Val Gln Glu Tyr Glu Pro Arg Val Val Asn Gln Leu Leu Glu Phe
            35                  40                  45

Thr Phe Arg Tyr Val Thr Cys Ile Leu Asp Asp Ala Lys Val Tyr Ala
    50                  55                  60

Asn His Ala Arg Lys Lys Thr Ile Asp Leu Asp Asp Val Arg Leu Ala
65                  70                  75                  80

Thr Glu Val Thr Leu Asp Lys Ser Phe Thr Gly Pro Leu Glu Arg His
                85                  90                  95

Val Leu Ala Lys Val Ala Asp Val Arg Asn Ser Met Pro Leu Pro Pro
            100                 105                 110

Ile Lys Pro His Cys Gly Leu Arg Leu Pro Pro Asp Arg Tyr Cys Leu
        115                 120                 125

Thr Gly Val Asn Tyr Lys Leu Arg Ala Thr Asn Gln Pro Lys Lys Met
    130                 135                 140

Thr Lys Ser Ala Val Glu Gly Arg Pro Leu Lys Thr Val Val Lys Pro
145                 150                 155                 160

Val Ser Ser Ala Asn Gly Pro Lys Arg Pro His Ser Val Val Ala Lys
                165                 170                 175

Gln Gln Val Val Thr Ile Pro Lys Pro Val Ile Lys Phe Thr Thr Thr
            180                 185                 190

Thr Thr Thr Lys Thr Val Gly Ser Ser Gly Gly Ser Gly Gly Gly Gly
        195                 200                 205

Gly Gln Glu Val Lys Ser Glu Ser Thr Gly Ala Gly Gly Asp Leu Lys
    210                 215                 220

Met Glu Val Asp Ser Asp Ala Ala Ala Val Gly Ser Ile Ala Gly Ala
225                 230                 235                 240

Ser Gly Ser Gly Ala Gly Ser Ala Ser Gly Gly Gly Gly Gly Gly Gly
                245                 250                 255

Ser Ser Gly Val Gly Val Ala Val Lys Arg Glu Arg Glu Glu Glu Glu
            260                 265                 270

Phe Glu Phe Val Thr Asn
        275
```

( 2 ) INFORMATION FOR SEQ ID NO:10:

( i ) SEQUENCE CHARACTERISTICS:
        ( A ) LENGTH: 5962 base pairs (B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 14..5692

(xi) SEQUENCE DESCRIPTION: SEQ ID NO:10:

| | | | | | | | | | | | | | | | | |
|---|---|---|---|---|---|---|---|---|---|---|---|---|---|---|---|---|
| TTATTTCCGG | CAT | ATG | GGA | CCC | GGC | TGC | GAT | TTG | CTG | CTG | CGG | ACA | GCA | | | 49 |
| | | Met | Gly | Pro | Gly | Cys | Asp | Leu | Leu | Leu | Arg | Thr | Ala | | | |
| | | 1 | | 5 | | | | | | 10 | | | | | | |
| GCT | ACC | ATC | ACT | GCT | GCC | GCC | ATC | ATG | TCA | GAC | ACG | GAC | AGC | GAC | GAA | 97 |
| Ala | Thr | Ile | Thr | Ala | Ala | Ala | Ile | Met | Ser | Asp | Thr | Asp | Ser | Asp | Glu | |
| | | 15 | | | | | 20 | | | | | 25 | | | | |
| GAT | TCC | GCT | GGA | GGC | GGC | CCA | TTT | TCT | TTA | GCG | GGT | TTC | CTT | TTC | GGC | 145 |
| Asp | Ser | Ala | Gly | Gly | Gly | Pro | Phe | Ser | Leu | Ala | Gly | Phe | Leu | Phe | Gly | |
| | | 30 | | | | 35 | | | | | 40 | | | | | |
| AAC | ATC | AAT | GGA | GCC | GGG | CAG | CTG | GAG | GGG | GAA | AGC | GTC | TTG | GAT | GAT | 193 |
| Asn | Ile | Asn | Gly | Ala | Gly | Gln | Leu | Glu | Gly | Glu | Ser | Val | Leu | Asp | Asp | |
| 45 | | | | | 50 | | | | | 55 | | | | | 60 | |
| GAA | TGT | AAG | AAG | CAC | TTG | GCA | GGC | TTG | GGG | GCT | TTG | GGG | CTG | GGC | AGC | 241 |
| Glu | Cys | Lys | Lys | His | Leu | Ala | Gly | Leu | Gly | Ala | Leu | Gly | Leu | Gly | Ser | |
| | | | | 65 | | | | | 70 | | | | | 75 | | |
| CTG | ATC | ACT | GAA | CTC | ACG | GCA | AAT | GAA | GAA | TTG | ACC | GGG | ACT | GAC | GGT | 289 |
| Leu | Ile | Thr | Glu | Leu | Thr | Ala | Asn | Glu | Glu | Leu | Thr | Gly | Thr | Asp | Gly | |
| | | | 80 | | | | | 85 | | | | | 90 | | | |
| GCC | TTG | GTA | AAT | GAT | GAA | GGG | TGG | GTT | AGG | AGT | ACA | GAA | GAT | GCT | GTG | 337 |
| Ala | Leu | Val | Asn | Asp | Glu | Gly | Trp | Val | Arg | Ser | Thr | Glu | Asp | Ala | Val | |
| | | 95 | | | | | 100 | | | | | 105 | | | | |
| GAC | TAT | TCA | GAC | ATC | AAT | GAG | GTG | GCA | GAA | GAT | GAA | AGC | CGA | AGA | TAC | 385 |
| Asp | Tyr | Ser | Asp | Ile | Asn | Glu | Val | Ala | Glu | Asp | Glu | Ser | Arg | Arg | Tyr | |
| | | 110 | | | | 115 | | | | | 120 | | | | | |
| CAG | CAG | ACG | ATG | GGG | AGC | TTG | CAG | CCC | CTT | TGC | CAC | TCA | GAT | TAT | GAT | 433 |
| Gln | Gln | Thr | Met | Gly | Ser | Leu | Gln | Pro | Leu | Cys | His | Ser | Asp | Tyr | Asp | |
| 125 | | | | | 130 | | | | | 135 | | | | | 140 | |
| GAA | GAT | GAC | TAT | GAT | GCT | GAT | TGT | GAA | GAC | ATT | GAT | TGC | AAG | TTG | ATG | 481 |
| Glu | Asp | Asp | Tyr | Asp | Ala | Asp | Cys | Glu | Asp | Ile | Asp | Cys | Lys | Leu | Met | |
| | | | | 145 | | | | | 150 | | | | | 155 | | |
| CCT | CCT | CCA | CCT | CCA | CCC | CCG | GGA | CCA | ATG | AAG | AAG | GAT | AAG | GAC | CAG | 529 |
| Pro | Pro | Pro | Pro | Pro | Pro | Pro | Gly | Pro | Met | Lys | Lys | Asp | Lys | Asp | Gln | |
| | | | | 160 | | | | | 165 | | | | | 170 | | |
| GAT | TCT | ATT | ACT | GGT | GTG | TCT | GAA | AAT | GGA | GAA | GGC | ATC | ATC | TTG | CCC | 577 |
| Asp | Ser | Ile | Thr | Gly | Val | Ser | Glu | Asn | Gly | Glu | Gly | Ile | Ile | Leu | Pro | |
| | | 175 | | | | | 180 | | | | | 185 | | | | |
| TCC | ATC | ATT | GCC | CCT | TCC | TCT | TTG | GCC | TCA | GAG | AAA | GTG | GAC | TTC | AGT | 625 |
| Ser | Ile | Ile | Ala | Pro | Ser | Ser | Leu | Ala | Ser | Glu | Lys | Val | Asp | Phe | Ser | |
| | 190 | | | | | 195 | | | | | 200 | | | | | |
| AGT | TCC | TCT | GAC | TCA | GAA | TCT | GAG | ATG | GGA | CCT | CAG | GAA | GCA | ACA | CAG | 673 |
| Ser | Ser | Ser | Asp | Ser | Glu | Ser | Glu | Met | Gly | Pro | Gln | Glu | Ala | Thr | Gln | |
| 205 | | | | | 210 | | | | | 215 | | | | | 220 | |
| GCA | GAA | TCT | GAA | GAT | GGA | AAG | CTG | ACC | CTT | CCA | TTG | GCT | GGG | ATT | ATG | 721 |
| Ala | Glu | Ser | Glu | Asp | Gly | Lys | Leu | Thr | Leu | Pro | Leu | Ala | Gly | Ile | Met | |
| | | | | 225 | | | | | 230 | | | | | 235 | | |
| CAG | CAT | GAT | GCC | ACC | AAG | CTG | TTG | CCA | AGT | GTC | ACA | GAA | CTT | TTT | CCA | 769 |
| Gln | His | Asp | Ala | Thr | Lys | Leu | Leu | Pro | Ser | Val | Thr | Glu | Leu | Phe | Pro | |
| | | | 240 | | | | | 245 | | | | | 250 | | | |
| GAA | TTT | CGA | CCT | GGA | AAG | GTG | TTA | CGT | TTT | CTA | CGT | CTT | TTT | GGA | CCA | 817 |
| Glu | Phe | Arg | Pro | Gly | Lys | Val | Leu | Arg | Phe | Leu | Arg | Leu | Phe | Gly | Pro | |
| | | 255 | | | | | 260 | | | | | 265 | | | | |

| | | | | | | | | | | | | | | | | |
|---|---|---|---|---|---|---|---|---|---|---|---|---|---|---|---|---|
| GGG | AAG | AAT | GTC | CCA | TCT | GTT | TGG | CGG | AGT | GCT | CGG | AGA | AAG | AGG | AAG | 865 |
| Gly | Lys 270 | Asn | Val | Pro | Ser | Val 275 | Trp | Arg | Ser | Ala | Arg 280 | Arg | Lys | Arg | Lys | |
| AAG | AAG | CAC | CGT | GAG | CTG | ATA | CAG | GAA | GAG | CAG | ATC | CAG | GAG | GTG | GAG | 913 |
| Lys 285 | Lys | His | Arg | Glu 290 | Leu | Ile | Gln | Glu | Glu 295 | Gln | Ile | Gln | Glu | Val 300 | Glu | |
| TGC | TCA | GTA | GAA | TCA | GAA | GTC | AGC | CAG | AAG | TCT | TTG | TGG | AAC | TAC | GAC | 961 |
| Cys | Ser | Val | Glu 305 | Ser | Glu | Val | Ser | Gln 310 | Lys | Ser | Leu | Trp | Asn 315 | Tyr | Asp | |
| TAC | GCT | CCA | CCA | CCA | CCT | CCA | GAG | CAG | TGT | CTC | TCT | GAT | GAT | GAA | ATC | 1009 |
| Tyr | Ala | Pro 320 | Pro | Pro | Pro | Pro | Glu 325 | Gln | Cys | Leu | Ser | Asp 330 | Asp | Glu | Ile | |
| ACG | ATG | ATG | GCT | CCT | GTG | GAG | TCC | AAA | TTT | TCC | CAA | TCA | ACT | GGA | GAT | 1057 |
| Thr | Met | Met 335 | Ala | Pro | Val | Glu | Ser 340 | Lys | Phe | Ser | Gln | Ser 345 | Thr | Gly | Asp | |
| ATA | GAT | AAA | GTG | ACA | GAT | ACC | AAA | CCA | AGA | GTG | GCT | GAG | TGG | CGT | TAT | 1105 |
| Ile | Asp 350 | Lys | Val | Thr | Asp | Thr 355 | Lys | Pro | Arg | Val | Ala 360 | Glu | Trp | Arg | Tyr | |
| GGG | CCT | GCC | CGA | CTG | TGG | TAT | GAT | ATG | CTG | GGT | GTC | CCT | GAA | GAT | GGC | 1153 |
| Gly 365 | Pro | Ala | Arg | Leu | Trp 370 | Tyr | Asp | Met | Leu | Gly 375 | Val | Pro | Glu | Asp | Gly 380 | |
| AGT | GGG | TTT | GAC | TAT | GGC | TTC | AAA | CTG | AGA | AAG | ACA | GAA | CAT | GAA | CCT | 1201 |
| Ser | Gly | Phe | Asp | Tyr 385 | Gly | Phe | Lys | Leu | Arg 390 | Lys | Thr | Glu | His | Glu 395 | Pro | |
| GTG | ATA | AAA | TCT | AGA | ATG | ATA | GAG | GAA | TTT | AGG | AAA | CTT | GAG | GAA | AAC | 1249 |
| Val | Ile | Lys | Ser 400 | Arg | Met | Ile | Glu | Glu 405 | Phe | Arg | Lys | Leu | Glu 410 | Glu | Asn | |
| AAT | GGC | ACT | GAT | CTT | CTG | GCT | GAT | GAA | AAC | TTC | CTG | ATG | GTG | ACA | CAG | 1297 |
| Asn | Gly | Thr 415 | Asp | Leu | Leu | Ala | Asp 420 | Glu | Asn | Phe | Leu | Met 425 | Val | Thr | Gln | |
| CTG | CAT | TGG | GAG | GAT | GAT | ATC | ATC | TGG | GAT | GGG | GAG | GAT | GTC | AAA | CAC | 1345 |
| Leu | His 430 | Trp | Glu | Asp | Asp | Ile 435 | Ile | Trp | Asp | Gly | Glu 440 | Asp | Val | Lys | His | |
| AAA | GGG | ACA | AAA | CCT | CAG | CGT | GCA | AGC | CTG | GCA | GGC | TGG | CTT | CCT | TCT | 1393 |
| Lys 445 | Gly | Thr | Lys | Pro | Gln 450 | Arg | Ala | Ser | Leu | Ala 455 | Gly | Trp | Leu | Pro | Ser 460 | |
| AGC | ATG | ACT | AGG | AAT | GCG | ATG | GCT | TAC | AAT | GTT | CAG | CAA | GGT | TTT | GCA | 1441 |
| Ser | Met | Thr | Arg | Asn 465 | Ala | Met | Ala | Tyr | Asn 470 | Val | Gln | Gln | Gly | Phe 475 | Ala | |
| GCC | ACT | CTT | GAT | GAT | GAC | AAA | CCT | TGG | TAC | TCC | ATT | TTT | CCC | ATT | GAC | 1489 |
| Ala | Thr | Leu | Asp 480 | Asp | Asp | Lys | Pro | Trp 485 | Tyr | Ser | Ile | Phe | Pro 490 | Ile | Asp | |
| AAT | GAG | GAT | CTG | GTA | TAT | GGA | CGC | TGG | GAG | GAC | AAT | ATC | ATT | TGG | GAT | 1537 |
| Asn | Glu | Asp 495 | Leu | Val | Tyr | Gly | Arg 500 | Trp | Glu | Asp | Asn | Ile 505 | Ile | Trp | Asp | |
| GCT | CAG | GCC | ATG | CCC | CGG | CTG | TTG | GAA | CCT | CCT | GTT | TTG | ACA | CTT | GAT | 1585 |
| Ala | Gln | Ala 510 | Met | Pro | Arg | Leu 515 | Leu | Glu | Pro | Pro | Val 520 | Leu | Thr | Leu | Asp | |
| CCC | AAT | GAT | GAG | AAC | CTC | ATT | TTG | GAA | ATT | CCT | GAT | GAG | AAG | GAA | GAG | 1633 |
| Pro 525 | Asn | Asp | Glu | Asn | Leu 530 | Ile | Leu | Glu | Ile | Pro 535 | Asp | Glu | Lys | Glu | Glu 540 | |
| GCC | ACC | TCT | AAC | TCC | CCC | TCC | AAG | GAG | AGT | AAG | AAG | GAA | TCA | TCT | CTG | 1681 |
| Ala | Thr | Ser | Asn | Ser 545 | Pro | Ser | Lys | Glu | Ser 550 | Lys | Lys | Glu | Ser | Ser 555 | Leu | |
| AAG | AAG | AGT | CGA | ATT | CTC | TTA | GGG | AAA | ACA | GGA | GTC | ATC | AAG | GAG | GAA | 1729 |
| Lys | Lys | Ser | Arg 560 | Ile | Leu | Leu | Gly | Lys 565 | Thr | Gly | Val | Ile | Lys 570 | Glu | Glu | |
| CCA | CAG | CAG | AAC | ATG | TCT | CAG | CCA | GAA | GTG | AAA | GAT | CCA | TGG | AAT | CTC | 1777 |
| Pro | Gln | Gln 575 | Asn | Met | Ser | Gln | Pro 580 | Glu | Val | Lys | Asp | Pro 585 | Trp | Asn | Leu | |

| | | | | | | | | | | | | | | | | |
|---|---|---|---|---|---|---|---|---|---|---|---|---|---|---|---|---|
| TCC | AAT | GAT | GAG | TAT | TAT | TAT | CCC | AAG | CAA | CAG | GGT | CTT | CGA | GGC | ACC | 1825 |
| Ser | Asn | Asp | Glu | Tyr | Tyr | Tyr | Pro | Lys | Gln | Gln | Gly | Leu | Arg | Gly | Thr | |
| | 590 | | | | 595 | | | | | | 600 | | | | | |
| TTT | GGA | GGG | AAT | ATT | ATC | CAG | CAT | TCA | ATT | CCT | GCT | GTG | GAA | TTA | CGG | 1873 |
| Phe | Gly | Gly | Asn | Ile | Ile | Gln | His | Ser | Ile | Pro | Ala | Val | Glu | Leu | Arg | |
| 605 | | | | | 610 | | | | | 615 | | | | | 620 | |
| CAG | CCC | TTC | TTT | CCC | ACC | CAC | ATG | GGG | CCC | ATC | AAA | CTC | CGG | CAG | TTC | 1921 |
| Gln | Pro | Phe | Phe | Pro | Thr | His | Met | Gly | Pro | Ile | Lys | Leu | Arg | Gln | Phe | |
| | | | | | 625 | | | | | 630 | | | | | 635 | |
| CAT | CGC | CCA | CCT | CTG | AAA | AAG | TAC | TCA | TTT | GGT | GCA | CTT | TCT | CAG | CCA | 1969 |
| His | Arg | Pro | Pro | Leu | Lys | Lys | Tyr | Ser | Phe | Gly | Ala | Leu | Ser | Gln | Pro | |
| | | | 640 | | | | | 645 | | | | | 650 | | | |
| GGT | CCC | CAC | TCA | GTC | CAA | CCT | TTG | CTA | AAG | CAC | ATC | AAA | AAA | AAG | GCC | 2017 |
| Gly | Pro | His | Ser | Val | Gln | Pro | Leu | Leu | Lys | His | Ile | Lys | Lys | Lys | Ala | |
| | | 655 | | | | | 660 | | | | | 665 | | | | |
| AAG | ATG | AGA | GAA | CAA | GAG | AGG | CAA | GCT | TCA | GGT | GGT | GGA | GAG | ATG | TTT | 2065 |
| Lys | Met | Arg | Glu | Gln | Glu | Arg | Gln | Ala | Ser | Gly | Gly | Gly | Glu | Met | Phe | |
| | | 670 | | | | | 675 | | | | | 680 | | | | |
| TTT | ATG | CGC | ACA | CCT | CAG | GAC | CTC | ACA | GGC | AAA | GAT | GGT | GAT | CTT | ATT | 2113 |
| Phe | Met | Arg | Thr | Pro | Gln | Asp | Leu | Thr | Gly | Lys | Asp | Gly | Asp | Leu | Ile | |
| 685 | | | | | 690 | | | | | 695 | | | | | 700 | |
| CTT | GCA | GAA | TAT | AGT | GAG | GAA | AAT | GGA | CCC | TTA | ATG | ATG | CAG | GTT | GGC | 2161 |
| Leu | Ala | Glu | Tyr | Ser | Glu | Glu | Asn | Gly | Pro | Leu | Met | Met | Gln | Val | Gly | |
| | | | | 705 | | | | | 710 | | | | | 715 | | |
| ATG | GCA | ACC | AAG | ATA | AAG | AAC | TAT | TAT | AAA | CGG | AAA | CCT | GGA | AAA | GAT | 2209 |
| Met | Ala | Thr | Lys | Ile | Lys | Asn | Tyr | Tyr | Lys | Arg | Lys | Pro | Gly | Lys | Asp | |
| | | | 720 | | | | | 725 | | | | | 730 | | | |
| CCT | GGA | GCA | CCA | GAT | TGT | AAA | TAT | GGG | GAA | ACT | GTT | TAC | TGC | CAT | ACA | 2257 |
| Pro | Gly | Ala | Pro | Asp | Cys | Lys | Tyr | Gly | Glu | Thr | Val | Tyr | Cys | His | Thr | |
| | | 735 | | | | | 740 | | | | | 745 | | | | |
| TCT | CCT | TTC | CTG | GGT | TCT | CTC | CAT | CCT | GGC | CAA | TTG | CTG | CAA | GCA | TTT | 2305 |
| Ser | Pro | Phe | Leu | Gly | Ser | Leu | His | Pro | Gly | Gln | Leu | Leu | Gln | Ala | Phe | |
| | 750 | | | | | 755 | | | | | 760 | | | | | |
| GAG | AAC | AAC | CTT | TTT | CGT | GCT | CCA | ATT | TAT | CTT | CAT | AAG | ATG | CCA | GAA | 2353 |
| Glu | Asn | Asn | Leu | Phe | Arg | Ala | Pro | Ile | Tyr | Leu | His | Lys | Met | Pro | Glu | |
| 765 | | | | | 770 | | | | | 775 | | | | | 780 | |
| ACT | GAT | TTC | TTG | ATC | ATT | CGG | ACA | AGA | CAG | GGT | TAC | TAT | ATT | CGG | GAA | 2401 |
| Thr | Asp | Phe | Leu | Ile | Ile | Arg | Thr | Arg | Gln | Gly | Tyr | Tyr | Ile | Arg | Glu | |
| | | | | 785 | | | | | 790 | | | | | 795 | | |
| TTA | GTG | GAT | ATT | TTT | GTG | GTT | GGC | CAG | CAG | TGT | CCC | TTG | TTT | GAA | GTT | 2449 |
| Leu | Val | Asp | Ile | Phe | Val | Val | Gly | Gln | Gln | Cys | Pro | Leu | Phe | Glu | Val | |
| | | | 800 | | | | | 805 | | | | | 810 | | | |
| CCT | GGG | CCT | AAC | TCC | AAA | AGG | GCC | AAT | ACG | CAT | ATT | CGA | GAC | TTT | CTA | 2497 |
| Pro | Gly | Pro | Asn | Ser | Lys | Arg | Ala | Asn | Thr | His | Ile | Arg | Asp | Phe | Leu | |
| | | 815 | | | | | 820 | | | | | 825 | | | | |
| CAG | GTT | TTT | ATT | TAC | CGC | CTT | TTC | TGG | AAA | AGT | AAA | GAT | CGG | CCA | CGG | 2545 |
| Gln | Val | Phe | Ile | Tyr | Arg | Leu | Phe | Trp | Lys | Ser | Lys | Asp | Arg | Pro | Arg | |
| | 830 | | | | | 835 | | | | | 840 | | | | | |
| AGG | ATA | CGA | ATG | GAA | GAT | ATA | AAA | AAA | GCC | TTT | CCT | TCC | CAT | TCA | GAA | 2593 |
| Arg | Ile | Arg | Met | Glu | Asp | Ile | Lys | Lys | Ala | Phe | Pro | Ser | His | Ser | Glu | |
| 845 | | | | | 850 | | | | | 855 | | | | | 860 | |
| AGC | AGC | ATC | CGG | AAG | AGG | CTA | AAG | CTC | TGC | GCT | GAC | TTC | AAA | CGC | ACA | 2641 |
| Ser | Ser | Ile | Arg | Lys | Arg | Leu | Lys | Leu | Cys | Ala | Asp | Phe | Lys | Arg | Thr | |
| | | | | 865 | | | | | 870 | | | | | 875 | | |
| GGG | ATG | GAC | TCA | AAC | TGG | TGG | GTG | CTT | AAG | TCT | GAT | TTT | CGT | TTA | CCA | 2689 |
| Gly | Met | Asp | Ser | Asn | Trp | Trp | Val | Leu | Lys | Ser | Asp | Phe | Arg | Leu | Pro | |
| | | | 880 | | | | | 885 | | | | | 890 | | | |
| ACG | GAA | GAA | GAG | ATC | AGA | GCT | ATG | GTG | TCA | CCA | GAG | CAG | TGC | TGT | GCT | 2737 |
| Thr | Glu | Glu | Glu | Ile | Arg | Ala | Met | Val | Ser | Pro | Glu | Gln | Cys | Cys | Ala | |
| | | 895 | | | | | 900 | | | | | 905 | | | | |

```
TAT TAT AGC ATG ATA GCT GCA GAG CAA CGA CTG AAG GAT GCT GGC TAT         2785
Tyr Tyr Ser Met Ile Ala Ala Glu Gln Arg Leu Lys Asp Ala Gly Tyr
910             915                 920

GGT GAG AAA TCC TTT TTT GCT CCA GAA GAA GAA AAT GAG GAA GAT TTC         2833
Gly Glu Lys Ser Phe Phe Ala Pro Glu Glu Glu Asn Glu Glu Asp Phe
925             930                 935                 940

CAG ATG AAG ATT GAT GAT GAA GTT CGC ACT GCC CCT TGG AAC ACC ACA         2881
Gln Met Lys Ile Asp Asp Glu Val Arg Thr Ala Pro Trp Asn Thr Thr
                945                 950                 955

AGG GCC TTC ATT GCT GCC ATG AAG GGC AAG TGT CTG CTA GAG GTG ACT         2929
Arg Ala Phe Ile Ala Ala Met Lys Gly Lys Cys Leu Leu Glu Val Thr
            960                 965                 970

GGG GTG GCA GAT CCC ACG GGG TGT GGT GAA GGA TTC TCC TAT GTG AAG         2977
Gly Val Ala Asp Pro Thr Gly Cys Gly Glu Gly Phe Ser Tyr Val Lys
        975                 980                 985

ATT CCA AAC AAA CCA ACA CAG CAG AAG GAT GAT AAA GAA CCG CAG CCA         3025
Ile Pro Asn Lys Pro Thr Gln Gln Lys Asp Asp Lys Glu Pro Gln Pro
    990                 995                 1000

GTG AAG AAG ACA GTG ACA GGA ACA GAT GCA GAC CTT CGT CGC CTT TCC         3073
Val Lys Lys Thr Val Thr Gly Thr Asp Ala Asp Leu Arg Arg Leu Ser
1005            1010                1015                1020

CTG AAA AAT GCC AAG CAA CTT CTA CGT AAA TTT GGT GTG CCT GAG GAA         3121
Leu Lys Asn Ala Lys Gln Leu Leu Arg Lys Phe Gly Val Pro Glu Glu
                1025                1030                1035

GAG ATT AAA AAG TTG TCC CGC TGG GAA GTG ATT GAT GTG GTG CGC ACA         3169
Glu Ile Lys Lys Leu Ser Arg Trp Glu Val Ile Asp Val Val Arg Thr
                1040                1045                1050

ATG TCA ACA GAA CAG GCT CGT TCT GGA GAG GGG CCC ATG AGT AAA TTT         3217
Met Ser Thr Glu Gln Ala Arg Ser Gly Glu Gly Pro Met Ser Lys Phe
            1055                1060                1065

GCC CGT GGA TCA AGG TTT TCT GTG GCT GAG CAT CAA GAG CGT TAC AAA         3265
Ala Arg Gly Ser Arg Phe Ser Val Ala Glu His Gln Glu Arg Tyr Lys
        1070                1075                1080

GAG GAA TGT CAG CGC ATC TTT GAC CTA CAG AAC AAG GTT CTG TCA TCA         3313
Glu Glu Cys Gln Arg Ile Phe Asp Leu Gln Asn Lys Val Leu Ser Ser
1085            1090                1095                1100

ACT GAA GTC TTA TCA ACT GAC ACA GAC AGC AGC TCA GCT GAA GAT AGT         3361
Thr Glu Val Leu Ser Thr Asp Thr Asp Ser Ser Ser Ala Glu Asp Ser
                1105                1110                1115

GAC TTT GAA GAA ATG GGA AAG AAC ATT GAG AAC ATG TTG CAG AAC AAG         3409
Asp Phe Glu Glu Met Gly Lys Asn Ile Glu Asn Met Leu Gln Asn Lys
            1120                1125                1130

AAA ACC AGC TCT CAG CTT TCA CGT GAA CGG GAG GAA CAG GAG CGG AAG         3457
Lys Thr Ser Ser Gln Leu Ser Arg Glu Arg Glu Glu Gln Glu Arg Lys
        1135                1140                1145

GAA CTA CAG CGA ATG CTA CTG GCA GCA GGC TCA GCA GCA TCC GGA AAC         3505
Glu Leu Gln Arg Met Leu Leu Ala Ala Gly Ser Ala Ala Ser Gly Asn
1150                1155                1160

AAT CAC AGA GAT GAT GAC ACA GCT TCC GTG ACT AGC CTT AAC TCT TCT         3553
Asn His Arg Asp Asp Asp Thr Ala Ser Val Thr Ser Leu Asn Ser Ser
1165                1170                1175                1180

GCC ACT GGA CGC TGT CTC AAG ATT TAT CGC ACG TTT CGA GAT GAA GAG         3601
Ala Thr Gly Arg Cys Leu Lys Ile Tyr Arg Thr Phe Arg Asp Glu Glu
            1185                1190                1195

GGG AAA GAG TAT GTT CGC TGT GAG ACA GTC CGA AAA CCA GCT GTC ATT         3649
Gly Lys Glu Tyr Val Arg Cys Glu Thr Val Arg Lys Pro Ala Val Ile
        1200                1205                1210

GAT GCC TAT GTG CGC ATA CGG ACT ACA AAA GAT GAG GAA TTC ATT CGA         3697
Asp Ala Tyr Val Arg Ile Arg Thr Thr Lys Asp Glu Glu Phe Ile Arg
1215                1220                1225
```

| | | | | | | | | | | | | | | | | |
|---|---|---|---|---|---|---|---|---|---|---|---|---|---|---|---|---|
| AAA | TTT | GCC | CTT | TTT | GAT | GAA | CAA | CAT | CGG | GAA | GAG | ATG | CGA | AAA | GAA | 3745 |
| Lys | Phe | Ala | Leu | Phe | Asp | Glu | Gln | His | Arg | Glu | Glu | Met | Arg | Lys | Glu | |
| | | | 1230 | | | | 1235 | | | | | 1240 | | | | |

| | | | | | | | | | | | | | | | | |
|---|---|---|---|---|---|---|---|---|---|---|---|---|---|---|---|---|
| CGG | CGG | AGG | ATT | CAA | GAG | CAA | CTG | AGG | CGG | CTT | AAG | AGG | AAC | CAG | GAA | 3793 |
| Arg | Arg | Arg | Ile | Gln | Glu | Gln | Leu | Arg | Arg | Leu | Lys | Arg | Asn | Gln | Glu | |
| 1245 | | | | | 1250 | | | | | 1255 | | | | | 1260 | |

| | | | | | | | | | | | | | | | | |
|---|---|---|---|---|---|---|---|---|---|---|---|---|---|---|---|---|
| AAG | GAG | AAG | CTT | AAG | GGT | CCT | CCT | GAG | AAG | AAG | CCC | AAG | AAA | ATG | AAG | 3841 |
| Lys | Glu | Lys | Leu | Lys | Gly | Pro | Pro | Glu | Lys | Lys | Pro | Lys | Lys | Met | Lys | |
| | | | | 1265 | | | | 1270 | | | | | 1275 | | | |

| | | | | | | | | | | | | | | | | |
|---|---|---|---|---|---|---|---|---|---|---|---|---|---|---|---|---|
| GAG | CGT | CCT | GAC | CTA | AAA | CTG | AAA | TGT | GGG | GCA | TGT | GGT | GCC | ATT | GGA | 3889 |
| Glu | Arg | Pro | Asp | Leu | Lys | Leu | Lys | Cys | Gly | Ala | Cys | Gly | Ala | Ile | Gly | |
| | | | 1280 | | | | 1285 | | | | | 1290 | | | | |

| | | | | | | | | | | | | | | | | |
|---|---|---|---|---|---|---|---|---|---|---|---|---|---|---|---|---|
| CAC | ATG | AGG | ACT | AAC | AAA | TTC | TGC | CCC | CTC | TAT | TAT | CAA | ACA | AAT | GCG | 3937 |
| His | Met | Arg | Thr | Asn | Lys | Phe | Cys | Pro | Leu | Tyr | Tyr | Gln | Thr | Asn | Ala | |
| | | 1295 | | | | | 1300 | | | | | 1305 | | | | |

| | | | | | | | | | | | | | | | | |
|---|---|---|---|---|---|---|---|---|---|---|---|---|---|---|---|---|
| CCA | CCT | TCC | AAC | CCT | GTT | GCC | ATG | ACA | GAA | GAA | CAG | GAG | GAG | GAG | TTG | 3985 |
| Pro | Pro | Ser | Asn | Pro | Val | Ala | Met | Thr | Glu | Glu | Gln | Glu | Glu | Glu | Leu | |
| 1310 | | | | | 1315 | | | | | 1320 | | | | | | |

| | | | | | | | | | | | | | | | | |
|---|---|---|---|---|---|---|---|---|---|---|---|---|---|---|---|---|
| GAA | AAG | ACA | GTC | ATT | CAT | AAT | GAT | AAT | GAA | GAA | CTT | ATC | AAG | GTT | GAA | 4033 |
| Glu | Lys | Thr | Val | Ile | His | Asn | Asp | Asn | Glu | Glu | Leu | Ile | Lys | Val | Glu | |
| 1325 | | | | | 1330 | | | | | 1335 | | | | | 1340 | |

| | | | | | | | | | | | | | | | | |
|---|---|---|---|---|---|---|---|---|---|---|---|---|---|---|---|---|
| GGG | ACC | AAA | ATT | GTC | TTG | GGG | AAA | CAG | CTA | ATT | GAG | AGT | GCG | GAT | GAG | 4081 |
| Gly | Thr | Lys | Ile | Val | Leu | Gly | Lys | Gln | Leu | Ile | Glu | Ser | Ala | Asp | Glu | |
| | | | | 1345 | | | | | 1350 | | | | | 1355 | | |

| | | | | | | | | | | | | | | | | |
|---|---|---|---|---|---|---|---|---|---|---|---|---|---|---|---|---|
| GTT | CGC | AGA | AAA | TCT | CTG | GTT | CTC | AAG | TTT | CCT | AAA | CAG | CAG | CTT | CCT | 4129 |
| Val | Arg | Arg | Lys | Ser | Leu | Val | Leu | Lys | Phe | Pro | Lys | Gln | Gln | Leu | Pro | |
| | | | | 1360 | | | | | 1365 | | | | | 1370 | | |

| | | | | | | | | | | | | | | | | |
|---|---|---|---|---|---|---|---|---|---|---|---|---|---|---|---|---|
| CCA | AAG | AAG | AAA | CGG | CGA | GTT | GGA | ACC | ACT | GTT | CAC | TGT | GAC | TAT | TTG | 4177 |
| Pro | Lys | Lys | Lys | Arg | Arg | Val | Gly | Thr | Thr | Val | His | Cys | Asp | Tyr | Leu | |
| | | 1375 | | | | | 1380 | | | | | 1385 | | | | |

| | | | | | | | | | | | | | | | | |
|---|---|---|---|---|---|---|---|---|---|---|---|---|---|---|---|---|
| AAT | AGA | CCT | CAT | AAG | TCC | ATC | CAC | CGG | CGC | CGC | ACA | GAC | CCT | ATG | GTG | 4225 |
| Asn | Arg | Pro | His | Lys | Ser | Ile | His | Arg | Arg | Arg | Thr | Asp | Pro | Met | Val | |
| 1390 | | | | | 1395 | | | | | 1400 | | | | | | |

| | | | | | | | | | | | | | | | | |
|---|---|---|---|---|---|---|---|---|---|---|---|---|---|---|---|---|
| ACG | CTG | TCG | TCC | ATC | TTG | GAG | TCT | ATC | ATC | AAT | GAC | ATG | AGA | GAT | CTT | 4273 |
| Thr | Leu | Ser | Ser | Ile | Leu | Glu | Ser | Ile | Ile | Asn | Asp | Met | Arg | Asp | Leu | |
| 1405 | | | | | 1410 | | | | | 1415 | | | | | 1420 | |

| | | | | | | | | | | | | | | | | |
|---|---|---|---|---|---|---|---|---|---|---|---|---|---|---|---|---|
| CCA | AAT | ACA | TAC | CCT | TTC | CAC | ACT | CCA | GTC | AAT | GCA | AAG | GTT | GTA | AAG | 4321 |
| Pro | Asn | Thr | Tyr | Pro | Phe | His | Thr | Pro | Val | Asn | Ala | Lys | Val | Val | Lys | |
| | | | | 1425 | | | | | 1430 | | | | | 1435 | | |

| | | | | | | | | | | | | | | | | |
|---|---|---|---|---|---|---|---|---|---|---|---|---|---|---|---|---|
| GAC | TAC | TAC | AAA | ATC | ATC | ACT | CGG | CCA | ATG | GAC | CTA | CAA | ACA | CTC | CGC | 4369 |
| Asp | Tyr | Tyr | Lys | Ile | Ile | Thr | Arg | Pro | Met | Asp | Leu | Gln | Thr | Leu | Arg | |
| | | | 1440 | | | | 1445 | | | | | 1450 | | | | |

| | | | | | | | | | | | | | | | | |
|---|---|---|---|---|---|---|---|---|---|---|---|---|---|---|---|---|
| GAA | AAC | GTG | CGT | AAA | CGC | CTC | TAC | CCA | TCT | CGG | GAA | GAG | TTC | AGA | GAG | 4417 |
| Glu | Asn | Val | Arg | Lys | Arg | Leu | Tyr | Pro | Ser | Arg | Glu | Glu | Phe | Arg | Glu | |
| | | | 1455 | | | | | 1460 | | | | | 1465 | | | |

| | | | | | | | | | | | | | | | | |
|---|---|---|---|---|---|---|---|---|---|---|---|---|---|---|---|---|
| CAT | CTG | GAG | CTA | ATT | GTG | AAA | AAT | AGT | GCA | ACC | TAC | AAT | GGG | CCA | AAA | 4465 |
| His | Leu | Glu | Leu | Ile | Val | Lys | Asn | Ser | Ala | Thr | Tyr | Asn | Gly | Pro | Lys | |
| | | 1470 | | | | | 1475 | | | | | 1480 | | | | |

| | | | | | | | | | | | | | | | | |
|---|---|---|---|---|---|---|---|---|---|---|---|---|---|---|---|---|
| CAC | TCA | TTG | ACT | CAG | ATC | TCT | CAA | TCC | ATG | CTG | GAT | CTC | TGT | GAT | GAA | 4513 |
| His | Ser | Leu | Thr | Gln | Ile | Ser | Gln | Ser | Met | Leu | Asp | Leu | Cys | Asp | Glu | |
| 1485 | | | | | 1490 | | | | | 1495 | | | | | 1500 | |

| | | | | | | | | | | | | | | | | |
|---|---|---|---|---|---|---|---|---|---|---|---|---|---|---|---|---|
| AAA | CTC | AAA | GAG | AAA | GAA | GAC | AAA | TTA | GCT | CGC | TTA | GAG | AAA | GCT | ATC | 4561 |
| Lys | Leu | Lys | Glu | Lys | Glu | Asp | Lys | Leu | Ala | Arg | Leu | Glu | Lys | Ala | Ile | |
| | | | | 1505 | | | | | 1510 | | | | | 1515 | | |

| | | | | | | | | | | | | | | | | |
|---|---|---|---|---|---|---|---|---|---|---|---|---|---|---|---|---|
| AAC | CCC | TTG | CTG | GAT | GAT | GAT | GAC | CAA | GTG | GCG | TTT | TCT | TTC | ATT | CTG | 4609 |
| Asn | Pro | Leu | Leu | Asp | Asp | Asp | Asp | Gln | Val | Ala | Phe | Ser | Phe | Ile | Leu | |
| | | | 1520 | | | | | 1525 | | | | | 1530 | | | |

| | | | | | | | | | | | | | | | | |
|---|---|---|---|---|---|---|---|---|---|---|---|---|---|---|---|---|
| GAC | AAC | ATT | GTC | ACC | CAG | AAA | ATG | ATG | GCA | GTT | CCA | GAT | TCT | TGG | CCA | 4657 |
| Asp | Asn | Ile | Val | Thr | Gln | Lys | Met | Met | Ala | Val | Pro | Asp | Ser | Trp | Pro | |
| | | | | 1535 | | | | | 1540 | | | | | 1545 | | |

| | | | | | | | | | | | | | | | |
|---|---|---|---|---|---|---|---|---|---|---|---|---|---|---|---|
| TTT | CAT | CAC | CCA | GTT | AAT | AAG | AAA | TTT | GTT | CCA | GAT | TAT | TAC | AAA | GTG | 4705
| Phe | His | His | Pro | Val | Asn | Lys | Lys | Phe | Val | Pro | Asp | Tyr | Tyr | Lys | Val |
| | | 1550 | | | | 1555 | | | | 1560 | | | | | |
| ATT | GTC | AAT | CCA | ATG | GAT | TTA | GAG | ACC | ATA | CGT | AAG | AAC | ATC | TCC | AAG | 4753
| Ile | Val | Asn | Pro | Met | Asp | Leu | Glu | Thr | Ile | Arg | Lys | Asn | Ile | Ser | Lys |
| 1565 | | | | | 1570 | | | | | 1575 | | | | | 1580 |
| CAC | AAG | TAT | CAG | AGT | CGG | GAG | AGC | TTT | CTG | GAT | GAT | GTA | AAC | CTT | ATT | 4801
| His | Lys | Tyr | Gln | Ser | Arg | Glu | Ser | Phe | Leu | Asp | Asp | Val | Asn | Leu | Ile |
| | | | | 1585 | | | | | 1590 | | | | | 1595 | |
| CTG | GCC | AAC | AGT | GTT | AAG | TAT | AAT | GGA | CCT | GAG | AGT | CAG | TAT | ACT | AAG | 4849
| Leu | Ala | Asn | Ser | Val | Lys | Tyr | Asn | Gly | Pro | Glu | Ser | Gln | Tyr | Thr | Lys |
| | | | 1600 | | | | | 1605 | | | | | 1610 | | |
| ACT | GCC | CAG | GAG | ATT | GTG | AAC | GTC | TGT | TAC | CAG | ACA | TTG | ACT | GAG | TAT | 4897
| Thr | Ala | Gln | Glu | Ile | Val | Asn | Val | Cys | Tyr | Gln | Thr | Leu | Thr | Glu | Tyr |
| | | 1615 | | | | | 1620 | | | | | 1625 | | | |
| GAT | GAA | CAT | TTG | ACT | CAA | CTT | GAG | AAG | GAT | ATT | TGT | ACT | GCT | AAA | GAA | 4945
| Asp | Glu | His | Leu | Thr | Gln | Leu | Glu | Lys | Asp | Ile | Cys | Thr | Ala | Lys | Glu |
| | 1630 | | | | | 1635 | | | | | 1640 | | | | |
| GCA | GCT | TTG | GAG | GAA | GCA | GAA | TTA | GAA | AGC | CTG | GAC | CCA | ATG | ACC | CCA | 4993
| Ala | Ala | Leu | Glu | Glu | Ala | Glu | Leu | Glu | Ser | Leu | Asp | Pro | Met | Thr | Pro |
| 1645 | | | | | 1650 | | | | | 1655 | | | | | 1660 |
| GGG | CCC | TAC | ACG | CCT | CAG | CCT | CCT | GAT | TTG | TAT | GAT | ACC | AAC | ACA | TCC | 5041
| Gly | Pro | Tyr | Thr | Pro | Gln | Pro | Pro | Asp | Leu | Tyr | Asp | Thr | Asn | Thr | Ser |
| | | | | 1665 | | | | | 1670 | | | | | 1675 | |
| CTC | AGT | ATG | TCT | CGA | GAT | GCC | TCT | GTA | TTT | CAA | GAT | GAG | AGC | AAT | ATG | 5089
| Leu | Ser | Met | Ser | Arg | Asp | Ala | Ser | Val | Phe | Gln | Asp | Glu | Ser | Asn | Met |
| | | | 1680 | | | | | 1685 | | | | | 1690 | | |
| TCT | GTC | TTG | GAT | ATC | CCC | AGT | GCC | ACT | CCA | GAA | AAG | CAG | GTA | ACA | CAG | 5137
| Ser | Val | Leu | Asp | Ile | Pro | Ser | Ala | Thr | Pro | Glu | Lys | Gln | Val | Thr | Gln |
| | | 1695 | | | | | 1700 | | | | | 1705 | | | |
| GAA | GGT | GAA | GAT | GGA | GAT | GGT | GAT | CTT | GCA | GAT | GAA | GAG | GAA | GGA | ACT | 5185
| Glu | Gly | Glu | Asp | Gly | Asp | Gly | Asp | Leu | Ala | Asp | Glu | Glu | Glu | Gly | Thr |
| | 1710 | | | | | 1715 | | | | | 1720 | | | | |
| GTA | CAA | CAG | CCT | CAA | GCC | AGT | GTC | CTG | TAT | GAG | GAT | TTG | CTT | ATG | TCT | 5233
| Val | Gln | Gln | Pro | Gln | Ala | Ser | Val | Leu | Tyr | Glu | Asp | Leu | Leu | Met | Ser |
| 1725 | | | | | 1730 | | | | | 1735 | | | | | 1740 |
| GAA | GGA | GAA | GAT | GAT | GAG | GAA | GAT | GCT | GGG | AGT | GAT | GAA | GAA | GGA | GAC | 5281
| Glu | Gly | Glu | Asp | Asp | Glu | Glu | Asp | Ala | Gly | Ser | Asp | Glu | Glu | Gly | Asp |
| | | | 1745 | | | | | 1750 | | | | | 1755 | | |
| AAT | CCT | TTC | TCT | GCT | ATC | CAG | CTG | AGT | GAA | AGT | GGA | AGT | GAC | TCT | GAT | 5329
| Asn | Pro | Phe | Ser | Ala | Ile | Gln | Leu | Ser | Glu | Ser | Gly | Ser | Asp | Ser | Asp |
| | | | 1760 | | | | | 1765 | | | | | 1770 | | |
| GTG | GGA | TCT | GGT | GGA | ATA | AGA | CCC | AAA | CAA | CCC | CGC | ATG | CTT | CAG | GAG | 5377
| Val | Gly | Ser | Gly | Gly | Ile | Arg | Pro | Lys | Gln | Pro | Arg | Met | Leu | Gln | Glu |
| | | | 1775 | | | | | 1780 | | | | | 1785 | | |
| AAC | ACA | AGG | ATG | GAC | ATG | GAA | AAT | GAA | GAA | AGC | ATG | ATG | TCC | TAT | GAG | 5425
| Asn | Thr | Arg | Met | Asp | Met | Glu | Asn | Glu | Glu | Ser | Met | Met | Ser | Tyr | Glu |
| | 1790 | | | | | 1795 | | | | | 1800 | | | | |
| GGA | GAC | GGT | GGG | GAG | GCT | TCC | CAT | GGT | TTG | GAG | GAT | AGC | AAC | ATC | AGT | 5473
| Gly | Asp | Gly | Gly | Glu | Ala | Ser | His | Gly | Leu | Glu | Asp | Ser | Asn | Ile | Ser |
| 1805 | | | | | 1810 | | | | | 1815 | | | | | 1820 |
| TAT | GGG | AGC | TAT | GAG | GAG | CCT | GAT | CCC | AAG | TCG | AAC | ACC | CAA | GAC | ACA | 5521
| Tyr | Gly | Ser | Tyr | Glu | Glu | Pro | Asp | Pro | Lys | Ser | Asn | Thr | Gln | Asp | Thr |
| | | | | 1825 | | | | | 1830 | | | | | 1835 | |
| AGC | TTC | AGC | AGC | ATC | GGT | GGG | TAT | GAG | GTA | TCA | GAG | GAG | GAA | GAT | 5569
| Ser | Phe | Ser | Ser | Ile | Gly | Gly | Tyr | Glu | Val | Ser | Glu | Glu | Glu | Asp |
| | | | 1840 | | | | | 1845 | | | | | 1850 | |
| GAG | GAG | GAG | GAA | GAG | CAG | CGC | TCT | GGG | CCG | AGC | GTA | CTA | AGC | CAG | GTC | 5617
| Glu | Glu | Glu | Glu | Glu | Gln | Arg | Ser | Gly | Pro | Ser | Val | Leu | Ser | Gln | Val |
| | | | | 1855 | | | | | 1860 | | | | | 1865 | |

| | | | | | | | | | | | | | | | | |
|---|---|---|---|---|---|---|---|---|---|---|---|---|---|---|---|---|
| CAC | CTG | TCA | GAG | GAC | GAG | GAG | GAC | AGT | GAG | GAT | TTC | CAC | TCC | ATT | GCT | 5665 |
| His | Leu | Ser | Glu | Asp | Glu | Glu | Asp | Ser | Glu | Asp | Phe | His | Ser | Ile | Ala | |
| | 1870 | | | | 1875 | | | | | 1880 | | | | | | |
| GGG | GAC | AGT | GAC | TTG | GAC | TCT | GAT | GAA | TGAGGCTTCC | | TTTGGGCCTC | | | | | 5712 |
| Gly | Asp | Ser | Asp | Leu | Asp | Ser | Asp | Glu | | | | | | | | |
| 1885 | | | | | 1890 | | | | | | | | | | | |

CTTGGTCAGC CTTCCCTGTT CTCCAGCCTA GGTGGTTCAC CTTTCCCCAA TTTGTTCATA 5772

TTTGTACAGT ATCTGATCCT GAAATCATGA AATTAACTAA CACCTTAGCC TTTTAAAAG 5832

TAGTAAGTAA ATGATAATAA ATCACCTCTC CTAATCTTCC TGGGGCAATG TCACCCTTTG 5892

ATTTAAAACA AAGCAACCCC CTTTCCCCTA CCACTACGGA AAAGAGCAAG CTCATTTTTC 5952

CGTGTCCTCC 5962

( 2 ) INFORMATION FOR SEQ ID NO:11:

( i ) SEQUENCE CHARACTERISTICS:
        ( A ) LENGTH: 1893 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

| | | | | | | | | | | | | | | |
|---|---|---|---|---|---|---|---|---|---|---|---|---|---|---|
| Met | Gly | Pro | Gly | Cys | Asp | Leu | Leu | Leu | Arg | Thr | Ala | Ala | Thr | Ile | Thr |
| 1 | | | | 5 | | | | | 10 | | | | | 15 | |
| Ala | Ala | Ala | Ile | Met | Ser | Asp | Thr | Ser | Asp | Glu | Asp | Ser | Ala | Gly | |
| | | | 20 | | | | | 25 | | | | | 30 | | |
| Gly | Gly | Pro | Phe | Ser | Leu | Ala | Gly | Phe | Leu | Phe | Gly | Asn | Ile | Asn | Gly |
| | | 35 | | | | | 40 | | | | | 45 | | | |
| Ala | Gly | Gln | Leu | Glu | Gly | Glu | Ser | Val | Leu | Asp | Asp | Glu | Cys | Lys | Lys |
| | 50 | | | | 55 | | | | | 60 | | | | | |
| His | Leu | Ala | Gly | Leu | Gly | Ala | Leu | Gly | Leu | Gly | Ser | Leu | Ile | Thr | Glu |
| 65 | | | | | 70 | | | | 75 | | | | | | 80 |
| Leu | Thr | Ala | Asn | Glu | Glu | Leu | Thr | Gly | Thr | Asp | Gly | Ala | Leu | Val | Asn |
| | | | | 85 | | | | | 90 | | | | | 95 | |
| Asp | Glu | Gly | Trp | Val | Arg | Ser | Thr | Glu | Asp | Ala | Val | Asp | Tyr | Ser | Asp |
| | | | 100 | | | | | 105 | | | | | 110 | | |
| Ile | Asn | Glu | Val | Ala | Glu | Asp | Glu | Ser | Arg | Arg | Tyr | Gln | Gln | Thr | Met |
| | | 115 | | | | | 120 | | | | | 125 | | | |
| Gly | Ser | Leu | Gln | Pro | Leu | Cys | His | Ser | Asp | Tyr | Asp | Glu | Asp | Asp | Tyr |
| | 130 | | | | | 135 | | | | | 140 | | | | |
| Asp | Ala | Asp | Cys | Glu | Asp | Ile | Asp | Cys | Lys | Leu | Met | Pro | Pro | Pro | Pro |
| 145 | | | | | 150 | | | | | 155 | | | | | 160 |
| Pro | Pro | Pro | Gly | Pro | Met | Lys | Lys | Asp | Lys | Asp | Gln | Asp | Ser | Ile | Thr |
| | | | | 165 | | | | | 170 | | | | | 175 | |
| Gly | Val | Ser | Glu | Asn | Gly | Glu | Gly | Ile | Ile | Leu | Pro | Ser | Ile | Ile | Ala |
| | | | | 180 | | | | | 185 | | | | | 190 | |
| Pro | Ser | Ser | Leu | Ala | Ser | Glu | Lys | Val | Asp | Phe | Ser | Ser | Ser | Ser | Asp |
| | | | 195 | | | | | 200 | | | | | 205 | | |
| Ser | Glu | Ser | Glu | Met | Gly | Pro | Gln | Glu | Ala | Thr | Gln | Ala | Glu | Ser | Glu |
| | 210 | | | | | 215 | | | | | 220 | | | | |
| Asp | Gly | Lys | Leu | Thr | Leu | Pro | Leu | Ala | Gly | Ile | Met | Gln | His | Asp | Ala |
| 225 | | | | | 230 | | | | | 235 | | | | | 240 |
| Thr | Lys | Leu | Leu | Pro | Ser | Val | Thr | Glu | Leu | Phe | Pro | Glu | Phe | Arg | Pro |
| | | | | 245 | | | | | 250 | | | | | 255 | |
| Gly | Lys | Val | Leu | Arg | Phe | Leu | Arg | Leu | Phe | Gly | Pro | Gly | Lys | Asn | Val |
| | | | 260 | | | | | 265 | | | | | 270 | | |

| | | | | | | | | | | | | | |
|---|---|---|---|---|---|---|---|---|---|---|---|---|---|
|Pro|Ser|Val 275|Trp|Arg|Ser|Ala|Arg 280|Arg|Lys|Arg|Lys 285|Lys|His|Arg|
|Glu|Leu 290|Ile|Gln|Glu|Glu 295|Gln|Ile|Gln|Glu|Val 300|Glu|Cys|Ser|Val|Glu|
|Ser 305|Glu|Val|Ser|Gln 310|Lys|Ser|Leu|Trp|Asn 315|Tyr|Asp|Tyr|Ala|Pro|Pro 320|
|Pro|Pro|Pro|Glu|Gln 325|Cys|Leu|Ser|Asp 330|Asp|Glu|Ile|Thr|Met 335|Met|Ala|
|Pro|Val|Glu|Ser 340|Lys|Phe|Ser|Gln|Ser 345|Thr|Gly|Asp|Ile|Asp 350|Lys|Val|
|Thr|Asp|Thr 355|Lys|Pro|Arg|Val|Ala 360|Glu|Trp|Arg|Tyr|Gly 365|Pro|Ala|Arg|
|Leu|Trp 370|Tyr|Asp|Met|Leu 375|Gly|Val|Pro|Glu|Asp 380|Gly|Ser|Gly|Phe|Asp|
|Tyr 385|Gly|Phe|Lys|Leu|Arg 390|Lys|Thr|Glu|His|Glu 395|Pro|Val|Ile|Lys|Ser 400|
|Arg|Met|Ile|Glu|Glu 405|Phe|Arg|Lys|Leu|Glu 410|Glu|Asn|Asn|Gly|Thr 415|Asp|
|Leu|Leu|Ala|Asp 420|Glu|Asn|Phe|Leu|Met 425|Val|Thr|Gln|Leu|His 430|Trp|Glu|
|Asp|Asp|Ile 435|Ile|Trp|Asp|Gly|Glu 440|Asp|Val|Lys|His|Lys 445|Gly|Thr|Lys|
|Pro|Gln|Arg 450|Ala|Ser|Leu|Ala|Gly 455|Trp|Leu|Pro|Ser|Ser 460|Met|Thr|Arg|
|Asn 465|Ala|Met|Ala|Tyr|Asn 470|Val|Gln|Gln|Gly|Phe 475|Ala|Ala|Thr|Leu|Asp 480|
|Asp|Asp|Lys|Pro|Trp 485|Tyr|Ser|Ile|Phe|Pro 490|Ile|Asp|Asn|Glu|Asp 495|Leu|
|Val|Tyr|Gly|Arg 500|Trp|Glu|Asp|Asn|Ile 505|Ile|Trp|Asp|Ala|Gln 510|Ala|Met|
|Pro|Arg|Leu 515|Leu|Glu|Pro|Pro|Val 520|Leu|Thr|Leu|Asp|Pro 525|Asn|Asp|Glu|
|Asn|Leu|Ile 530|Leu|Glu|Ile|Pro 535|Asp|Glu|Lys|Glu|Glu 540|Ala|Thr|Ser|Asn|
|Ser 545|Pro|Ser|Lys|Glu|Ser 550|Lys|Lys|Glu|Ser|Ser 555|Leu|Lys|Lys|Ser|Arg 560|
|Ile|Leu|Leu|Gly|Lys 565|Thr|Gly|Val|Ile|Lys 570|Glu|Glu|Pro|Gln|Gln 575|Asn|
|Met|Ser|Gln|Pro 580|Glu|Val|Lys|Asp|Pro 585|Trp|Asn|Leu|Ser|Asn 590|Asp|Glu|
|Tyr|Tyr|Tyr|Pro 595|Lys|Gln|Gln|Gly|Leu 600|Arg|Gly|Thr|Phe 605|Gly|Gly|Asn|
|Ile|Ile|Gln|His 610|Ser|Ile|Pro|Ala 615|Val|Glu|Leu|Arg|Gln 620|Pro|Phe|Phe|
|Pro|Thr|His 625|Met|Gly|Pro 630|Ile|Lys|Leu|Arg|Gln 635|Phe|His|Arg|Pro|Pro 640|
|Leu|Lys|Lys|Tyr|Ser 645|Phe|Gly|Ala|Leu|Ser 650|Gln|Pro|Gly|Pro|His 655|Ser|
|Val|Gln|Pro|Leu 660|Leu|Lys|His|Ile|Lys 665|Lys|Lys|Ala|Lys|Met 670|Arg|Glu|
|Gln|Glu|Arg 675|Gln|Ala|Ser|Gly|Gly 680|Gly|Glu|Met|Phe|Phe 685|Met|Arg|Thr|

| | | | | | | | | | | | | | | |
|---|---|---|---|---|---|---|---|---|---|---|---|---|---|---|
| Pro | Gln | Asp | Leu | Thr | Gly | Lys | Asp | Gly | Asp | Leu | Ile | Leu | Ala | Glu | Tyr |
| | 690 | | | | 695 | | | | 700 | | | | | |
| Ser | Glu | Glu | Asn | Gly | Pro | Leu | Met | Met | Gln | Val | Gly | Met | Ala | Thr | Lys |
| 705 | | | | | 710 | | | | 715 | | | | | 720 |
| Ile | Lys | Asn | Tyr | Tyr | Lys | Arg | Lys | Pro | Gly | Lys | Asp | Pro | Gly | Ala | Pro |
| | | | | 725 | | | | | 730 | | | | 735 | |
| Asp | Cys | Lys | Tyr | Gly | Glu | Thr | Val | Tyr | Cys | His | Thr | Ser | Pro | Phe | Leu |
| | | | 740 | | | | 745 | | | | | 750 | | |
| Gly | Ser | Leu | His | Pro | Gly | Gln | Leu | Gln | Ala | Phe | Glu | Asn | Asn | Leu |
| | | 755 | | | | 760 | | | | 765 | | | | |
| Phe | Arg | Ala | Pro | Ile | Tyr | Leu | His | Lys | Met | Pro | Glu | Thr | Asp | Phe | Leu |
| | 770 | | | | 775 | | | | | 780 | | | | | |
| Ile | Ile | Arg | Thr | Arg | Gln | Gly | Tyr | Tyr | Ile | Arg | Glu | Leu | Val | Asp | Ile |
| 785 | | | | | 790 | | | | 795 | | | | | 800 | |
| Phe | Val | Val | Gly | Gln | Gln | Cys | Pro | Leu | Phe | Glu | Val | Pro | Gly | Pro | Asn |
| | | | 805 | | | | | 810 | | | | | 815 | | |
| Ser | Lys | Arg | Ala | Asn | Thr | His | Ile | Arg | Asp | Phe | Leu | Gln | Val | Phe | Ile |
| | | 820 | | | | | 825 | | | | 830 | | | | |
| Tyr | Arg | Leu | Phe | Trp | Lys | Ser | Lys | Asp | Arg | Pro | Arg | Arg | Ile | Arg | Met |
| | 835 | | | | | 840 | | | | | 845 | | | | |
| Glu | Asp | Ile | Lys | Lys | Ala | Phe | Pro | Ser | His | Ser | Glu | Ser | Ser | Ile | Arg |
| 850 | | | | | 855 | | | | | 860 | | | | | |
| Lys | Arg | Leu | Lys | Leu | Cys | Ala | Asp | Phe | Lys | Arg | Thr | Gly | Met | Asp | Ser |
| 865 | | | | | 870 | | | | | 875 | | | | | 880 |
| Asn | Trp | Trp | Val | Leu | Lys | Ser | Asp | Phe | Arg | Leu | Pro | Thr | Glu | Glu |
| | | | | 885 | | | | | 890 | | | | | 895 |
| Ile | Arg | Ala | Met | Val | Ser | Pro | Glu | Gln | Cys | Cys | Ala | Tyr | Tyr | Ser | Met |
| | | | | 900 | | | | 905 | | | | | 910 | | |
| Ile | Ala | Ala | Glu | Gln | Arg | Leu | Lys | Asp | Ala | Gly | Tyr | Gly | Glu | Lys | Ser |
| | | | 915 | | | | 920 | | | | | 925 | | | |
| Phe | Phe | Ala | Pro | Glu | Glu | Glu | Asn | Glu | Glu | Asp | Phe | Gln | Met | Lys | Ile |
| | 930 | | | | | 935 | | | | | 940 | | | | |
| Asp | Asp | Glu | Val | Arg | Thr | Ala | Pro | Trp | Asn | Thr | Thr | Arg | Ala | Phe | Ile |
| 945 | | | | | 950 | | | | | 955 | | | | | 960 |
| Ala | Ala | Met | Lys | Gly | Lys | Cys | Leu | Leu | Glu | Val | Thr | Gly | Val | Ala | Asp |
| | | | | 965 | | | | | 970 | | | | | 975 | |
| Pro | Thr | Gly | Cys | Gly | Glu | Gly | Phe | Ser | Tyr | Val | Lys | Ile | Pro | Asn | Lys |
| | | | 980 | | | | | 985 | | | | | 990 | | |
| Pro | Thr | Gln | Gln | Lys | Asp | Asp | Lys | Glu | Pro | Gln | Pro | Val | Lys | Lys | Thr |
| | | 995 | | | | 1000 | | | | | 1005 | | | | |
| Val | Thr | Gly | Thr | Asp | Ala | Asp | Leu | Arg | Arg | Leu | Ser | Leu | Lys | Asn | Ala |
| | 1010 | | | | 1015 | | | | | 1020 | | | | | |
| Lys | Gln | Leu | Leu | Arg | Lys | Phe | Gly | Val | Pro | Glu | Glu | Glu | Ile | Lys | Lys |
| 1025 | | | | | 1030 | | | | | 1035 | | | | | 1040 |
| Leu | Ser | Arg | Trp | Glu | Val | Ile | Asp | Val | Val | Arg | Thr | Met | Ser | Thr | Glu |
| | | | | 1045 | | | | | 1050 | | | | | 1055 | |
| Gln | Ala | Arg | Ser | Gly | Glu | Gly | Pro | Met | Ser | Lys | Phe | Ala | Arg | Gly | Ser |
| | | | 1060 | | | | | 1065 | | | | | 1070 | | |
| Arg | Phe | Ser | Val | Ala | Glu | His | Gln | Glu | Arg | Tyr | Lys | Glu | Glu | Cys | Gln |
| | | | 1075 | | | | | 1080 | | | | | 1085 | | |
| Arg | Ile | Phe | Asp | Leu | Gln | Asn | Lys | Val | Leu | Ser | Ser | Thr | Glu | Val | Leu |
| | | 1090 | | | | | 1095 | | | | | 1100 | | | |
| Ser | Thr | Asp | Thr | Asp | Ser | Ser | Ser | Ala | Glu | Asp | Ser | Asp | Phe | Glu | Glu |
| 1105 | | | | | 1110 | | | | | 1115 | | | | | 1120 |

Met Gly Lys Asn Ile Glu Asn Met Leu Gln Asn Lys Lys Thr Ser Ser
             1125                1130                1135

Gln Leu Ser Arg Glu Arg Glu Glu Gln Glu Arg Lys Glu Leu Gln Arg
             1140                1145                1150

Met Leu Leu Ala Ala Gly Ser Ala Ala Ser Gly Asn Asn His Arg Asp
             1155                1160                1165

Asp Asp Thr Ala Ser Val Thr Ser Leu Asn Ser Ser Ala Thr Gly Arg
             1170                1175                1180

Cys Leu Lys Ile Tyr Arg Thr Phe Arg Asp Glu Glu Gly Lys Glu Tyr
1185             1190                1195                1200

Val Arg Cys Glu Thr Val Arg Lys Pro Ala Val Ile Asp Ala Tyr Val
             1205                1210                1215

Arg Ile Arg Thr Thr Lys Asp Glu Glu Phe Ile Arg Lys Phe Ala Leu
             1220                1225                1230

Phe Asp Glu Gln His Arg Glu Glu Met Arg Lys Glu Arg Arg Arg Ile
             1235                1240                1245

Gln Glu Gln Leu Arg Arg Leu Lys Arg Asn Gln Glu Lys Glu Lys Leu
             1250                1255                1260

Lys Gly Pro Pro Glu Lys Lys Pro Lys Lys Met Lys Glu Arg Pro Asp
1265             1270                1275                1280

Leu Lys Leu Lys Cys Gly Ala Cys Gly Ala Ile Gly His Met Arg Thr
             1285                1290                1295

Asn Lys Phe Cys Pro Leu Tyr Tyr Gln Thr Asn Ala Pro Pro Ser Asn
             1300                1305                1310

Pro Val Ala Met Thr Glu Glu Gln Glu Glu Glu Leu Glu Lys Thr Val
             1315                1320                1325

Ile His Asn Asp Asn Glu Glu Leu Ile Lys Val Glu Gly Thr Lys Ile
             1330                1335                1340

Val Leu Gly Lys Gln Leu Ile Glu Ser Ala Asp Glu Val Arg Arg Lys
1345             1350                1355                1360

Ser Leu Val Leu Lys Phe Pro Lys Gln Gln Leu Pro Pro Lys Lys Lys
             1365                1370                1375

Arg Arg Val Gly Thr Thr Val His Cys Asp Tyr Leu Asn Arg Pro His
             1380                1385                1390

Lys Ser Ile His Arg Arg Arg Thr Asp Pro Met Val Thr Leu Ser Ser
             1395                1400                1405

Ile Leu Glu Ser Ile Ile Asn Asp Met Arg Asp Leu Pro Asn Thr Tyr
             1410                1415                1420

Pro Phe His Thr Pro Val Asn Ala Lys Val Val Lys Asp Tyr Tyr Lys
1425             1430                1435                1440

Ile Ile Thr Arg Pro Met Asp Leu Gln Thr Leu Arg Glu Asn Val Arg
             1445                1450                1455

Lys Arg Leu Tyr Pro Ser Arg Glu Glu Phe Arg Glu His Leu Glu Leu
             1460                1465                1470

Ile Val Lys Asn Ser Ala Thr Tyr Asn Gly Pro Lys His Ser Leu Thr
             1475                1480                1485

Gln Ile Ser Gln Ser Met Leu Asp Leu Cys Asp Glu Lys Leu Lys Glu
             1490                1495                1500

Lys Glu Asp Lys Leu Ala Arg Leu Glu Lys Ala Ile Asn Pro Leu Leu
1505             1510                1515                1520

Asp Asp Asp Asp Gln Val Ala Phe Ser Phe Ile Leu Asp Asn Ile Val
             1525                1530                1535

Thr Gln Lys Met Met Ala Val Pro Asp Ser Trp Pro Phe His His Pro
        1540                1545                1550

Val Asn Lys Lys Phe Val Pro Asp Tyr Tyr Lys Val Ile Val Asn Pro
        1555                1560                1565

Met Asp Leu Glu Thr Ile Arg Lys Asn Ile Ser Lys His Lys Tyr Gln
1570                1575                1580

Ser Arg Glu Ser Phe Leu Asp Asp Val Asn Leu Ile Leu Ala Asn Ser
1585                1590                1595                1600

Val Lys Tyr Asn Gly Pro Glu Ser Gln Tyr Thr Lys Thr Ala Gln Glu
            1605                1610                1615

Ile Val Asn Val Cys Tyr Gln Thr Leu Thr Glu Tyr Asp Glu His Leu
            1620                1625                1630

Thr Gln Leu Glu Lys Asp Ile Cys Thr Ala Lys Glu Ala Ala Leu Glu
        1635                1640                1645

Glu Ala Glu Leu Glu Ser Leu Asp Pro Met Thr Pro Gly Pro Tyr Thr
1650                1655                1660

Pro Gln Pro Pro Asp Leu Tyr Asp Thr Asn Thr Ser Leu Ser Met Ser
1665                1670                1675                1680

Arg Asp Ala Ser Val Phe Gln Asp Glu Ser Asn Met Ser Val Leu Asp
            1685                1690                1695

Ile Pro Ser Ala Thr Pro Glu Lys Gln Val Thr Gln Glu Gly Glu Asp
            1700                1705                1710

Gly Asp Gly Asp Leu Ala Asp Glu Glu Glu Gly Thr Val Gln Gln Pro
        1715                1720                1725

Gln Ala Ser Val Leu Tyr Glu Asp Leu Leu Met Ser Glu Gly Glu Asp
        1730                1735                1740

Asp Glu Glu Asp Ala Gly Ser Asp Glu Glu Gly Asp Asn Pro Phe Ser
1745                1750                1755                1760

Ala Ile Gln Leu Ser Glu Ser Gly Ser Asp Ser Asp Val Gly Ser Gly
            1765                1770                1775

Gly Ile Arg Pro Lys Gln Pro Arg Met Leu Gln Glu Asn Thr Arg Met
            1780                1785                1790

Asp Met Glu Asn Glu Glu Ser Met Met Ser Tyr Glu Gly Asp Gly Gly
        1795                1800                1805

Glu Ala Ser His Gly Leu Glu Asp Ser Asn Ile Ser Tyr Gly Ser Tyr
    1810                1815                1820

Glu Glu Pro Asp Pro Lys Ser Asn Thr Gln Asp Thr Ser Phe Ser Ser
1825                1830                1835                1840

Ile Gly Gly Tyr Glu Val Ser Glu Glu Glu Asp Glu Glu Glu
            1845                1850                1855

Glu Gln Arg Ser Gly Pro Ser Val Leu Ser Gln Val His Leu Ser Glu
            1860                1865                1870

Asp Glu Glu Asp Ser Glu Asp Phe His Ser Ile Ala Gly Asp Ser Asp
            1875                1880                1885

Leu Asp Ser Asp Glu
        1890

( 2 ) INFORMATION FOR SEQ ID NO:12:

( i ) SEQUENCE CHARACTERISTICS:
       ( A ) LENGTH: 3182 base pairs
       ( B ) TYPE: nucleic acid
       ( C ) STRANDEDNESS: double
       ( D ) TOPOLOGY: linear ( i i ) MOLECULE TYPE: cDNA ( i x ) FEATURE:
 ( A ) NAME/KEY: CDS
 ( B ) LOCATION: 972..3002

( x i ) SEQUENCE DESCRIPTION: SEQ ID NO:12:

```
CGAGTTTTTT TTTTTTTTT TTTTACAAGA GCACAAATCC ACATTTATTT ATTGATTTTT      60
CGTTAGTTTA AATCCTTGAG GGGTACAGCA TCACTCGGAT TCTGTGTCCA ATGGCCTTAG    120
CAGGAAGATT GCTTCGGAAT TTGGCACGAA CCATGCCACT GTTTCCATGG GCCCGAGTTA    180
CTTTTCCCCA GATGACTCTG GTTTTGTTTG GTTTGCCGCC AGGAGTGACT GTGTTGTTCT    240
TTGCTTTATA TACATAAGCG CATCTCTTGC CCAAATAGAA TTCTGTTTCA TCTCGGGCGT    300
AAACACCTTC AATTTTAAGA AGAGCTGTGT GCTCCCTTTG GTTCCGGAGA CCCCGCTTAT    360
AGCCAGCAAA AATGGCCTTG GACCACAGCC TTCCAGACAT AGTTCCTTTT AGAAGTCCCG    420
TTCCAGCAG GCCTCCACAG GAGCCAAGAT GGCGCCGAGC CGGGTGAGCA GCGTCTCGGC     480
TGCCGCTAGA GTTTTCCTGC TCCCCGCGCT CGGGTGGCGG GGGCGGGTCT GAGTGGTACC    540
CCGGAGGAGA CCCTTTGAAG GTCCCTTGTG GGGACTGGAA AGAGGACGGT TGGTTGTGTG    600
TCTGTGCTCG TGGGGACCCC GTGTGTGTGC CTGCATTGGA GAGATGTTGC AGGAGATGGG    660
GTGGGCTCTC TGAACCTCCT TTCGCGCTGC CCGGGGATCT TCGACCTGCT TCTCTGCTGG    720
GATCTCGCTT AAGTTAACCC TTCCCTGGGA CGCCTTCCTG CCGCCTCCAC TGATCTGAGG    780
AGATCCTGTG ACTGTAGCGT GTTTTATGAG CCTTTACTGG CAGAGGGTAC CGCCGGGTAT    840
TGAAGGATTC GTAGGAGTTC GCCAGGAAG TGGGACACGA CCCCCTCTTG TAAACCCGGC     900
GCCAGGCACA GAGGTCTCCG TCTCTCCACC GGGGGCTTCA TCCTTCCAGG GAGGAGAAGA    960
GGGACTCCAG A ATG GCT GAG GAG AAG AAG CTG AAG CTT AGC AAC ACT GTG   1010
            Met Ala Glu Glu Lys Lys Leu Lys Leu Ser Asn Thr Val
              1               5                  10
CTG CCC TCG GAG TCC ATG AAG GTG GTG GCT GAA TCC ATG GGC ATC GCC    1058
Leu Pro Ser Glu Ser Met Lys Val Val Ala Glu Ser Met Gly Ile Ala
     15              20                  25
CAG ATT CAG GAG GAG ACC TGC CAG CTG CTA ACG GAT GAG GTC AGC TAC    1106
Gln Ile Gln Glu Glu Thr Cys Gln Leu Leu Thr Asp Glu Val Ser Tyr
 30              35                  40                     45
CGC ATC AAA GAG ATC GCA CAG GAT GCC TTG AAG TTC ATG CAC ATG GGG    1154
Arg Ile Lys Glu Ile Ala Gln Asp Ala Leu Lys Phe Met His Met Gly
                 50                  55                  60
AAG CGG CAG AAG CTC ACC ACC AGT GAC ATT GAC TAC GCC TTG AAG CTA    1202
Lys Arg Gln Lys Leu Thr Thr Ser Asp Ile Asp Tyr Ala Leu Lys Leu
         65                  70                  75
AAG AAT GTC GAG CCA CTC TAT GGC TTC CAC GCC CAG GAG TTC ATT CCT    1250
Lys Asn Val Glu Pro Leu Tyr Gly Phe His Ala Gln Glu Phe Ile Pro
             80                  85                  90
TTC CGC TTC GCC TCT GGT GGG GGC CGG GAG CTT TAC TTC TAT GAG GAG    1298
Phe Arg Phe Ala Ser Gly Gly Gly Arg Glu Leu Tyr Phe Tyr Glu Glu
         95                 100                 105
AAG GAG GTT GAT CTG AGC GAC ATC ATC AAT ACC CCT CTG CCC CGG GTG    1346
Lys Glu Val Asp Leu Ser Asp Ile Ile Asn Thr Pro Leu Pro Arg Val
110             115                 120                     125
CCC CTG GAC GTC TGC CTC AAA GCT CAT TGG CTG AGC ATC GAG GGC TGC    1394
Pro Leu Asp Val Cys Leu Lys Ala His Trp Leu Ser Ile Glu Gly Cys
             130                 135                 140
CAG CCA GCT ATC CCC GAG AAC CCG CCC CCA GCT CCC AAA GAG CAA CAG    1442
Gln Pro Ala Ile Pro Glu Asn Pro Pro Pro Ala Pro Lys Glu Gln Gln
         145                 150                 155
```

-continued

| | | | | | | | | | | | | | | | |
|---|---|---|---|---|---|---|---|---|---|---|---|---|---|---|---|
| AAG | GCT | GAA | GCC | ACA | GAA | CCC | CTG | AAG | TCA | GCC | AAG | CCA | GGC | CAG | GAG | 1490
| Lys | Ala | Glu | Ala | Thr | Glu | Pro | Leu | Lys | Ser | Ala | Lys | Pro | Gly | Gln | Glu |
| | 160 | | | | | 165 | | | | 170 | | | | | |

| | | | | | | | | | | | | | | | |
|---|---|---|---|---|---|---|---|---|---|---|---|---|---|---|---|
| GAA | GAC | GGA | CCC | CTG | AAG | GGC | AAA | GGT | CAA | GGG | GCC | ACC | ACA | GCC | GAC | 1538
| Glu | Asp | Gly | Pro | Leu | Lys | Gly | Lys | Gly | Gln | Gly | Ala | Thr | Thr | Ala | Asp |
| | 175 | | | | | 180 | | | | | 185 | | | | |

| | | | | | | | | | | | | | | | |
|---|---|---|---|---|---|---|---|---|---|---|---|---|---|---|---|
| GGC | AAA | GGG | AAA | GAG | AAG | AAG | GCG | CCG | CCC | TTG | CTG | GAG | GGG | GCC | CCC | 1586
| Gly | Lys | Gly | Lys | Glu | Lys | Lys | Ala | Pro | Pro | Leu | Leu | Glu | Gly | Ala | Pro |
| 190 | | | | | 195 | | | | | 200 | | | | | 205 |

| | | | | | | | | | | | | | | | |
|---|---|---|---|---|---|---|---|---|---|---|---|---|---|---|---|
| TTG | CGA | CTG | AAG | CCC | CGG | AGC | ATC | CAC | GAG | TTG | TCT | GTG | GAG | CAG | CAG | 1634
| Leu | Arg | Leu | Lys | Pro | Arg | Ser | Ile | His | Glu | Leu | Ser | Val | Glu | Gln | Gln |
| | | | | 210 | | | | | 215 | | | | | 220 | |

| | | | | | | | | | | | | | | | |
|---|---|---|---|---|---|---|---|---|---|---|---|---|---|---|---|
| CTC | TAC | TAC | AAG | GAG | ATC | ACC | GAG | GCC | TGC | GTG | GGC | TCC | TGC | GAG | GCC | 1682
| Leu | Tyr | Tyr | Lys | Glu | Ile | Thr | Glu | Ala | Cys | Val | Gly | Ser | Cys | Glu | Ala |
| | | | 225 | | | | | 230 | | | | | 235 | | |

| | | | | | | | | | | | | | | | |
|---|---|---|---|---|---|---|---|---|---|---|---|---|---|---|---|
| AAG | AGG | GCG | GAA | GCC | CTG | CAA | AGC | ATT | GCC | ACG | GAC | CCT | GGA | CTG | TAT | 1730
| Lys | Arg | Ala | Glu | Ala | Leu | Gln | Ser | Ile | Ala | Thr | Asp | Pro | Gly | Leu | Tyr |
| | | 240 | | | | | 245 | | | | | 250 | | | |

| | | | | | | | | | | | | | | | |
|---|---|---|---|---|---|---|---|---|---|---|---|---|---|---|---|
| CAG | ATG | CTG | CCA | CGG | TTC | AGT | ACC | TTT | ATC | TCG | GAG | GGG | GTC | CGT | GTG | 1778
| Gln | Met | Leu | Pro | Arg | Phe | Ser | Thr | Phe | Ile | Ser | Glu | Gly | Val | Arg | Val |
| 255 | | | | | | 260 | | | | | 265 | | | | |

| | | | | | | | | | | | | | | | |
|---|---|---|---|---|---|---|---|---|---|---|---|---|---|---|---|
| AAC | GTG | GTT | CAG | AAC | AAC | CTG | GCC | CTA | CTC | ATC | TAC | CTG | ATG | CGT | ATG | 1826
| Asn | Val | Val | Gln | Asn | Asn | Leu | Ala | Leu | Leu | Ile | Tyr | Leu | Met | Arg | Met |
| 270 | | | | | 275 | | | | | 280 | | | | | 285 |

| | | | | | | | | | | | | | | | |
|---|---|---|---|---|---|---|---|---|---|---|---|---|---|---|---|
| GTG | AAA | GCG | CTG | ATG | GAC | AAC | CCC | ACG | CTC | TAT | CTA | GAA | AAA | TAC | GTC | 1874
| Val | Lys | Ala | Leu | Met | Asp | Asn | Pro | Thr | Leu | Tyr | Leu | Glu | Lys | Tyr | Val |
| | | | | 290 | | | | | 295 | | | | | 300 | |

| | | | | | | | | | | | | | | | |
|---|---|---|---|---|---|---|---|---|---|---|---|---|---|---|---|
| CAT | GAG | CTG | ATT | CCA | GCT | GTG | ATG | ACC | TGC | ATC | GTG | AGC | AGA | CAG | TTG | 1922
| His | Glu | Leu | Ile | Pro | Ala | Val | Met | Thr | Cys | Ile | Val | Ser | Arg | Gln | Leu |
| | | | | 305 | | | | | 310 | | | | | 315 | |

| | | | | | | | | | | | | | | | |
|---|---|---|---|---|---|---|---|---|---|---|---|---|---|---|---|
| TGC | CTG | CGA | CCA | GAT | GTG | GAC | AAT | CAC | TGG | GCA | CTC | CGA | GAC | TTT | GCT | 1970
| Cys | Leu | Arg | Pro | Asp | Val | Asp | Asn | His | Trp | Ala | Leu | Arg | Asp | Phe | Ala |
| | | 320 | | | | | 325 | | | | | 330 | | | |

| | | | | | | | | | | | | | | | |
|---|---|---|---|---|---|---|---|---|---|---|---|---|---|---|---|
| GCC | CGC | CTG | GTG | GCC | CAG | ATC | TGC | AAG | CAT | TTT | AGC | ACA | ACC | ACT | AAC | 2018
| Ala | Arg | Leu | Val | Ala | Gln | Ile | Cys | Lys | His | Phe | Ser | Thr | Thr | Thr | Asn |
| | 335 | | | | | 340 | | | | | 345 | | | | |

| | | | | | | | | | | | | | | | |
|---|---|---|---|---|---|---|---|---|---|---|---|---|---|---|---|
| AAC | ATC | CAG | TCC | CGG | ATC | ACC | AAG | ACC | TTC | ACC | AAG | AGC | TGG | GTG | GAC | 2066
| Asn | Ile | Gln | Ser | Arg | Ile | Thr | Lys | Thr | Phe | Thr | Lys | Ser | Trp | Val | Asp |
| 350 | | | | | 355 | | | | | 360 | | | | | 365 |

| | | | | | | | | | | | | | | | |
|---|---|---|---|---|---|---|---|---|---|---|---|---|---|---|---|
| GAG | AAG | ACG | CCC | TGG | ACG | ACT | CGT | TAT | GGC | TCC | ATC | GCA | GGC | TTG | GCT | 2114
| Glu | Lys | Thr | Pro | Trp | Thr | Thr | Arg | Tyr | Gly | Ser | Ile | Ala | Gly | Leu | Ala |
| | | | | 370 | | | | | 375 | | | | | 380 | |

| | | | | | | | | | | | | | | | |
|---|---|---|---|---|---|---|---|---|---|---|---|---|---|---|---|
| GAG | CTG | GGA | CAC | GAT | GTT | ATC | AAG | ACT | CTG | ATT | CTG | CCC | CGG | CTG | CAG | 2162
| Glu | Leu | Gly | His | Asp | Val | Ile | Lys | Thr | Leu | Ile | Leu | Pro | Arg | Leu | Gln |
| | | | 385 | | | | | 390 | | | | | 395 | | |

| | | | | | | | | | | | | | | | |
|---|---|---|---|---|---|---|---|---|---|---|---|---|---|---|---|
| CAG | GAA | GGG | GAG | CGG | ATC | CGC | AGT | GTG | CTG | GAC | GGC | CCT | GTG | CTG | AGC | 2210
| Gln | Glu | Gly | Glu | Arg | Ile | Arg | Ser | Val | Leu | Asp | Gly | Pro | Val | Leu | Ser |
| | | 400 | | | | | 405 | | | | | 410 | | | |

| | | | | | | | | | | | | | | | |
|---|---|---|---|---|---|---|---|---|---|---|---|---|---|---|---|
| AAC | ATT | GAC | CGG | ATT | GGA | GCA | GAC | CAT | GTG | CAG | AGC | CTC | CTG | CTG | AAA | 2258
| Asn | Ile | Asp | Arg | Ile | Gly | Ala | Asp | His | Val | Gln | Ser | Leu | Leu | Leu | Lys |
| | 415 | | | | | 420 | | | | | 425 | | | | |

| | | | | | | | | | | | | | | | |
|---|---|---|---|---|---|---|---|---|---|---|---|---|---|---|---|
| CAC | TGT | GCT | CCT | GTT | CTG | GCA | AAG | CTG | CGC | CCA | CCG | CCT | GAC | AAT | CAG | 2306
| His | Cys | Ala | Pro | Val | Leu | Ala | Lys | Leu | Arg | Pro | Pro | Pro | Asp | Asn | Gln |
| 430 | | | | | 435 | | | | | 440 | | | | | 445 |

| | | | | | | | | | | | | | | | |
|---|---|---|---|---|---|---|---|---|---|---|---|---|---|---|---|
| GAC | GCC | TAT | CGG | GCA | GAA | TTC | GGG | TCC | CTT | GGG | CCC | CTC | CTC | TGC | TCC | 2354
| Asp | Ala | Tyr | Arg | Ala | Glu | Phe | Gly | Ser | Leu | Gly | Pro | Leu | Leu | Cys | Ser |
| | | | 450 | | | | | 455 | | | | | 460 | | |

| | | | | | | | | | | | | | | | |
|---|---|---|---|---|---|---|---|---|---|---|---|---|---|---|---|
| CAG | GTG | GTC | AAG | GCT | CGG | GCC | CAG | GCT | GCT | CTG | CAG | GCT | CAG | CAG | GTC | 2402
| Gln | Val | Val | Lys | Ala | Arg | Ala | Gln | Ala | Ala | Leu | Gln | Ala | Gln | Gln | Val |
| | | | 465 | | | | | 470 | | | | | 475 | | |

| | | | | | | | | | | | | | | | |
|---|---|---|---|---|---|---|---|---|---|---|---|---|---|---|---|
| AAC | AGG | ACC | ACT | CTG | ACC | ATC | ACG | CAG | CCC | CGG | CCC | ACG | CTG | ACC | CTC | 2450 |
| Asn | Arg | Thr 480 | Thr | Leu | Thr | Ile | Thr 485 | Gln | Pro | Arg | Pro | Thr 490 | Leu | Thr | Leu | |
| TCG | CAG | GCC | CCA | CAG | CCT | GGC | CCT | CGC | ACC | CCT | GGC | TTG | CTG | AAG | GTT | 2498 |
| Ser | Gln 495 | Ala | Pro | Gln | Pro | Gly 500 | Pro | Arg | Thr | Pro | Gly 505 | Leu | Leu | Lys | Val | |
| CCT | GGC | TCC | ATC | GCA | CTT | CCT | GTC | CAG | ACA | CTG | GTG | TCT | GCA | CGA | GCG | 2546 |
| Pro 510 | Gly | Ser | Ile | Ala | Leu 515 | Pro | Val | Gln | Thr | Leu 520 | Val | Ser | Ala | Arg | Ala 525 | |
| GCT | GCC | CCA | CCA | CAG | CCT | TCC | CCT | CCT | CCA | ACC | AAG | TTT | ATT | GTA | ATG | 2594 |
| Ala | Ala | Pro | Pro | Gln 530 | Pro | Ser | Pro | Pro | Pro 535 | Thr | Lys | Phe | Ile | Val 540 | Met | |
| TCA | TCG | TCC | TCC | AGC | GCC | CCA | TCC | ACC | CAG | CAG | GTC | CTG | TCC | CTC | AGC | 2642 |
| Ser | Ser | Ser | Ser 545 | Ser | Ala | Pro | Ser | Thr 550 | Gln | Gln | Val | Leu | Ser 555 | Leu | Ser | |
| ACC | TCG | GCC | CCC | GGC | TCA | GGT | TCC | ACC | ACC | ACT | TCG | CCC | GTC | ACC | ACC | 2690 |
| Thr | Ser | Ala 560 | Pro | Gly | Ser | Gly | Ser 565 | Thr | Thr | Thr | Ser | Pro 570 | Val | Thr | Thr | |
| ACC | GTC | CCC | AGC | GTG | CAG | CCC | ATC | GTC | AAG | TTG | GTC | TCC | ACC | GCC | ACC | 2738 |
| Thr | Val 575 | Pro | Ser | Val | Gln | Pro 580 | Ile | Val | Lys | Leu | Val 585 | Ser | Thr | Ala | Thr | |
| ACC | GCA | CCC | CCC | AGC | ACT | GCT | CCC | TCT | GGT | CCT | GGG | AGT | GTC | CAG | AAG | 2786 |
| Thr 590 | Ala | Pro | Pro | Ser | Thr 595 | Ala | Pro | Ser | Gly | Pro 600 | Gly | Ser | Val | Gln | Lys 605 | |
| TAC | ATC | GTG | GTC | TCA | CTT | CCC | CCA | ACA | GGG | GAG | GGC | AAA | GGA | GGC | CCC | 2834 |
| Tyr | Ile | Val | Val | Ser 610 | Leu | Pro | Pro | Thr | Gly 615 | Glu | Gly | Lys | Gly | Gly 620 | Pro | |
| ACC | TCC | CAT | CCT | TCT | CCA | GTT | CCT | CCC | CCG | GCA | TCG | TCC | CCG | TCC | CCA | 2882 |
| Thr | Ser | His | Pro 625 | Ser | Pro | Val | Pro | Pro 630 | Pro | Ala | Ser | Ser | Pro 635 | Ser | Pro | |
| CTC | AGC | GGC | AGT | GCC | CTT | TGT | GGG | GGG | AAG | CAG | GAG | GCT | GGG | GAC | AGT | 2930 |
| Leu | Ser | Gly 640 | Ser | Ala | Leu | Cys | Gly 645 | Gly | Lys | Gln | Glu | Ala 650 | Gly | Asp | Ser | |
| CCC | CCT | CCA | GCT | CCA | GGG | ACT | CCA | AAA | GCC | AAT | GGC | TCC | CAG | CCC | AAC | 2978 |
| Pro | Pro 655 | Pro | Ala | Pro | Gly | Thr 660 | Pro | Lys | Ala | Asn | Gly 665 | Ser | Gln | Pro | Asn | |
| TCC | GGC | TCC | CCT | CAG | CCT | GCT | CCG | TGATGCTCCA | | | CCTGCCAGCC | | | CCCGGATTCC | | 3032 |
| Ser 670 | Gly | Ser | Pro | Gln | Pro 675 | Ala | Pro | | | | | | | | | |
| CACACATGCA | | | GACATGTACA | | | CACGTGCACG | | | TACACACATG | | | CATGCTCGCT | | AAGCGGAAGG | 3092 |
| AAGTTGTAGA | | | TTGCTTCCTT | | | CATGTCACTT | | | TCTTTTTAGA | | | TATTGTACAG | | CCAGTTTCTC | 3152 |
| AGAATAAAAG | | | TTTGGTTTGT | | | AAAAAAAAAA | | | | | | | | | 3182 |

( 2 ) INFORMATION FOR SEQ ID NO:13:

( i ) SEQUENCE CHARACTERISTICS:
        ( A ) LENGTH: 677 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| | | | | | | | | | | | | | | | |
|---|---|---|---|---|---|---|---|---|---|---|---|---|---|---|---|
| Met 1 | Ala | Glu | Glu | Lys 5 | Lys | Leu | Lys | Leu | Ser 10 | Asn | Thr | Val | Leu | Pro 15 | Ser |
| Glu | Ser | Met | Lys 20 | Val | Val | Ala | Glu | Ser 25 | Met | Gly | Ile | Ala | Gln 30 | Ile | Gln |
| Glu | Glu | Thr 35 | Cys | Gln | Leu | Leu | Thr 40 | Asp | Glu | Val | Ser | Tyr 45 | Arg | Ile | Lys |

```
Glu  Ile  Ala  Gln  Asp  Ala  Leu  Lys  Phe  Met  His  Met  Gly  Lys  Arg  Gln
      50                  55                  60

Lys  Leu  Thr  Thr  Ser  Asp  Ile  Asp  Tyr  Ala  Leu  Lys  Leu  Lys  Asn  Val
 65                  70                  75                                  80

Glu  Pro  Leu  Tyr  Gly  Phe  His  Ala  Gln  Glu  Phe  Ile  Pro  Phe  Arg  Phe
                85                  90                            95

Ala  Ser  Gly  Gly  Gly  Arg  Glu  Leu  Tyr  Phe  Tyr  Glu  Glu  Lys  Glu  Val
           100                 105                      110

Asp  Leu  Ser  Asp  Ile  Ile  Asn  Thr  Pro  Leu  Pro  Arg  Val  Pro  Leu  Asp
           115                 120                 125

Val  Cys  Leu  Lys  Ala  His  Trp  Leu  Ser  Ile  Glu  Gly  Cys  Gln  Pro  Ala
     130                 135                 140

Ile  Pro  Glu  Asn  Pro  Pro  Ala  Pro  Lys  Glu  Gln  Gln  Lys  Ala  Glu
145                      150                 155                      160

Ala  Thr  Glu  Pro  Leu  Lys  Ser  Ala  Lys  Pro  Gln  Glu  Glu  Asp  Gly
                     165                 170                      175

Pro  Leu  Lys  Gly  Lys  Gly  Gln  Gly  Ala  Thr  Thr  Ala  Asp  Gly  Lys  Gly
                180                      185                      190

Lys  Glu  Lys  Lys  Ala  Pro  Pro  Leu  Leu  Glu  Gly  Ala  Pro  Leu  Arg  Leu
           195                      200                 205

Lys  Pro  Arg  Ser  Ile  His  Glu  Leu  Ser  Val  Glu  Gln  Gln  Leu  Tyr  Tyr
     210                      215                 220

Lys  Glu  Ile  Thr  Glu  Ala  Cys  Val  Gly  Ser  Cys  Glu  Ala  Lys  Arg  Ala
225                      230                 235                      240

Glu  Ala  Leu  Gln  Ser  Ile  Ala  Thr  Asp  Pro  Gly  Leu  Tyr  Gln  Met  Leu
                245                      250                      255

Pro  Arg  Phe  Ser  Thr  Phe  Ile  Ser  Glu  Gly  Val  Arg  Val  Asn  Val  Val
           260                      265                      270

Gln  Asn  Asn  Leu  Ala  Leu  Leu  Ile  Tyr  Leu  Met  Arg  Met  Val  Lys  Ala
           275                      280                 285

Leu  Met  Asp  Asn  Pro  Thr  Leu  Tyr  Leu  Glu  Lys  Tyr  Val  His  Glu  Leu
     290                      295                 300

Ile  Pro  Ala  Val  Met  Thr  Cys  Ile  Val  Ser  Arg  Gln  Leu  Cys  Leu  Arg
305                      310                 315                      320

Pro  Asp  Val  Asp  Asn  His  Trp  Ala  Leu  Arg  Asp  Phe  Ala  Ala  Arg  Leu
                     325                 330                      335

Val  Ala  Gln  Ile  Cys  Lys  His  Phe  Ser  Thr  Thr  Thr  Asn  Asn  Ile  Gln
                340                 345                      350

Ser  Arg  Ile  Thr  Lys  Thr  Phe  Thr  Lys  Ser  Trp  Val  Asp  Glu  Lys  Thr
           355                 360                      365

Pro  Trp  Thr  Thr  Arg  Tyr  Gly  Ser  Ile  Ala  Gly  Leu  Ala  Glu  Leu  Gly
     370                      375                 380

His  Asp  Val  Ile  Lys  Thr  Leu  Ile  Leu  Pro  Arg  Leu  Gln  Gln  Glu  Gly
385                      390                      395                      400

Glu  Arg  Ile  Arg  Ser  Val  Leu  Asp  Gly  Pro  Val  Leu  Ser  Asn  Ile  Asp
                405                      410                      415

Arg  Ile  Gly  Ala  Asp  His  Val  Gln  Ser  Leu  Leu  Leu  Lys  His  Cys  Ala
                420                      425                 430

Pro  Val  Leu  Ala  Lys  Leu  Arg  Pro  Pro  Asp  Asn  Gln  Asp  Ala  Tyr
                435                      440                 445

Arg  Ala  Glu  Phe  Gly  Ser  Leu  Gly  Pro  Leu  Leu  Cys  Ser  Gln  Val  Val
     450                      455                 460

Lys  Ala  Arg  Ala  Gln  Ala  Ala  Leu  Gln  Ala  Gln  Gln  Val  Asn  Arg  Thr
465                      470                 475                      480
```

| | | | | | | | | | | | | | | |
|---|---|---|---|---|---|---|---|---|---|---|---|---|---|---|
|Thr|Leu|Thr|Ile|Thr<br>485|Gln|Pro|Arg|Pro|Thr<br>490|Leu|Thr|Leu|Ser|Gln<br>495|Ala|
|Pro|Gln|Pro|Gly<br>500|Pro|Arg|Thr|Pro|Gly<br>505|Leu|Leu|Lys|Val|Pro<br>510|Gly|Ser|
|Ile|Ala|Leu<br>515|Pro|Val|Gln|Thr|Leu<br>520|Val|Ser|Ala|Arg|Ala<br>525|Ala|Ala|Pro|
|Pro|Gln<br>530|Pro|Ser|Pro|Pro|Pro<br>535|Thr|Lys|Phe|Ile|Val<br>540|Met|Ser|Ser|Ser|
|Ser<br>545|Ser|Ala|Pro|Ser|Thr<br>550|Gln|Gln|Val|Leu|Ser<br>555|Leu|Ser|Thr|Ser|Ala<br>560|
|Pro|Gly|Ser|Gly|Ser<br>565|Thr|Thr|Thr|Ser|Pro<br>570|Val|Thr|Thr|Thr|Val<br>575|Pro|
|Ser|Val|Gln|Pro<br>580|Ile|Val|Lys|Leu|Val<br>585|Ser|Thr|Ala|Thr|Thr<br>590|Ala|Pro|
|Pro|Ser|Thr<br>595|Ala|Pro|Ser|Gly|Pro<br>600|Gly|Ser|Val|Gln|Lys<br>605|Tyr|Ile|Val|
|Val|Ser<br>610|Leu|Pro|Pro|Thr|Gly<br>615|Glu|Gly|Lys|Gly|Pro<br>620|Thr|Ser|His|
|Pro<br>625|Ser|Pro|Val|Pro|Pro<br>630|Pro|Ala|Ser|Ser|Pro<br>635|Ser|Pro|Leu|Ser|Gly<br>640|
|Ser|Ala|Leu|Cys|Gly<br>645|Gly|Lys|Gln|Glu|Ala<br>650|Gly|Asp|Ser|Pro|Pro<br>655|Pro|
|Ala|Pro|Gly|Thr<br>660|Pro|Lys|Ala|Asn|Gly<br>665|Ser|Gln|Pro|Asn|Ser<br>670|Gly|Ser|
|Pro|Gln|Pro|Ala<br>675|Pro| | | | | | | | | | | |

( 2 ) INFORMATION FOR SEQ ID NO:14:

( i ) SEQUENCE CHARACTERISTICS:
        ( A ) LENGTH: 1872 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

| | | | | | | | | | | | | | | |
|---|---|---|---|---|---|---|---|---|---|---|---|---|---|---|
|Met<br>1|Gly|Pro|Gly|Cys<br>5|Asp|Leu|Leu|Leu|Arg<br>10|Thr|Ala|Ala|Thr|Ile<br>15|Thr|
|Ala|Ala|Ala|Ile<br>20|Met|Ser|Asp|Thr|Asp<br>25|Ser|Asp|Glu|Asp|Ser<br>30|Ala|Gly|
|Gly|Gly|Pro<br>35|Phe|Ser|Leu|Ala|Gly<br>40|Phe|Leu|Phe|Gly|Asn<br>45|Ile|Asn|Gly|
|Ala|Gly<br>50|Gln|Leu|Glu|Gly|Glu<br>55|Ser|Val|Leu|Asp|Asp<br>60|Glu|Cys|Lys|Lys|
|His<br>65|Leu|Ala|Gly|Leu|Gly<br>70|Ala|Leu|Gly|Leu|Gly<br>75|Ser|Leu|Ile|Thr|Glu<br>80|
|Leu|Thr|Ala|Asn|Glu<br>85|Glu|Leu|Thr|Gly|Thr<br>90|Asp|Gly|Ala|Leu|Val<br>95|Asn|
|Asp|Glu|Gly|Trp<br>100|Val|Arg|Ser|Thr|Glu<br>105|Asp|Ala|Val|Asp|Tyr<br>110|Ser|Asp|
|Ile|Asn|Glu<br>115|Val|Ala|Glu|Asp|Glu<br>120|Ser|Arg|Arg|Tyr|Gln<br>125|Gln|Thr|Met|
|Gly|Ser<br>130|Leu|Gln|Pro|Leu|Cys<br>135|His|Ser|Asp|Tyr|Asp<br>140|Glu|Asp|Asp|Tyr|

```
Asp Ala Asp Cys Glu Asp Ile Asp Cys Lys Leu Met Pro Pro Pro
145                 150                 155                 160
Pro Pro Pro Gly Pro Met Lys Lys Asp Lys Asp Gln Asp Ser Ile Thr
                165                 170                 175
Gly Glu Lys Val Asp Phe Ser Ser Ser Asp Ser Glu Ser Glu Met
                180                 185                 190
Gly Pro Gln Glu Ala Thr Gln Ala Glu Ser Glu Asp Gly Lys Leu Thr
            195                 200                 205
Leu Pro Leu Ala Gly Ile Met Gln His Asp Ala Thr Lys Leu Leu Pro
        210                 215                 220
Ser Val Thr Glu Leu Phe Pro Glu Phe Arg Pro Gly Lys Val Leu Arg
225                 230                 235                 240
Phe Leu Arg Leu Phe Gly Pro Gly Lys Asn Val Pro Ser Val Trp Arg
                245                 250                 255
Ser Ala Arg Arg Lys Arg Lys Lys Lys His Arg Glu Leu Ile Gln Glu
            260                 265                 270
Glu Gln Ile Gln Glu Val Glu Cys Ser Val Glu Ser Glu Val Ser Gln
        275                 280                 285
Lys Ser Leu Trp Asn Tyr Asp Tyr Ala Pro Pro Pro Pro Pro Glu Gln
    290                 295                 300
Cys Leu Ser Asp Asp Glu Ile Thr Met Met Ala Pro Val Glu Ser Lys
305                 310                 315                 320
Phe Ser Gln Ser Thr Gly Asp Ile Asp Lys Val Thr Asp Thr Lys Pro
                325                 330                 335
Arg Val Ala Glu Trp Arg Tyr Gly Pro Ala Arg Leu Trp Tyr Asp Met
            340                 345                 350
Leu Gly Val Pro Glu Asp Gly Ser Gly Phe Asp Tyr Gly Phe Lys Leu
        355                 360                 365
Arg Lys Thr Glu His Glu Pro Val Ile Lys Ser Arg Met Ile Glu Glu
370                 375                 380
Phe Arg Lys Leu Glu Glu Asn Asn Gly Thr Asp Leu Leu Ala Asp Glu
385                 390                 395                 400
Asn Phe Leu Met Val Thr Gln Leu His Trp Glu Asp Asp Ile Ile Trp
                405                 410                 415
Asp Gly Glu Asp Val Lys His Lys Gly Thr Lys Pro Gln Arg Ala Ser
            420                 425                 430
Leu Ala Gly Trp Leu Pro Ser Ser Met Thr Arg Asn Ala Met Ala Tyr
        435                 440                 445
Asn Val Gln Gln Gly Phe Ala Ala Thr Leu Asp Asp Lys Pro Trp
450                 455                 460
Tyr Ser Ile Phe Pro Ile Asp Asn Glu Asp Leu Val Tyr Gly Arg Trp
465                 470                 475                 480
Glu Asp Asn Ile Ile Trp Asp Ala Gln Ala Met Pro Arg Leu Leu Glu
                485                 490                 495
Pro Pro Val Leu Thr Leu Asp Pro Asn Asp Glu Asn Leu Ile Leu Glu
            500                 505                 510
Ile Pro Asp Glu Lys Glu Glu Ala Thr Ser Asn Ser Pro Ser Lys Glu
        515                 520                 525
Ser Lys Lys Glu Ser Ser Leu Lys Lys Ser Arg Ile Leu Leu Gly Lys
    530                 535                 540
Thr Gly Val Ile Lys Glu Glu Pro Gln Gln Asn Met Ser Gln Pro Glu
545                 550                 555                 560
Val Lys Asp Pro Trp Asn Leu Ser Asn Asp Glu Tyr Tyr Tyr Pro Lys
                565                 570                 575
```

| Gln | Gln | Gly | Leu | Arg | Gly | Thr | Phe | Gly | Gly | Asn | Ile | Ile | Gln | His | Ser |
|---|---|---|---|---|---|---|---|---|---|---|---|---|---|---|---|
| | | | 580 | | | | 585 | | | | | | 590 | | |
| Ile | Pro | Ala | Val | Glu | Leu | Arg | Gln | Pro | Phe | Phe | Pro | Thr | His | Met | Gly |
| | | 595 | | | | 600 | | | | | 605 | | | | |
| Pro | Ile | Lys | Leu | Arg | Gln | Phe | His | Arg | Pro | Pro | Leu | Lys | Lys | Tyr | Ser |
| | 610 | | | | | 615 | | | | | 620 | | | | |
| Phe | Gly | Ala | Leu | Ser | Gln | Pro | Gly | Pro | His | Ser | Val | Gln | Pro | Leu | Leu |
| 625 | | | | | 630 | | | | 635 | | | | | | 640 |
| Lys | His | Ile | Lys | Lys | Ala | Lys | Met | Arg | Glu | Gln | Glu | Arg | Gln | Ala | |
| | | | | 645 | | | | 650 | | | | | 655 | | |
| Ser | Gly | Gly | Gly | Glu | Met | Phe | Phe | Met | Arg | Thr | Pro | Gln | Asp | Leu | Thr |
| | | | 660 | | | | | 665 | | | | | 670 | | |
| Gly | Lys | Asp | Gly | Asp | Leu | Ile | Leu | Ala | Glu | Tyr | Ser | Glu | Glu | Asn | Gly |
| | | 675 | | | | 680 | | | | | | 685 | | | |
| Pro | Leu | Met | Met | Gln | Val | Gly | Met | Ala | Thr | Lys | Ile | Lys | Asn | Tyr | Tyr |
| | 690 | | | | | 695 | | | | | 700 | | | | |
| Lys | Arg | Lys | Pro | Gly | Lys | Asp | Pro | Gly | Ala | Pro | Asp | Cys | Lys | Tyr | Gly |
| 705 | | | | | 710 | | | | 715 | | | | | | 720 |
| Glu | Thr | Val | Tyr | Cys | His | Thr | Ser | Pro | Phe | Leu | Gly | Ser | Leu | His | Pro |
| | | | | 725 | | | | | 730 | | | | | 735 | |
| Gly | Gln | Leu | Leu | Gln | Ala | Phe | Glu | Asn | Asn | Leu | Phe | Arg | Ala | Pro | Ile |
| | | | 740 | | | | | 745 | | | | | 750 | | |
| Tyr | Leu | His | Lys | Met | Pro | Glu | Thr | Asp | Phe | Leu | Ile | Ile | Arg | Thr | Arg |
| | | 755 | | | | | 760 | | | | | 765 | | | |
| Gln | Gly | Tyr | Tyr | Ile | Arg | Glu | Leu | Val | Asp | Ile | Phe | Val | Val | Gly | Gln |
| | 770 | | | | | 775 | | | | | 780 | | | | |
| Gln | Cys | Pro | Leu | Phe | Glu | Val | Pro | Gly | Pro | Asn | Ser | Lys | Arg | Ala | Asn |
| 785 | | | | | 790 | | | | | 795 | | | | | 800 |
| Thr | His | Ile | Arg | Asp | Phe | Leu | Gln | Val | Phe | Ile | Tyr | Arg | Leu | Phe | Trp |
| | | | | 805 | | | | | 810 | | | | | 815 | |
| Lys | Ser | Lys | Asp | Arg | Pro | Arg | Arg | Ile | Arg | Met | Glu | Asp | Ile | Lys | Lys |
| | | | 820 | | | | | 825 | | | | | 830 | | |
| Ala | Phe | Pro | Ser | His | Ser | Glu | Ser | Ser | Ile | Arg | Lys | Arg | Leu | Lys | Leu |
| | | | 835 | | | | | 840 | | | | | 845 | | |
| Cys | Ala | Asp | Phe | Lys | Arg | Thr | Gly | Met | Asp | Ser | Asn | Trp | Trp | Val | Leu |
| | 850 | | | | | 855 | | | | | 860 | | | | |
| Lys | Ser | Asp | Phe | Arg | Leu | Pro | Thr | Glu | Glu | Ile | Arg | Ala | Met | Val | |
| 865 | | | | | 870 | | | | 875 | | | | | 880 | |
| Ser | Pro | Glu | Gln | Cys | Cys | Ala | Tyr | Tyr | Ser | Met | Ile | Ala | Ala | Glu | Gln |
| | | | | 885 | | | | | 890 | | | | | 895 | |
| Arg | Leu | Lys | Asp | Ala | Gly | Tyr | Gly | Glu | Lys | Ser | Phe | Phe | Ala | Pro | Glu |
| | | | 900 | | | | | 905 | | | | | 910 | | |
| Glu | Glu | Asn | Glu | Glu | Asp | Phe | Gln | Met | Lys | Ile | Asp | Asp | Glu | Val | Arg |
| | | | 915 | | | | 920 | | | | | 925 | | | |
| Thr | Ala | Pro | Trp | Asn | Thr | Thr | Arg | Ala | Phe | Ile | Ala | Ala | Met | Lys | Gly |
| | | | 930 | | | | 935 | | | | | 940 | | | |
| Lys | Cys | Leu | Leu | Glu | Val | Thr | Gly | Val | Ala | Asp | Pro | Thr | Gly | Cys | Gly |
| 945 | | | | | 950 | | | | | 955 | | | | | 960 |
| Glu | Gly | Phe | Ser | Tyr | Val | Lys | Ile | Pro | Asn | Lys | Pro | Thr | Gln | Gln | Lys |
| | | | | 965 | | | | | 970 | | | | | 975 | |
| Asp | Asp | Lys | Glu | Pro | Gln | Pro | Val | Lys | Lys | Thr | Val | Thr | Gly | Thr | Asp |
| | | | 980 | | | | | 985 | | | | | 990 | | |
| Ala | Asp | Leu | Arg | Arg | Leu | Ser | Leu | Lys | Asn | Ala | Lys | Gln | Leu | Leu | Arg |

|  |  |  |
|---|---|---|
| 995 | 1000 | 1005 |

Lys Phe Gly Val Pro Glu Glu Ile Lys Lys Leu Ser Arg Trp Glu
1010                     1015                    1020

Val Ile Asp Val Val Arg Thr Met Ser Thr Glu Gln Ala Arg Ser Gly
1025                    1030                    1035                    1040

Glu Gly Pro Met Ser Lys Phe Ala Arg Gly Ser Arg Phe Ser Val Ala
                    1045                    1050                    1055

Glu His Gln Glu Arg Tyr Lys Glu Cys Gln Arg Ile Phe Asp Leu
                1060                    1065                    1070

Gln Asn Lys Val Leu Ser Ser Thr Glu Val Leu Ser Thr Asp Thr Asp
1075                    1080                    1085

Ser Ser Ser Ala Glu Asp Ser Asp Phe Glu Glu Met Gly Lys Asn Ile
1090                    1095                    1100

Glu Asn Met Leu Gln Asn Lys Lys Thr Ser Ser Gln Leu Ser Arg Glu
1105                    1110                    1115                    1120

Arg Glu Glu Gln Glu Arg Lys Glu Leu Gln Arg Met Leu Leu Ala Ala
                    1125                    1130                    1135

Gly Ser Ala Ala Ser Gly Asn Asn His Arg Asp Asp Asp Thr Ala Ser
                1140                    1145                    1150

Val Thr Ser Leu Asn Ser Ser Ala Thr Gly Arg Cys Leu Lys Ile Tyr
                1155                    1160                    1165

Arg Thr Phe Arg Asp Glu Glu Gly Lys Glu Tyr Val Arg Cys Glu Thr
1170                    1175                    1180

Val Arg Lys Pro Ala Val Ile Asp Ala Tyr Val Arg Ile Arg Thr Thr
1185                    1190                    1195                    1200

Lys Asp Glu Glu Phe Ile Arg Lys Phe Ala Leu Phe Asp Glu Gln His
                    1205                    1210                    1215

Arg Glu Glu Met Arg Lys Glu Arg Arg Ile Gln Glu Gln Leu Arg
                1220                    1225                    1230

Arg Leu Lys Arg Asn Gln Glu Lys Glu Lys Leu Lys Gly Pro Pro Glu
                1235                    1240                    1245

Lys Lys Pro Lys Lys Met Lys Glu Arg Pro Asp Leu Lys Leu Lys Cys
1250                    1255                    1260

Gly Ala Cys Gly Ala Ile Gly His Met Arg Thr Asn Lys Phe Cys Pro
1265                    1270                    1275                    1280

Leu Tyr Tyr Gln Thr Asn Ala Pro Pro Ser Asn Pro Val Ala Met Thr
                    1285                    1290                    1295

Glu Glu Gln Glu Glu Glu Leu Glu Lys Thr Val Ile His Asn Asp Asn
                1300                    1305                    1310

Glu Glu Leu Ile Lys Val Glu Gly Thr Lys Ile Val Leu Gly Lys Gln
                1315                    1320                    1325

Leu Ile Glu Ser Ala Asp Glu Val Arg Arg Lys Ser Leu Val Leu Lys
1330                    1335                    1340

Phe Pro Lys Gln Gln Leu Pro Pro Lys Lys Lys Arg Arg Val Gly Thr
1345                    1350                    1355                    1360

Thr Val His Cys Asp Tyr Leu Asn Arg Pro His Lys Ser Ile His Arg
                    1365                    1370                    1375

Arg Arg Thr Asp Pro Met Val Thr Leu Ser Ser Ile Leu Glu Ser Ile
                1380                    1385                    1390

Ile Asn Asp Met Arg Asp Leu Pro Asn Thr Tyr Pro Phe His Thr Pro
                1395                    1400                    1405

Val Asn Ala Lys Val Val Lys Asp Tyr Tyr Lys Ile Ile Thr Arg Pro
1410                    1415                    1420

```
Met Asp Leu Gln Thr Leu Arg Glu Asn Val Arg Lys Arg Leu Tyr Pro
1425                1430                1435                1440

Ser Arg Glu Glu Phe Arg Glu His Leu Glu Leu Ile Val Lys Asn Ser
                1445                1450                1455

Ala Thr Tyr Asn Gly Pro Lys His Ser Leu Thr Gln Ile Ser Gln Ser
                1460                1465                1470

Met Leu Asp Leu Cys Asp Glu Lys Leu Lys Glu Lys Glu Asp Lys Leu
        1475                1480                1485

Ala Arg Leu Glu Lys Ala Ile Asn Pro Leu Leu Asp Asp Asp Asp Gln
        1490                1495                1500

Val Ala Phe Ser Phe Ile Leu Asp Asn Ile Val Thr Gln Lys Met Met
1505                1510                1515                1520

Ala Val Pro Asp Ser Trp Pro Phe His His Pro Val Asn Lys Lys Phe
                1525                1530                1535

Val Pro Asp Tyr Tyr Lys Val Ile Val Asn Pro Met Asp Leu Glu Thr
                1540                1545                1550

Ile Arg Lys Asn Ile Ser Lys His Lys Tyr Gln Ser Arg Glu Ser Phe
                1555                1560                1565

Leu Asp Asp Val Asn Leu Ile Leu Ala Asn Ser Val Lys Tyr Asn Gly
        1570                1575                1580

Pro Glu Ser Gln Tyr Thr Lys Thr Ala Gln Glu Ile Val Asn Val Cys
1585                1590                1595                1600

Tyr Gln Thr Leu Thr Glu Tyr Asp Glu His Leu Thr Gln Leu Glu Lys
                1605                1610                1615

Asp Ile Cys Thr Ala Lys Glu Ala Ala Leu Glu Glu Ala Glu Leu Glu
                1620                1625                1630

Ser Leu Asp Pro Met Thr Pro Gly Pro Tyr Thr Pro Gln Pro Pro Asp
        1635                1640                1645

Leu Tyr Asp Thr Asn Thr Ser Leu Ser Met Ser Arg Asp Ala Ser Val
        1650                1655                1660

Phe Gln Asp Glu Ser Asn Met Ser Val Leu Asp Ile Pro Ser Ala Thr
1665                1670                1675                1680

Pro Glu Lys Gln Val Thr Gln Glu Gly Glu Asp Gly Asp Gly Asp Leu
                1685                1690                1695

Ala Asp Glu Glu Glu Gly Thr Val Gln Gln Pro Gln Ala Ser Val Leu
        1700                1705                1710

Tyr Glu Asp Leu Leu Met Ser Glu Gly Glu Asp Asp Glu Glu Asp Ala
        1715                1720                1725

Gly Ser Asp Glu Glu Gly Asp Asn Pro Phe Ser Ala Ile Gln Leu Ser
        1730                1735                1740

Glu Ser Gly Ser Asp Ser Asp Val Gly Ser Gly Gly Ile Arg Pro Lys
1745                1750                1755                1760

Gln Pro Arg Met Leu Gln Glu Asn Thr Arg Met Asp Met Glu Asn Glu
                1765                1770                1775

Glu Ser Met Met Ser Tyr Glu Gly Asp Gly Gly Glu Ala Ser His Gly
                1780                1785                1790

Leu Glu Asp Ser Asn Ile Ser Tyr Gly Ser Tyr Glu Glu Pro Asp Pro
        1795                1800                1805

Lys Ser Asn Thr Gln Asp Thr Ser Phe Ser Ser Ile Gly Gly Tyr Glu
        1810                1815                1820

Val Ser Glu Glu Glu Glu Asp Glu Glu Glu Glu Gln Arg Ser Gly
1825                1830                1835                1840

Pro Ser Val Leu Ser Gln Val His Leu Ser Glu Asp Glu Glu Asp Ser
                1845                1850                1855
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Glu | Asp | Phe | His | Ser | Ile | Ala | Gly | Asp | Ser | Asp | Leu | Asp | Ser | Asp | Glu | |
|     |     |     |     | 1860 |     |     |     |     | 1865 |     |     |     |     | 1870 |     |     |

( 2 ) INFORMATION FOR SEQ ID NO:15:

( i ) SEQUENCE CHARACTERISTICS:
        ( A ) LENGTH: 3603 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..2214

( x i ) SEQUENCE DESCRIPTION: SEQ ID NO:15:

| | | | | | | | | | | | | | | | | |
|---|---|---|---|---|---|---|---|---|---|---|---|---|---|---|---|---|
| AGA | GGT | GGT | GCA | GGC | GGC | GCC | CCC | GGC | GGC | GCA | GAC | CCT | GGC | GCC | AGC | 48 |
| Arg | Gly | Gly | Ala | Gly | Gly | Ala | Pro | Gly | Gly | Ala | Asp | Pro | Gly | Ala | Ser | |
| 1 | | | | 5 | | | | | 10 | | | | | 15 | | |
| GGC | CCG | GCC | AGC | ACG | GCG | GCC | AGC | ATG | GTC | ATC | GGG | CCA | ACT | ATG | CAA | 96 |
| Gly | Pro | Ala | Ser | Thr | Ala | Ala | Ser | Met | Val | Ile | Gly | Pro | Thr | Met | Gln | |
| | | | 20 | | | | | 25 | | | | | 30 | | | |
| GGG | CGC | TGC | CCA | GCC | CGG | CCG | CCG | TCC | CGC | CGC | CCG | CCC | CCG | GGA | CCC | 144 |
| Gly | Arg | Cys | Pro | Ala | Arg | Pro | Pro | Ser | Arg | Arg | Pro | Pro | Pro | Gly | Pro | |
| | | 35 | | | | | 40 | | | | | 45 | | | | |
| CCA | CCG | GGC | TGC | CCA | AAA | GGC | GCG | GCC | GGC | GCA | GTG | ACC | CAG | AGC | CTG | 192 |
| Pro | Pro | Gly | Cys | Pro | Lys | Gly | Ala | Ala | Gly | Ala | Val | Thr | Gln | Ser | Leu | |
| | 50 | | | | | 55 | | | | | 60 | | | | | |
| TCC | CGG | ACG | CCC | ACG | GCC | ACC | ACC | AGC | GGG | ATT | CGG | GCC | ACC | CTG | ACG | 240 |
| Ser | Arg | Thr | Pro | Thr | Ala | Thr | Thr | Ser | Gly | Ile | Arg | Ala | Thr | Leu | Thr | |
| 65 | | | | 70 | | | | | 75 | | | | | 80 | | |
| CCC | ACC | GTG | CTG | GCC | CCC | CGC | TTG | CCG | CAG | CCG | CCT | CAG | AAC | CCG | ACC | 288 |
| Pro | Thr | Val | Leu | Ala | Pro | Arg | Leu | Pro | Gln | Pro | Pro | Gln | Asn | Pro | Thr | |
| | | | 85 | | | | | 90 | | | | | 95 | | | |
| AAC | ATC | CAG | AAC | TTC | CAG | CTG | CCC | CCA | GGA | ATG | GTC | CTC | GTC | CGA | AGT | 336 |
| Asn | Ile | Gln | Asn | Phe | Gln | Leu | Pro | Pro | Gly | Met | Val | Leu | Val | Arg | Ser | |
| | | | 100 | | | | | 105 | | | | | 110 | | | |
| GAG | AAT | GGG | CAG | TTG | TTA | ATG | ATT | CCT | CAG | CAG | GCC | TTG | GCC | CAG | ATG | 384 |
| Glu | Asn | Gly | Gln | Leu | Leu | Met | Ile | Pro | Gln | Gln | Ala | Leu | Ala | Gln | Met | |
| | | 115 | | | | | 120 | | | | | 125 | | | | |
| CAG | GCG | CAG | GCC | CAT | GCC | CAG | CCT | CAG | ACC | ACC | ATG | GCG | CCT | CGC | CCT | 432 |
| Gln | Ala | Gln | Ala | His | Ala | Gln | Pro | Gln | Thr | Thr | Met | Ala | Pro | Arg | Pro | |
| | 130 | | | | | 135 | | | | | 140 | | | | | |
| GCC | ACC | CCC | ACA | AGT | GCC | CCT | CCC | GTC | CAG | ATC | TCC | ACC | GTA | CAG | GCA | 480 |
| Ala | Thr | Pro | Thr | Ser | Ala | Pro | Pro | Val | Gln | Ile | Ser | Thr | Val | Gln | Ala | |
| 145 | | | | 150 | | | | | 155 | | | | | 160 | | |
| CCT | GGA | ACA | CCT | ATC | ATT | GCA | CGG | CAG | GTG | ACC | CCA | ACT | ACC | ATA | ATT | 528 |
| Pro | Gly | Thr | Pro | Ile | Ile | Ala | Arg | Gln | Val | Thr | Pro | Thr | Thr | Ile | Ile | |
| | | | 165 | | | | | 170 | | | | | 175 | | | |
| AAG | CAA | GTG | TCT | CAG | GCC | CAG | ACA | ACG | GTG | CAG | CCC | AGT | GCA | ACC | CTG | 576 |
| Lys | Gln | Val | Ser | Gln | Ala | Gln | Thr | Thr | Val | Gln | Pro | Ser | Ala | Thr | Leu | |
| | | | 180 | | | | | 185 | | | | | 190 | | | |
| CAG | CGC | TCG | CCC | GGC | GTC | CAG | CCT | CAG | CTC | GTT | CTG | GGT | GGC | GCT | GCC | 624 |
| Gln | Arg | Ser | Pro | Gly | Val | Gln | Pro | Gln | Leu | Val | Leu | Gly | Gly | Ala | Ala | |
| | | 195 | | | | | 200 | | | | | 205 | | | | |
| CAG | ACG | GCT | TCA | CTT | GGG | ACG | GCG | ACG | GCT | GTT | CAG | ACG | GGG | ACT | CCT | 672 |
| Gln | Thr | Ala | Ser | Leu | Gly | Thr | Ala | Thr | Ala | Val | Gln | Thr | Gly | Thr | Pro | |
| | 210 | | | | | 215 | | | | | 220 | | | | | |
| CAG | CGC | ACG | GTA | CCA | GGG | GCG | ACC | ACC | ACT | TCC | TCA | GCT | GCC | ACG | GAA | 720 |
| Gln | Arg | Thr | Val | Pro | Gly | Ala | Thr | Thr | Thr | Ser | Ser | Ala | Ala | Thr | Glu | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| ACT | ATG | GAA | AAC | GTG | AAG | AAA | TGT | AAA | AAT | TTC | CTA | TCT | ACG | TTA | ATA | 768 |
| Thr | Met | Glu | Asn | Val<br>245 | Lys | Lys | Cys | Lys | Asn<br>250 | Phe | Leu | Ser | Thr | Leu<br>255 | Ile | |
| AAA | CTG | GCT | TCA | TCT | GGC | AAG | CAG | TCT | ACA | GAG | ACA | GCA | GCT | AAT | GTG | 816 |
| Lys | Leu | Ala | Ser<br>260 | Ser | Gly | Lys | Gln | Ser<br>265 | Thr | Glu | Thr | Ala | Ala<br>270 | Asn | Val | |
| AAA | GAG | CTC | GTG | CAG | AAT | TTA | CTG | GAT | GGA | AAA | ATA | GAA | GCA | GAA | GAT | 864 |
| Lys | Glu | Leu<br>275 | Val | Gln | Asn | Leu | Leu<br>280 | Asp | Gly | Lys | Ile | Glu<br>285 | Ala | Glu | Asp | |
| TTC | ACA | AGC | AGG | TTA | TAC | CGA | GAA | CTT | AAT | TCT | TCA | CCT | CAA | CCT | TAC | 912 |
| Phe | Thr | Ser<br>290 | Arg | Leu | Tyr | Arg | Glu<br>295 | Leu | Asn | Ser | Ser | Pro<br>300 | Gln | Pro | Tyr | |
| CTT | GTG | CCT | TTC | CTG | AAG | AGG | AGC | TTA | CCC | GCC | TTG | AGA | CAG | CTG | ACC | 960 |
| Leu<br>305 | Val | Pro | Phe | Leu | Lys<br>310 | Arg | Ser | Leu | Pro | Ala<br>315 | Leu | Arg | Gln | Leu | Thr<br>320 | |
| CCC | GAC | TCC | GCG | GCC | TTC | ATC | CAG | CAG | AGC | CAG | CAG | CAG | CCG | CCA | CCG | 1008 |
| Pro | Asp | Ser | Ala | Ala<br>325 | Phe | Ile | Gln | Gln | Ser<br>330 | Gln | Gln | Gln | Pro | Pro<br>335 | Pro | |
| CCC | ACC | TCG | CAG | GCC | ACC | ACT | GCG | CTC | ACG | GCC | GTG | GTG | CTG | AGT | AGC | 1056 |
| Pro | Thr | Ser | Gln<br>340 | Ala | Thr | Thr | Ala | Leu<br>345 | Thr | Ala | Val | Val | Leu<br>350 | Ser | Ser | |
| TCG | GTC | CAG | CGC | ACG | GCC | GGG | AAG | ACG | GCG | GCC | ACC | GTG | ACC | AGT | GCC | 1104 |
| Ser | Val | Gln<br>355 | Arg | Thr | Ala | Gly | Lys<br>360 | Thr | Ala | Ala | Thr | Val<br>365 | Thr | Ser | Ala | |
| CTC | CAG | CCC | CCT | GTG | CTC | AGC | CTC | ACG | CAG | CCC | ACG | CAG | GTC | GGC | GTC | 1152 |
| Leu | Gln | Pro<br>370 | Pro | Val | Leu | Ser<br>375 | Leu | Thr | Gln | Pro | Thr<br>380 | Gln | Val | Gly | Val | |
| GGC | AAG | CAG | GGG | CAA | CCC | ACA | CCG | CTG | GTC | ATC | CAG | CAG | CCT | CCG | AAG | 1200 |
| Gly<br>385 | Lys | Gln | Gly | Gln | Pro<br>390 | Thr | Pro | Leu | Val | Ile<br>395 | Gln | Gln | Pro | Pro | Lys<br>400 | |
| CCA | GGA | GCC | CTG | ATC | CGG | CCC | CCG | CAG | GTG | ACG | TTG | ACG | CAG | ACA | CCC | 1248 |
| Pro | Gly | Ala | Leu | Ile<br>405 | Arg | Pro | Pro | Gln | Val<br>410 | Thr | Leu | Thr | Gln | Thr<br>415 | Pro | |
| ATG | GTC | GCC | CTG | CGG | CAG | CCT | CAC | AAC | CGG | ATC | ATG | CTC | ACC | ACG | CCT | 1296 |
| Met | Val | Ala | Leu<br>420 | Arg | Gln | Pro | His | Asn<br>425 | Arg | Ile | Met | Leu | Thr<br>430 | Thr | Pro | |
| CAG | CAG | ATC | CAG | CTG | AAC | CCA | CTG | CAG | CCA | GTC | CCT | GTG | GTG | AAA | CCC | 1344 |
| Gln | Gln | Ile<br>435 | Gln | Leu | Asn | Pro | Leu<br>440 | Gln | Pro | Val | Pro | Val<br>445 | Val | Lys | Pro | |
| GCC | GTG | TTA | CCT | GGA | ACC | AAA | GCC | CTT | TCT | GCT | GTC | TCG | GCA | CAA | GCA | 1392 |
| Ala | Val | Leu<br>450 | Pro | Gly | Thr | Lys<br>455 | Ala | Leu | Ser | Ala | Val<br>460 | Ser | Ala | Gln | Ala | |
| GCT | GCT | GCA | CAG | AAA | AAT | AAA | CTC | AAG | GAG | CCT | GGG | GGA | GGT | TCG | TTT | 1440 |
| Ala | Ala | Ala<br>465 | Gln | Lys | Asn | Lys<br>470 | Leu | Lys | Glu | Pro | Gly<br>475 | Gly | Gly | Ser | Phe<br>480 | |
| CGG | GAC | GAT | GAT | GAC | ATT | AAT | GAT | GTT | GCA | TCG | ATG | GCT | GGA | GTA | AAC | 1488 |
| Arg | Asp | Asp | Asp | Asp<br>485 | Ile | Asn | Asp | Val | Ala<br>490 | Ser | Met | Ala | Gly | Val<br>495 | Asn | |
| TTG | TCA | GAA | GAA | AGT | GCA | AGA | ATA | TTA | GCC | ACG | AAC | TCT | GAA | TTG | GTG | 1536 |
| Leu | Ser | Glu | Glu<br>500 | Ser | Ala | Arg | Ile | Leu<br>505 | Ala | Thr | Asn | Ser | Glu<br>510 | Leu | Val | |
| GGC | ACG | CTA | ACG | CGG | TCC | TGT | AAA | GAT | GAA | ACC | TTC | CTC | CTC | CAA | GCG | 1584 |
| Gly | Thr | Leu<br>515 | Thr | Arg | Ser | Cys | Lys<br>520 | Asp | Glu | Thr | Phe | Leu<br>525 | Leu | Gln | Ala | |
| CCT | TTG | CAG | AGA | AGA | ATA | TTA | GAA | ATA | GGT | AAA | AAA | CAT | GGT | ATA | ACG | 1632 |
| Pro | Leu | Gln<br>530 | Arg | Arg | Ile | Leu | Glu<br>535 | Ile | Gly | Lys | Lys | His<br>540 | Gly | Ile | Thr | |
| GAA | TTA | CAT | CCA | GAT | GTA | GTA | AGT | TAT | GTA | TCA | CAT | GCC | ACG | CAA | CAA | 1680 |
| Glu<br>545 | Leu | His | Pro | Asp | Val<br>550 | Val | Ser | Tyr | Val | Ser<br>555 | His | Ala | Thr | Gln | Gln<br>560 | |

| | | | | | | | | | | | | | | | | |
|---|---|---|---|---|---|---|---|---|---|---|---|---|---|---|---|---|
| AGG | CTA | CAG | AAT | CTT | GTA | GAG | AAA | ATA | TCA | GAA | ACA | GCT | CAG | CAG | AAG | 1728 |
| Arg | Leu | Gln | Asn | Leu | Val | Glu | Lys | Ile | Ser | Glu | Thr | Ala | Gln | Gln | Lys | |
| | | | 565 | | | | | 570 | | | | | | 575 | | |
| AAC | TTT | TCT | TAC | AAG | GAT | GAC | GAC | AGA | TAT | GAG | CAG | GCG | AGT | GAC | GTC | 1776 |
| Asn | Phe | Ser | Tyr | Lys | Asp | Asp | Asp | Arg | Tyr | Glu | Gln | Ala | Ser | Asp | Val | |
| | | | 580 | | | | | 585 | | | | | 590 | | | |
| CGG | GCA | CAG | CTC | AAG | TTT | TTT | GAA | CAG | CTT | GAT | CAA | ATC | GAA | AAG | CAG | 1824 |
| Arg | Ala | Gln | Leu | Lys | Phe | Phe | Glu | Gln | Leu | Asp | Gln | Ile | Glu | Lys | Gln | |
| | | 595 | | | | | 600 | | | | | 605 | | | | |
| AGG | AAG | GAT | GAG | CAG | GAG | CGG | GAG | ATC | CTG | ATG | AGG | GCA | GCA | AAG | TCT | 1872 |
| Arg | Lys | Asp | Glu | Gln | Glu | Arg | Glu | Ile | Leu | Met | Arg | Ala | Ala | Lys | Ser | |
| | 610 | | | | | 615 | | | | | 620 | | | | | |
| CGG | TCA | AGA | CAA | GAA | GAT | CCA | GAA | CAG | TTA | AGG | CTG | AAA | CAG | AAG | GCA | 1920 |
| Arg | Ser | Arg | Gln | Glu | Asp | Pro | Glu | Gln | Leu | Arg | Leu | Lys | Gln | Lys | Ala | |
| 625 | | | | 630 | | | | | 635 | | | | | 640 | | |
| AAG | GAG | ATG | CAG | CAA | CAG | GAA | CTG | GCA | CAA | ATG | AGA | CAG | CGG | GAC | GCC | 1968 |
| Lys | Glu | Met | Gln | Gln | Gln | Glu | Leu | Ala | Gln | Met | Arg | Gln | Arg | Asp | Ala | |
| | | | 645 | | | | | 650 | | | | | 655 | | | |
| AAC | CTC | ACA | GCA | CTA | GCA | GCG | ATC | GGG | CCC | AGG | AAA | AAG | AGG | AAA | GTG | 2016 |
| Asn | Leu | Thr | Ala | Leu | Ala | Ala | Ile | Gly | Pro | Arg | Lys | Lys | Arg | Lys | Val | |
| | | | 660 | | | | | 665 | | | | | 670 | | | |
| GAC | TGT | CCG | GGG | CCG | GGC | TCA | GGA | GCA | GAG | GGG | TCG | GGC | CCC | GGC | TCA | 2064 |
| Asp | Cys | Pro | Gly | Pro | Gly | Ser | Gly | Ala | Glu | Gly | Ser | Gly | Pro | Gly | Ser | |
| | | 675 | | | | | 680 | | | | | 685 | | | | |
| GTG | GTC | CCA | GGC | AGC | TCG | GGT | GTC | GGA | ACC | CCC | AGA | CAG | TTC | ACG | CGA | 2112 |
| Val | Val | Pro | Gly | Ser | Ser | Gly | Val | Gly | Thr | Pro | Arg | Gln | Phe | Thr | Arg | |
| | | 690 | | | | | 695 | | | | | 700 | | | | |
| CAA | AGA | ATC | ACG | CGG | GTC | AAC | CTC | AGG | GAC | CTC | ATA | TTT | TGT | TTA | GAA | 2160 |
| Gln | Arg | Ile | Thr | Arg | Val | Asn | Leu | Arg | Asp | Leu | Ile | Phe | Cys | Leu | Glu | |
| 705 | | | | | 710 | | | | | 715 | | | | | 720 | |
| AAT | GAA | CGT | GAG | ACA | AGC | CAT | TCA | CTG | CTG | CTC | TAC | AAA | GCA | TTC | CTT | 2208 |
| Asn | Glu | Arg | Glu | Thr | Ser | His | Ser | Leu | Leu | Leu | Tyr | Lys | Ala | Phe | Leu | |
| | | | | 725 | | | | | 730 | | | | | 735 | | |

| | | | | | |
|---|---|---|---|---|---|
| AAG | TGACACAGGA | GGACGCCTGG | GGACTTTTTA | TATATTTGCA | GATTACGCCT | 2261 |
| Lys | | | | | | |
| TTTTGTAACG | AGCAAATGGG | ATATTGTTTA | AAAAACAGCC | ACCTCTTTAC | AATGGAACAG | 2321 |
| TTTTATATTC | CTGTTTCTAA | ATCAGCTCTT | CAGTGTGAAA | GAAAACACGT | TTCTGTAACA | 2381 |
| GAGAGAACAC | AAAGGCCTGT | GGATACTCTT | AAAGGACAAT | TAAATCTTAA | CTCATCTTGA | 2441 |
| TTGAGTGGCC | TTCCTGCCAA | ACAAGCCATA | TATAAAGACT | GATGGAATCG | TTAGCAAATA | 2501 |
| ATTAGCTGCC | CTCTGTCAAC | TCATAGCAGT | TTCTGCATTA | TTTGTGCATT | TTGGTTTAGT | 2561 |
| TCTACCTAAC | TTACTATGTA | GGTGTATGTC | TACAGCCGAT | GACCTCATTT | CGTTTATTTT | 2621 |
| ATTTTTGTAA | TAGTCAGTTG | GCAAAGCAAA | CTGATTTTTT | AGACTATTTA | TCTTCCTTCC | 2681 |
| CTTCCCCTCC | CACCCCGCTC | TCCTCTCTGC | CCCCTGCCCT | CCCCTCCCCT | CCCTTCCCCT | 2741 |
| CCACTCCGCT | GAGAATCCTG | GAGGAATACA | CAATTCATCG | TTGCACCCCC | ACCTCAGAGT | 2801 |
| GTAATCGCAT | TTCTGCTTGG | TAGAGGCCGA | GCCCAGCAAA | GGTGGCTCCT | TCTGAATGTG | 2861 |
| TGGTCAGCAT | CTGTACAAAT | GCATTTTATT | TGCTATAGTT | TGTAAAGCTG | TAAAGTTAAA | 2921 |
| AGAGATGAAA | ACCTTTTCAG | CATAAATATA | TTTTACTTGC | ACTGTGTTTT | TTAGCTAAAA | 2981 |
| GTGAAAACCT | AGATTAAATA | AAATCAAAGT | TGAGAAGAAT | CATCAAAAGA | CTGTTTCTCG | 3041 |
| GTGTGAATCA | AGTGTTGAAA | AATGGTTGGT | GTATTTGTC | AGTAATTGTA | CATAACTTTT | 3101 |
| GGCACATGAC | ATAGAAATGG | CTATGTAAAC | TATAATTATT | TTGCTAAGAG | ACTGTATGCA | 3161 |
| AGCCTTGGGC | CGACTTTACA | GACGTCCAGA | GCAAAGCCCC | TTCTTTGTAC | CTATTTTTTT | 3221 |

```
ATTACAAATA TACTAATTGG TTCTTTCTAT TTTCAGAGGT TATTGTATGA AATTGTCTAT    3281

TGATAGTACT TTTATGACTG TAAATACTCT GGCTTTCTCC GTGTGAATTC TCACATTAGA    3341

CTTTAATTCG AGCGCGTGTG AACTGAACGC TGATCAGTAT TTTTTATCAA CACCTGAGAA    3401

CTGTTACACC TTTTATTTTG TCTTTTAGGA AATCCCTGTC TTTCCATTTT TTCATGTAAA    3461

TTTTGCACAG TTACTTGTTC ATATGTAAAT ATTTTACTTT CAGAAATGAA GTTTTTAATT    3521

GCTATTGTTT TATATAGGAT TGAAAGAAAA TTAACTCCTT TATTAAAAAC AAATTTATCT    3581

GTAAAAAAAA AAAAAAAAA AA                                              3603
```

(2) INFORMATION FOR SEQ ID NO:16:

(i) SEQUENCE CHARACTERISTICS:
        (A) LENGTH: 737 amino acids
        (B) TYPE: amino acid
        (D) TOPOLOGY: linear (ii) MOLECULE TYPE: protein (xi) SEQUENCE DESCRIPTION: SEQ ID NO:16:

```
Arg Gly Gly Ala Gly Gly Ala Pro Gly Gly Ala Asp Pro Gly Ala Ser
 1               5                  10                  15

Gly Pro Ala Ser Thr Ala Ala Ser Met Val Ile Gly Pro Thr Met Gln
                20                  25                  30

Gly Arg Cys Pro Ala Arg Pro Pro Ser Arg Arg Pro Pro Gly Pro
            35                  40                  45

Pro Pro Gly Cys Pro Lys Gly Ala Ala Gly Ala Val Thr Gln Ser Leu
        50                  55                  60

Ser Arg Thr Pro Thr Ala Thr Thr Ser Gly Ile Arg Ala Thr Leu Thr
65                  70                  75                  80

Pro Thr Val Leu Ala Pro Arg Leu Pro Gln Pro Pro Gln Asn Pro Thr
                85                  90                  95

Asn Ile Gln Asn Phe Gln Leu Pro Pro Gly Met Val Leu Val Arg Ser
               100                 105                 110

Glu Asn Gly Gln Leu Leu Met Ile Pro Gln Gln Ala Leu Ala Gln Met
            115                 120                 125

Gln Ala Gln Ala His Ala Gln Pro Gln Thr Thr Met Ala Pro Arg Pro
130                 135                 140

Ala Thr Pro Thr Ser Ala Pro Pro Val Gln Ile Ser Thr Val Gln Ala
145                 150                 155                 160

Pro Gly Thr Pro Ile Ile Ala Arg Gln Val Thr Pro Thr Thr Ile Ile
                165                 170                 175

Lys Gln Val Ser Gln Ala Gln Thr Thr Val Gln Pro Ser Ala Thr Leu
            180                 185                 190

Gln Arg Ser Pro Gly Val Gln Pro Gln Leu Val Leu Gly Gly Ala Ala
        195                 200                 205

Gln Thr Ala Ser Leu Gly Thr Ala Thr Ala Val Gln Thr Gly Thr Pro
210                 215                 220

Gln Arg Thr Val Pro Gly Ala Thr Thr Ser Ser Ala Ala Thr Glu
225                 230                 235                 240

Thr Met Glu Asn Val Lys Lys Cys Lys Asn Phe Leu Ser Thr Leu Ile
                245                 250                 255

Lys Leu Ala Ser Ser Gly Lys Gln Ser Thr Glu Thr Ala Ala Asn Val
            260                 265                 270

Lys Glu Leu Val Gln Asn Leu Leu Asp Gly Lys Ile Glu Ala Glu Asp
        275                 280                 285
```

-continued

| | | | | | | | | | | | | | | |
|---|---|---|---|---|---|---|---|---|---|---|---|---|---|---|
| Phe | Thr | Ser | Arg | Leu | Tyr | Arg | Glu | Leu | Asn | Ser | Ser | Pro | Gln | Pro | Tyr |
| | 290 | | | | | 295 | | | | | 300 | | | | |
| Leu | Val | Pro | Phe | Leu | Lys | Arg | Ser | Leu | Pro | Ala | Leu | Arg | Gln | Leu | Thr |
| 305 | | | | | 310 | | | | | 315 | | | | | 320 |
| Pro | Asp | Ser | Ala | Ala | Phe | Ile | Gln | Gln | Ser | Gln | Gln | Gln | Pro | Pro | Pro |
| | | | | 325 | | | | | 330 | | | | | 335 | |
| Pro | Thr | Ser | Gln | Ala | Thr | Thr | Ala | Leu | Thr | Ala | Val | Val | Leu | Ser | Ser |
| | | | 340 | | | | | 345 | | | | | 350 | | |
| Ser | Val | Gln | Arg | Thr | Ala | Gly | Lys | Thr | Ala | Ala | Thr | Val | Thr | Ser | Ala |
| | | 355 | | | | | 360 | | | | | 365 | | | |
| Leu | Gln | Pro | Pro | Val | Leu | Ser | Leu | Thr | Gln | Pro | Thr | Gln | Val | Gly | Val |
| | 370 | | | | | 375 | | | | | 380 | | | | |
| Gly | Lys | Gln | Gly | Gln | Pro | Thr | Pro | Leu | Val | Ile | Gln | Gln | Pro | Pro | Lys |
| 385 | | | | | 390 | | | | | 395 | | | | | 400 |
| Pro | Gly | Ala | Leu | Ile | Arg | Pro | Pro | Gln | Val | Thr | Leu | Thr | Gln | Thr | Pro |
| | | | | 405 | | | | | 410 | | | | | 415 | |
| Met | Val | Ala | Leu | Arg | Gln | Pro | His | Asn | Arg | Ile | Met | Leu | Thr | Thr | Pro |
| | | | 420 | | | | | 425 | | | | | 430 | | |
| Gln | Gln | Ile | Gln | Leu | Asn | Pro | Leu | Gln | Pro | Val | Pro | Val | Val | Lys | Pro |
| | | | 435 | | | | | 440 | | | | | 445 | | |
| Ala | Val | Leu | Pro | Gly | Thr | Lys | Ala | Leu | Ser | Ala | Val | Ser | Ala | Gln | Ala |
| | 450 | | | | | 455 | | | | | 460 | | | | |
| Ala | Ala | Ala | Gln | Lys | Asn | Lys | Leu | Lys | Glu | Pro | Gly | Gly | Gly | Ser | Phe |
| 465 | | | | | 470 | | | | | 475 | | | | | 480 |
| Arg | Asp | Asp | Asp | Asp | Ile | Asn | Asp | Val | Ala | Ser | Met | Ala | Gly | Val | Asn |
| | | | | 485 | | | | | 490 | | | | | 495 | |
| Leu | Ser | Glu | Glu | Ser | Ala | Arg | Ile | Leu | Ala | Thr | Asn | Ser | Glu | Leu | Val |
| | | | | 500 | | | | | 505 | | | | | 510 | |
| Gly | Thr | Leu | Thr | Arg | Ser | Cys | Lys | Asp | Glu | Thr | Phe | Leu | Leu | Gln | Ala |
| | | | 515 | | | | | 520 | | | | | 525 | | |
| Pro | Leu | Gln | Arg | Arg | Ile | Leu | Glu | Ile | Gly | Lys | Lys | His | Gly | Ile | Thr |
| | | 530 | | | | | 535 | | | | | 540 | | | |
| Glu | Leu | His | Pro | Asp | Val | Val | Ser | Tyr | Val | Ser | His | Ala | Thr | Gln | Gln |
| 545 | | | | | 550 | | | | | 555 | | | | | 560 |
| Arg | Leu | Gln | Asn | Leu | Val | Glu | Lys | Ile | Ser | Glu | Thr | Ala | Gln | Gln | Lys |
| | | | | 565 | | | | | 570 | | | | | 575 | |
| Asn | Phe | Ser | Tyr | Lys | Asp | Asp | Asp | Arg | Tyr | Glu | Gln | Ala | Ser | Asp | Val |
| | | | | 580 | | | | | 585 | | | | | 590 | |
| Arg | Ala | Gln | Leu | Lys | Phe | Phe | Glu | Gln | Leu | Asp | Gln | Ile | Glu | Lys | Gln |
| | | | | 595 | | | | | 600 | | | | | 605 | |
| Arg | Lys | Asp | Glu | Gln | Glu | Arg | Glu | Ile | Leu | Met | Arg | Ala | Ala | Lys | Ser |
| | | | 610 | | | | | 615 | | | | | 620 | | |
| Arg | Ser | Arg | Gln | Glu | Asp | Pro | Glu | Gln | Leu | Arg | Leu | Lys | Gln | Lys | Ala |
| 625 | | | | | 630 | | | | | 635 | | | | | 640 |
| Lys | Glu | Met | Gln | Gln | Gln | Glu | Leu | Ala | Gln | Met | Arg | Gln | Arg | Asp | Ala |
| | | | | 645 | | | | | 650 | | | | | 655 | |
| Asn | Leu | Thr | Ala | Leu | Ala | Ala | Ile | Gly | Pro | Arg | Lys | Lys | Arg | Lys | Val |
| | | | 660 | | | | | 665 | | | | | 670 | | |
| Asp | Cys | Pro | Gly | Pro | Gly | Ser | Gly | Ala | Glu | Gly | Ser | Gly | Pro | Gly | Ser |
| | | 675 | | | | | 680 | | | | | 685 | | | |
| Val | Val | Pro | Gly | Ser | Ser | Gly | Val | Gly | Thr | Pro | Arg | Gln | Phe | Thr | Arg |
| | | 690 | | | | | 695 | | | | | 700 | | | |
| Gln | Arg | Ile | Thr | Arg | Val | Asn | Leu | Arg | Asp | Leu | Ile | Phe | Cys | Leu | Glu |
| 705 | | | | | 710 | | | | | 715 | | | | | 720 |

Asn Glu Arg Glu Thr Ser His Ser Leu Leu Leu Tyr Lys Ala Phe Leu
            725                 730                 735

Lys ( 2 ) INFORMATION FOR SEQ ID NO:17:

( i ) SEQUENCE CHARACTERISTICS:
        ( A ) LENGTH: 2152 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..2112

( x i ) SEQUENCE DESCRIPTION: SEQ ID NO:17:

| | | | | | | | | | | | | | | | | |
|---|---|---|---|---|---|---|---|---|---|---|---|---|---|---|---|---|
| CTA | CTG | GCC | GTG | CTG | CAG | TTC | CTA | CGG | CAG | AGC | AAA | CTC | CGC | GAG | GCC | 48 |
| Leu | Leu | Ala | Val | Leu | Gln | Phe | Leu | Arg | Gln | Ser | Lys | Leu | Arg | Glu | Ala | |
| 1 | | | | 5 | | | | | 10 | | | | | 15 | | |
| GAA | GAG | GCG | CTG | CGC | CGT | GAG | GCC | GGG | CTG | CTG | GAG | GAG | GCA | GTG | GCG | 96 |
| Glu | Glu | Ala | Leu | Arg | Arg | Glu | Ala | Gly | Leu | Leu | Glu | Glu | Ala | Val | Ala | |
| | | | 20 | | | | 25 | | | | | 30 | | | | |
| GGC | TCC | GGA | GCC | CCG | GGA | GAG | GTG | GAC | AGC | GCC | GGC | GCT | GAG | GTG | ACC | 144 |
| Gly | Ser | Gly | Ala | Pro | Gly | Glu | Val | Asp | Ser | Ala | Gly | Ala | Glu | Val | Thr | |
| | | 35 | | | | 40 | | | | | 45 | | | | | |
| AGC | GCG | CTT | CTC | AGC | CGG | GTG | ACC | GCC | TCG | GCC | CCT | GGC | CCT | GCG | GCC | 192 |
| Ser | Ala | Leu | Leu | Ser | Arg | Val | Thr | Ala | Ser | Ala | Pro | Gly | Pro | Ala | Ala | |
| | 50 | | | | | 55 | | | | | 60 | | | | | |
| CCC | GAC | CCT | CCG | GGC | ACT | GGC | GCT | TCG | GGG | GCC | ACG | GTC | GTC | TCA | GGT | 240 |
| Pro | Asp | Pro | Pro | Gly | Thr | Gly | Ala | Ser | Gly | Ala | Thr | Val | Val | Ser | Gly | |
| 65 | | | | | 70 | | | | | 75 | | | | | 80 | |
| TCA | GCC | TCA | GGT | CCT | GCG | GCT | CCG | GGT | AAA | GTT | GGA | AGT | GTT | GCT | GTG | 288 |
| Ser | Ala | Ser | Gly | Pro | Ala | Ala | Pro | Gly | Lys | Val | Gly | Ser | Val | Ala | Val | |
| | | | | 85 | | | | | 90 | | | | | 95 | | |
| GAA | GAC | CAG | CCA | GAT | GTC | AGT | GCC | GTG | TTG | TCA | GCC | TAC | AAC | CAA | CAA | 336 |
| Glu | Asp | Gln | Pro | Asp | Val | Ser | Ala | Val | Leu | Ser | Ala | Tyr | Asn | Gln | Gln | |
| | | | 100 | | | | | 105 | | | | | 110 | | | |
| GGA | GAT | CCC | ACA | ATG | TAT | GAA | GAA | TAC | TAT | AGT | GGA | CTG | AAA | CAC | TTC | 384 |
| Gly | Asp | Pro | Thr | Met | Tyr | Glu | Glu | Tyr | Tyr | Ser | Gly | Leu | Lys | His | Phe | |
| | | | 115 | | | | 120 | | | | | 125 | | | | |
| ATT | GAA | TGT | TCC | CTG | GAC | TGC | CAT | CGG | GCA | GAG | TTG | TCC | CAA | CTT | TTT | 432 |
| Ile | Glu | Cys | Ser | Leu | Asp | Cys | His | Arg | Ala | Glu | Leu | Ser | Gln | Leu | Phe | |
| | | 130 | | | | | 135 | | | | | 140 | | | | |
| TAT | CCT | CTG | TTT | GTG | CAC | ATG | TAC | TTG | GAG | CTA | GTC | TAC | AAT | CAA | CAT | 480 |
| Tyr | Pro | Leu | Phe | Val | His | Met | Tyr | Leu | Glu | Leu | Val | Tyr | Asn | Gln | His | |
| 145 | | | | | 150 | | | | | 155 | | | | | 160 | |
| GAG | AAT | GAA | GCA | AAG | TCA | TTC | TTT | GAG | AAG | TTC | CAT | GGA | GAT | CAG | GAA | 528 |
| Glu | Asn | Glu | Ala | Lys | Ser | Phe | Phe | Glu | Lys | Phe | His | Gly | Asp | Gln | Glu | |
| | | | | 165 | | | | | 170 | | | | | 175 | | |
| TGT | TAT | TAC | CAG | GAT | GAC | CTA | CGA | GTA | TTA | TCT | AGT | CTT | ACC | AAA | AAG | 576 |
| Cys | Tyr | Tyr | Gln | Asp | Asp | Leu | Arg | Val | Leu | Ser | Ser | Leu | Thr | Lys | Lys | |
| | | | 180 | | | | | 185 | | | | | 190 | | | |
| GAA | CAC | ATG | AAA | GGG | AAT | GAG | ACC | ATG | TTG | GAT | TTT | CGA | ACA | AGT | AAA | 624 |
| Glu | His | Met | Lys | Gly | Asn | Glu | Thr | Met | Leu | Asp | Phe | Arg | Thr | Ser | Lys | |
| | | | 195 | | | | 200 | | | | | 205 | | | | |
| TTT | GTT | CTG | CGT | ATT | TCC | CGT | GAC | TCG | TAC | CAA | CTC | TTG | AAG | AGG | CAT | 672 |
| Phe | Val | Leu | Arg | Ile | Ser | Arg | Asp | Ser | Tyr | Gln | Leu | Leu | Lys | Arg | His | |
| | | 210 | | | | | 215 | | | | | 220 | | | | |

| | | | | | | | | | | | | | | | | |
|---|---|---|---|---|---|---|---|---|---|---|---|---|---|---|---|---|
| CTT | CAG | GAG | AAA | CAG | AAC | AAT | CAG | ATA | TGG | AAC | ATA | GTT | CAG | GAG | CAC | 720 |
| Leu | Gln | Glu | Lys | Gln | Asn | Asn | Gln | Ile | Trp | Asn | Ile | Val | Gln | Glu | His | |
| 225 | | | | 230 | | | | 235 | | | | | | | 240 | |
| CTC | TAC | ATT | GAC | ATC | TTT | GAT | GGG | ATG | CCG | CGT | AGT | AAG | CAA | CAG | ATA | 768 |
| Leu | Tyr | Ile | Asp | Ile | Phe | Asp | Gly | Met | Pro | Arg | Ser | Lys | Gln | Gln | Ile | |
| | | | | 245 | | | | | 250 | | | | | | 255 | |
| GAT | GCG | ATG | GTG | GGA | AGT | TTG | GCA | GGA | GAG | GCT | AAA | CGA | GAG | GCA | AAC | 816 |
| Asp | Ala | Met | Val | Gly | Ser | Leu | Ala | Gly | Glu | Ala | Lys | Arg | Glu | Ala | Asn | |
| | | | 260 | | | | | 265 | | | | | 270 | | | |
| AAA | TCA | AAG | GTA | TTT | TTT | GGT | TTA | TTA | AAA | GAA | CCA | GAA | ATT | GAG | GTA | 864 |
| Lys | Ser | Lys | Val | Phe | Phe | Gly | Leu | Leu | Lys | Glu | Pro | Glu | Ile | Glu | Val | |
| | | 275 | | | | | 280 | | | | | 285 | | | | |
| CCT | TTG | GAT | GAC | GAG | GAT | GAA | GAG | GGA | GAA | AAT | GAA | GAA | GGA | AAA | CCT | 912 |
| Pro | Leu | Asp | Asp | Glu | Asp | Glu | Glu | Gly | Glu | Asn | Glu | Glu | Gly | Lys | Pro | |
| | 290 | | | | | 295 | | | | | 300 | | | | | |
| AAA | AAG | AAG | AAG | CCT | AAA | AAA | GAT | AGT | ATT | GGA | TCC | AAA | AGC | AAA | AAA | 960 |
| Lys | Lys | Lys | Lys | Pro | Lys | Lys | Asp | Ser | Ile | Gly | Ser | Lys | Ser | Lys | Lys | |
| 305 | | | | | 310 | | | | | 315 | | | | | 320 | |
| CAA | GAT | CCC | AAT | GCT | CCA | CCT | CAG | AAC | AGA | ATC | CCT | CTT | CCT | GAG | TTG | 1008 |
| Gln | Asp | Pro | Asn | Ala | Pro | Pro | Gln | Asn | Arg | Ile | Pro | Leu | Pro | Glu | Leu | |
| | | | | 325 | | | | | 330 | | | | | 335 | | |
| AAA | GAT | TCA | GAT | AAG | TTG | GAT | AAG | ATA | ATG | AAT | ATG | AAA | GAA | ACC | ACC | 1056 |
| Lys | Asp | Ser | Asp | Lys | Leu | Asp | Lys | Ile | Met | Asn | Met | Lys | Glu | Thr | Thr | |
| | | | 340 | | | | | 345 | | | | | 350 | | | |
| AAA | CGA | GTA | CGC | CTT | GGG | CCG | GAC | TGC | TTA | CCC | TCC | ATT | TGT | TTC | TAT | 1104 |
| Lys | Arg | Val | Arg | Leu | Gly | Pro | Asp | Cys | Leu | Pro | Ser | Ile | Cys | Phe | Tyr | |
| | | 355 | | | | | 360 | | | | | 365 | | | | |
| ACA | TTT | CTC | AAT | GCT | TAC | CAG | GGT | CTC | ACT | GCA | GTG | GAT | GTC | ACT | GAT | 1152 |
| Thr | Phe | Leu | Asn | Ala | Tyr | Gln | Gly | Leu | Thr | Ala | Val | Asp | Val | Thr | Asp | |
| | 370 | | | | | 375 | | | | | 380 | | | | | |
| GAT | TCT | AGT | CTG | ATT | GCT | GGA | GGT | TTT | GCA | GAT | TCA | ACT | GTC | AGA | GTG | 1200 |
| Asp | Ser | Ser | Leu | Ile | Ala | Gly | Gly | Phe | Ala | Asp | Ser | Thr | Val | Arg | Val | |
| 385 | | | | | 390 | | | | | 395 | | | | | 400 | |
| TGG | TCG | GTA | ACA | CCC | AAA | AAG | CTT | CGT | AGT | GTC | AAA | CAA | GCA | TCA | GAT | 1248 |
| Trp | Ser | Val | Thr | Pro | Lys | Lys | Leu | Arg | Ser | Val | Lys | Gln | Ala | Ser | Asp | |
| | | | | 405 | | | | | 410 | | | | | 415 | | |
| CTT | AGT | CTT | ATA | GAC | AAA | GAA | TCA | GAT | GAT | GTC | TTA | GAA | AGA | ATC | ATG | 1296 |
| Leu | Ser | Leu | Ile | Asp | Lys | Glu | Ser | Asp | Asp | Val | Leu | Glu | Arg | Ile | Met | |
| | | | 420 | | | | | 425 | | | | | 430 | | | |
| GAT | GAG | AAA | ACA | GCA | AGT | GAG | TTG | AAG | ATT | TTG | TAT | GGT | CAC | AGT | GGG | 1344 |
| Asp | Glu | Lys | Thr | Ala | Ser | Glu | Leu | Lys | Ile | Leu | Tyr | Gly | His | Ser | Gly | |
| | | 435 | | | | | 440 | | | | | 445 | | | | |
| CCT | GTC | TAC | GGA | GCC | AGC | TTC | AGT | CCG | GAT | AGG | AAC | TAT | CTG | CTT | TCC | 1392 |
| Pro | Val | Tyr | Gly | Ala | Ser | Phe | Ser | Pro | Asp | Arg | Asn | Tyr | Leu | Leu | Ser | |
| | 450 | | | | | 455 | | | | | 460 | | | | | |
| TCT | TCA | GAG | GAC | GGA | ACT | GTT | AGA | TTG | TGG | AGC | CTT | CAA | ACA | TTT | ACT | 1440 |
| Ser | Ser | Glu | Asp | Gly | Thr | Val | Arg | Leu | Trp | Ser | Leu | Gln | Thr | Phe | Thr | |
| 465 | | | | | 470 | | | | | 475 | | | | | 480 | |
| TGT | TTG | GTG | GGA | TAT | AAA | GGA | CAC | AAC | TAT | CCA | GTA | TGG | GAC | ACA | CAA | 1488 |
| Cys | Leu | Val | Gly | Tyr | Lys | Gly | His | Asn | Tyr | Pro | Val | Trp | Asp | Thr | Gln | |
| | | | | 485 | | | | | 490 | | | | | 495 | | |
| TTT | TCT | CCA | TAT | GGA | TAT | TAT | TTT | GTG | TCA | GGG | GGC | CAT | GAC | CGA | GTA | 1536 |
| Phe | Ser | Pro | Tyr | Gly | Tyr | Tyr | Phe | Val | Ser | Gly | Gly | His | Asp | Arg | Val | |
| | | | 500 | | | | | 505 | | | | | 510 | | | |
| GCT | CGG | CTC | TGG | GCT | ACA | GAC | CAC | TAT | CAG | CCT | TTA | AGA | ATA | TTT | GCC | 1584 |
| Ala | Arg | Leu | Trp | Ala | Thr | Asp | His | Tyr | Gln | Pro | Leu | Arg | Ile | Phe | Ala | |
| | | 515 | | | | | 520 | | | | | 525 | | | | |
| GGC | CAT | CTT | GCT | GAT | GTG | AAT | TGT | ACC | AGA | TTC | CAT | CCA | AAT | TCT | AAT | 1632 |
| Gly | His | Leu | Ala | Asp | Val | Asn | Cys | Thr | Arg | Phe | His | Pro | Asn | Ser | Asn | |
| | 530 | | | | | 535 | | | | | 540 | | | | | |

```
TAT GTT GCT ACG GGC TCT GCA GAC AGA ACT GTG CGG CTC TGG GAC GTC      1680
Tyr Val Ala Thr Gly Ser Ala Asp Arg Thr Val Arg Leu Trp Asp Val
545                 550                 555                 560

CTG AAT GGT AAC TGT GTA AGG ATC TTC ACT GGA CAC AAG GGA CCA ATT      1728
Leu Asn Gly Asn Cys Val Arg Ile Phe Thr Gly His Lys Gly Pro Ile
                    565                 570                 575

CAT TCC TTG ACA TTT TCT CCC AAT GGG AGA TTC CTG GCT ACA GGA GCA      1776
His Ser Leu Thr Phe Ser Pro Asn Gly Arg Phe Leu Ala Thr Gly Ala
                580                 585                 590

ACA GAT GGC AGA GTG CTT CTT TGG GAT ATT GGA CAT GGT TTG ATG GTT      1824
Thr Asp Gly Arg Val Leu Leu Trp Asp Ile Gly His Gly Leu Met Val
            595                 600                 605

GGA GAA TTA AAA GGC CAC ACT GAT ACA GTC TGT TCA CTT AGG TTT AGT      1872
Gly Glu Leu Lys Gly His Thr Asp Thr Val Cys Ser Leu Arg Phe Ser
610                 615                 620

AGA GAT GGT GAA ATT TTG GCA TCA GGT TCA ATG GAT AAT ACA GTT CGA      1920
Arg Asp Gly Glu Ile Leu Ala Ser Gly Ser Met Asp Asn Thr Val Arg
625                 630                 635                 640

TTA TGG GAT GCT ATC AAA GCC TTT GAA GAT TTA GAG ACC GAT GAC TTT      1968
Leu Trp Asp Ala Ile Lys Ala Phe Glu Asp Leu Glu Thr Asp Asp Phe
                    645                 650                 655

ACT ACA GCC ACT GGG CAT ATA AAT TTA CCT GAG AAT TCA CAG GAG TTA      2016
Thr Thr Ala Thr Gly His Ile Asn Leu Pro Glu Asn Ser Gln Glu Leu
                660                 665                 670

TTG TTG GGA ACA TAT ATG ACC AAA TCA ACA CCA GTT GTA CAC CTT CAT      2064
Leu Leu Gly Thr Tyr Met Thr Lys Ser Thr Pro Val Val His Leu His
            675                 680                 685

TTT ACT CGA AGA AAC CTG GTT CTA GCT GCA GGA GCT TAT AGT CCA CAA      2112
Phe Thr Arg Arg Asn Leu Val Leu Ala Ala Gly Ala Tyr Ser Pro Gln
690                 695                 700

TAAACCATCG GTATTAAAGA CCAAAAAAAA AAAAAAAAA                           2152
```

(2) INFORMATION FOR SEQ ID NO:18:

(i) SEQUENCE CHARACTERISTICS:
        (A) LENGTH: 704 amino acids
        (B) TYPE: amino acid
        (D) TOPOLOGY: linear (ii) MOLECULE TYPE: protein (xi) SEQUENCE DESCRIPTION: SEQ ID NO:18:

```
Leu Leu Ala Val Leu Gln Phe Leu Arg Gln Ser Lys Leu Arg Glu Ala
 1               5                  10                  15

Glu Glu Ala Leu Arg Arg Glu Ala Gly Leu Leu Glu Glu Ala Val Ala
                20                  25                  30

Gly Ser Gly Ala Pro Gly Glu Val Asp Ser Ala Gly Ala Glu Val Thr
            35                  40                  45

Ser Ala Leu Leu Ser Arg Val Thr Ala Ser Ala Pro Gly Pro Ala Ala
        50                  55                  60

Pro Asp Pro Pro Gly Thr Gly Ala Ser Gly Ala Thr Val Val Ser Gly
65                  70                  75                  80

Ser Ala Ser Gly Pro Ala Ala Pro Gly Lys Val Gly Ser Val Ala Val
                85                  90                  95

Glu Asp Gln Pro Asp Val Ser Ala Val Leu Ser Ala Tyr Asn Gln Gln
                100                 105                 110

Gly Asp Pro Thr Met Tyr Glu Glu Tyr Tyr Ser Gly Leu Lys His Phe
            115                 120                 125

Ile Glu Cys Ser Leu Asp Cys His Arg Ala Glu Leu Ser Gln Leu Phe
        130                 135                 140
```

| | | | | | | | | | | | | | | |
|---|---|---|---|---|---|---|---|---|---|---|---|---|---|---|
| Tyr | Pro | Leu | Phe | Val | His | Met | Tyr | Leu | Glu | Leu | Val | Tyr | Asn | Gln | His |
| 145 | | | | | 150 | | | | 155 | | | | | | 160 |
| Glu | Asn | Glu | Ala | Lys | Ser | Phe | Phe | Glu | Lys | Phe | His | Gly | Asp | Gln | Glu |
| | | | | 165 | | | | | 170 | | | | | 175 | |
| Cys | Tyr | Tyr | Gln | Asp | Asp | Leu | Arg | Val | Leu | Ser | Ser | Leu | Thr | Lys | Lys |
| | | | 180 | | | | | 185 | | | | | 190 | | |
| Glu | His | Met | Lys | Gly | Asn | Glu | Thr | Met | Leu | Asp | Phe | Arg | Thr | Ser | Lys |
| | | 195 | | | | | 200 | | | | | 205 | | | |
| Phe | Val | Leu | Arg | Ile | Ser | Arg | Asp | Ser | Tyr | Gln | Leu | Leu | Lys | Arg | His |
| | 210 | | | | | 215 | | | | 220 | | | | | |
| Leu | Gln | Glu | Lys | Gln | Asn | Asn | Gln | Ile | Trp | Asn | Ile | Val | Gln | Glu | His |
| 225 | | | | | 230 | | | | | 235 | | | | | 240 |
| Leu | Tyr | Ile | Asp | Ile | Phe | Asp | Gly | Met | Pro | Arg | Ser | Lys | Gln | Gln | Ile |
| | | | | 245 | | | | | 250 | | | | | 255 | |
| Asp | Ala | Met | Val | Gly | Ser | Leu | Ala | Gly | Glu | Ala | Lys | Arg | Glu | Ala | Asn |
| | | | 260 | | | | | 265 | | | | | 270 | | |
| Lys | Ser | Lys | Val | Phe | Phe | Gly | Leu | Leu | Lys | Glu | Pro | Glu | Ile | Glu | Val |
| | | 275 | | | | | 280 | | | | | 285 | | | |
| Pro | Leu | Asp | Asp | Glu | Asp | Glu | Glu | Gly | Glu | Asn | Glu | Glu | Gly | Lys | Pro |
| | 290 | | | | | 295 | | | | | 300 | | | | |
| Lys | Lys | Lys | Lys | Pro | Lys | Lys | Asp | Ser | Ile | Gly | Ser | Lys | Ser | Lys | Lys |
| 305 | | | | | 310 | | | | | 315 | | | | | 320 |
| Gln | Asp | Pro | Asn | Ala | Pro | Pro | Gln | Asn | Arg | Ile | Pro | Leu | Pro | Glu | Leu |
| | | | | 325 | | | | | 330 | | | | | 335 | |
| Lys | Asp | Ser | Asp | Lys | Leu | Asp | Lys | Ile | Met | Asn | Met | Lys | Glu | Thr | Thr |
| | | | 340 | | | | | 345 | | | | | 350 | | |
| Lys | Arg | Val | Arg | Leu | Gly | Pro | Asp | Cys | Leu | Pro | Ser | Ile | Cys | Phe | Tyr |
| | | 355 | | | | | 360 | | | | | 365 | | | |
| Thr | Phe | Leu | Asn | Ala | Tyr | Gln | Gly | Leu | Thr | Ala | Val | Asp | Val | Thr | Asp |
| | 370 | | | | | 375 | | | | | 380 | | | | |
| Asp | Ser | Ser | Leu | Ile | Ala | Gly | Gly | Phe | Ala | Asp | Ser | Thr | Val | Arg | Val |
| 385 | | | | | 390 | | | | | 395 | | | | | 400 |
| Trp | Ser | Val | Thr | Pro | Lys | Lys | Leu | Arg | Ser | Val | Lys | Gln | Ala | Ser | Asp |
| | | | | 405 | | | | | 410 | | | | | 415 | |
| Leu | Ser | Leu | Ile | Asp | Lys | Glu | Ser | Asp | Asp | Val | Leu | Glu | Arg | Ile | Met |
| | | | 420 | | | | | 425 | | | | | 430 | | |
| Asp | Glu | Lys | Thr | Ala | Ser | Glu | Leu | Lys | Ile | Leu | Tyr | Gly | His | Ser | Gly |
| | | 435 | | | | | 440 | | | | | 445 | | | |
| Pro | Val | Tyr | Gly | Ala | Ser | Phe | Ser | Pro | Asp | Arg | Asn | Tyr | Leu | Leu | Ser |
| | 450 | | | | | 455 | | | | | 460 | | | | |
| Ser | Ser | Glu | Asp | Gly | Thr | Val | Arg | Leu | Trp | Ser | Leu | Gln | Thr | Phe | Thr |
| 465 | | | | | 470 | | | | | 475 | | | | | 480 |
| Cys | Leu | Val | Gly | Tyr | Lys | Gly | His | Asn | Tyr | Pro | Val | Trp | Asp | Thr | Gln |
| | | | | 485 | | | | | 490 | | | | | 495 | |
| Phe | Ser | Pro | Tyr | Gly | Tyr | Tyr | Phe | Val | Ser | Gly | Gly | His | Asp | Arg | Val |
| | | | 500 | | | | | 505 | | | | | 510 | | |
| Ala | Arg | Leu | Trp | Ala | Thr | Asp | His | Tyr | Gln | Pro | Leu | Arg | Ile | Phe | Ala |
| | | 515 | | | | | 520 | | | | | 525 | | | |
| Gly | His | Leu | Ala | Asp | Val | Asn | Cys | Thr | Arg | Phe | His | Pro | Asn | Ser | Asn |
| | 530 | | | | | 535 | | | | | 540 | | | | |
| Tyr | Val | Ala | Thr | Gly | Ser | Ala | Asp | Arg | Thr | Val | Arg | Leu | Trp | Asp | Val |
| 545 | | | | | 550 | | | | | 555 | | | | | 560 |
| Leu | Asn | Gly | Asn | Cys | Val | Arg | Ile | Phe | Thr | Gly | His | Lys | Gly | Pro | Ile |

|  |  |  |  |  | 565 |  |  |  |  | 570 |  |  |  |  | 575 |  |
|---|---|---|---|---|---|---|---|---|---|---|---|---|---|---|---|---|
| His | Ser | Leu | Thr<br>580 | Phe | Ser | Pro | Asn | Gly<br>585 | Arg | Phe | Leu | Ala | Thr<br>590 | Gly | Ala |
| Thr | Asp | Gly<br>595 | Arg | Val | Leu | Leu | Trp | Asp<br>600 | Ile | Gly | His | Gly<br>605 | Leu | Met | Val |
| Gly | Glu<br>610 | Leu | Lys | Gly | His | Thr<br>615 | Asp | Thr | Val | Cys | Ser<br>620 | Leu | Arg | Phe | Ser |
| Arg<br>625 | Asp | Gly | Glu | Ile | Leu<br>630 | Ala | Ser | Gly | Ser | Met<br>635 | Asp | Asn | Thr | Val | Arg<br>640 |
| Leu | Trp | Asp | Ala | Ile<br>645 | Lys | Ala | Phe | Glu | Asp<br>650 | Leu | Glu | Thr | Asp | Asp<br>655 | Phe |
| Thr | Thr | Ala | Thr<br>660 | Gly | His | Ile | Asn | Leu<br>665 | Pro | Glu | Asn | Ser | Gln<br>670 | Glu | Leu |
| Leu | Leu | Gly<br>675 | Thr | Tyr | Met | Thr | Lys<br>680 | Ser | Thr | Pro | Val | Val<br>685 | His | Leu | His |
| Phe | Thr<br>690 | Arg | Arg | Asn | Leu | Val<br>695 | Leu | Ala | Ala | Gly | Ala<br>700 | Tyr | Ser | Pro | Gln |

( 2 ) INFORMATION FOR SEQ ID NO:19:

( i ) SEQUENCE CHARACTERISTICS:
 ( A ) LENGTH: 3812 base pairs
 ( B ) TYPE: nucleic acid
 ( C ) STRANDEDNESS: double
 ( D ) TOPOLOGY: linear ( i i ) MOLECULE TYPE: cDNA ( i x ) FEATURE:
 ( A ) NAME/KEY: CDS
 ( B ) LOCATION: 60..3701

( x i ) SEQUENCE DESCRIPTION: SEQ ID NO:19:

| TTTTTATAA | CAAACGCAAA | TTAGTTAATA | AATTCTGGCG | CAGAACCGGC | ATTTGAGCG | 59 |
|---|---|---|---|---|---|---|

| ATG | GAA | ACG | CAA | CCT | GAG | GTG | CCC | GAG | GTG | CCG | CTG | CGA | CCG | TTT | AAA | 107 |
|---|---|---|---|---|---|---|---|---|---|---|---|---|---|---|---|---|
| Met<br>1 | Glu | Thr | Gln | Pro<br>5 | Glu | Val | Pro | Glu | Val<br>10 | Pro | Leu | Arg | Pro | Phe<br>15 | Lys | |

| TTG | GCG | CAT | CAG | GTT | GTG | AGC | CTC | ACG | GGC | ATC | AGT | TTC | GAG | CGG | AGG | 155 |
|---|---|---|---|---|---|---|---|---|---|---|---|---|---|---|---|---|
| Leu | Ala | His | Gln<br>20 | Val | Val | Ser | Leu | Thr<br>25 | Gly | Ile | Ser | Phe | Glu<br>30 | Arg | Arg | |

| AGC | ATA | ATC | GGC | GTG | GTC | GAG | CTG | ACC | ATT | GTG | CCG | AAC | AGC | GAG | AAT | 203 |
|---|---|---|---|---|---|---|---|---|---|---|---|---|---|---|---|---|
| Ser | Ile | Ile<br>35 | Gly | Val | Val | Glu | Leu<br>40 | Thr | Ile | Val | Pro | Asn<br>45 | Ser | Glu | Asn | |

| CTG | CGC | CTG | ATA | AGC | CTG | AAT | GCC | AAG | CAG | CTG | AGA | ATC | TAC | AGC | GTC | 251 |
|---|---|---|---|---|---|---|---|---|---|---|---|---|---|---|---|---|
| Leu | Arg<br>50 | Leu | Ile | Ser | Leu | Asn<br>55 | Ala | Lys | Gln | Leu | Arg<br>60 | Ile | Tyr | Ser | Val | |

| GTT | TTG | AAC | GAT | GTC | TGC | CAG | GCG | GAT | TTC | ACG | TAC | TTC | GAT | CCC | TTC | 299 |
|---|---|---|---|---|---|---|---|---|---|---|---|---|---|---|---|---|
| Val<br>65 | Leu | Asn | Asp | Val<br>70 | Cys | Gln | Ala | Asp | Phe<br>75 | Thr | Tyr | Phe | Asp | Pro<br>80 | Phe | |

| CAG | AAC | ATC | TGC | TAC | AAG | GAG | CCC | AAG | AGC | CGC | GCT | CTG | GAG | GTC | TAC | 347 |
|---|---|---|---|---|---|---|---|---|---|---|---|---|---|---|---|---|
| Gln | Asn | Ile | Cys | Tyr<br>85 | Lys | Glu | Pro | Lys | Ser<br>90 | Arg | Ala | Leu | Glu | Val<br>95 | Tyr | |

| TCC | AAG | CAT | CAT | CTG | ACC | GCC | GCT | CAG | TAC | ACC | GAT | CCC | GAT | GTG | AAC | 395 |
|---|---|---|---|---|---|---|---|---|---|---|---|---|---|---|---|---|
| Ser | Lys | His | His<br>100 | Leu | Thr | Ala | Ala | Gln<br>105 | Tyr | Thr | Asp | Pro | Asp<br>110 | Val | Asn | |

| AAC | GGC | GAA | CTG | CTC | ATC | CAG | GTT | CCG | CCC | GAG | GGC | TAC | TCT | ATG | ATC | 443 |
|---|---|---|---|---|---|---|---|---|---|---|---|---|---|---|---|---|
| Asn | Gly | Glu<br>115 | Leu | Leu | Ile | Gln | Val<br>120 | Pro | Pro | Glu | Gly | Tyr<br>125 | Ser | Met | Ile | |

| CAG | GAG | GGT | CAG | GGT | CTG | CGC | ATC | CGC | ATT | GAG | TTC | TCG | TTG | GAG | AAT | 491 |
|---|---|---|---|---|---|---|---|---|---|---|---|---|---|---|---|---|
| Gln | Glu | Gly<br>130 | Gln | Gly | Leu | Arg | Ile<br>135 | Arg | Ile | Glu | Phe | Ser<br>140 | Leu | Glu | Asn | |

| | | | | | | | | | | | | | | | | |
|---|---|---|---|---|---|---|---|---|---|---|---|---|---|---|---|---|
| CCC | AAA | TGC | GGC | GTA | CAT | TTT | GTC | ATA | CCA | CCC | GCT | TCA | ACG | GAC | GAG | 539 |
| Pro | Lys | Cys | Gly | Val | His | Phe | Val | Ile | Pro | Pro | Ala | Ser | Thr | Asp | Glu | |
| 145 | | | | 150 | | | | | 155 | | | | | 160 | | |
| GAG | ACA | CAG | ATG | AAC | AGC | TCG | CAT | ATG | TTC | ACC | AAT | TGC | TAT | GAA | AAC | 587 |
| Glu | Thr | Gln | Met | Asn | Ser | Ser | His | Met | Phe | Thr | Asn | Cys | Tyr | Glu | Asn | |
| | | | | 165 | | | | | 170 | | | | | 175 | | |
| TCG | TCG | AGA | TTG | TGG | TTT | CCC | TGC | GTG | GAC | AGT | TTC | GCC | GAT | CCC | TGC | 635 |
| Ser | Ser | Arg | Leu | Trp | Phe | Pro | Cys | Val | Asp | Ser | Phe | Ala | Asp | Pro | Cys | |
| | | | 180 | | | | | 185 | | | | | 190 | | | |
| ACC | TGG | CGG | CTG | GAG | TTC | ACT | GTC | GAC | AAA | AAT | ATG | ACC | GCC | GTT | TCG | 683 |
| Thr | Trp | Arg | Leu | Glu | Phe | Thr | Val | Asp | Lys | Asn | Met | Thr | Ala | Val | Ser | |
| | | | 195 | | | | | 200 | | | | | 205 | | | |
| TGT | GGA | GAA | CTT | CTA | GAA | GTC | ATT | ATG | ACC | CCA | GAT | CTG | CGA | AAG | AAA | 731 |
| Cys | Gly | Glu | Leu | Leu | Glu | Val | Ile | Met | Thr | Pro | Asp | Leu | Arg | Lys | Lys | |
| 210 | | | | | 215 | | | | | 220 | | | | | | |
| ACC | TTC | CAC | TAT | TCG | GTT | AGC | ACA | CCA | GTA | TGT | GCA | CCA | AAT | ATT | GCG | 779 |
| Thr | Phe | His | Tyr | Ser | Val | Ser | Thr | Pro | Val | Cys | Ala | Pro | Asn | Ile | Ala | |
| 225 | | | | | 230 | | | | | 235 | | | | | 240 | |
| CTG | GCT | GTG | GGT | CAG | TTT | GAG | ATC | TAC | GTG | GAT | CCG | CAC | ATG | CAT | GAA | 827 |
| Leu | Ala | Val | Gly | Gln | Phe | Glu | Ile | Tyr | Val | Asp | Pro | His | Met | His | Glu | |
| | | | | 245 | | | | | 250 | | | | | 255 | | |
| GTG | ACC | CAC | TTT | TGT | CTG | CCC | GGA | TTG | TTG | CCG | CTG | TTA | AAA | AAT | ACG | 875 |
| Val | Thr | His | Phe | Cys | Leu | Pro | Gly | Leu | Leu | Pro | Leu | Leu | Lys | Asn | Thr | |
| | | | 260 | | | | | 265 | | | | | 270 | | | |
| GTT | CGC | TAT | TTG | CAC | GAG | GCA | TTT | GAA | TTT | TAC | GAG | GAG | ACC | TTA | TCT | 923 |
| Val | Arg | Tyr | Leu | His | Glu | Ala | Phe | Glu | Phe | Tyr | Glu | Glu | Thr | Leu | Ser | |
| | | 275 | | | | | 280 | | | | | 285 | | | | |
| ACG | CGC | TAC | CCA | TTC | AGT | TGC | TAC | AAA | CAA | GTG | TTT | GTA | GAC | GAA | TTG | 971 |
| Thr | Arg | Tyr | Pro | Phe | Ser | Cys | Tyr | Lys | Gln | Val | Phe | Val | Asp | Glu | Leu | |
| | 290 | | | | | 295 | | | | | 300 | | | | | |
| GAC | ACG | GAC | ATA | AGT | GCC | TAT | GCC | ACT | ATG | AGC | ATT | GCT | TCG | GTG | AAC | 1019 |
| Asp | Thr | Asp | Ile | Ser | Ala | Tyr | Ala | Thr | Met | Ser | Ile | Ala | Ser | Val | Asn | |
| 305 | | | | 310 | | | | | 315 | | | | | 320 | | |
| CTG | CTG | CAC | TCC | ATA | GCT | ATC | ATC | GAT | CAG | ACC | TAT | ATA | TCT | CGA | ACC | 1067 |
| Leu | Leu | His | Ser | Ile | Ala | Ile | Ile | Asp | Gln | Thr | Tyr | Ile | Ser | Arg | Thr | |
| | | | | 325 | | | | | 330 | | | | | 335 | | |
| TTT | ATG | TCG | CGC | GCT | GTG | GCT | GAG | CAA | TTC | TTC | GGC | TGC | TTT | ATT | ACA | 1115 |
| Phe | Met | Ser | Arg | Ala | Val | Ala | Glu | Gln | Phe | Phe | Gly | Cys | Phe | Ile | Thr | |
| | | | 340 | | | | | 345 | | | | | 350 | | | |
| TCG | CAT | CAT | TGG | TCG | GAC | ACC | TGG | CTG | GCC | AAG | GGC | ATT | GCG | GAG | TAC | 1163 |
| Ser | His | His | Trp | Ser | Asp | Thr | Trp | Leu | Ala | Lys | Gly | Ile | Ala | Glu | Tyr | |
| | | 355 | | | | | 360 | | | | | 365 | | | | |
| CTG | TGT | GGA | TTG | TAT | TCC | AGG | AAG | TGC | TTC | GGC | AAC | AAC | GAG | TAC | CGT | 1211 |
| Leu | Cys | Gly | Leu | Tyr | Ser | Arg | Lys | Cys | Phe | Gly | Asn | Asn | Glu | Tyr | Arg | |
| | 370 | | | | | 375 | | | | | 380 | | | | | |
| GCT | TGG | GTG | CAA | TCT | GAA | CTG | GCG | CGT | GTC | GTT | CGC | TAC | GAG | GAG | CAG | 1259 |
| Ala | Trp | Val | Gln | Ser | Glu | Leu | Ala | Arg | Val | Val | Arg | Tyr | Glu | Glu | Gln | |
| 385 | | | | 390 | | | | | 395 | | | | | 400 | | |
| TAT | GGC | GGC | ATT | ATT | CTC | GAT | TGC | AGT | CAG | CCG | CCA | GCA | CCT | TTG | CCT | 1307 |
| Tyr | Gly | Gly | Ile | Ile | Leu | Asp | Cys | Ser | Gln | Pro | Pro | Ala | Pro | Leu | Pro | |
| | | | | 405 | | | | | 410 | | | | | 415 | | |
| GTT | TCG | GGC | ACA | AAT | CAA | TCG | GCT | GCT | TCC | AGC | AAA | CAG | CAG | GAG | ATT | 1355 |
| Val | Ser | Gly | Thr | Asn | Gln | Ser | Ala | Ala | Ser | Ser | Lys | Gln | Gln | Glu | Ile | |
| | | | 420 | | | | | 425 | | | | | 430 | | | |
| GTC | CAC | TAT | TTT | CCC | ATC | AAG | AGT | TTG | CAC | ACC | GTA | TCG | CCG | AAG | TAT | 1403 |
| Val | His | Tyr | Phe | Pro | Ile | Lys | Ser | Leu | His | Thr | Val | Ser | Pro | Lys | Tyr | |
| | | 435 | | | | | 440 | | | | | 445 | | | | |
| GTG | GAG | GCG | ATG | CGA | AGG | AAA | GCG | CAT | TTC | GTA | ATC | CGA | ATG | CTG | GAG | 1451 |
| Val | Glu | Ala | Met | Arg | Arg | Lys | Ala | His | Phe | Val | Ile | Arg | Met | Leu | Glu | |
| | 450 | | | | | 455 | | | | | 460 | | | | | |

| | | | | | | | | | | | | | | | | |
|---|---|---|---|---|---|---|---|---|---|---|---|---|---|---|---|---|
| AAC | CGC | ATC | GGG | CAG | GAG | CTG | CTG | ATT | CAG | GTG | TTC | AAT | AAG | CAA | TTG | 1499 |
| Asn | Arg | Ile | Gly | Gln | Glu | Leu | Leu | Ile | Gln | Val | Phe | Asn | Lys | Gln | Leu | |
| 465 | | | | 470 | | | | | 475 | | | | | 480 | | |
| GCT | TTG | GCT | TCT | AGT | GCG | GCA | ACG | ACG | AAG | ATC | GGT | GCA | GGA | CTC | TGG | 1547 |
| Ala | Leu | Ala | Ser | Ser | Ala | Ala | Thr | Thr | Lys | Ile | Gly | Ala | Gly | Leu | Trp | |
| | | | | 485 | | | | | 490 | | | | | 495 | | |
| TCT | CAG | CTG | CTC | ATC | TCG | ACC | AAC | ATT | TTT | ATC | AAG | GCC | ATC | TTC | ACC | 1595 |
| Ser | Gln | Leu | Leu | Ile | Ser | Thr | Asn | Ile | Phe | Ile | Lys | Ala | Ile | Phe | Thr | |
| | | | 500 | | | | | 505 | | | | | 510 | | | |
| GTA | ACC | GGA | AAA | GAT | ATG | TCT | GTC | TTC | ATG | GAC | CAG | TGG | GTG | CGC | ACT | 1643 |
| Val | Thr | Gly | Lys | Asp | Met | Ser | Val | Phe | Met | Asp | Gln | Trp | Val | Arg | Thr | |
| | | | 515 | | | | | 520 | | | | | 525 | | | |
| GGA | GGG | CAC | GCC | AAG | TTT | TCG | CTC | ACA | TCT | GTG | TTC | AAT | CGC | AAG | AGA | 1691 |
| Gly | Gly | His | Ala | Lys | Phe | Ser | Leu | Thr | Ser | Val | Phe | Asn | Arg | Lys | Arg | |
| | 530 | | | | | 535 | | | | | 540 | | | | | |
| AAC | ACG | ATT | GAA | CTG | GAA | ATC | CGC | CAG | GAC | TAT | GTT | AAT | CAG | CGG | GGA | 1739 |
| Asn | Thr | Ile | Glu | Leu | Glu | Ile | Arg | Gln | Asp | Tyr | Val | Asn | Gln | Arg | Gly | |
| 545 | | | | | 550 | | | | | 555 | | | | | 560 | |
| ATT | AGA | AAA | TAC | AAT | GGT | CCA | TTG | ATG | GTG | CAG | CTG | CAG | GAG | TTG | GAT | 1787 |
| Ile | Arg | Lys | Tyr | Asn | Gly | Pro | Leu | Met | Val | Gln | Leu | Gln | Glu | Leu | Asp | |
| | | | | 565 | | | | | 570 | | | | | 575 | | |
| GGA | ACG | TTT | AAG | CAC | ACA | TTG | CAG | ATT | GAG | AGT | ACC | CTG | GTA | AAG | TCC | 1835 |
| Gly | Thr | Phe | Lys | His | Thr | Leu | Gln | Ile | Glu | Ser | Thr | Leu | Val | Lys | Ser | |
| | | | 580 | | | | | 585 | | | | | 590 | | | |
| GAT | ATC | ACT | TGT | CAC | TCG | AAG | AGC | AGG | CGT | AAC | AAA | AAG | AAG | AAG | ATC | 1883 |
| Asp | Ile | Thr | Cys | His | Ser | Lys | Ser | Arg | Arg | Asn | Lys | Lys | Lys | Lys | Ile | |
| | | 595 | | | | | 600 | | | | | 605 | | | | |
| CCC | TTG | TGC | ACC | GGT | GAG | GAA | GTG | GAT | ATG | GAT | TTA | TCA | GCC | ATG | GAC | 1931 |
| Pro | Leu | Cys | Thr | Gly | Glu | Glu | Val | Asp | Met | Asp | Leu | Ser | Ala | Met | Asp | |
| 610 | | | | | 615 | | | | | 620 | | | | | | |
| GAC | TCA | CCT | GTG | CTT | TGG | ATC | CGC | CTC | GAT | CCC | GAA | ATG | ATT | CTG | CTG | 1979 |
| Asp | Ser | Pro | Val | Leu | Trp | Ile | Arg | Leu | Asp | Pro | Glu | Met | Ile | Leu | Leu | |
| 625 | | | | | 630 | | | | | 635 | | | | | 640 | |
| CGC | GAC | CTC | ATA | ATC | GAA | CAG | CCC | GAC | TTC | CAG | TGG | CAG | TAT | CAG | CTT | 2027 |
| Arg | Asp | Leu | Ile | Ile | Glu | Gln | Pro | Asp | Phe | Gln | Trp | Gln | Tyr | Gln | Leu | |
| | | | | 645 | | | | | 650 | | | | | 655 | | |
| CGG | CAT | GAA | CGT | GAT | GTT | ACT | GCT | CAA | TTT | CAG | GCG | ATT | CAA | GCC | CTG | 2075 |
| Arg | His | Glu | Arg | Asp | Val | Thr | Ala | Gln | Phe | Gln | Ala | Ile | Gln | Ala | Leu | |
| | | | 660 | | | | | 665 | | | | | 670 | | | |
| CAA | AAG | TAC | CCC | ACG | AAT | GCC | ACC | AGG | CTT | GCT | TTA | ACC | GAC | ACC | ATA | 2123 |
| Gln | Lys | Tyr | Pro | Thr | Asn | Ala | Thr | Arg | Leu | Ala | Leu | Thr | Asp | Thr | Ile | |
| | | 675 | | | | | 680 | | | | | 685 | | | | |
| GAA | AGC | GAA | CGT | TGC | TTC | TAT | CAG | GTG | CGC | TGC | GAG | GCA | GCC | CAC | AGC | 2171 |
| Glu | Ser | Glu | Arg | Cys | Phe | Tyr | Gln | Val | Arg | Cys | Glu | Ala | Ala | His | Ser | |
| | 690 | | | | | 695 | | | | | 700 | | | | | |
| TTG | ACC | AAA | GTG | GCC | AAC | CAG | ATG | GTG | GCC | TCC | TGG | AGT | GGA | CCG | CCC | 2219 |
| Leu | Thr | Lys | Val | Ala | Asn | Gln | Met | Val | Ala | Ser | Trp | Ser | Gly | Pro | Pro | |
| 705 | | | | | 710 | | | | | 715 | | | | | 720 | |
| GCC | ATG | CTG | AAC | ATA | TTT | AGG | AAG | TTT | TTC | GGC | TCA | TTT | AGT | GCT | CCG | 2267 |
| Ala | Met | Leu | Asn | Ile | Phe | Arg | Lys | Phe | Phe | Gly | Ser | Phe | Ser | Ala | Pro | |
| | | | | 725 | | | | | 730 | | | | | 735 | | |
| CAC | ATT | ATC | AAA | CTG | AAC | AAC | TTC | TCC | AAC | TTT | CAG | CTG | TAC | TTC | CTG | 2315 |
| His | Ile | Ile | Lys | Leu | Asn | Asn | Phe | Ser | Asn | Phe | Gln | Leu | Tyr | Phe | Leu | |
| | | | 740 | | | | | 745 | | | | | 750 | | | |
| CAG | AAG | GCT | ATT | CCC | GTA | GCC | ATG | GCA | GGT | CTG | CGC | ACA | TCT | CAT | GGT | 2363 |
| Gln | Lys | Ala | Ile | Pro | Val | Ala | Met | Ala | Gly | Leu | Arg | Thr | Ser | His | Gly | |
| | | 755 | | | | | 760 | | | | | 765 | | | | |
| ATT | TGC | CCG | CCG | GAA | GTG | ATG | CGT | TTT | CTT | TTC | GAT | CTC | TTC | AAG | TAC | 2411 |
| Ile | Cys | Pro | Pro | Glu | Val | Met | Arg | Phe | Leu | Phe | Asp | Leu | Phe | Lys | Tyr | |
| | 770 | | | | | 775 | | | | | 780 | | | | | |

| | | | | | | | | | | | | | | | | |
|---|---|---|---|---|---|---|---|---|---|---|---|---|---|---|---|---|
| AAC | GAG | AAT | TCG | CGT | AAC | CAT | TAC | ACG | GAT | GCA | TAC | TAC | AGG | GCA | GCT | 2459 |
| Asn | Glu | Asn | Ser | Arg | Asn | His | Tyr | Thr | Asp | Ala | Tyr | Tyr | Arg | Ala | Ala | |
| 785 | | | | | 790 | | | | 795 | | | | | | 800 | |
| TTG | GTA | GAA | GCT | CTA | GGC | GAA | ACC | TTA | ACA | CCT | GTG | GTC | TCC | GTT | GCT | 2507 |
| Leu | Val | Glu | Ala | Leu | Gly | Glu | Thr | Leu | Thr | Pro | Val | Val | Ser | Val | Ala | |
| | | | | 805 | | | | | 810 | | | | | 815 | | |
| ATC | CAT | GGC | ACA | CAA | ATC | ACT | ACG | GAC | AGT | CTA | TCC | ACG | GAT | GCG | AAA | 2555 |
| Ile | His | Gly | Thr | Gln | Ile | Thr | Thr | Asp | Ser | Leu | Ser | Thr | Asp | Ala | Lys | |
| | | | 820 | | | | | 825 | | | | | 830 | | | |
| CTT | GTG | CTA | GAT | GAA | GTT | ACA | CGT | CTG | CTG | AAC | ATG | GAG | AAA | CAT | CTA | 2603 |
| Leu | Val | Leu | Asp | Glu | Val | Thr | Arg | Leu | Leu | Asn | Met | Glu | Lys | His | Leu | |
| | | 835 | | | | | 840 | | | | | 845 | | | | |
| CCC | TCG | TAC | AAG | TAC | ATG | GTG | TCC | GTG | TCG | TGT | CTG | AAG | GTC | ATC | CGG | 2651 |
| Pro | Ser | Tyr | Lys | Tyr | Met | Val | Ser | Val | Ser | Cys | Leu | Lys | Val | Ile | Arg | |
| | 850 | | | | | 855 | | | | | 860 | | | | | |
| AAG | CTG | CAA | AAA | TTC | GGT | CAT | CTG | CCC | TCA | CTG | CCG | CAC | ATT | TAC | CGC | 2699 |
| Lys | Leu | Gln | Lys | Phe | Gly | His | Leu | Pro | Ser | Leu | Pro | His | Ile | Tyr | Arg | |
| 865 | | | | | 870 | | | | | 875 | | | | | 880 | |
| AGC | TAT | GCC | GAA | TAT | GGA | ATA | TAT | CTC | GAT | CTC | CGC | ATT | GCT | GCT | ATG | 2747 |
| Ser | Tyr | Ala | Glu | Tyr | Gly | Ile | Tyr | Leu | Asp | Leu | Arg | Ile | Ala | Ala | Met | |
| | | | | 885 | | | | | 890 | | | | | 895 | | |
| GAG | TGT | CTC | GTG | GAC | TTT | GTG | AAA | GTG | GAT | GGG | CGC | AGC | GAG | GAT | TTG | 2795 |
| Glu | Cys | Leu | Val | Asp | Phe | Val | Lys | Val | Asp | Gly | Arg | Ser | Glu | Asp | Leu | |
| | | | 900 | | | | | 905 | | | | | 910 | | | |
| GAA | CAT | TTG | ATT | ACT | CTG | CTG | GAA | ACT | GAT | CCG | GAT | CCG | GCT | GCT | CGC | 2843 |
| Glu | His | Leu | Ile | Thr | Leu | Leu | Glu | Thr | Asp | Pro | Asp | Pro | Ala | Ala | Arg | |
| | | 915 | | | | | 920 | | | | | 925 | | | | |
| CAT | GCA | CTG | GCC | CAA | CTG | CTG | ATC | GAT | AAT | CCG | CCT | TTC | ACA | CGC | GAA | 2891 |
| His | Ala | Leu | Ala | Gln | Leu | Leu | Ile | Asp | Asn | Pro | Pro | Phe | Thr | Arg | Glu | |
| | | 930 | | | | | 935 | | | | | 940 | | | | |
| TCT | CGC | AGC | CGT | CTG | GAT | AAA | CCC | AAT | CTC | GTG | GAT | CGT | CTA | TGG | TTC | 2939 |
| Ser | Arg | Ser | Arg | Leu | Asp | Lys | Pro | Asn | Leu | Val | Asp | Arg | Leu | Trp | Phe | |
| 945 | | | | | 950 | | | | | 955 | | | | | 960 | |
| AGT | ATT | AAC | CGC | TTG | CCC | TAC | GAT | ACC | AAG | CTG | CGC | TGC | GAT | ATT | GTC | 2987 |
| Ser | Ile | Asn | Arg | Leu | Pro | Tyr | Asp | Thr | Lys | Leu | Arg | Cys | Asp | Ile | Val | |
| | | | | 965 | | | | | 970 | | | | | 975 | | |
| GAT | CTG | TAC | TAC | GCA | CTG | TAC | GGA | ACT | AAG | CGT | CCG | AAT | TGC | TTG | CAG | 3035 |
| Asp | Leu | Tyr | Tyr | Ala | Leu | Tyr | Gly | Thr | Lys | Arg | Pro | Asn | Cys | Leu | Gln | |
| | | | 980 | | | | | 985 | | | | | 990 | | | |
| GCC | GGC | GAG | AAC | CAA | AGC | TTC | TAC | AAG | GAT | TTG | ATG | AAG | GAC | AAT | AAT | 3083 |
| Ala | Gly | Glu | Asn | Gln | Ser | Phe | Tyr | Lys | Asp | Leu | Met | Lys | Asp | Asn | Asn | |
| | | 995 | | | | | 1000 | | | | | 1005 | | | | |
| AGC | AGT | GTA | GGC | AGC | GTA | ACC | GGC | AGC | TTC | AAG | AAG | ACC | AGT | GAT | TCA | 3131 |
| Ser | Ser | Val | Gly | Ser | Val | Thr | Gly | Ser | Phe | Lys | Lys | Thr | Ser | Asp | Ser | |
| | | 1010 | | | | | 1015 | | | | | 1020 | | | | |
| AAG | TCA | CAT | TTG | CCA | ACA | CCA | ACG | AAT | ACT | TTG | GAC | AAT | GAG | CCA | CAG | 3179 |
| Lys | Ser | His | Leu | Pro | Thr | Pro | Thr | Asn | Thr | Leu | Asp | Asn | Glu | Pro | Gln | |
| 1025 | | | | | 1030 | | | | | 1035 | | | | | 1040 | |
| GAG | CGG | CAA | AAG | CCG | GCA | ATG | GTT | ACC | ATC | AAG | CGA | ACG | GCC | ACA | GAA | 3227 |
| Glu | Arg | Gln | Lys | Pro | Ala | Met | Val | Thr | Ile | Lys | Arg | Thr | Ala | Thr | Glu | |
| | | | | 1045 | | | | | 1050 | | | | | 1055 | | |
| GCA | TTT | GAG | GTG | GGC | GAT | GAG | ATT | ATC | AAG | CTG | GAA | CGC | AGC | GAG | GAG | 3275 |
| Ala | Phe | Glu | Val | Gly | Asp | Glu | Ile | Ile | Lys | Leu | Glu | Arg | Ser | Glu | Glu | |
| | | | | 1060 | | | | | 1065 | | | | | 1070 | | |
| ATC | ACC | GTG | CTA | GAT | GAA | CCA | GTT | AAC | GTG | CAG | GCC | TAT | GAC | AGT | GAG | 3323 |
| Ile | Thr | Val | Leu | Asp | Glu | Pro | Val | Asn | Val | Gln | Ala | Tyr | Asp | Ser | Glu | |
| | | | 1075 | | | | | 1080 | | | | | 1085 | | | |
| ACC | AAA | GTG | AAT | GCC | CTG | CAG | GCA | GAT | GAA | GAA | GCA | CGT | GAT | ACC | CAT | 3371 |
| Thr | Lys | Val | Asn | Ala | Leu | Gln | Ala | Asp | Glu | Glu | Ala | Arg | Asp | Thr | His | |
| | | | 1090 | | | | | 1095 | | | | | 1100 | | | |

```
CAG GCT GCC AAG CGC CTT AAG AAC GAA ATG TAC GCC GAG GAT GAT AAC        3419
Gln Ala Ala Lys Arg Leu Lys Asn Glu Met Tyr Ala Glu Asp Asp Asn
1105                1110                1115                1120

TCA TCC ACA ATG CTC GAC GTG GGC GAC TCC ACC AGA TAT GAG AGT AGC        3467
Ser Ser Thr Met Leu Asp Val Gly Asp Ser Thr Arg Tyr Glu Ser Ser
            1125                1130                1135

CAC GAG GAG GGC AAA TTG AAG TCC GGC GAT GGT GGG CTC AAG AAG AAA        3515
His Glu Glu Gly Lys Leu Lys Ser Gly Asp Gly Gly Leu Lys Lys Lys
        1140                1145                1150

AAG AAG AAG GAG AAG AAG AAG CAT AAG CAC AAA CAC AAG CAT AGG CAC        3563
Lys Lys Lys Glu Lys Lys Lys His Lys His Lys His Lys His Arg His
    1155                1160                1165

AGC AAG GAC AAG GAC AAG GAG CGA AAG GAT AAG GAC AAG CGT GAC CCG        3611
Ser Lys Asp Lys Asp Lys Glu Arg Lys Asp Lys Asp Lys Arg Asp Pro
1170                1175                1180

CAT ATA TCA CGC CTG CAG GCC GCG AGA CAG CCA CTC CGG ACA CTC TCA        3659
His Ile Ser Arg Leu Gln Ala Ala Arg Gln Pro Leu Arg Thr Leu Ser
1185                1190                1195                1200

GCT CGG AGG ACA GTA GCA ACA GCA ATA GCC TGC CGC CCA TGAACCTTAA         3708
Ala Arg Arg Thr Val Ala Thr Ala Ile Ala Cys Arg Pro
                1205                1210

CTAAGTGAGG GTTCCTACAG GTGGGGAAAT TGCAATGTTT GGGGGATAGA TGACAGAATA     3768

AAGGTATAAT ACCTTAAAAA AAAAAAAAAA AAAAAAAAA AAAA                        3812
```

( 2 ) INFORMATION FOR SEQ ID NO:20:

( i ) SEQUENCE CHARACTERISTICS:
        ( A ) LENGTH: 1213 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Met Glu Thr Gln Pro Glu Val Pro Glu Val Pro Leu Arg Pro Phe Lys
1               5                   10                  15

Leu Ala His Gln Val Val Ser Leu Thr Gly Ile Ser Phe Glu Arg Arg
            20                  25                  30

Ser Ile Ile Gly Val Val Glu Leu Thr Ile Val Pro Asn Ser Glu Asn
        35                  40                  45

Leu Arg Leu Ile Ser Leu Asn Ala Lys Gln Leu Arg Ile Tyr Ser Val
    50                  55                  60

Val Leu Asn Asp Val Cys Gln Ala Asp Phe Thr Tyr Phe Asp Pro Phe
65                  70                  75                  80

Gln Asn Ile Cys Tyr Lys Glu Pro Lys Ser Arg Ala Leu Glu Val Tyr
                85                  90                  95

Ser Lys His His Leu Thr Ala Ala Gln Tyr Thr Asp Pro Asp Val Asn
            100                 105                 110

Asn Gly Glu Leu Leu Ile Gln Val Pro Pro Glu Gly Tyr Ser Met Ile
        115                 120                 125

Gln Glu Gly Gln Gly Leu Arg Ile Arg Ile Glu Phe Ser Leu Glu Asn
    130                 135                 140

Pro Lys Cys Gly Val His Phe Val Ile Pro Ala Ser Thr Asp Glu
145                 150                 155                 160

Glu Thr Gln Met Asn Ser Ser His Met Phe Thr Asn Cys Tyr Glu Asn
                165                 170                 175

Ser Ser Arg Leu Trp Phe Pro Cys Val Asp Ser Phe Ala Asp Pro Cys
            180                 185                 190
```

| | | | | | | | | | | | | | | | |
|---|---|---|---|---|---|---|---|---|---|---|---|---|---|---|---|
| Thr | Trp | Arg 195 | Leu | Glu | Phe | Thr | Val 200 | Asp | Lys | Asn | Met | Thr 205 | Ala | Val | Ser |
| Cys | Gly 210 | Glu | Leu | Leu | Glu | Val 215 | Ile | Met | Thr | Pro | Asp 220 | Leu | Arg | Lys | Lys |
| Thr 225 | Phe | His | Tyr | Ser | Val 230 | Ser | Thr | Pro | Val | Cys 235 | Ala | Pro | Asn | Ile | Ala 240 |
| Leu | Ala | Val | Gly | Gln 245 | Phe | Glu | Ile | Tyr | Val 250 | Asp | Pro | His | Met | His 255 | Glu |
| Val | Thr | His | Phe 260 | Cys | Leu | Pro | Gly | Leu 265 | Leu | Pro | Leu | Leu | Lys 270 | Asn | Thr |
| Val | Arg | Tyr 275 | Leu | His | Glu | Ala | Phe 280 | Glu | Phe | Tyr | Glu | Thr 285 | Leu | Ser |
| Thr | Arg 290 | Tyr | Pro | Phe | Ser | Cys 295 | Tyr | Lys | Gln | Val | Phe 300 | Val | Asp | Glu | Leu |
| Asp 305 | Thr | Asp | Ile | Ser | Ala 310 | Tyr | Ala | Thr | Met | Ser 315 | Ile | Ala | Ser | Val | Asn 320 |
| Leu | Leu | His | Ser | Ile 325 | Ala | Ile | Ile | Asp | Gln 330 | Thr | Tyr | Ile | Ser | Arg 335 | Thr |
| Phe | Met | Ser | Arg 340 | Ala | Val | Ala | Glu | Gln 345 | Phe | Phe | Gly | Cys | Phe 350 | Ile | Thr |
| Ser | His | His 355 | Trp | Ser | Asp | Thr | Trp 360 | Leu | Ala | Lys | Gly | Ile 365 | Ala | Glu | Tyr |
| Leu | Cys 370 | Gly | Leu | Tyr | Ser | Arg 375 | Lys | Cys | Phe | Gly | Asn 380 | Asn | Glu | Tyr | Arg |
| Ala 385 | Trp | Val | Gln | Ser | Glu 390 | Leu | Ala | Arg | Val | Val 395 | Arg | Tyr | Glu | Glu | Gln 400 |
| Tyr | Gly | Gly | Ile | Ile 405 | Leu | Asp | Cys | Ser | Gln 410 | Pro | Pro | Ala | Pro | Leu 415 | Pro |
| Val | Ser | Gly | Thr 420 | Asn | Gln | Ser | Ala | Ala 425 | Ser | Ser | Lys | Gln | Gln 430 | Glu | Ile |
| Val | His | Tyr 435 | Phe | Pro | Ile | Lys | Ser 440 | Leu | His | Thr | Val | Ser 445 | Pro | Lys | Tyr |
| Val | Glu 450 | Ala | Met | Arg | Arg | Lys 455 | Ala | His | Phe | Val | Ile 460 | Arg | Met | Leu | Glu |
| Asn 465 | Arg | Ile | Gly | Gln | Glu 470 | Leu | Leu | Ile | Gln | Val 475 | Phe | Asn | Lys | Gln | Leu 480 |
| Ala | Leu | Ala | Ser | Ser 485 | Ala | Ala | Thr | Thr | Lys 490 | Ile | Gly | Ala | Gly | Leu 495 | Trp |
| Ser | Gln | Leu | Leu 500 | Ile | Ser | Thr | Asn | Ile 505 | Phe | Ile | Lys | Ala | Ile 510 | Phe | Thr |
| Val | Thr | Gly 515 | Lys | Asp | Met | Ser | Val 520 | Phe | Met | Asp | Gln | Trp 525 | Val | Arg | Thr |
| Gly | Gly 530 | His | Ala | Lys | Phe | Ser 535 | Leu | Thr | Ser | Val | Phe 540 | Asn | Arg | Lys | Arg |
| Asn 545 | Thr | Ile | Glu | Leu | Glu 550 | Ile | Arg | Gln | Asp | Tyr 555 | Val | Asn | Gln | Arg | Gly 560 |
| Ile | Arg | Lys | Tyr | Asn 565 | Gly | Pro | Leu | Met | Val 570 | Gln | Leu | Gln | Glu | Leu 575 | Asp |
| Gly | Thr | Phe | Lys 580 | His | Thr | Leu | Gln | Ile 585 | Glu | Ser | Thr | Leu | Val 590 | Lys | Ser |
| Asp | Ile | Thr 595 | Cys | His | Ser | Lys | Ser 600 | Arg | Arg | Asn | Lys | Lys 605 | Lys | Lys | Ile |
| Pro | Leu | Cys | Thr | Gly | Glu | Glu | Val | Asp | Met | Asp | Leu | Ser | Ala | Met | Asp |

```
              610                        615                        620
Asp  Ser  Pro  Val  Leu  Trp  Ile  Arg  Leu  Asp  Pro  Glu  Met  Ile  Leu  Leu
625                      630                      635                      640
Arg  Asp  Leu  Ile  Ile  Glu  Gln  Pro  Asp  Phe  Gln  Trp  Gln  Tyr  Gln  Leu
                    645                      650                      655
Arg  His  Glu  Arg  Asp  Val  Thr  Ala  Gln  Phe  Gln  Ala  Ile  Gln  Ala  Leu
               660                      665                      670
Gln  Lys  Tyr  Pro  Thr  Asn  Ala  Thr  Arg  Leu  Ala  Leu  Thr  Asp  Thr  Ile
          675                      680                      685
Glu  Ser  Glu  Arg  Cys  Phe  Tyr  Gln  Val  Arg  Cys  Glu  Ala  Ala  His  Ser
     690                      695                      700
Leu  Thr  Lys  Val  Ala  Asn  Gln  Met  Val  Ala  Ser  Trp  Ser  Gly  Pro  Pro
705                      710                      715                      720
Ala  Met  Leu  Asn  Ile  Phe  Arg  Lys  Phe  Phe  Gly  Ser  Phe  Ser  Ala  Pro
                    725                      730                      735
His  Ile  Ile  Lys  Leu  Asn  Asn  Phe  Ser  Asn  Phe  Gln  Leu  Tyr  Phe  Leu
               740                      745                      750
Gln  Lys  Ala  Ile  Pro  Val  Ala  Met  Ala  Gly  Leu  Arg  Thr  Ser  His  Gly
          755                      760                      765
Ile  Cys  Pro  Pro  Glu  Val  Met  Arg  Phe  Leu  Phe  Asp  Leu  Phe  Lys  Tyr
     770                      775                      780
Asn  Glu  Asn  Ser  Arg  Asn  His  Tyr  Thr  Asp  Ala  Tyr  Tyr  Arg  Ala  Ala
785                      790                      795                      800
Leu  Val  Glu  Ala  Leu  Gly  Glu  Thr  Leu  Thr  Pro  Val  Val  Ser  Val  Ala
                    805                      810                      815
Ile  His  Gly  Thr  Gln  Ile  Thr  Thr  Asp  Ser  Leu  Ser  Thr  Asp  Ala  Lys
               820                      825                      830
Leu  Val  Leu  Asp  Glu  Val  Thr  Arg  Leu  Leu  Asn  Met  Glu  Lys  His  Leu
          835                      840                      845
Pro  Ser  Tyr  Lys  Tyr  Met  Val  Ser  Val  Ser  Cys  Leu  Lys  Val  Ile  Arg
     850                      855                      860
Lys  Leu  Gln  Lys  Phe  Gly  His  Leu  Pro  Ser  Leu  Pro  His  Ile  Tyr  Arg
865                      870                      875                      880
Ser  Tyr  Ala  Glu  Tyr  Gly  Ile  Tyr  Leu  Asp  Leu  Arg  Ile  Ala  Ala  Met
                    885                      890                      895
Glu  Cys  Leu  Val  Asp  Phe  Val  Lys  Val  Asp  Gly  Arg  Ser  Glu  Asp  Leu
               900                      905                      910
Glu  His  Leu  Ile  Thr  Leu  Leu  Glu  Thr  Asp  Pro  Asp  Pro  Ala  Ala  Arg
          915                      920                      925
His  Ala  Leu  Ala  Gln  Leu  Leu  Ile  Asp  Asn  Pro  Pro  Phe  Thr  Arg  Glu
     930                      935                      940
Ser  Arg  Ser  Arg  Leu  Asp  Lys  Pro  Asn  Leu  Val  Asp  Arg  Leu  Trp  Phe
945                      950                      955                      960
Ser  Ile  Asn  Arg  Leu  Pro  Tyr  Asp  Thr  Lys  Leu  Arg  Cys  Asp  Ile  Val
                    965                      970                      975
Asp  Leu  Tyr  Tyr  Ala  Leu  Tyr  Gly  Thr  Lys  Arg  Pro  Asn  Cys  Leu  Gln
               980                      985                      990
Ala  Gly  Glu  Asn  Gln  Ser  Phe  Tyr  Lys  Asp  Leu  Met  Lys  Asp  Asn  Asn
          995                      1000                     1005
Ser  Ser  Val  Gly  Ser  Val  Thr  Gly  Ser  Phe  Lys  Lys  Thr  Ser  Asp  Ser
     1010                     1015                     1020
Lys  Ser  His  Leu  Pro  Thr  Pro  Thr  Asn  Thr  Leu  Asp  Asn  Glu  Pro  Gln
1025                     1030                     1035                     1040
```

| | | | | | | | | | | | | | | |
|---|---|---|---|---|---|---|---|---|---|---|---|---|---|---|
| Glu | Arg | Gln | Lys | Pro | Ala | Met | Val | Thr | Ile | Lys | Arg | Thr | Ala | Thr | Glu |
| | | | | 1045 | | | | 1050 | | | | | 1055 | | |
| Ala | Phe | Glu | Val | Gly | Asp | Glu | Ile | Ile | Lys | Leu | Glu | Arg | Ser | Glu | Glu |
| | | | | 1060 | | | | 1065 | | | | | 1070 | | |
| Ile | Thr | Val | Leu | Asp | Glu | Pro | Val | Asn | Val | Gln | Ala | Tyr | Asp | Ser | Glu |
| | | | | 1075 | | | | 1080 | | | | | 1085 | | |
| Thr | Lys | Val | Asn | Ala | Leu | Gln | Ala | Asp | Glu | Glu | Ala | Arg | Asp | Thr | His |
| | | | | 1090 | | | | 1095 | | | | | 1100 | | |
| Gln | Ala | Ala | Lys | Arg | Leu | Lys | Asn | Glu | Met | Tyr | Ala | Glu | Asp | Asp | Asn |
| 1105 | | | | | 1110 | | | | 1115 | | | | | 1120 | |
| Ser | Ser | Thr | Met | Leu | Asp | Val | Gly | Asp | Ser | Thr | Arg | Tyr | Glu | Ser | Ser |
| | | | | 1125 | | | | 1130 | | | | | 1135 | | |
| His | Glu | Glu | Gly | Lys | Leu | Lys | Ser | Gly | Asp | Gly | Gly | Leu | Lys | Lys | Lys |
| | | | | 1140 | | | | 1145 | | | | | 1150 | | |
| Lys | Lys | Lys | Glu | Lys | Lys | Lys | His | Lys | His | Lys | His | Lys | His | Arg | His |
| | | | | 1155 | | | | 1160 | | | | | 1165 | | |
| Ser | Lys | Asp | Lys | Asp | Lys | Glu | Arg | Lys | Asp | Lys | Asp | Lys | Arg | Asp | Pro |
| | | | | 1170 | | | | 1175 | | | | | 1180 | | |
| His | Ile | Ser | Arg | Leu | Gln | Ala | Ala | Arg | Gln | Pro | Leu | Arg | Thr | Leu | Ser |
| 1185 | | | | | 1190 | | | | 1195 | | | | | 1200 | |
| Ala | Arg | Arg | Thr | Val | Ala | Thr | Ala | Ile | Ala | Cys | Arg | Pro | | | |
| | | | | 1205 | | | | 1210 | | | | | | | |

( 2 ) INFORMATION FOR SEQ ID NO:21:

( i ) SEQUENCE CHARACTERISTICS:
        ( A ) LENGTH: 872 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 96..686

( x i ) SEQUENCE DESCRIPTION: SEQ ID NO:21:

```
CCAAAAATCC  GCCCAACTTA  CTGTACTTTC  CCCAAACACT  TCCAACCAAC  CGACCTACCA           60

CCCACTTGAT  TTGACTCTGA  AGAAACCCAA  AAGCA ATG TCG GAT CTC TTT ACC               113
                                         Met Ser Asp Leu Phe Thr
                                          1               5

ACT TTC GAT AGC AAC GGC GTC GCG AGG CAC CAC CTG CAC CAC AAC CAC                  161
Thr Phe Asp Ser Asn Gly Val Ala Arg His His Leu His His Asn His
            10                  15                  20

AAC TCC ACA TCG TCC GCC AGC GGA CTG CTC CAC GAC CCA CCC ATG GCC                  209
Asn Ser Thr Ser Ser Ala Ser Gly Leu Leu His Asp Pro Pro Met Ala
        25                  30                  35

TCG CCC TCC CAG CAC AGT CCG ATG ACC AAC AAC AGC AAC TCA TCC TCG                  257
Ser Pro Ser Gln His Ser Pro Met Thr Asn Asn Ser Asn Ser Ser Ser
    40                  45                  50

CAG AAC GGC GGA CCG GTT TCC GGT TTG GGT ACG GGA ACG GGC CCC ATA                  305
Gln Asn Gly Gly Pro Val Ser Gly Leu Gly Thr Gly Thr Gly Pro Ile
 55                  60                  65                  70

TCT GGT GGT AGC AAG TCA TCC AAT CAC ACA TCA TCC GCC GCC GGT TCC                  353
Ser Gly Gly Ser Lys Ser Ser Asn His Thr Ser Ser Ala Ala Gly Ser
                75                  80                  85

GAG AAC ACT CCC ATG CTT ACC AAA CCG CGT CTC ACA GAG CTC GTC CGA                  401
Glu Asn Thr Pro Met Leu Thr Lys Pro Arg Leu Thr Glu Leu Val Arg
            90                  95                 100
```

| | | | | | | | | | | | | | | | |
|---|---|---|---|---|---|---|---|---|---|---|---|---|---|---|---|
| GAG | GTG | GAT | ACC | ACC | ACG | CAG | CTG | GAC | GAG | GAT | GTT | GAG | GAG | CTT | CTG | 449
| Glu | Val | Asp | Thr | Thr | Thr | Gln | Leu | Asp | Glu | Asp | Val | Glu | Glu | Leu | Leu |
| | | 105 | | | | | 110 | | | | 115 | | | | |
| CTT | CAG | ATC | ATC | GAC | GAC | TTT | GTG | AGG | GAC | ACC | GTC | AAG | TCG | ACG | AGC | 497
| Leu | Gln | Ile | Ile | Asp | Asp | Phe | Val | Arg | Asp | Thr | Val | Lys | Ser | Thr | Ser |
| | 120 | | | | | 125 | | | | | 130 | | | | |
| GCC | TTC | GCC | AAG | CAC | CGA | AAG | TCT | AAC | AAG | ATC | GAG | GTG | CGC | GAC | GTG | 545
| Ala | Phe | Ala | Lys | His | Arg | Lys | Ser | Asn | Lys | Ile | Glu | Val | Arg | Asp | Val |
| 135 | | | | | 140 | | | | 145 | | | | | | 150 |
| CAG | CTG | CAC | TTT | GAG | CGG | AAG | TAC | AAC | ATG | TGG | ATA | CCC | GGC | TTC | GGT | 593
| Gln | Leu | His | Phe | Glu | Arg | Lys | Tyr | Asn | Met | Trp | Ile | Pro | Gly | Phe | Gly |
| | | | | 155 | | | | | 160 | | | | | 165 | |
| ACG | GAC | GAA | CTG | CGT | CCC | TAC | AAG | CGG | GCA | GCT | GTC | ACG | GAG | GCG | CAC | 641
| Thr | Asp | Glu | Leu | Arg | Pro | Tyr | Lys | Arg | Ala | Ala | Val | Thr | Glu | Ala | His |
| | | | 170 | | | | | 175 | | | | | 180 | | |
| AAA | CAG | CGC | CTT | GCC | CTC | ATA | CGG | AAA | ACG | ATC | AAG | AAA | TAC | TAGAGGATTG | | 693
| Lys | Gln | Arg | Leu | Ala | Leu | Ile | Arg | Lys | Thr | Ile | Lys | Lys | Tyr | | |
| | | 185 | | | | | 190 | | | | | 195 | | | |

```
GATCTAATCG GGTCGAGGCT CTGTTTCGGT TTGCCGGATT TCGCGTATGC TAAACGTGCA     753

CACGCCACAA ACTAATTTAA GCTCCAATTT AGATTAAATA ACAAATTATC GTCGCTCTAT     813

TGTAGATTTA TTGTAATAAA AGTGCACTAT TGATTTCACA TTCAAAAAAA AAAAAAAA      872
```

( 2 ) INFORMATION FOR SEQ ID NO:22:

( i ) SEQUENCE CHARACTERISTICS:
        ( A ) LENGTH: 196 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Met  Ser  Asp  Leu  Phe  Thr  Thr  Phe  Asp  Ser  Asn  Gly  Val  Ala  Arg  His
 1              5                   10                  15

His  Leu  His  His  Asn  His  Asn  Ser  Thr  Ser  Ser  Ala  Ser  Gly  Leu  Leu
              20                  25                  30

His  Asp  Pro  Pro  Met  Ala  Ser  Pro  Ser  Gln  His  Ser  Pro  Met  Thr  Asn
             35                  40                  45

Asn  Ser  Asn  Ser  Ser  Ser  Gln  Asn  Gly  Gly  Pro  Val  Ser  Gly  Leu  Gly
     50                  55                      60

Thr  Gly  Thr  Gly  Pro  Ile  Ser  Gly  Gly  Ser  Lys  Ser  Ser  Asn  His  Thr
65                   70                  75                              80

Ser  Ser  Ala  Ala  Gly  Ser  Glu  Asn  Thr  Pro  Met  Leu  Thr  Lys  Pro  Arg
                 85                  90                  95

Leu  Thr  Glu  Leu  Val  Arg  Glu  Val  Asp  Thr  Thr  Thr  Gln  Leu  Asp  Glu
         100                 105                 110

Asp  Val  Glu  Glu  Leu  Leu  Leu  Gln  Ile  Ile  Asp  Asp  Phe  Val  Arg  Asp
         115                 120                 125

Thr  Val  Lys  Ser  Thr  Ser  Ala  Phe  Ala  Lys  His  Arg  Lys  Ser  Asn  Lys
     130                 135                 140

Ile  Glu  Val  Arg  Asp  Val  Gln  Leu  His  Phe  Glu  Arg  Lys  Tyr  Asn  Met
145                  150                 155                         160

Trp  Ile  Pro  Gly  Phe  Gly  Thr  Asp  Glu  Leu  Arg  Pro  Tyr  Lys  Arg  Ala
                 165                 170                 175

Ala  Val  Thr  Glu  Ala  His  Lys  Gln  Arg  Leu  Ala  Leu  Ile  Arg  Lys  Thr
             180                 185                 190

Ile  Lys  Lys  Tyr
         195
```

( 2 ) INFORMATION FOR SEQ ID NO:23:

( i ) SEQUENCE CHARACTERISTICS:
        ( A ) LENGTH: 738 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 31..624

( x i ) SEQUENCE DESCRIPTION: SEQ ID NO:23:

```
CCCCCCCCCC CCCCCCCCGA TTTTTTTAA ATG GAC GAA ATC CTC TTT CCC ACG         54
                                 Met Asp Glu Ile Leu Phe Pro Thr
                                  1               5

CAG CAA AAG AGC AAC TCC CTA AGC GAC GGC GAC GAT GTC GAC CTG AAA        102
Gln Gln Lys Ser Asn Ser Leu Ser Asp Gly Asp Asp Val Asp Leu Lys
         10              15                  20

TTC TTC CAG TCG GGC CTC CGG GGG AGG CGA AAG GAC AGC GAC ACC TCG        150
Phe Phe Gln Ser Gly Leu Arg Gly Arg Arg Lys Asp Ser Asp Thr Ser
 25              30                  35                      40

GAT CCG GGA AAC GAT GCG GAT CGT GAT GGC AAA GAT GCG GAT GGG GAC        198
Asp Pro Gly Asn Asp Ala Asp Arg Asp Gly Lys Asp Ala Asp Gly Asp
                 45                  50                  55

AAC GAC AAC AAG AAC ACG GAC GGA GAT GGT GAC TCT GGC GAG CCG GCG        246
Asn Asp Asn Lys Asn Thr Asp Gly Asp Gly Asp Ser Gly Glu Pro Ala
             60                  65                  70

CAC AAA AAG CTC AAA ACC AAG AAG GAA CTG GAG GAG GAG GAG CGC GAA        294
His Lys Lys Leu Lys Thr Lys Lys Glu Leu Glu Glu Glu Glu Arg Glu
         75                  80                  85

CGA ATG CAG GTT CTC GTT TCC AAC TTT ACT GAA GAA CAG CTG GAT CGC        342
Arg Met Gln Val Leu Val Ser Asn Phe Thr Glu Glu Gln Leu Asp Arg
 90                  95                 100

TAC GAA ATG TAT CGT CGC TCA GCC TTT CCC AAG GCC GCC GTC AAG CGT        390
Tyr Glu Met Tyr Arg Arg Ser Ala Phe Pro Lys Ala Ala Val Lys Arg
105              110                 115                     120

CTA ATG CAA ACT ATC ACC GGC TGT TCC GTG TCC CAA AAT GTT GTG ATA        438
Leu Met Gln Thr Ile Thr Gly Cys Ser Val Ser Gln Asn Val Val Ile
                 125                 130                 135

GCC ATG TCC GGC ATT GCG AAG GTC TTC GTC GGC GAG GTT GTG GAG GAA        486
Ala Met Ser Gly Ile Ala Lys Val Phe Val Gly Glu Val Val Glu Glu
             140                 145                 150

GCC CTC GAC GTG ATG GAG GCC CAA GGT GAA TCC GGT GCC CTG CAG CCC        534
Ala Leu Asp Val Met Glu Ala Gln Gly Glu Ser Gly Ala Leu Gln Pro
         155                 160                 165

AAA TTC ATA CGA GAG GCA GTG CGA CGA CTG AGG ACC AAG GAT CGG ATG        582
Lys Phe Ile Arg Glu Ala Val Arg Arg Leu Arg Thr Lys Asp Arg Met
170                 175                 180

CCC ATA GGC AGA TAC CAG CAG CCC TAT TTC AGA CTG AAC TAGCGAGTCG         631
Pro Ile Gly Arg Tyr Gln Gln Pro Tyr Phe Arg Leu Asn
185                 190                 195

AGACATTAAG AAATATAGTT TGTAAATCTG TTAGTGAATA TAAAAATACA TAAACAAGTA      691

AAAAGTAAAT AAATATAAAG ATTTTTCAA GAAAAAAAAA AAAAAA                      738
```

( 2 ) INFORMATION FOR SEQ ID NO:24:

( i ) SEQUENCE CHARACTERISTICS:
        ( A ) LENGTH: 197 amino acids
        ( B ) TYPE: amino acid ( D ) TOPOLOGY: linear ( i i ) MOLECULE TYPE: protein ( x i ) SEQUENCE DESCRIPTION: SEQ ID NO:24:

| Met | Asp | Glu | Ile | Leu | Phe | Pro | Thr | Gln | Gln | Lys | Ser | Asn | Ser | Leu | Ser |
|---|---|---|---|---|---|---|---|---|---|---|---|---|---|---|---|
| 1 | | | | 5 | | | | | 10 | | | | | 15 | |

| Asp | Gly | Asp | Asp | Val | Asp | Leu | Lys | Phe | Phe | Gln | Ser | Gly | Leu | Arg | Gly |
|---|---|---|---|---|---|---|---|---|---|---|---|---|---|---|---|
| | | | 20 | | | | | 25 | | | | | 30 | | |

| Arg | Arg | Lys | Asp | Ser | Asp | Thr | Ser | Asp | Pro | Gly | Asn | Asp | Ala | Asp | Arg |
|---|---|---|---|---|---|---|---|---|---|---|---|---|---|---|---|
| | | 35 | | | | | 40 | | | | | 45 | | | |

| Asp | Gly | Lys | Asp | Ala | Asp | Gly | Asp | Asn | Asp | Asn | Lys | Asn | Thr | Asp | Gly |
|---|---|---|---|---|---|---|---|---|---|---|---|---|---|---|---|
| | 50 | | | | | 55 | | | | | 60 | | | | |

| Asp | Gly | Asp | Ser | Gly | Glu | Pro | Ala | His | Lys | Lys | Leu | Lys | Thr | Lys | Lys |
|---|---|---|---|---|---|---|---|---|---|---|---|---|---|---|---|
| 65 | | | | | 70 | | | | | 75 | | | | | 80 |

| Glu | Leu | Glu | Glu | Glu | Glu | Arg | Glu | Arg | Met | Gln | Val | Leu | Val | Ser | Asn |
|---|---|---|---|---|---|---|---|---|---|---|---|---|---|---|---|
| | | | | 85 | | | | | 90 | | | | | 95 | |

| Phe | Thr | Glu | Glu | Gln | Leu | Asp | Arg | Tyr | Glu | Met | Tyr | Arg | Arg | Ser | Ala |
|---|---|---|---|---|---|---|---|---|---|---|---|---|---|---|---|
| | | | 100 | | | | | 105 | | | | | 110 | | |

| Phe | Pro | Lys | Ala | Ala | Val | Lys | Arg | Leu | Met | Gln | Thr | Ile | Thr | Gly | Cys |
|---|---|---|---|---|---|---|---|---|---|---|---|---|---|---|---|
| | | 115 | | | | | 120 | | | | | 125 | | | |

| Ser | Val | Ser | Gln | Asn | Val | Val | Ile | Ala | Met | Ser | Gly | Ile | Ala | Lys | Val |
|---|---|---|---|---|---|---|---|---|---|---|---|---|---|---|---|
| | 130 | | | | | 135 | | | | | 140 | | | | |

| Phe | Val | Gly | Glu | Val | Val | Glu | Glu | Ala | Leu | Asp | Val | Met | Glu | Ala | Gln |
|---|---|---|---|---|---|---|---|---|---|---|---|---|---|---|---|
| 145 | | | | | 150 | | | | | 155 | | | | | 160 |

| Gly | Glu | Ser | Gly | Ala | Leu | Gln | Pro | Lys | Phe | Ile | Arg | Glu | Ala | Val | Arg |
|---|---|---|---|---|---|---|---|---|---|---|---|---|---|---|---|
| | | | | 165 | | | | | 170 | | | | | 175 | |

| Arg | Leu | Arg | Thr | Lys | Asp | Arg | Met | Pro | Ile | Gly | Arg | Tyr | Gln | Gln | Pro |
|---|---|---|---|---|---|---|---|---|---|---|---|---|---|---|---|
| | | | 180 | | | | | 185 | | | | | 190 | | |

| Tyr | Phe | Arg | Leu | Asn |
|---|---|---|---|---|
| | | | | 195 |

( 2 ) INFORMATION FOR SEQ ID NO:25:

( i ) SEQUENCE CHARACTERISTICS:
        ( A ) LENGTH: 1183 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 161..952

( x i ) SEQUENCE DESCRIPTION: SEQ ID NO:25:

```
GAATTCGCGG CCGCCGGGGA CCATGTTGCT TCCGAACATC CTGCTCACCG GTACACCAGG      60

GGTTGGAAAA ACCACACTAG GCAAAGAACT TGCGTCAAAA TCAGGACTGA AATACATTAA     120

TGTGGGTGAT TTAGCTCGAG AAGTCTGATC ATCGGATATG ATG GAG TCT GGC AAG      175
                                              Met Glu Ser Gly Lys
                                               1               5

ACG GCT TCT CCC AAG AGC ATG CCG AAA GAT GCA CAG ATG ATG GCA CAA     223
Thr Ala Ser Pro Lys Ser Met Pro Lys Asp Ala Gln Met Met Ala Gln
                10              15                  20

ATC CTG AAG GAT ATG GGG ATT ACA GAA TAT GAG CCA AGA GTT ATA AAT     271
Ile Leu Lys Asp Met Gly Ile Thr Glu Tyr Glu Pro Arg Val Ile Asn
            25              30                  35

CAG ATG TTG GAG TTT GCC TTC CGA TAT GTG ACC ACA ATT CTA GAT GAT     319
Gln Met Leu Glu Phe Ala Phe Arg Tyr Val Thr Thr Ile Leu Asp Asp
```

|  |  |  |  |  |  |  |  |  |  |  |  |  |  |  |  |
|---|---|---|---|---|---|---|---|---|---|---|---|---|---|---|---|
|  |  |  | 40 |  |  |  | 45 |  |  |  | 50 |  |  |  |  |
| GCA | AAA | ATT | TAT | TCA | AGC | CAT | GCT | AAG | AAA | GCT | ACT | GTT | GAT | GCA | GAT | 367 |
| Ala | Lys | Ile | Tyr | Ser | Ser | His | Ala | Lys | Lys | Ala | Thr | Val | Asp | Ala | Asp |
|  | 55 |  |  |  |  | 60 |  |  |  |  | 65 |  |  |  |  |
| GAT | GTG | CGA | TTG | GCA | ATC | CAG | TGC | CGC | GCT | GAT | CAG | TCT | TTT | ACC | TCT | 415 |
| Asp | Val | Arg | Leu | Ala | Ile | Gln | Cys | Arg | Ala | Asp | Gln | Ser | Phe | Thr | Ser |
| 70 |  |  |  |  | 75 |  |  |  |  | 80 |  |  |  |  | 85 |
| CCT | CCC | CCA | AGA | GAT | TTT | TTA | TTA | GAT | ATT | GCA | AGG | CAA | AGA | AAT | CAA | 463 |
| Pro | Pro | Pro | Arg | Asp | Phe | Leu | Leu | Asp | Ile | Ala | Arg | Gln | Arg | Asn | Gln |
|  |  |  |  | 90 |  |  |  |  | 95 |  |  |  |  | 100 |  |
| ACC | CCT | TTG | CCA | TTG | ATC | AAG | CCA | TAT | TCA | GGT | CCT | AGG | TTG | CCA | CCT | 511 |
| Thr | Pro | Leu | Pro | Leu | Ile | Lys | Pro | Tyr | Ser | Gly | Pro | Arg | Leu | Pro | Pro |
|  |  |  |  | 105 |  |  |  |  | 110 |  |  |  |  | 115 |  |
| GAT | AGA | TAC | TGC | TTA | ACA | GCT | CCA | AAC | TAT | AGG | CTG | AAA | TCT | TTA | CAG | 559 |
| Asp | Arg | Tyr | Cys | Leu | Thr | Ala | Pro | Asn | Tyr | Arg | Leu | Lys | Ser | Leu | Gln |
|  |  |  | 120 |  |  |  |  | 125 |  |  |  |  | 130 |  |  |
| AAA | AAG | GCA | TCA | ACT | TCT | GCG | GGA | AGA | ATA | ACA | GTC | CCG | CGG | TTA | AGT | 607 |
| Lys | Lys | Ala | Ser | Thr | Ser | Ala | Gly | Arg | Ile | Thr | Val | Pro | Arg | Leu | Ser |
|  | 135 |  |  |  |  | 140 |  |  |  |  | 145 |  |  |  |  |
| GTT | GGT | TCA | GTT | ACT | AGC | AGA | CCA | AGT | ACT | CCC | ACA | CTA | GGC | ACA | CCA | 655 |
| Val | Gly | Ser | Val | Thr | Ser | Arg | Pro | Ser | Thr | Pro | Thr | Leu | Gly | Thr | Pro |
| 150 |  |  |  |  | 155 |  |  |  |  | 160 |  |  |  |  | 165 |
| ACC | CCA | CAG | ACC | ATG | TCT | GTT | TCA | ACT | AAA | GTA | GGG | ACT | CCC | ATG | TCC | 703 |
| Thr | Pro | Gln | Thr | Met | Ser | Val | Ser | Thr | Lys | Val | Gly | Thr | Pro | Met | Ser |
|  |  |  |  | 170 |  |  |  |  | 175 |  |  |  |  | 180 |  |
| CTC | ACA | GGT | CAA | AGG | TTT | ACA | GTA | CAG | ATG | CCT | ACT | TCT | CAG | TCT | CCA | 751 |
| Leu | Thr | Gly | Gln | Arg | Phe | Thr | Val | Gln | Met | Pro | Thr | Ser | Gln | Ser | Pro |
|  |  |  | 185 |  |  |  |  | 190 |  |  |  |  | 195 |  |  |
| GCT | GTA | AAA | GCT | TCA | ATT | CCT | GCA | ACC | TCA | GCA | GTT | CAG | AAT | GTT | CTG | 799 |
| Ala | Val | Lys | Ala | Ser | Ile | Pro | Ala | Thr | Ser | Ala | Val | Gln | Asn | Val | Leu |
|  | 200 |  |  |  |  | 205 |  |  |  |  | 210 |  |  |  |  |
| ATT | AAT | CCA | TCA | TTA | ATC | GGG | TCC | AAA | AAC | ATT | CTT | ATT | ACC | ACT | AAT | 847 |
| Ile | Asn | Pro | Ser | Leu | Ile | Gly | Ser | Lys | Asn | Ile | Leu | Ile | Thr | Thr | Asn |
|  | 215 |  |  |  |  | 220 |  |  |  |  | 225 |  |  |  |  |
| ATG | ATG | TCA | TCA | CAA | AAT | ACT | GCC | AAT | GAA | TCA | TCA | AAT | GCA | TTG | AAA | 895 |
| Met | Met | Ser | Ser | Gln | Asn | Thr | Ala | Asn | Glu | Ser | Ser | Asn | Ala | Leu | Lys |
| 230 |  |  |  |  | 235 |  |  |  |  | 240 |  |  |  |  | 245 |
| AGA | AAA | CGT | GAA | GAT | GAT | GAT | GAT | GAC | GAT | GAT | GAT | GAT | GAT | GAC | TAT | 943 |
| Arg | Lys | Arg | Glu | Asp | Asp | Asp | Asp | Asp | Asp | Asp | Asp | Asp | Asp | Asp | Tyr |
|  |  |  |  | 250 |  |  |  |  | 255 |  |  |  |  | 260 |  |

```
GAT AAT CTG  TAATCTAGCC  TTGCTGAATG  TAACATGTAT  ACTTGGTCTT                    992
Asp Asn Leu

GAATTCATTG  TACTGATATT  AAACATGCAT  GCTGGATGTT  TTCAAGTTGT  GTTTTAGAAA        1052

ACTAATAATA  ATGAGTAAAC  ACAGTTACCA  TACTTTTCAA  TTGAAATGAA  GGTTTTTCAT        1112

CAGCCTTAAA  AGTGTAAGAA  AAATAAAGTT  GTCATTCATT  CGATAAAAAA  AAAAAAAGCG        1172

GCCGCGAATT  C                                                                  1183
```

( 2 ) INFORMATION FOR SEQ ID NO:26:

( i ) SEQUENCE CHARACTERISTICS:
        ( A ) LENGTH: 264 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Met Glu Ser Gly Lys Thr Ala Ser Pro Lys Ser Met Pro Lys Asp Ala
 1               5                  10                  15
```

```
Gln  Met  Met  Ala  Gln  Ile  Leu  Lys  Asp  Met  Gly  Ile  Thr  Glu  Tyr  Glu
               20                  25                       30

Pro  Arg  Val  Ile  Asn  Gln  Met  Leu  Glu  Phe  Ala  Phe  Arg  Tyr  Val  Thr
          35                       40                       45

Thr  Ile  Leu  Asp  Asp  Ala  Lys  Ile  Tyr  Ser  Ser  His  Ala  Lys  Lys  Ala
     50                       55                       60

Thr  Val  Asp  Ala  Asp  Asp  Val  Arg  Leu  Ala  Ile  Gln  Cys  Arg  Ala  Asp
65                       70                       75                        80

Gln  Ser  Phe  Thr  Ser  Pro  Pro  Arg  Asp  Phe  Leu  Leu  Asp  Ile  Ala
                    85                  90                       95

Arg  Gln  Arg  Asn  Gln  Thr  Pro  Leu  Pro  Leu  Ile  Lys  Pro  Tyr  Ser  Gly
               100                 105                      110

Pro  Arg  Leu  Pro  Pro  Asp  Arg  Tyr  Cys  Leu  Thr  Ala  Pro  Asn  Tyr  Arg
          115                      120                      125

Leu  Lys  Ser  Leu  Gln  Lys  Lys  Ala  Ser  Thr  Ser  Ala  Gly  Arg  Ile  Thr
     130                 135                      140

Val  Pro  Arg  Leu  Ser  Val  Gly  Ser  Val  Thr  Ser  Arg  Pro  Ser  Thr  Pro
145                      150                      155                       160

Thr  Leu  Gly  Thr  Pro  Thr  Pro  Gln  Thr  Met  Ser  Val  Ser  Thr  Lys  Val
               165                      170                      175

Gly  Thr  Pro  Met  Ser  Leu  Thr  Gly  Gln  Arg  Phe  Thr  Val  Gln  Met  Pro
               180                      185                      190

Thr  Ser  Gln  Ser  Pro  Ala  Val  Lys  Ala  Ser  Ile  Pro  Ala  Thr  Ser  Ala
          195                      200                      205

Val  Gln  Asn  Val  Leu  Ile  Asn  Pro  Ser  Leu  Ile  Gly  Ser  Lys  Asn  Ile
     210                      215                      220

Leu  Ile  Thr  Thr  Asn  Met  Met  Ser  Ser  Gln  Asn  Thr  Ala  Asn  Glu  Ser
225                      230                      235                       240

Ser  Asn  Ala  Leu  Lys  Arg  Lys  Arg  Glu  Asp  Asp  Asp  Asp  Asp  Asp  Asp
                    245                      250                      255

Asp  Asp  Asp  Asp  Tyr  Asp  Asn  Leu
               260
```

( 2 ) INFORMATION FOR SEQ ID NO:27:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

```
Asp  Val  Gln  Leu  His  Leu  Glu  Arg  Gln  Asn  Met  Ile  Pro  Gly  Phe  Gly
1                   5                        10                       15

Ser  Glu  Glu  Ile  Pro  Tyr  Lys
               20
```

( 2 ) INFORMATION FOR SEQ ID NO:28:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

|  |  | Val | Phe | Val | Gly | Glu | Val | Val | Glu | Glu | Ala | Leu | Asp | Val | Glu | Glu | Lys |
|---|---|---|---|---|---|---|---|---|---|---|---|---|---|---|---|---|---|
|  |  | 1 |  |  |  | 5 |  |  |  |  | 10 |  |  |  |  | 15 |  |

Pro ( 2 ) INFORMATION FOR SEQ ID NO:29:

( i ) SEQUENCE CHARACTERISTICS:
        ( A ) LENGTH: 1578 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 25..1377

( x i ) SEQUENCE DESCRIPTION: SEQ ID NO:29:

```
ATTCCAAGCT AAATTTAGGC GGGT ATG AGT GAT TTC AGT GAA GAA TTA AAA         51
                          Met Ser Asp Phe Ser Glu Glu Leu Lys
                           1               5

GGG CCT GTG ACA GAT GAT GAA GAA GTG GAA ACA TCT GTG CTC AGT GGT        99
Gly Pro Val Thr Asp Asp Glu Glu Val Glu Thr Ser Val Leu Ser Gly
 10              15                  20                  25

GCA GGA ATG CAT TTT CCT TGG CTT CAA ACA TAC GTA GAA ACT GTG GCC       147
Ala Gly Met His Phe Pro Trp Leu Gln Thr Tyr Val Glu Thr Val Ala
             30                  35                  40

ATT GGA GGG AAA AGG AGG AAG GAT TTT GCT CAG ACA ACA AGT GCT TGT       195
Ile Gly Gly Lys Arg Arg Lys Asp Phe Ala Gln Thr Thr Ser Ala Cys
         45                  50                  55

TTA AGT TTT ATC CAA GAA GCT CTG CTG AAG CAC CAA TGG CAG CAA GCT       243
Leu Ser Phe Ile Gln Glu Ala Leu Leu Lys His Gln Trp Gln Gln Ala
         60                  65                  70

GCA GAA TAC ATG TAC AGT TAT TTT CAG ACC TTG GAA GAT TCA GAT AGC       291
Ala Glu Tyr Met Tyr Ser Tyr Phe Gln Thr Leu Glu Asp Ser Asp Ser
 75                  80                  85

TAC AAA AGG CAG GCT GCA CCT GAG ATT ATT TGG AAG CTC GGA AGT GAA       339
Tyr Lys Arg Gln Ala Ala Pro Glu Ile Ile Trp Lys Leu Gly Ser Glu
 90                  95                  100                 105

ATT CTA TTT TAT CAT CCC AAA AGC AAC ATG GAG AGT TTC AAT ACT TTT       387
Ile Leu Phe Tyr His Pro Lys Ser Asn Met Glu Ser Phe Asn Thr Phe
             110                 115                 120

GCT AAC CGG ATG AAA AAT ATT GGC GTC ATG AAT TAT TTA AAG ATC TCC       435
Ala Asn Arg Met Lys Asn Ile Gly Val Met Asn Tyr Leu Lys Ile Ser
             125                 130                 135

TTA CAA CAT GCA TTA TAC CTT CTG CAT CAT GGA ATG CTT AAA GAT GCT       483
Leu Gln His Ala Leu Tyr Leu Leu His His Gly Met Leu Lys Asp Ala
         140                 145                 150

AAG AGA AAT CTG AGT GAG GCA GAG ACA TGG AGA CAT GGT GAA AAT ACG       531
Lys Arg Asn Leu Ser Glu Ala Glu Thr Trp Arg His Gly Glu Asn Thr
 155                 160                 165

TCT TCC CGG GAA ATA TTA ATC AAC CTT ATT CAG GCC TAT AAA GGG CTT       579
Ser Ser Arg Glu Ile Leu Ile Asn Leu Ile Gln Ala Tyr Lys Gly Leu
 170                 175                 180                 185

TTA CAG TAT TAT ACC TGG TCT GAA AAG AAG ATG GAA TTG TCA AAG CTT       627
Leu Gln Tyr Tyr Thr Trp Ser Glu Lys Lys Met Glu Leu Ser Lys Leu
             190                 195                 200

GAT AAG GAT GAT TAT GCT TAC AAT GCA GTA GCC CAG GAT GTG TTC AAC       675
Asp Lys Asp Asp Tyr Ala Tyr Asn Ala Val Ala Gln Asp Val Phe Asn
             205                 210                 215

CAC AGC TGG AAG ACA TCT GCA AAT ATT TCT GCA TTG ATT AAA ATT CCT       723
His Ser Trp Lys Thr Ser Ala Asn Ile Ser Ala Leu Ile Lys Ile Pro
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
|     |     |     | 220 |     |     |     |     | 225 |     |     |     |     | 230 |     |     |      |
| GGA | GTT | TGG | GAC | CCT | TTT | GTG | AAG | AGT | TAT | GTA | GAA | ATG | CTG | GAA | TTC | 771  |
| Gly | Val | Trp | Asp | Pro | Phe | Val | Lys | Ser | Tyr | Val | Glu | Met | Leu | Glu | Phe |      |
|     | 235 |     |     |     | 240 |     |     |     |     | 245 |     |     |     |     |     |      |
| TAT | GGG | GAT | CGA | GAT | GGA | GCC | CAA | GAG | GTA | CTC | ACC | AAT | TAT | GCA | TAT | 819  |
| Tyr | Gly | Asp | Arg | Asp | Gly | Ala | Gln | Glu | Val | Leu | Thr | Asn | Tyr | Ala | Tyr |      |
| 250 |     |     |     |     | 255 |     |     |     |     | 260 |     |     |     |     | 265 |      |
| GAT | GAA | AAG | TTT | CCA | TCA | AAT | CCA | AAT | GCC | CAT | ATC | TAC | TTA | TAC | AAC | 867  |
| Asp | Glu | Lys | Phe | Pro | Ser | Asn | Pro | Asn | Ala | His | Ile | Tyr | Leu | Tyr | Asn |      |
|     |     |     |     | 270 |     |     |     |     | 275 |     |     |     |     | 280 |     |      |
| TTT | CTA | AAG | AGA | CAG | AAG | GCA | CCA | AGA | TCA | AAA | TTG | ATA | AGT | GTG | CTT | 915  |
| Phe | Leu | Lys | Arg | Gln | Lys | Ala | Pro | Arg | Ser | Lys | Leu | Ile | Ser | Val | Leu |      |
|     |     |     | 285 |     |     |     |     | 290 |     |     |     |     | 295 |     |     |      |
| AAG | ATT | TTG | TAT | CAG | ATT | GTA | CCA | TCT | CAT | AAA | TTG | ATG | TTG | GAA | TTC | 963  |
| Lys | Ile | Leu | Tyr | Gln | Ile | Val | Pro | Ser | His | Lys | Leu | Met | Leu | Glu | Phe |      |
|     |     | 300 |     |     |     |     | 305 |     |     |     |     | 310 |     |     |     |      |
| CAT | ACA | TTA | CTT | AGA | AAA | TCA | GAA | AAA | GAA | GAA | CAC | CGT | AAA | CTG | GGG | 1011 |
| His | Thr | Leu | Leu | Arg | Lys | Ser | Glu | Lys | Glu | Glu | His | Arg | Lys | Leu | Gly |      |
|     | 315 |     |     |     |     | 320 |     |     |     |     | 325 |     |     |     |     |      |
| TTG | GAG | GTA | TTA | TTT | GGA | GTC | TTA | GAT | TTT | GCC | GGA | TGC | ACT | AAG | AAT | 1059 |
| Leu | Glu | Val | Leu | Phe | Gly | Val | Leu | Asp | Phe | Ala | Gly | Cys | Thr | Lys | Asn |      |
| 330 |     |     |     |     | 335 |     |     |     |     | 340 |     |     |     |     | 345 |      |
| ATA | ACT | GCT | TGG | AAA | TAC | TTG | GCA | AAA | TAT | CTG | AAA | AAT | ATC | TTA | ATG | 1107 |
| Ile | Thr | Ala | Trp | Lys | Tyr | Leu | Ala | Lys | Tyr | Leu | Lys | Asn | Ile | Leu | Met |      |
|     |     |     |     | 350 |     |     |     |     | 355 |     |     |     |     | 360 |     |      |
| GGA | AAC | CAC | CTT | GCG | TGG | GTT | CAA | GAA | GAG | TGG | AAC | TCC | AGG | AAA | AAC | 1155 |
| Gly | Asn | His | Leu | Ala | Trp | Val | Gln | Glu | Glu | Trp | Asn | Ser | Arg | Lys | Asn |      |
|     |     |     | 365 |     |     |     |     | 370 |     |     |     |     | 375 |     |     |      |
| TGG | TGG | CCA | GGG | TTT | CAT | TTC | AGC | TAC | TTT | TGG | GCA | AAA | AGT | GAT | TGG | 1203 |
| Trp | Trp | Pro | Gly | Phe | His | Phe | Ser | Tyr | Phe | Trp | Ala | Lys | Ser | Asp | Trp |      |
|     |     | 380 |     |     |     |     | 385 |     |     |     |     | 390 |     |     |     |      |
| AAG | GAA | GAT | ACA | GCT | TTG | GCC | TGT | GAG | AAA | GCT | TTT | GTG | GCT | GGT | TTA | 1251 |
| Lys | Glu | Asp | Thr | Ala | Leu | Ala | Cys | Glu | Lys | Ala | Phe | Val | Ala | Gly | Leu |      |
|     | 395 |     |     |     |     | 400 |     |     |     |     | 405 |     |     |     |     |      |
| CTG | TTA | GGA | AAA | GGT | TGT | AGA | TAT | TTC | CGG | TAT | ATT | TTA | AAG | CAA | GAT | 1299 |
| Leu | Leu | Gly | Lys | Gly | Cys | Arg | Tyr | Phe | Arg | Tyr | Ile | Leu | Lys | Gln | Asp |      |
| 410 |     |     |     |     | 415 |     |     |     |     | 420 |     |     |     |     | 425 |      |
| CAC | CAA | ATC | TTA | GGG | AAG | AAA | ATT | AAG | CGG | ATG | AAG | AGA | TCT | GTG | AAA | 1347 |
| His | Gln | Ile | Leu | Gly | Lys | Lys | Ile | Lys | Arg | Met | Lys | Arg | Ser | Val | Lys |      |
|     |     |     |     | 430 |     |     |     |     | 435 |     |     |     |     | 440 |     |      |
| AAA | TAC | AGT | ATT | GTA | AAT | CCA | AGA | CTC | TGATACTGAA | | | TTTAGTTAT | | | | 1394 |
| Lys | Tyr | Ser | Ile | Val | Asn | Pro | Arg | Leu |     |     |     |     |     |     |     |      |
|     |     |     | 445 |     |     |     |     | 450 |     |     |     |     |     |     |     |      |

| | |
|---|---|
| TTCACAGTTG TAGCTACACA GTAAGTAGCT TGGTAGATAG TTATTGAATG TATTTATGTA | 1454 |
| GTGTATTAAG AAGCTTATAT TACTACAAAA AACTTATTTT TATATATTTT TATATTTTTG | 1514 |
| TATTATTTAT AGCTAGAGAA ACAATATTAC TGCCTTTGCT CTTTGTAACT ATGTCTGTTT | 1574 |
| TCTT | 1578 |

( 2 ) INFORMATION FOR SEQ ID NO:30:

( i ) SEQUENCE CHARACTERISTICS:
        ( A ) LENGTH: 450 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

| | | | | | | | | | | | | | | |
|---|---|---|---|---|---|---|---|---|---|---|---|---|---|---|
| Met | Ser | Asp | Phe | Ser | Glu | Glu | Leu | Lys | Gly | Pro | Val | Thr | Asp | Asp | Glu |
| 1 | | | | 5 | | | | | 10 | | | | | 15 | |

-continued

| | | | | | | | | | | | | | | |
|---|---|---|---|---|---|---|---|---|---|---|---|---|---|---|
|Glu|Val|Glu|Thr 20|Ser|Val|Leu|Ser|Gly 25|Ala|Gly|Met|His|Phe 30|Pro|Trp|
|Leu|Gln|Thr 35|Tyr|Val|Glu|Thr|Val 40|Ala|Ile|Gly|Gly|Lys 45|Arg|Arg|Lys|
|Asp|Phe 50|Ala|Gln|Thr|Thr|Ser 55|Ala|Cys|Leu|Ser|Phe 60|Ile|Gln|Glu|Ala|
|Leu 65|Leu|Lys|His|Gln|Trp 70|Gln|Gln|Ala|Ala|Glu 75|Tyr|Met|Tyr|Ser|Tyr 80|
|Phe|Gln|Thr|Leu|Glu 85|Asp|Ser|Asp|Ser|Tyr 90|Lys|Arg|Gln|Ala|Ala 95|Pro|
|Glu|Ile|Ile|Trp 100|Lys|Leu|Gly|Ser|Glu 105|Ile|Leu|Phe|Tyr|His 110|Pro|Lys|
|Ser|Asn|Met 115|Glu|Ser|Phe|Asn|Thr 120|Phe|Ala|Asn|Arg|Met 125|Lys|Asn|Ile|
|Gly|Val 130|Met|Asn|Tyr|Leu|Lys 135|Ile|Ser|Leu|Gln|His 140|Ala|Leu|Tyr|Leu|
|Leu 145|His|His|Gly|Met|Leu 150|Lys|Asp|Ala|Lys|Arg 155|Asn|Leu|Ser|Glu|Ala 160|
|Glu|Thr|Trp|Arg|His 165|Gly|Glu|Asn|Thr|Ser 170|Ser|Arg|Glu|Ile|Leu 175|Ile|
|Asn|Leu|Ile|Gln 180|Ala|Tyr|Lys|Gly|Leu 185|Leu|Gln|Tyr|Tyr|Thr 190|Trp|Ser|
|Glu|Lys|Lys 195|Met|Glu|Leu|Ser|Lys 200|Leu|Asp|Lys|Asp|Asp 205|Tyr|Ala|Tyr|
|Asn|Ala 210|Val|Ala|Gln|Asp|Val 215|Phe|Asn|His|Ser|Trp 220|Lys|Thr|Ser|Ala|
|Asn 225|Ile|Ser|Ala|Leu|Ile 230|Lys|Ile|Pro|Gly|Val 235|Trp|Asp|Pro|Phe|Val 240|
|Lys|Ser|Tyr|Val|Glu 245|Met|Leu|Glu|Phe|Tyr 250|Gly|Asp|Arg|Asp|Gly 255|Ala|
|Gln|Glu|Val|Leu 260|Thr|Asn|Tyr|Ala|Tyr 265|Asp|Glu|Lys|Phe|Pro 270|Ser|Asn|
|Pro|Asn|Ala 275|His|Ile|Tyr|Leu|Tyr 280|Asn|Phe|Leu|Lys|Arg 285|Gln|Lys|Ala|
|Pro|Arg 290|Ser|Lys|Leu|Ile|Ser 295|Val|Leu|Lys|Ile|Leu 300|Tyr|Gln|Ile|Val|
|Pro|Ser 305|His|Lys|Leu|Met 310|Leu|Glu|Phe|His|Thr 315|Leu|Leu|Arg|Lys|Ser 320|
|Glu|Lys|Glu|Glu|His 325|Arg|Lys|Leu|Gly|Leu 330|Glu|Val|Leu|Phe|Gly 335|Val|
|Leu|Asp|Phe|Ala 340|Gly|Cys|Thr|Lys|Asn 345|Ile|Thr|Ala|Trp|Lys 350|Tyr|Leu|
|Ala|Lys|Tyr 355|Leu|Lys|Asn|Ile|Leu 360|Met|Gly|Asn|His|Leu 365|Ala|Trp|Val|
|Gln|Glu|Glu 370|Trp|Asn|Ser|Arg|Lys 375|Asn|Trp|Trp|Pro|Gly 380|Phe|His|Phe|
|Ser 385|Tyr|Phe|Trp|Ala|Lys 390|Ser|Asp|Trp|Lys|Glu 395|Asp|Thr|Ala|Leu|Ala 400|
|Cys|Glu|Lys|Ala|Phe 405|Val|Ala|Gly|Leu|Leu 410|Leu|Gly|Lys|Gly|Cys 415|Arg|
|Tyr|Phe|Arg|Tyr 420|Ile|Leu|Lys|Gln|Asp 425|His|Gln|Ile|Leu|Gly 430|Lys|Lys|
|Ile|Lys|Arg|Met|Lys|Arg|Ser|Val|Lys|Lys|Tyr|Ser|Ile|Val|Asn|Pro|

-continued

```
                            435                     440                     445
Arg Leu
    450
```

( 2 ) INFORMATION FOR SEQ ID NO:31:

( i ) SEQUENCE CHARACTERISTICS:
        ( A ) LENGTH: 3901 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 185..2791

( x i ) SEQUENCE DESCRIPTION: SEQ ID NO:31:

```
GCTCGAGTGC CAAAGCTGGG GTTCTACTTG AGATTTCCCT CGTGGTGCCA GGGTCCGGCG      60

AGCATCACGC CGAGGCCCAT TTTCCAGACG ACCACGACGA GGCCGGGGTC ACGAACTCTG     120

GCGCCCCTTA CCAGCTTCCA GTCTCTCGAG GTGGCCAGTG TGGTGCTTGG TCCTTGTTTC     180

CAGG ATG GAC TTC CCC AGC TCC CTC CGC CCT GCG TTG TTT CTG ACC GGC      229
     Met Asp Phe Pro Ser Ser Leu Arg Pro Ala Leu Phe Leu Thr Gly
     1               5                  10                  15

CCC CTT GGT CTG AGC GAC GTC CCT GAC CTC TCT TTC ATG TGC AGC TGG      277
Pro Leu Gly Leu Ser Asp Val Pro Asp Leu Ser Phe Met Cys Ser Trp
             20                  25                  30

CGA GAC GCA CTG ACT CTG CCA GAG GCC CAG CCC CAG AAC TCA GAG AAT      325
Arg Asp Ala Leu Thr Leu Pro Glu Ala Gln Pro Gln Asn Ser Glu Asn
                 35                  40                  45

GGG GCA CTG CAT GTG ACC AAG GAC CTG CTG TGG GAG CCG GCA ACC CCT      373
Gly Ala Leu His Val Thr Lys Asp Leu Leu Trp Glu Pro Ala Thr Pro
         50                  55                  60

GGG CCT CTC CCC ATG CTG CCT CCC CTC ATC GAT CCC TGG GAC CCT GGC      421
Gly Pro Leu Pro Met Leu Pro Pro Leu Ile Asp Pro Trp Asp Pro Gly
     65                  70                  75

CTG ACT GCC CGG GAC CTG CTT TTC CGC GGA GGG TAC CGG TAT CGG AAG      469
Leu Thr Ala Arg Asp Leu Leu Phe Arg Gly Gly Tyr Arg Tyr Arg Lys
 80                  85                  90                  95

CGG CCC CGA GTC GTG CTG GAT GTG ACT GAG CAG ATC AGC CGG TTC CTC      517
Arg Pro Arg Val Val Leu Asp Val Thr Glu Gln Ile Ser Arg Phe Leu
                 100                 105                 110

TTG GAT CAT GGA GAC GTA GCC TTT GCG CCC CTG GGG AAG CTG ATG CTG      565
Leu Asp His Gly Asp Val Ala Phe Ala Pro Leu Gly Lys Leu Met Leu
             115                 120                 125

GAG AAT TTC AAG CTG GAG GGA GCG GGG AGC CGC ACT AAG AAG AAG ACA      613
Glu Asn Phe Lys Leu Glu Gly Ala Gly Ser Arg Thr Lys Lys Lys Thr
         130                 135                 140

GTG GTC AGT GTG AAG AAG CTG CTC CAG GAC CTC GGT GGA CAC CAG CCC      661
Val Val Ser Val Lys Lys Leu Leu Gln Asp Leu Gly Gly His Gln Pro
     145                 150                 155

TGG GGG TGT CCC TGG GCT TAC CTC AGC AAC CGA CAG CGC CGC TTC TCT      709
Trp Gly Cys Pro Trp Ala Tyr Leu Ser Asn Arg Gln Arg Arg Phe Ser
160                 165                 170                 175

ATC CTC GGG GGC CCC ATC CTG GGC ACG TCG GTG GCG AGC CAC TTG GCA      757
Ile Leu Gly Gly Pro Ile Leu Gly Thr Ser Val Ala Ser His Leu Ala
                 180                 185                 190

GAG CTG CTG CAC GAG GAG CTG GTG CTG CGG TGG GAG CAG CTG CTT CTG      805
Glu Leu Leu His Glu Glu Leu Val Leu Arg Trp Glu Gln Leu Leu Leu
             195                 200                 205
```

```
GAT GAG GCC TGC ACT GGG GGC GCG CTG GCC TGG GTT CCT GGA AGG ACA        853
Asp Glu Ala Cys Thr Gly Gly Ala Leu Ala Trp Val Pro Gly Arg Thr
        210                 215                 220

CCC CAG TTC GGG CAG CTG GTC TAC CCT GCT GGA GGC GCC CAG GAC AGG        901
Pro Gln Phe Gly Gln Leu Val Tyr Pro Ala Gly Gly Ala Gln Asp Arg
225                 230                 235

CTG CAT TTC CAA GAG GTC GTT CTG ACC CCA GGT GAC AAT CCC CAA TTC        949
Leu His Phe Gln Glu Val Val Leu Thr Pro Gly Asp Asn Pro Gln Phe
240                 245                 250                 255

CTT GGG AAA CCT GGA CGC ATC CAG CTC CAG GGA CCT GTC CGG CAA GTG        997
Leu Gly Lys Pro Gly Arg Ile Gln Leu Gln Gly Pro Val Arg Gln Val
                260                 265                 270

GTG ACA TGC ACC GTC CAG GGA GAA AGT AAG GCC CTT ATA TAC ACT TTC       1045
Val Thr Cys Thr Val Gln Gly Glu Ser Lys Ala Leu Ile Tyr Thr Phe
        275                 280                 285

CTC CCT CAC TGG CTG ACC TGC TAC CTG ACC CCT GGC CCT TTC CAT CCC       1093
Leu Pro His Trp Leu Thr Cys Tyr Leu Thr Pro Gly Pro Phe His Pro
        290                 295                 300

TCC TCA GCT CTG CTG GCC GTC CGC TCT GAC TAC CAC TGT GCC GTG TGG       1141
Ser Ser Ala Leu Leu Ala Val Arg Ser Asp Tyr His Cys Ala Val Trp
305                 310                 315

AAG TTT GGT AAA CAG TGG CAG CCA ACC CTT CTG CAG GCG ATG CAG GTG       1189
Lys Phe Gly Lys Gln Trp Gln Pro Thr Leu Leu Gln Ala Met Gln Val
320                 325                 330                 335

GAG AAA GGG GCC ACG GGG ATC AGC CTC AGC CCT CAC CTG CCC GGG GAG       1237
Glu Lys Gly Ala Thr Gly Ile Ser Leu Ser Pro His Leu Pro Gly Glu
                340                 345                 350

CTG GCC ATC TGC AGC CGC TCG GGA GCC GTC TGC CTG TGG AGC CCT GAG       1285
Leu Ala Ile Cys Ser Arg Ser Gly Ala Val Cys Leu Trp Ser Pro Glu
        355                 360                 365

GAT GGG CTG CGG CAA ATC TAC AGG GAC CCT GAG ACC CTC GTG TTC CGG       1333
Asp Gly Leu Arg Gln Ile Tyr Arg Asp Pro Glu Thr Leu Val Phe Arg
        370                 375                 380

GAC TCC TCT TCG TGG CGT TGG GCA GAC TTC ACT GCG CAC CCT CGG GTG       1381
Asp Ser Ser Ser Trp Arg Trp Ala Asp Phe Thr Ala His Pro Arg Val
385                 390                 395

CTG ACC GTG GGT GAC CGC ACC GGA GTG AAG ATG CTG GAC ACT CAG GGC       1429
Leu Thr Val Gly Asp Arg Thr Gly Val Lys Met Leu Asp Thr Gln Gly
400                 405                 410                 415

CCG CCG GGC TGT GGT CTG TTG CTT TTT CGT TTG GGG GCA GAG GCT TCG       1477
Pro Pro Gly Cys Gly Leu Leu Leu Phe Arg Leu Gly Ala Glu Ala Ser
                420                 425                 430

TGC CAG AAA GGG GAA CGT GTC CTG CTT ACC CAG TAC CTG GGG CAC TCC       1525
Cys Gln Lys Gly Glu Arg Val Leu Leu Thr Gln Tyr Leu Gly His Ser
        435                 440                 445

AGC CCC AAA TGC CTC CCC CCT ACT CTT CAT CTC GTC TGT ACC CAG TTC       1573
Ser Pro Lys Cys Leu Pro Pro Thr Leu His Leu Val Cys Thr Gln Phe
        450                 455                 460

TCT CTC TAC CTA GTG GAC GAG CGC CTT CCC CTG GTG CCG ATG CTG AAG       1621
Ser Leu Tyr Leu Val Asp Glu Arg Leu Pro Leu Val Pro Met Leu Lys
465                 470                 475

TGG AAC CAT GGC CTC CCC TCC CCG CTC CTG CTG GCC CGA CTG CTG CCT       1669
Trp Asn His Gly Leu Pro Ser Pro Leu Leu Leu Ala Arg Leu Leu Pro
480                 485                 490                 495

CCG CCC CGG CCC AGC TGC GTG CAG CCC CTG CTC CTC GGA GGC CAG GGT       1717
Pro Pro Arg Pro Ser Cys Val Gln Pro Leu Leu Leu Gly Gly Gln Gly
                500                 505                 510

GGG CAG CTG CAG CTG CTG CAC CTG GCA GGA GAA GGG GCG TCG GTG CCC       1765
Gly Gln Leu Gln Leu Leu His Leu Ala Gly Glu Gly Ala Ser Val Pro
        515                 520                 525
```

| | | | | | | | | | | | | | | | | |
|---|---|---|---|---|---|---|---|---|---|---|---|---|---|---|---|---|
| CGC | CTG | GCA | GGC | CCC | CCC | CAG | TCT | CTT | CCT | TCC | AGG | ATC | GAC | TCC | CTC | 1813 |
| Arg | Leu | Ala | Gly | Pro | Pro | Gln | Ser | Leu | Pro | Ser | Arg | Ile | Asp | Ser | Leu | |
| | | 530 | | | | | 535 | | | | | 540 | | | | |
| CCT | GCA | TTT | CCT | CTG | CTG | GAG | CCT | AAG | ATC | CAG | TGG | CGG | CTG | CAG | GAG | 1861 |
| Pro | Ala | Phe | Pro | Leu | Leu | Glu | Pro | Lys | Ile | Gln | Trp | Arg | Leu | Gln | Glu | |
| 545 | | | | | 550 | | | | | 555 | | | | | | |
| CGC | CTG | AAA | GCA | CCG | ACC | ATA | GGT | CTG | GCT | GCC | GTC | GTC | CCG | CCC | TTG | 1909 |
| Arg | Leu | Lys | Ala | Pro | Thr | Ile | Gly | Leu | Ala | Ala | Val | Val | Pro | Pro | Leu | |
| 560 | | | | | 565 | | | | | 570 | | | | | 575 | |
| CCC | TCA | GCG | CCC | ACA | CCA | GGC | CTG | GTG | CTC | TTC | CAG | CTC | TCG | GCG | GCG | 1957 |
| Pro | Ser | Ala | Pro | Thr | Pro | Gly | Leu | Val | Leu | Phe | Gln | Leu | Ser | Ala | Ala | |
| | | | | 580 | | | | | 585 | | | | | 590 | | |
| GGA | GAT | GTC | TTC | TAC | CAG | CAG | CTC | CGC | CCC | CAG | GTG | GAC | TCC | AGC | CTC | 2005 |
| Gly | Asp | Val | Phe | Tyr | Gln | Gln | Leu | Arg | Pro | Gln | Val | Asp | Ser | Ser | Leu | |
| | | | | 595 | | | | | 600 | | | | | 605 | | |
| CGC | AGA | GAT | GCT | GGG | CCT | CCT | GGC | GAC | ACC | CAA | CCT | GAC | TGC | CAT | GCC | 2053 |
| Arg | Arg | Asp | Ala | Gly | Pro | Pro | Gly | Asp | Thr | Gln | Pro | Asp | Cys | His | Ala | |
| | | 610 | | | | | 615 | | | | | 620 | | | | |
| CCC | ACA | GCT | TCC | TGG | ACC | TCC | CAG | GAC | ACT | GCC | GGC | TGC | AGC | CAG | TGG | 2101 |
| Pro | Thr | Ala | Ser | Trp | Thr | Ser | Gln | Asp | Thr | Ala | Gly | Cys | Ser | Gln | Trp | |
| 625 | | | | | 630 | | | | | 635 | | | | | | |
| CTG | AAG | GCC | CTG | CTA | AAA | GTG | CCC | CTG | GCT | CCT | CCT | GTG | TGG | ACA | GCA | 2149 |
| Leu | Lys | Ala | Leu | Leu | Lys | Val | Pro | Leu | Ala | Pro | Pro | Val | Trp | Thr | Ala | |
| 640 | | | | | 645 | | | | | 650 | | | | | 655 | |
| CCC | ACC | TTC | ACC | CAC | CGC | CAG | ATG | CTG | GGC | AGC | ACA | GAG | CTG | CGG | AGG | 2197 |
| Pro | Thr | Phe | Thr | His | Arg | Gln | Met | Leu | Gly | Ser | Thr | Glu | Leu | Arg | Arg | |
| | | | | 660 | | | | | 665 | | | | | 670 | | |
| GAG | GAA | GAG | GAA | GGG | CAG | CGG | CTG | GGT | GTG | CTC | CGC | AAG | GCC | ATG | GCC | 2245 |
| Glu | Glu | Glu | Glu | Gly | Gln | Arg | Leu | Gly | Val | Leu | Arg | Lys | Ala | Met | Ala | |
| | | | | 675 | | | | | 680 | | | | | 685 | | |
| CGA | GGG | CAG | CTC | CTG | CTG | CAG | AGA | GAC | CTG | GGC | TCC | CTC | CCT | GCG | GCA | 2293 |
| Arg | Gly | Gln | Leu | Leu | Leu | Gln | Arg | Asp | Leu | Gly | Ser | Leu | Pro | Ala | Ala | |
| | | | | 690 | | | | | 695 | | | | | 700 | | |
| GAG | CCA | CCC | CCT | GCA | CCC | GAG | TCA | GGC | CTA | GAG | GAC | AAG | CTC | AGT | GAG | 2341 |
| Glu | Pro | Pro | Pro | Ala | Pro | Glu | Ser | Gly | Leu | Glu | Asp | Lys | Leu | Ser | Glu | |
| | | 705 | | | | | 710 | | | | | 715 | | | | |
| CGC | CTG | GGG | GAA | GCC | TGG | GCA | GGC | CGA | GGG | GCT | GCC | TGG | TGG | GAG | AGG | 2389 |
| Arg | Leu | Gly | Glu | Ala | Trp | Ala | Gly | Arg | Gly | Ala | Ala | Trp | Trp | Glu | Arg | |
| 720 | | | | | 725 | | | | | 730 | | | | | 735 | |
| CAG | CAG | GGC | AGG | ACC | TCG | GAG | CCC | GGG | AGA | CAG | ACC | AGG | CGG | CCC | AAG | 2437 |
| Gln | Gln | Gly | Arg | Thr | Ser | Glu | Pro | Gly | Arg | Gln | Thr | Arg | Arg | Pro | Lys | |
| | | | | 740 | | | | | 745 | | | | | 750 | | |
| CGC | CGG | ACC | CAG | CTG | TCC | AGC | AGC | TTT | TCG | CTC | AGT | GGC | CAT | GTG | GAT | 2485 |
| Arg | Arg | Thr | Gln | Leu | Ser | Ser | Ser | Phe | Ser | Leu | Ser | Gly | His | Val | Asp | |
| | | | | 755 | | | | | 760 | | | | | 765 | | |
| CCG | TCA | GAG | GAC | ACC | AGC | TCC | CCT | CAT | AGC | CCT | GAG | TGG | CCA | CCT | GCT | 2533 |
| Pro | Ser | Glu | Asp | Thr | Ser | Ser | Pro | His | Ser | Pro | Glu | Trp | Pro | Pro | Ala | |
| | | 770 | | | | | 775 | | | | | 780 | | | | |
| GAT | GCT | CTG | CCC | CTG | CCC | CCC | ACG | ACC | CCG | CCC | TCC | CAG | GAG | TTG | ACT | 2581 |
| Asp | Ala | Leu | Pro | Leu | Pro | Pro | Thr | Thr | Pro | Pro | Ser | Gln | Glu | Leu | Thr | |
| 785 | | | | | 790 | | | | | 795 | | | | | | |
| CCG | GAT | GCA | TGC | GCC | CAG | GGC | GTC | CCA | TCA | GAG | CAG | CGG | CAG | ATG | CTC | 2629 |
| Pro | Asp | Ala | Cys | Ala | Gln | Gly | Val | Pro | Ser | Glu | Gln | Arg | Gln | Met | Leu | |
| 800 | | | | | 805 | | | | | 810 | | | | | 815 | |
| CGT | GAC | TAC | ATG | GCC | AAG | CTA | CCA | CCC | CAG | AGG | GAC | ACC | CCA | GGC | TGT | 2677 |
| Arg | Asp | Tyr | Met | Ala | Lys | Leu | Pro | Pro | Gln | Arg | Asp | Thr | Pro | Gly | Cys | |
| | | | | 820 | | | | | 825 | | | | | 830 | | |
| GCC | ACC | ACA | CCT | CCC | CAC | TCC | CAG | GCC | TCC | AGC | GTC | CGG | GCC | ACT | CGC | 2725 |
| Ala | Thr | Thr | Pro | Pro | His | Ser | Gln | Ala | Ser | Ser | Val | Arg | Ala | Thr | Arg | |
| | | | | 835 | | | | | 840 | | | | | 845 | | |

| | | | | | | | | | | | | | | | |
|---|---|---|---|---|---|---|---|---|---|---|---|---|---|---|---|
| TCC | CAG | CAG | CAC | ACA | CCC | GTC | CTC | TCT | AGC | TCT | CAG | CCC | CTC | CGG AAG | 2773 |
| Ser | Gln | Gln | His | Thr | Pro | Val | Leu | Ser | Ser | Ser | Gln | Pro | Leu | Arg Lys | |
| | | 850 | | | | | 855 | | | | 860 | | | | |

| | | | | | |
|---|---|---|---|---|---|
| AAG | CCT | CGA ATG GGC TTC | TGAGGACACA | AGGTGGGCTG | CCCTCAAGCC | 2821 |
| Lys | Pro | Arg Met Gly Phe | | | | |
| | 865 | | | | | |

| | | | | |
|---|---|---|---|---|
| CCAGAGAGCC | CCTCATCCTT | CCTCTGGGAC | CAGATGTGCC | TTCCACAGTT GAAACTTGAG | 2881 |
| AAGCAGAGCT | CGCCACCTTC | TGGAGGCCAC | TGTGATGATG | AGCCAAGCAA TTTGGAGCCA | 2941 |
| AGTTGAAGGG | ACAGGGCAAC | AAAATACAGT | AGTAGTTTCT | TTTGTATTTT GTATATTCGC | 3001 |
| CTGAAGATCA | TCCCGCAAGG | CAGGCTGGAG | GTGCCGGTGG | GCCTGTGTTG CTGGGATTTT | 3061 |
| AGTCTGTGCT | GGGAGGCAGG | GCTCCGTGCG | CCTCAGCTGT | GGGGCCTCA GCAGGTCCC | 3121 |
| TCAGTTCTCA | CGCCTTCCTG | TCCAGTGGAA | TGGGGCCAG | GAGTGCTGGC TCCTCGTGTT | 3181 |
| TGGTGAGGGT | GGAGTGAGGC | CCCTGCAGAG | CTGCTGATGA | GGTGGGCACA GCGGCCGTTG | 3241 |
| GCAGCTGCTG | TTGTGGGTTG | CTTTGTCAAT | CTCTGCCCCG | GTCTGATGTT TCCTACAGGG | 3301 |
| AGATGCCGTG | GATCCAGGTT | CAGGGACTAA | ATACACTTGG | CAGCTGAAGA TGAATTGGAA | 3361 |
| TGGTCACGTT | TTTTAGGCTG | GACAGCGTCC | CGCCACAGCT | ACTACCTGAC ACTGAGCTCA | 3421 |
| TGCAGAGAGA | TGATGGCTGA | TGTTCCTTCT | CCCTTGGGAC | ATGGGTCTGG CACCTGTGGG | 3481 |
| CTGTCGATAG | TGCCCTCTGA | GCAGAGGGTC | ACGGTCATGT | CAGTTTGGGG GAATTCTCTG | 3541 |
| TTGTGCCTCA | GAGACTCCCC | CCTTTCTTTC | CTCCCTCCCC | TTCTCATTTT GATGTCTAAA | 3601 |
| GCATCAAGTC | CCTCTTCCTC | AGAGTTTCTC | TAGCTGCAGT | GGAAGATTCT GTTTCCTGT | 3661 |
| GGGGAAAATG | CTCACTTGAG | ATTTTGCAGG | GACCCGGGTC | TGTCTGGTTT CTGATGACAT | 3721 |
| AGTAAGAGAA | AGGTCTTTTT | TCAGGTTGGC | TGGTGAAAGG | AATTGCATGT GACTCACACA | 3781 |
| AACAGGAGCT | AGCCCAATCA | TACACTGACT | CGCGTGGGTG | TTTAAATGTT TATCATGCCT | 3841 |
| AAGGGAGACA | TTTATAATTA | AACCATTTAT | GCTACATAAA | AAAAAAAAA AAAAAAAAA | 3901 |

( 2 ) INFORMATION FOR SEQ ID NO:32:

( i ) SEQUENCE CHARACTERISTICS:
  ( A ) LENGTH: 869 amino acids
  ( B ) TYPE: amino acid
  ( D ) TOPOLOGY: linear ( i i ) MOLECULE TYPE: protein ( x i ) SEQUENCE DESCRIPTION: SEQ ID NO:32:

| Met | Asp | Phe | Pro | Ser | Ser | Leu | Arg | Pro | Ala | Leu | Phe | Leu | Thr | Gly | Pro |
|---|---|---|---|---|---|---|---|---|---|---|---|---|---|---|---|
| 1 | | | | 5 | | | | | 10 | | | | | 15 | |
| Leu | Gly | Leu | Ser | Asp | Val | Pro | Asp | Leu | Ser | Phe | Met | Cys | Ser | Trp | Arg |
| | | | 20 | | | | | 25 | | | | | 30 | | |
| Asp | Ala | Leu | Thr | Leu | Pro | Glu | Ala | Gln | Pro | Gln | Asn | Ser | Glu | Asn | Gly |
| | | | 35 | | | | 40 | | | | | 45 | | | |
| Ala | Leu | His | Val | Thr | Lys | Asp | Leu | Leu | Trp | Glu | Pro | Ala | Thr | Pro | Gly |
| | | | 50 | | | | 55 | | | | 60 | | | | |
| Pro | Leu | Pro | Met | Leu | Pro | Pro | Leu | Ile | Asp | Pro | Trp | Asp | Pro | Gly | Leu |
| 65 | | | | | 70 | | | | 75 | | | | | | 80 |
| Thr | Ala | Arg | Asp | Leu | Leu | Phe | Arg | Gly | Gly | Tyr | Arg | Tyr | Arg | Lys | Arg |
| | | | | 85 | | | | | 90 | | | | | 95 | |
| Pro | Arg | Val | Val | Leu | Asp | Val | Thr | Glu | Gln | Ile | Ser | Arg | Phe | Leu | Leu |
| | | | 100 | | | | | 105 | | | | | 110 | | |
| Asp | His | Gly | Asp | Val | Ala | Phe | Ala | Pro | Leu | Gly | Lys | Leu | Met | Leu | Glu |
| | | | 115 | | | | 120 | | | | | 125 | | | |

```
Asn  Phe  Lys  Leu  Glu  Gly  Ala  Gly  Ser  Arg  Thr  Lys  Lys  Thr  Val
     130                 135                      140

Val  Ser  Val  Lys  Lys  Leu  Leu  Gln  Asp  Leu  Gly  Gly  His  Gln  Pro  Trp
145                      150                      155                      160

Gly  Cys  Pro  Trp  Ala  Tyr  Leu  Ser  Asn  Arg  Gln  Arg  Arg  Phe  Ser  Ile
                    165                      170                      175

Leu  Gly  Gly  Pro  Ile  Leu  Gly  Thr  Ser  Val  Ala  Ser  His  Leu  Ala  Glu
               180                      185                      190

Leu  Leu  His  Glu  Glu  Leu  Val  Leu  Arg  Trp  Glu  Gln  Leu  Leu  Leu  Asp
          195                      200                      205

Glu  Ala  Cys  Thr  Gly  Gly  Ala  Leu  Ala  Trp  Val  Pro  Gly  Arg  Thr  Pro
     210                      215                      220

Gln  Phe  Gly  Gln  Leu  Val  Tyr  Pro  Ala  Gly  Gly  Ala  Gln  Asp  Arg  Leu
225                      230                      235                      240

His  Phe  Gln  Glu  Val  Val  Leu  Thr  Pro  Gly  Asp  Asn  Pro  Gln  Phe  Leu
                    245                      250                      255

Gly  Lys  Pro  Gly  Arg  Ile  Gln  Leu  Gln  Gly  Pro  Val  Arg  Gln  Val  Val
               260                      265                      270

Thr  Cys  Thr  Val  Gln  Gly  Glu  Ser  Lys  Ala  Leu  Ile  Tyr  Thr  Phe  Leu
          275                      280                      285

Pro  His  Trp  Leu  Thr  Cys  Tyr  Leu  Thr  Pro  Gly  Pro  Phe  His  Pro  Ser
     290                      295                      300

Ser  Ala  Leu  Leu  Ala  Val  Arg  Ser  Asp  Tyr  His  Cys  Ala  Val  Trp  Lys
305                      310                      315                      320

Phe  Gly  Lys  Gln  Trp  Gln  Pro  Thr  Leu  Leu  Gln  Ala  Met  Gln  Val  Glu
                    325                      330                      335

Lys  Gly  Ala  Thr  Gly  Ile  Ser  Leu  Ser  Pro  His  Leu  Pro  Gly  Glu  Leu
               340                      345                      350

Ala  Ile  Cys  Ser  Arg  Ser  Gly  Ala  Val  Cys  Leu  Trp  Ser  Pro  Glu  Asp
          355                      360                      365

Gly  Leu  Arg  Gln  Ile  Tyr  Arg  Asp  Pro  Glu  Thr  Leu  Val  Phe  Arg  Asp
     370                      375                      380

Ser  Ser  Ser  Trp  Arg  Trp  Ala  Asp  Phe  Thr  Ala  His  Pro  Arg  Val  Leu
385                      390                      395                      400

Thr  Val  Gly  Asp  Arg  Thr  Gly  Val  Lys  Met  Leu  Asp  Thr  Gln  Gly  Pro
               405                      410                      415

Pro  Gly  Cys  Gly  Leu  Leu  Leu  Phe  Arg  Leu  Gly  Ala  Glu  Ala  Ser  Cys
               420                      425                      430

Gln  Lys  Gly  Glu  Arg  Val  Leu  Leu  Thr  Gln  Tyr  Leu  Gly  His  Ser  Ser
          435                      440                      445

Pro  Lys  Cys  Leu  Pro  Pro  Thr  Leu  His  Leu  Val  Cys  Thr  Gln  Phe  Ser
     450                      455                      460

Leu  Tyr  Leu  Val  Asp  Glu  Arg  Leu  Pro  Leu  Val  Pro  Met  Leu  Lys  Trp
465                      470                      475                      480

Asn  His  Gly  Leu  Pro  Ser  Pro  Leu  Leu  Leu  Ala  Arg  Leu  Leu  Pro  Pro
                    485                      490                      495

Pro  Arg  Pro  Ser  Cys  Val  Gln  Pro  Leu  Leu  Leu  Gly  Gly  Gln  Gly  Gly
               500                      505                      510

Gln  Leu  Gln  Leu  Leu  His  Leu  Ala  Gly  Glu  Gly  Ala  Ser  Val  Pro  Arg
          515                      520                      525

Leu  Ala  Gly  Pro  Pro  Gln  Ser  Leu  Pro  Ser  Arg  Ile  Asp  Ser  Leu  Pro
     530                      535                      540

Ala  Phe  Pro  Leu  Leu  Glu  Pro  Lys  Ile  Gln  Trp  Arg  Leu  Gln  Glu  Arg
```

|  |  |  |  |  |  |  |  |  |  |  |  |  |  |  |
|---|---|---|---|---|---|---|---|---|---|---|---|---|---|---|
| 545 |  |  |  |  | 550 |  |  |  |  | 555 |  |  |  | 560 |
| Leu | Lys | Ala | Pro | Thr | Ile | Gly | Leu | Ala | Ala | Val | Val | Pro | Pro | Leu | Pro |
|  |  |  |  | 565 |  |  |  |  | 570 |  |  |  |  | 575 |
| Ser | Ala | Pro | Thr | Pro | Gly | Leu | Val | Leu | Phe | Gln | Leu | Ser | Ala | Ala | Gly |
|  |  |  | 580 |  |  |  |  | 585 |  |  |  |  | 590 |  |
| Asp | Val | Phe | Tyr | Gln | Gln | Leu | Arg | Pro | Gln | Val | Asp | Ser | Ser | Leu | Arg |
|  |  | 595 |  |  |  |  | 600 |  |  |  |  | 605 |  |  |  |
| Arg | Asp | Ala | Gly | Pro | Pro | Gly | Asp | Thr | Gln | Pro | Asp | Cys | His | Ala | Pro |
|  | 610 |  |  |  |  | 615 |  |  |  |  | 620 |  |  |  |  |
| Thr | Ala | Ser | Trp | Thr | Ser | Gln | Asp | Thr | Ala | Gly | Cys | Ser | Gln | Trp | Leu |
| 625 |  |  |  |  | 630 |  |  |  |  | 635 |  |  |  |  | 640 |
| Lys | Ala | Leu | Leu | Lys | Val | Pro | Leu | Ala | Pro | Pro | Val | Trp | Thr | Ala | Pro |
|  |  |  |  | 645 |  |  |  |  | 650 |  |  |  |  | 655 |  |
| Thr | Phe | Thr | His | Arg | Gln | Met | Leu | Gly | Ser | Thr | Glu | Leu | Arg | Arg | Glu |
|  |  |  | 660 |  |  |  |  | 665 |  |  |  |  | 670 |  |  |
| Glu | Glu | Glu | Gly | Gln | Arg | Leu | Gly | Val | Leu | Arg | Lys | Ala | Met | Ala | Arg |
|  |  | 675 |  |  |  |  | 680 |  |  |  |  | 685 |  |  |  |
| Gly | Gln | Leu | Leu | Leu | Gln | Arg | Asp | Leu | Gly | Ser | Leu | Pro | Ala | Ala | Glu |
|  | 690 |  |  |  |  | 695 |  |  |  |  | 700 |  |  |  |  |
| Pro | Pro | Pro | Ala | Pro | Glu | Ser | Gly | Leu | Glu | Asp | Lys | Leu | Ser | Glu | Arg |
| 705 |  |  |  |  | 710 |  |  |  |  | 715 |  |  |  |  | 720 |
| Leu | Gly | Glu | Ala | Trp | Ala | Gly | Arg | Gly | Ala | Ala | Trp | Trp | Glu | Arg | Gln |
|  |  |  |  | 725 |  |  |  |  | 730 |  |  |  |  | 735 |  |
| Gln | Gly | Arg | Thr | Ser | Glu | Pro | Gly | Arg | Gln | Thr | Arg | Arg | Pro | Lys | Arg |
|  |  |  | 740 |  |  |  |  | 745 |  |  |  |  | 750 |  |  |
| Arg | Thr | Gln | Leu | Ser | Ser | Ser | Phe | Ser | Leu | Ser | Gly | His | Val | Asp | Pro |
|  |  | 755 |  |  |  |  | 760 |  |  |  |  | 765 |  |  |  |
| Ser | Glu | Asp | Thr | Ser | Ser | Pro | His | Ser | Pro | Glu | Trp | Pro | Pro | Ala | Asp |
|  | 770 |  |  |  |  | 775 |  |  |  |  | 780 |  |  |  |  |
| Ala | Leu | Pro | Leu | Pro | Pro | Thr | Thr | Pro | Pro | Ser | Gln | Glu | Leu | Thr | Pro |
| 785 |  |  |  |  | 790 |  |  |  |  | 795 |  |  |  |  | 800 |
| Asp | Ala | Cys | Ala | Gln | Gly | Val | Pro | Ser | Glu | Gln | Arg | Gln | Met | Leu | Arg |
|  |  |  |  | 805 |  |  |  |  | 810 |  |  |  |  | 815 |  |
| Asp | Tyr | Met | Ala | Lys | Leu | Pro | Pro | Gln | Arg | Asp | Thr | Pro | Gly | Cys | Ala |
|  |  |  | 820 |  |  |  |  | 825 |  |  |  |  | 830 |  |  |
| Thr | Thr | Pro | Pro | His | Ser | Gln | Ala | Ser | Ser | Val | Arg | Ala | Thr | Arg | Ser |
|  |  | 835 |  |  |  |  | 840 |  |  |  |  | 845 |  |  |  |
| Gln | Gln | His | Thr | Pro | Val | Leu | Ser | Ser | Ser | Gln | Pro | Leu | Arg | Lys | Lys |
|  | 850 |  |  |  |  | 855 |  |  |  |  | 860 |  |  |  |  |
| Pro | Arg | Met | Gly | Phe |  |  |  |  |  |  |  |  |  |  |  |
| 865 |  |  |  |  |  |  |  |  |  |  |  |  |  |  |  |

( 2 ) INFORMATION FOR SEQ ID NO:33:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

| Lys | Lys | Leu | Gln | Asp | Leu | Val | Arg | Glu | Val | Asp | Pro | Asn | Glu | Gln | Leu |
|---|---|---|---|---|---|---|---|---|---|---|---|---|---|---|---|
| 1 |  |  |  | 5 |  |  |  |  | 10 |  |  |  |  | 15 |  |
| Asp | Glu | Asp | Val | Glu | Met | Leu | Leu | Gln | Ile | Ala | Asp | Asp |  |  |  |
|  |  |  | 20 |  |  |  |  | 25 |  |  |  |  |  |  |  |

( 2 ) INFORMATION FOR SEQ ID NO:34:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:34:

```
Leu  Gln  Asp  Leu  Val  Arg  Glu  Val  Asp  Pro  Asn
 1              5                           10
```

( 2 ) INFORMATION FOR SEQ ID NO:35:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:35:

```
His  Met  Arg  Glu  Ala  Val  Arg  Arg  Leu  Lys
 1              5                           10
```

( 2 ) INFORMATION FOR SEQ ID NO:36:

( i ) SEQUENCE CHARACTERISTICS:
    ( A ) LENGTH: 24 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:36:

```
Met  Gln  Ile  Leu  Val  Ser  Ser  Phe  Glu  Glu  Glu  Gln  Leu  Asn  Tyr  Glu
 1              5                           10                          15
Met  Tyr  Asn  Lys  Ala  Tyr  Gly  Gln
               20
```